(12) United States Patent
Kim et al.

(10) Patent No.: US 11,819,556 B2
(45) Date of Patent: *Nov. 21, 2023

(54) STABILIZED COMPOSITIONS OF RADIONUCLIDES AND USES THEREOF

(71) Applicant: RayzeBio, Inc., San Diego, CA (US)

(72) Inventors: Daniel Kim, San Diego, CA (US); Gang Chen, San Diego, CA (US); Ken Song, San Diego, CA (US); Matthew Moran, Ontario (CA); Susan Arangio, San Diego, CA (US)

(73) Assignee: RAYZEBIO, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/324,420

(22) Filed: May 26, 2023

(65) Prior Publication Data

US 2023/0293737 A1    Sep. 21, 2023

Related U.S. Application Data

(60) Continuation of application No. 17/976,664, filed on Oct. 28, 2022, now Pat. No. 11,707,540, which is a continuation of application No. 17/858,859, filed on Jul. 6, 2022, now Pat. No. 11,497,822, which is a division of application No. 17/665,202, filed on Feb. 4, 2022, now Pat. No. 11,541,134.

(60) Provisional application No. 63/228,535, filed on Aug. 2, 2021.

(51) Int. Cl.
  *A61K 51/08*    (2006.01)
  *A61P 35/00*    (2006.01)
  *A61K 51/12*    (2006.01)

(52) U.S. Cl.
  CPC .......... *A61K 51/088* (2013.01); *A61K 51/121* (2013.01); *A61P 35/00* (2018.01)

(58) Field of Classification Search
  CPC .......... A61K 51/08; A61K 51/12; A61P 35/00
  See application file for complete search history.

(56) References Cited

U.S. PATENT DOCUMENTS

| | | |
|---|---|---|
| 4,457,489 A | 7/1984 | Gilmore |
| 6,017,512 A | 1/2000 | Dean et al. |
| 8,293,873 B2 | 10/2012 | De et al. |
| 8,349,391 B2 | 1/2013 | Harfensteller et al. |
| 8,603,435 B2 | 12/2013 | Miao et al. |
| 9,351,997 B2 | 5/2016 | Bender |
| 9,480,759 B2 | 11/2016 | Stevenson et al. |
| 9,610,371 B2 | 4/2017 | Norenberg |
| 9,790,573 B2 | 10/2017 | Moreno et al. |
| 10,159,759 B2 | 12/2018 | Kjaer et al. |
| 10,172,967 B2 | 1/2019 | Norenberg |
| 10,596,276 B2 | 3/2020 | De et al. |
| 10,596,278 B2 | 3/2020 | De et al. |
| 11,497,822 B1* | 11/2022 | Kim .................. A61P 35/00 |
| 11,541,134 B1* | 1/2023 | Kim ................... A61K 51/121 |
| 11,707,540 B2* | 7/2023 | Kim ................... A61K 51/088 |
| | | 424/1.69 |
| 2012/0219495 A1 | 8/2012 | Yoo et al. |
| 2013/0183235 A1 | 7/2013 | Ramdahl |
| 2018/0185524 A1 | 7/2018 | Buono et al. |
| 2019/0134240 A1 | 5/2019 | Zeng et al. |
| 2019/0282715 A1 | 9/2019 | Harris et al. |
| 2019/0336623 A1 | 11/2019 | Tworowska et al. |
| 2020/0030464 A1 | 1/2020 | De Palo et al. |
| 2020/0030465 A1 | 1/2020 | De Palo et al. |
| 2020/0131224 A1 | 4/2020 | Fugazza et al. |
| 2020/0353106 A1 | 11/2020 | De Palo et al. |
| 2021/0290789 A1 | 9/2021 | Burak et al. |
| 2021/0316019 A1 | 10/2021 | Fugazza et al. |
| 2021/0346527 A1 | 11/2021 | Mariani et al. |
| 2021/0379212 A1 | 12/2021 | De Palo et al. |

(Continued)

FOREIGN PATENT DOCUMENTS

| | | |
|---|---|---|
| EP | 1673492 B1 | 3/2009 |
| EP | 2021012 B1 | 12/2017 |

(Continued)

OTHER PUBLICATIONS

Sanjana Ballal et al. Broadening horizons with 225Ac-DOTATATE targeted alpha therapy for gastroenteropancreatic neuroendocrine tumour patients stable or refractory to 177LU-DOTATATE PRRT:first clinical experience on the efficacy and safety, Eur.J Nucl Med and Mol Imaging,47,934-946. (Year: 2020).*

Bal et al. Long-term outcome of 225Ac-DOTATATE Targeted Alpha Therapy in Patients with Metastic Gastroenteropancreatic Neurendocrine Tumors. Power Point presentation 17 pgs. (2018).

Ballal et al. Broadening horizons with 225Ac-DOTATATE targeted alpha therapy for gastroenteropancreatic neuroendocrine tumour patients stable or refractory to 177 Lu-DOTATATE PRRT: first clinical experience on the efficacy and safety. Eur J Nucl Med Mol Imaging 47(4):934-946 (2020).

(Continued)

*Primary Examiner* — Michael G. Hartley
*Assistant Examiner* — Jagadishwar R Samala
(74) *Attorney, Agent, or Firm* — WILSON SONSINI GOODRICH & ROSATI

(57) ABSTRACT

Provided herein are radiopharmaceutical compositions and uses thereof. The radiopharmaceutical compositions can comprise one or more stabilizing agents, an aqueous vehicle, and a conjugate that comprises a targeting ligand and a radionuclide bound to a metal chelator. The targeting ligand can be a small molecule compound or a peptide such as a monocyclic peptide. The targeting ligand can be configured to bind with a tumor target. The stabilizing agent can comprise a radiolysis stabilizer, a free metal chelator, and/or a pH stabilizer. Further provided herein are methods of preparing the radiopharmaceutical compositions and methods of treating cancer by administering the described radiopharmaceutical compositions.

22 Claims, 22 Drawing Sheets

Specification includes a Sequence Listing.

(56) References Cited

U.S. PATENT DOCUMENTS

| | | |
|---|---|---|
| 2021/0379213 A1 | 12/2021 | De Palo et al. |
| 2022/0072166 A1 | 3/2022 | Buono et al. |
| 2023/0144360 A1 | 5/2023 | Kim et al. |

FOREIGN PATENT DOCUMENTS

| | | |
|---|---|---|
| WO | WO-2012174136 A1 | 12/2012 |
| WO | WO-2016207732 A1 | 12/2016 |
| WO | WO-2018132751 A1 | 7/2018 |
| WO | WO-2020021310 A1 | 1/2020 |
| WO | WO-2020021322 A1 | 1/2020 |
| WO | WO-2020021465 A1 | 1/2020 |
| WO | WO-2020064693 A1 | 4/2020 |
| WO | WO-2020089379 A1 | 5/2020 |
| WO | WO-2020099398 A1 | 5/2020 |
| WO | WO-2020113047 A1 | 6/2020 |
| WO | WO-2020131930 A1 | 6/2020 |
| WO | WO-2020225447 A1 | 11/2020 |
| WO | WO-2021142231 A1 | 7/2021 |
| WO | WO-2021154921 A1 | 8/2021 |
| WO | WO-2022002022 A1 | 1/2022 |
| WO | WO-2022031925 A1 | 2/2022 |
| WO | WO-2022081791 A1 | 4/2022 |
| WO | WO-2022111800 A1 | 6/2022 |
| WO | WO-2022112323 A1 | 6/2022 |

OTHER PUBLICATIONS

Ballal et al. Survival Outcomes in Metastatic Gastroenteropancreatic Neuroendocrine Tumor Patients receiving Concomitant 225 Ac-DOTATATE Targeted Alpha Therapy and Capecitabine: A Real-world Scenario Management Based Long-term Outcome Study. J Nucl Med. jnumed. 122.264043 (2022) (online ahead of print).

Ballinger. Theranostic radiopharmaceuticals: established agents in current use. Br J Radiol 91(1091):20170969 (2018).

Baranyai et al. The Use of the Macrocyclic Chelator DOTA in Radiochemical Sepa-rations. Eur. J. Inorg. Chem. pp. 36-56 (2020).

Baum et al. Peptide receptor radionuclide therapy (PRRT) of neuroendocrine tumors: current state and future perspectives. Int J Endo Oncol 2(2):151-158 (2015).

Belder. Dextran 18-1166-12 (Edition AA). Amersham Biosciences 64 pgs. (2003).

Blom et al. Chapter 2: Radiolabelled Somatostatin Analogues For Use In Molecular Imaging. Somatostatin. Editors: A. Anderson and T. McAnulty. Nova Science Publishers, Inc. pp. 41-78 (2013).

Brahmer et al. Nivolumab versus Docetaxel in Advanced Squamous-Cell Non-Small-Cell Lung Cancer. N Engl J Med 373(2):123-135 (2015).

Brechbiel. Bifunctional Chelates for Metal Nuclides. Q J Nucl Med Mol Imaging 52(2):166-173 (2008).

cancer.net. Lung Cancer—Small Cell: Statistics. Available at https://www.cancer.net/cancer-types/lung-cancer-small-cell/statistics (Jan. 2021).

Carrasquillo. Chapter 21: Alpha Radionuclide Therapy: Principles and Applications to NETs. Diagnostic and Therapeutic Nuclear Medicine for Neuroendocrine Tumors. Humana Press, Cham. pp. 429-445 (2017).

Chan et al. Improved safety and efficacy of 213Bi-DOTATATE-targeted alpha therapy of somatostatin receptor-expressing neuroendocrine tumors in mice pre-treated with L-lysine. EJNMMI Res. 6:83 (2016).

Chan et al. Influence of tumour size on the efficacy of targeted alpha therapy with (213)Bi-[DOTA(0), Tyr(3)]-octreotate. EJNMMI Res 6(1):6 (2016).

Chan et al. Optimizing labelling conditions of 213Bi-DOTATATE for preclinical applications of peptide receptor targeted alpha therapy. EJNMMI Radiopharm Chem 1(1):9 (2017).

Collins et al. Acquired Resistance to Antibody-Drug Conjugates. Cancers (Basel) 11(3):394 (2019).

Dai et al. Chiral DOTA chelators as an improved platform for biomedical imaging and therapy applications. Nature Commun 9:857 (2018).

Das et al. Epidemiology, Incidence, and Prevalence of Neuroendocrine Neoplasms: Are There Global Differences? Curr Oncol Rep 23(4):43 (2021).

Delpassand et al. Targeted Alpha-Emitter Therapy With 212Pb-DOTAMTATE for the Treatment of Metastatic SSTR-Expressing Neuroendocrine Tumors: First-in-Human, Dose-Escalation Clinical Trial. J Nucl Med jnumed.121.263230 (24 pgs.) (2022).

Ede et al. Conformationally constrained peptide analogs with hypoglycaemic activity. Peptides: Chemistry and Biology. Smith and Rivier (Eds.), Escom, Leiden pp. 268-270 (1991).

Erchegyi et al. Novel sst(4)-selective somatostatin (SRIF) agonists. 2. Analogues with beta-methyl-3-(2-naphthyl)alanine substitutions at position 8. J Med Chem 46:5587-5596 (2003).

Erchegyi et al. Somatostatin receptor 1 selective analogues: 2. N(alpha)-Methylated scan. J Med Chem 48(2):507-14 (2005).

Esser et al. Comparison of [177Lu-DOTAO, Tyr3]octreotate and [177Lu-DOTAO, Tyr3]octreotide: which peptide is preferable for PRRT? Eur. J. Nucl. Med. Mol. Imag. 33:1346-1351 (2006).

Essler et al. Therapeutic efficacy and toxicity of 225Ac-labelled vs. 213Bi-labelled tumour-homing peptides in a preclinical mouse model of peritoneal carcinomatosis. Eur J Nucl Med Mol Imaging 39(4):602-12 (2012).

Eychenne et al. Overview of Radiolabeled Somatostatin Analogs for Cancer Imaging and Therapy. Molecules 25(17):4012 (2020).

Feijtel et al. Peptide Receptor Radionuclide Therapy: Looking Back, Looking Forward. Curr Top Med Chem 20(32):2959-2969 (2020).

Feuerecker et al. Activity and Adverse Events of Actinium-225-PSMA-617 in Advanced Metastatic Castration-resistant Prostate Cancer After Failure of Lutetium-177-PSMA. Eur Urol 79(3):343-350 (2021).

Fidelman. NCT03457948—Pembrolizumab in With Liver-Directed or Peptide Receptor Radionuclide Therapy in Neuroendocrine Tumors With Metastases—ClinicalTrials.gov. First Posted Mar. 8, 2018.

Formenti et al. Combining radiotherapy and Cancer Immunotherapy: a Paradigm Shift. J Natl Cancer Inst 105(4):256-65 (2013).

Gianfaldoni et al. An Overview on Radiotherapy: From Its History to Its Current Applications in Dermatology. Open Access Maced J Med Sci 5(4):521-525 (2017).

Grace et al. Novel sst4-Selective Somatostatin (SRIF) Agonists. 4. Three-Dimensional Consensus Structure by NMR. J Med Chem 46:5606-5618 (2003).

Grace et al. Somatostatin Receptor 1 Selective Analogues: 4. Three-Dimensional Consensus Structure by NMR. J Med Chem 48:523-533 (2005).

Graf et al., DNA double strand breaks as predictor of efficacy of the alpha-particle emitter Ac-225 and the electron emitter Lu-177 for somatostatin receptor targeted radiotherapy. PLOS One 9(2):e88239 (2014).

Hanaoka et al. Evaluation of (64)Cu-labeled DOTA-D-Phe(1)-Tyr(3)-octreotide ((64)Cu-DOTA-TOC) for imaging somatostatin receptor-expressing tumors. Ann Nucl Med 23:559-567 (2009).

Hocart et al. Highly Potent Cyclic Disulfide Antagonists of Somatostatin. J Med Chem 42(11):1863-71 (1999).

Hooijman et al. Development of [225 Ac]Ac-PSMA-I&T for Targeted Alpha Therapy According to GMP Guidelines for Treatment of mCRPC. Pharmaceutics 13(5):715 (2021).

Iori et al. Labelling of 90 Y- and 177 Lu-DOTA-Bioconjugates for Targeted Radionuclide Therapy: A Comparison among Manual, Semiautomated, and Fully Automated Synthesis. Contrast Media & Molecular Imaging 2017:8160134 (2017).

Iwasaki et al. A Fluorescent Imaging Probe Based on a Macrocyclic Scaffold That Binds to Cellular EpCAM. J Mol Evol 81:210-217 (2015).

Jamous et al. Synthesis of Peptide Radiopharmaceuticals for the Therapy and Diagnosis of Tumor Diseases. Molecules 18(3):3379-409 (2013).

Kamaleshwaran et al. Whole-body and Single-Photon Emission Computed Tomography/Computed Tomography Postpeptide Receptor Alpha Radionuclide Therapy Images of Actinium 225-

(56) References Cited

OTHER PUBLICATIONS

Tetraazacyclododecanetetraacetic Acid—Octreotide as a Primary Modality of Treatment in a Patient with Advanced Rectal Neuroendocrine Tumor with Metastases. Indian J Nucl Med 35(3):226-228 (2020).
Kassis. Therapeutic radionuclides: biophysical and radiobiologic principles. Semin Nucl Med 38(5):358-66 (2008).
Katunumaa et al. Catechin derivatives: specific inhibitor for caspases-3, 7 and 2, and the prevention of apoptosis at the cell and animal levels. FEBS Lett 580(3):741-6 (2006).
Kelly et al. A consensus time for performing quality control of 225Ac-labeled radiopharmaceuticals. Available at https://assets.researchsquare.com/files/rs-39342/v2_covered.pdf?c=1631863217. Research Square (26 pgs) (2021).
Kelly et al. Extensive-stage small cell lung cancer: initial management. UpToDate. UpToDate, Waltham, MA (34 pgs.) (2020).
Kim et al. Phase I study of the 177 Lu-DOTA 0-Tyr 3-Octreotate (lutathera) in combination with nivolumab in patients with neuroendocrine tumors of the lung. J Immunother Cancer 8(2):e000980 (2020).
Kratochwil et al. 225Ac-PSMA-617 for PSMA-Targeted α-Radiation Therapy of Metastatic Castration-Resistant Prostate Cancer. J Nucl Med 57(12):1941-1944 (2016).
Kratochwil et al. Ac-225-DOTATOC—an empiric dose finding for alpha particle emitter based radionuclide therapy of neuroendocrine tumors. J Nuc Med 56(supp 3):1232 (2015).
Kratochwil et al. Ac-225-DOTATOC—dose finding for alpha particle emitter based radionuclide therapy of neuroendocrine tumors. Annual meeting of the European association of nuclear medicine and molecular imaging. S1 vol. 42:S36, Abstract OP089 (2015).
Le Caër. Water Radiolysis: Influence of Oxide Surfaces on H2 Production under Ionizing Radiation. Water 3:235-253 (2011).
Lewin et al. Peptide receptor chemoradionuclide therapy in small cell carcinoma: from bench to bedside. Eur J Nucl Med Mol Imaging 42(1):25-32 (2015).
Li et al. Functionally Versatile and Highly Stable Chelator for 111 In and 177 Lu: Proof-of-Principle Prostate-Specific Membrane Antigen Targeting. Bioconjugate Chem. 30(5):1539-1553 (2019).
Liu et al. Bayesian optimal interval designs for phase I clinical trials. Journal of the Royal Statistical Society. 64(3):507-23 (2015).
LUTATHERA® (lutetium Lu 177 dotatate) injection, for intravenous use. Product label. Advanced Accelerator Applications USA, Inc. Initial U.S. Approval 2018.
Ma et al. Breakthrough of 225Ac and its radionuclide daughters from an 225Ac/213Bi generator: development of new methods, quantitative characterization, and implications for clinical use. Appl Radiat Isot 55(5):667-78 (2001).
Marcu et al. Global comparison of targeted alpha vs targeted beta therapy for cancer: In vitro, in vivo and clinical trials. Crit Rev Oncol Hematol 123:7-20 (2018).
Mehmood et al. Excipients use in parenteral and lyophilized formulation development. Open Science Journal of Pharmacy and Pharmacology 3(3):19-27 (2015).
Miederer et al. Preclinical evaluation of the alpha-particle generator nuclide 225Ac for somatostatin receptor radiotherapy of neuroendocrine tumors. Clin Cancer Res 14(11):3555-61 (2008).
Mitin. Radiation therapy techniques in cancer treatment. UpToDate. UpToDate, Waltham, MA (23 pgs.) (last updated Jan. 14, 2022).
Morgenstern et al. Bismuth-213 and actinium-225—generator performance and evolving therapeutic applications of two generator-derived alpha-emitting radioisotopes. Curr Radiopharm 5(3):221-7 (2012).
Navalkissoor et al. Targeted Alpha Particle Therapy for Neuroendocrine Tumours: The Next Generation of Peptide Receptor Radionuclide Therapy. Neuroendocrinology 108(3):256-264 (2019).
Negi et al. Ligand design for somatostatin receptor isoforms 4 and 5. Eur J Med Chem 163:148-159 (2019).

Nema et al. Excipients and their role in approved injectable products: current usage and future directions. PDA J Pharm Sci Technol 65(3):287-332 (2011).
Pandya et al. Preliminary Therapy Evaluation of (225)Ac-DOTA-c(RGDyK) Demonstrates that Cerenkov Radiation Derived from (225)Ac Daughter Decay Can Be Detected by Optical Imaging for In Vivo Tumor Visualization. Theranostics 6(5):698-709 (2016).
PLENVU®(polyethylene glycol 3350, sodium ascorbate, sodium sulfate, ascorbic acid, sodium chloride and potassium chloride for oral solution). Norgine B.V Initial U.S. Approval 2006.
Portalatin et al. Medical Management of Constipation. Clin Colon Rectal Surg 25(1):12-19 (2012).
Price et al. Matching chelators to radiometals for radiopharmaceuticals. Chem Soc Rev 43(1):260-90 (2014).
Ramogida et al. Evaluation of polydentate picolinic acid chelating ligands and an α-melanocyte-stimulating hormone derivative for targeted alpha therapy using ISOL-produced225 Ac. EJNMMI radiopharm. chem. 4:21 (2019).
Rivier et al. Novel sst(4)-selective somatostatin (SRIF) agonists. 1. Lead identification using a betide scan. J Med Chem 46:5579-5586 (2003).
Rivier et al. Potent Somatostatin Undecapeptide Agonists Selective for Somatostatin Receptor 1 (sst1). J Med Chem 44:2238-2246 (2001).
Rivier et al. Somatostatin receptor 1 selective analogues: 3. Dicyclic peptides. J Med Chem 48:515-522 (2005).
Rohrer et al. Identification and characterization of subtype selective somatostatin receptor agonists. J Physiol Paris 94(3-4):211-5 (2000).
Sartor et al. Lutetium-177-PSMA-617 for Metastatic Castration-Resistant Prostate Cancer. N Engl J Med 385(12):1091-1103 (2021).
Sgouros et al. Radiopharmaceutical therapy in cancer: clinical advances and challenges. Nat Rev Drug Discov 19(9):589-608 (2020).
Singh et al. Lutetium DOTATATE whole body scans: A novel approach for evaluation of neuroendocrine tumors. Indian J Nucl Med 26(3):135-8 (2011).
Smith et al. Tritiated D-ala1-Peptide T Binding. Drug Development Res. 15:371-379 (1988).
Strosberg et al. Phase 3 Trial of 177Lu-Dotatate for Midgut Neuroendocrine Tumors. N Engl J Med 376(2):125-135 (2017).
Tafreshi et al. Lipophilicity Determines Routes of Uptake and Clearance, and Toxicity of an Alpha-Particle-Emitting Peptide Receptor Radiotherapy. ACS Pharmacol Transl Sci 4(2):953-965 (2021).
Tafreshi et al. Melanocortin 1 Receptor-Targeted α-Particle Therapy for Metastatic Uveal Melanoma. J Nucl Med 60(8):1124-1133 (2019).
Tafreshi et al. Preclinical evaluation of [ 225 Ac]Ac-DOTA-TATE for treatment of lung neuroendocrine neoplasms. Eur J Nucl Med Mol Imaging 48(11):3408-3421 (2021).
Thiele et al. Actinium-225 for Targeted a Therapy: Coordination Chemistry and Cur-rent Chelation Approaches. Cancer Biother Radiopharm 33(8):336-348 (2018).
Thompson et al. Practice-changing radiation therapy trials for the treatment of cancer: where are we 150 years after the birth of Marie Curie? Br J Cancer 119(4):389-407 (2018).
Tsionou et al. Comparison of macrocyclic and acyclic chelators for gallium-68 radiolabelling. RSC Adv 7(78):49586-49599 (2017).
Xu et al. Epidemiologic Trends of and Factors Associated With Overall Survival for Patients With Gastroenteropancreatic Neuroendocrine Tumors in the United States. JAMA Netw Open 4(9):e2124750 (2021).
Yang et al. Synthesis and Evaluation of a Macrocyclic Actinium-225 Chelator, Quality Control and In Vivo Evaluation of 225 Ac-crown-αMSH Peptide. Chemistry 26(50):11435-11440 (2020).
Yuan et al. Bayesian Optimal Interval Design: A Simple and Well-Performing Design for Phase I Oncology Trials. Clin Cancer Res. 22(17):4291-301 (2016).

* cited by examiner p-NO2-Bn-TETA

TACN-TM, N,N',N'', tris(2-mercaptoethyl)-1,4,7-triazacyclononane p-NH2-Bn-TE3A

3p-C-NETA

DOTAGA, R = amide, NHS ester

C-NE3TA-NCS

3p-C-DEPA,

H2dedpa, 1,2-[[6-(carboxy)-pyridin-2-yl]-methylamino]ethane (HBED-CC)TFP

HEHA, 1,4,7,10,13,16-hexaazacyclo-hexadecane-$N,N',N'',N''',N'''',N'''''$-hexaacetic acid $p$-SCN-Bn-DFO Bifunctional derivative $p$-SCN-Bn-H$_6$phospa 2,2',2'',2'''-((2S,5S,8S,11S)-2,5,8,11-tetramethyl-1,4,7,10-tetraazacyclododecane-1,4,7,10-tetrayl)tetraacetic acid 2,2',2'',2'''-((2S,5S,8S,11S)-2,5,8,11-tetraethyl-1,4,7,10-tetraazacyclododecane-1,4,7,10-tetrayl)tetraacetic acid Cbm: carbamoyl- 4Amp (Amp): 4-aminomethylphenylalanine Nal: *L*-3-(1-Naphthyl)alanine GABA: γ-aminobutyric acid threo-(2R,3S)C$^\beta$Me 4Aph: 4-aminophenyl propanoic acid 4Iamp: 4-(*N*-isopropyl)-aminomethylphenylalanine 2Nal: *L*-3-(2-Naphthyl)alanine 3Pal: Pyridyl-L-alanine threo-(2S,3R)C$^\beta$Me LAgl(NβMe,benzoyl)     DAgl(NβMe,benzoyl)     LAgl(NβMe, βAla)

DAgl(NβMe, βAla)     LAgl(βAla)     DAgl(βAla)

LAgl-(NβMe,HO-Ac)     DAgl-(NβMe,HO-Ac)

STABILIZED COMPOSITIONS OF RADIONUCLIDES AND USES THEREOF

CROSS REFERENCE

This application is a continuation of U.S. application Ser. No. 17/976,664, filed on Oct. 28, 2022, which is a continuation of U.S. application Ser. No. 17/858,859, filed Jul. 6, 2022, now issued as U.S. Pat. No. 11,497,822 on Oct. 26, 2022, which is a divisional of U.S. application Ser. No. 17/665,202, filed on Feb. 4, 2022, now issued as U.S. Pat. No. 11,541,134 on Dec. 14, 2022, which claims the benefit of U.S. Provisional Application No. 63/228,535, filed on Aug. 2, 2021, each of which is incorporated herein by reference in their entirety.

SEQUENCE LISTING

The instant application contains a Sequence Listing which has been submitted electronically in XML format and is hereby incorporated by reference in its entirety. Said XML file, created on Oct. 28, 2022, is named 59541-718_302_SL.xml and is 155,945 bytes in size.

BACKGROUND

In the United States, cancer is the leading cause of death for those under 65 years of age, and it accounted for about 21% of all death in 2018. Neuroendocrine tumors (NETs) arise from neuroendocrine cells and most commonly develop in lung, digestive tract and pancreas. NETs are one of the cancers that need systemic therapies because either they are inoperable, or they are diagnosed at the advanced stage with distant spread of tumor cells. Traditional radiotherapies such as external beam radiation therapy have been used for decades as a standard-of-care treatment for diagnosed cancer patients. While some patients respond to external beam radiation therapy, many others do not. Further, metastasis and circulating tumor cells can spread and remain in the bloodstream or bodily fluids after standard-of-care treatment and lead to resistance to therapy. The presence of cancer cells in various parts of the body reduces the therapeutic efficacy of traditional radiotherapies. Accordingly, strategies for targeted radiotherapies are being developed for better cancer treatment and diagnosis. One of the major challenges in the production of radiopharmaceutical drugs is to extend the shelf-life of product to allow treatment of patients at remote locations to the manufacturer site. There remains a need for compositions of radionuclides, e.g., alpha-particle emitting radionuclides, that have improved stability and shelf lives.

SUMMARY

One of the major challenges in the production of radiopharmaceutical drugs is to extend the shelf-life of product to allow treatment of patients at remote locations to the manufacturer site. As radionuclide such as Actinium-225 decays, a series of highly reactive chemicals are generated. In some cases, they can react with the drug substance, e.g., causing degradation of the radioisotope-containing drug and increasing radioactive impurity overtime. In one aspect, provided herein are liquid radiopharmaceutical formulations that provide enhanced stability for alpha-emitting radionuclide such as Actinium-225. In one aspect, provided herein are liquid radiopharmaceutical formulations comprising $^{225}$Ac-DOTA-TATE that are stable for at least 120 hours.

In one aspect, provided herein is a liquid radiopharmaceutical composition comprising: (i) a conjugate, which the conjugate is $^{225}$Ac-DOTA-TATE; (ii) one or more stabilizing agents; and (iii) an aqueous vehicle.

In one aspect, provided herein is a liquid radiopharmaceutical composition comprising: (i) a conjugate, which the conjugate is $^{225}$Ac-DOTA-TOC; (ii) one or more stabilizing agents; and (iii) an aqueous vehicle.

In one aspect, the present disclosure relates to a liquid radiopharmaceutical composition comprising, a conjugate, optionally one or more stabilizing agents, and an aqueous vehicle. The conjugate further comprises a targeting ligand, a metal chelator covalently attached to the targeting ligand, and a radionuclide that is bound to the metal chelator. In some embodiments, the targeting ligand binds to a somatostatin receptor (SSR), such as a somatostatin receptor type 1 (SSTR1), somatostatin receptor type 2 (SSTR2), somatostatin receptor type 3 (SSTR3), somatostatin receptor type 4 (SSTR4), and/or somatostatin receptor type 5 (SSTR5). In some embodiments, the targeting ligand binds to a somatostatin receptor type 2 (SSTR2). In some embodiments, the targeting ligand is a binding peptide, which comprises 6 to 14 amino acid residues. In some embodiments, the binding peptide comprises an amino acid sequence with at least 90% identity to a sequence selected from SEQ IDs 1 to 96. In some embodiments, the binding peptide comprises an amino acid sequence selected from SEQ IDs 1 to 96. In some embodiments, the targeting ligand is octreotate, octreotide, D-Phe$^1$-cyclo(Cys$^2$-Tyr$^3$-D-Trp$^4$-Lys$^5$-Thr$^6$-Cys$^7$)Thr$^8$ (SEQ ID NO: 97) (tyr3-octreotate or TATE), D-Phe$^1$-cyclo(Cys$^2$-Tyr$^3$-D-Trp$^4$-Lys$^5$-Thr$^6$-Cys$^7$)Thr(ol)$^8$ (SEQ ID NO: 98) (Phe$^1$-Tyr$^3$octreotide, edotreotide, or TOC), D-Phe$^1$-cyclo(Cys$^2$-Phe$^3$-D-Trp$^4$-Lys$^5$-Thr$^6$-Cys$^7$)Thr(ol)$^8$ (SEQ ID NO: 99) (OC), D-Phe$^1$-cyclo(Cys$^2$-1-Nal-D-Trp$^4$-Lys$^5$-Thr$^6$-Cys$^7$)Thr(ol)$^8$ (SEQ ID NO: 100) (NOC), p-Cl-Phe-cyclo(D-Cys-Aph(Hor)-D-Aph(Cbm)-Lys-Thr-Cys)D-Tyr-NH$_2$) (SEQ ID NO: 101) (JR11), or p-Cl-Phe-cyclo(D-Cys-Tyr-D-Aph(Cbm)-Lys-Thr-Cys)-D-Tyr-NH$_2$ (SEQ ID NO: 102) (LM3). In some embodiments, the targeting ligand is tyr3-octreotate, edotreotide, octreotate, or octreotide. In some embodiments, the targeting ligand is tyr3-octreotate. The targeting ligand can be an agonist of the SSR. The targeting ligand can be an antagonist of the SSR. In another embodiment, the targeting ligand is a small molecule compound, such as L-797,591, L-779,976, L-796,778, L-803,087, or L-817,818. In some embodiments, a binding affinity of the targeting ligand to a human SSR is not more than 250 nM, not more than 100 nM, not more than 50 nM, not more than 5 nM, as determined by half maximal inhibitory concentration (IC$_{50}$). In some embodiments, the binding affinity of the targeting ligand to a human SSR is not more than 250 nM, as determined by half maximal inhibitory concentration (IC$_{50}$). In some embodiments, the binding affinity of the targeting ligand to a human SSR is not more than 100 nM, as determined by half maximal inhibitory concentration (IC$_{50}$). In some embodiments, the binding affinity of the targeting ligand to a human SSR is not more than 50 nM, as determined by half maximal inhibitory concentration (IC$_{50}$). In some embodiments, the binding affinity of the targeting ligand to a human SSR is not more than 5 nM, as determined by half maximal inhibitory concentration (IC$_{50}$). In some embodiments, the binding affinity of the targeting ligand to a human SSR is not more than 2 nM, as determined by half maximal inhibitory concentration (IC$_{50}$). In some embodiments, the human SSR is SSTR2. The targeting ligand can covalently link to the metal chelator through a linker.

In one aspect, the disclosure described herein is a radiopharmaceutical composition comprising a conjugate that further comprises a targeting ligand that covalently links to a metal chelator through a linker. In some embodiments, the metal chelator is selected from AAZTA, BAT, BAT-TM, Crown, Cyclen, DO2A, CB-DO2A, DO3A, H3HP-DO3A, Oxo-DO3A, p-NH$_2$-Bn-Oxo-DO3A, DOTA, DOTA-3py, DOTA-PA, DOTA-GA, DOTA-4AMP, DOTA-2py, DOTA-1py, p-SCN-Bn-DOTA, CHX-A"-EDTA, MeO-DOTA-NCS EDTA, DOTAMAP, DOTAGA, DOTAGA-anhydride, DOTMA, DOTASA, DOTAM, DOTP, CB-Cyclam, TE2A, CB-TE2A, CB-TE2P, DM-TE2A, MM-TE2A, NOTA, NOTP, HEHA, HEHA-NCS, p-SCN-Bn-HEHA, DTPA, CHX-A"-DTPA, p-NH$_2$-Bn-CHX-A"-DTPA, p-SCN-DTPA, p-SCN-Bz-Mx-DTPA, 1B4M-DTPA-DTPA, p-SCN-Bn1B-DTPA, p-SCN-Bn-1B4M-DTPA, p-SCN-Bn-CHX-A"-DTPA, PEPA, p-SCN-Bn-PEPA, 1,4,8,11-tetraazacyclo tetradecane-1,4,8,11-tetrapropionic acid (TETPA), DOTPA, DOTMP, DOTPM, t-Bu-calix[4]arene-tetracarboxylic acid, macropa, macropa-NCS, macropid, H$_3$L$^1$, H$_3$L$^4$, H2azapa, H$_5$decapa, bispa$^2$, H$_4$pypa, H$_4$octapa, H$_4$CHXoctapa, p-SCN-Bn-H$_4$octapa, p-SCN-Bn-H$_4$octapa, TTHA, p-NO$_2$-Bn-neunpa, H$_4$octox, H$_2$macropa, H$_2$bispa$^2$, H$_4$phospa, H$_6$phospa, p-SCN-Bn-H$_6$phospa, TETA, p-NO2-Bn-TETA, TRAP, TRAP-Pr, TPA, HBED, SHBED, HBED-CC, (HBED-CC)TFP, DMSA, DMPS, DHLA, lipoic acid, TGA, BAL, Bis-thioseminarabazones, p-SCN-NOTA, nNOTA, NODAGA, CB-TE1A1P, 3P-C-NETA-NCS, 3p-C-DEPA, 3P-C-DEPA-NCS, TCMC, PCTA, NODIA-Me, TACN, pycuplAiB, pycup2A, THP, DEDPA, H$_2$DEDPA, p-SCN-Bn-H$_2$DEDPA, p-SCN-Bn-TCMC, motexafin, NTA, NOC, 3p-C-NETA, p-NH$_2$-Bn-TE3A, SarAr, DiAmSar, SarAr-NCS, AmBaSar, BaBaSar, TACN-TM, CP256, C-NE3TA, C-NE3TA-NCS, NODASA, NETA-monoamide, C-NETA, TACN-HSB, NOPO, BPCA, p-SCN-Bn-DRO, DRO-ChX-Mal, DFO, DFO-IAC, DFO-BAC, DiP-LICAM, EC, SBAD, BAPEN, TACHPYR, NEC-SP, L$^{py}$, L1, L2, L3, and EuK-106. In another embodiment, the metal chelator is a metal chelator in FIG. 3 to FIG. 17. In some embodiments, the metal chelator is DOTA, HEHA, or macropa. The metal chelator can be DOTA.

In one aspect, the disclosure described herein is a radiopharmaceutical composition comprising one or more stabilizing agents. The stabilizing agent can comprise a radiolysis stabilizer, which can be an amino acid or a peptide or a derivative thereof, a vitamin or a derivative thereof, a lipid or a derivative thereof, a carbohydrate or a derivative thereof, a volume expander or an antioxidant. In some embodiments, the amino acid or peptide is selected from N-Acetyl-L-cysteine, Glutathione, L-Lysine, Selenol-L-methionine, Glutathione, Albumin, Melatonin, Taurine, Alanine, Arginine, Asparagine, Aspartic acid, Cysteine, Glutamine, Glutamic acid, Glycine, Histidine, Isoleucine, Lysine, Methionine, Phenylalanine, Proline, Serine, Threonine, Tryptophan, Tyrosine, Valine, and derivatives thereof. In some embodiments, the amino acid is Methionine. In some embodiments, the radiolysis stabilizer is an antioxidant, such as a flavonoid or a derivative thereof. In some embodiments, the flavonoid is (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), 3,3',4',5,5',7-Hexahydroxyflavylium chloride, (−)-cis-3,3',4',5,7-Pentahydroxyflavane (Epi-Catechin or EC), 7-Hydroxy-3-(4'-methoxyphenyl)-4H-benzopyran-4-one, 3,4,5-Trihydroxybenzoic acid (Gallic acid), 3,4',5,7-Tetrahydroxyflavone (Kaempferol), Luteolin, 2-(3,4-dihydroxyphenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxychromen-4-one (Rutin hydrate), Quercetin, (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), or (2R,3S)-2-(3,4,5-trihydroxyphenyl)-3,4-dihydro-2H-chromene-3,5,7-triol (Gallo-Catechin or GC). In some embodiments, the flavonoid is a catechin or a derivative thereof, for example, (2S,3R)-2-(3,4-Dihydroxyphenyl)-3,4-dihydro-1 (2H)-benzopyran-3,5,7-triol 3-(3,4,5-trihydroxybenzoate ((−) Catechin gallate or CG), (−)-cis-3,3',4',5,7-Pentahydroxyflavane (Epi-Catechin or EC), 3,4,5-Trihydroxybenzoic acid (Gallic acid), (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl] 3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), or (2R,3S)-2-(3,4,5-trihydroxyphenyl)-3,4-dihydro-2H-chromene-3,5,7-triol (Gallo-Catechin or GC). The antioxidant can also be a carotenoid or a derivative thereof, such as all-trans-Fucoxanthin, Lycopene, Xanthophyll, Beta carotene, Lycopene, or Lutein. In some embodiments, the antioxidant is N-acetyl cysteine, L-Ascorbic acid, N-tert-Butyl-α-phenylnitrone, 3-(3,4-Dihydroxyphenyl)-2-propenoic acid (Caffeic Acid), β-Carotene, Provitamin A, (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), 1,4,5-Trihydroxycyclohexanecarboxylic acid, trans-4-Hydroxy cinnamic acid (p-Coumaric acid), 3,3',4',5,5',7-Hexahydroxyflavylium chloride, Thiocytic Acid (Dihydrolipoic Acid, DHLA), 4,4',5,5',6,6'-Hexahydroxydiphenic acid 2,6,2',6'-dilactone (Ellagic acid), (−)-cis-3,3',4',5,7-Pentahydroxyflavane (Epi-Catechin or EC), 2-Methoxy-4-(2-propenyl) phenol, trans-4-Hydroxy-3-methoxycinnamic acid (Ferulic acid), 7-Hydroxy-3-(4'-methoxyphenyl)-4H-benzopyran-4-one, all-trans-Fucoxanthin, 3,4,5-Trihydroxybenzoic acid (Gallic acid), (2S,3R)-2-(3,4,5-Trihydroxyphenyl)-3,4-dihydro-1 (2H)-benzopyran-3,5,7-triol ((−)-Gallocatechin), Glutathione, 2-(3,4-Dihydroxyphenyl) ethanol, 3,4',5,7-Tetrahydroxyflavone (Kaempferol), (±)-1,2-Dithiolane-3-pentanoic acid, Luteolin, Lycopene, L-Lysine, Neochlorogenic acid, Oleic acid, trans-3,5,4'-Trihydroxystilbene (Resveratrol), 2-(3,4-dihydroxyphenyl)-5,7-dihydroxy-3-[(2S,3R,4S,5S,6R)-3,4,5-trihydroxy-6-[[(2R,3R,4R,5R,6 S)-3,4,5-trihydroxy-6-methyloxan-2-yl] oxymethyl] oxan-2-yl] oxychromen-4-one, Rutin hydrate, Selenol-L-methionine, Thiourea, (+)-α-Tocopherol, Xanthophyll, Citric acid (CA), Gentisic acid (GA), Salicylic acid (SA), Erythorbic acid (EA), Phenol, Sodium bisulfite, Butylated hydroxy anisole, Butylated hydroxy toluene, Metabisulfite, Benzyl alcohol, Thymol, Lipoic acid (LA), Thioglycolic acid (TGA), 2,3 Dimercaptopropan-1-ol (BAL), Zinc, Selenium, Albumin, Ethanol, Mannitol, Sucrose, Melatonin, Ebselen, Pyruvic acid, Carboxy-PTIO, Trolox, Uric acid, Edaravone, Beta carotene, NADPH, Lycopene, Lutein, Catalase, Estrogen, Estradiol, Estriol, Ubiquinol, Copper, Quercetin, Cortisone, Taurine, (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl] 3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), (2R,3S)-2-(3,4,5-trihydroxyphenyl)-3,4-dihydro-2H-chromene-3,5,7-triol (Gallo-Catechin or GC), (−)-Epigalocatechin-3-O-Gallate, 5-Aminolevulibic Acid hydrate, Ploysorbate 80, Garlic Acid, Sodium L-Ascorbate, Hyaluronic Acid, Dextran 60-90, Selenol, and LysaKare. The radiolysis stabilizer can also be a vitamin or a derivative thereof, for example, L-Ascorbic acid, β-Carotene, Provitamin A, (+)-α-Tocopherol, Erythorbic acid (EA), Trolox, and Lutein. In some embodiments, radiolysis stabilizer is a lipid. The lipid can be a fatty acid, such as a saturated or unsaturated $C_6$ to $C_{30}$ fatty acid. In some embodiments, the fatty acid is oleic acid, Myristoleic acid, Palmitoleic acid, Sapienic acid, Elaidic acid, Vaccenic acid, or Linoleic acid, α-Linolenic acid. In another embodiment, the lipid is a steroid or derivatives thereof, for example, Estrogen, Estradiol, Estriol, or Cortisone. The radiolysis stabilizer can also be a carbohydrate or a derivative thereof, such as Mannitol, Sucrose, Dextran (e.g., Dextran 40, Dextran 70), and Cyclodextrins, (e.g., α (alpha)-cyclodextrin, β (beta)-cyclodextrin, and γ (gamma)-cyclodextrin). In some embodiments, the radiolysis stabilizer is a volume expander. The volume expander can be a polymer or a polymer mixture, such as PEG 3350, PEG 4000, Polygeline, Haemaccel, Gelofusine, and PLENVU (polyethylene glycol 3350, sodium sulfate, ascorbic acid, sodium chloride and potassium chloride US FDA 2018 Label). In some embodiments, volume expander is selected from Dextran, Dextran 40, Dextran 70, Cyclodextrins, a (alpha)-cyclodextrin, (beta)-cyclodextrin, and γ (gamma)-cyclodextrin, PEG 3350, PEG 4000, Polygeline, Gelofusine, and PLENVU (polyethylene glycol 3350, sodium sulfate, ascorbic acid, sodium chloride and potassium chloride US FDA 2018 Label). In some embodiments, radiolysis stabilizer is selected from N-Acetyl-L-cysteine, L-Ascorbic acid, N-tert-Butyl-α-phenylnitrone, 3-(3,4-Dihydroxyphenyl)-2-propenoic acid (Caffeic Acid), β-Carotene, Provitamin A, (2S,3R)-2-(3,4-Dihydroxyphenyl)-3,4-dihydro-1(2H)-benzopyran-3,5,7-triol 3-(3,4,5-trihydroxybenzoate ((−) Catechin gallate, or CG), 1,4,5-Trihydroxycyclohexanecarboxylic acid, trans-4-Hydroxycinnamic acid (p-Coumaric acid), 3,3',4',5,5',7-Hexahydroxyflavylium chloride, Thiocytic Acid (Dihydrolipoic Acid, DHLA), 4,4',5,5',6,6'-Hexahydroxydiphenic acid 2,6,2',6'-dilactone (Ellagic acid), (−)-cis-3,3',4',5,7-Pentahydroxyflavane (Epi-Catechin or EC), 2-Methoxy-4-(2-propenyl) phenol, trans-4-Hydroxy-3-methoxycinnamic acid (Ferulic acid), 7-Hydroxy-3-(4'-methoxyphenyl)-4H-benzopyran-4-one, all-trans-Fucoxanthin, 3,4,5-Trihydroxybenzoic acid (Gallic acid), (2S,3R)-2-(3,4,5-Trihydroxyphenyl)-3,4-dihydro-1 (2H)-benzopyran-3,5,7-triol ((−)-Gallocatechin), Glutathione, 2-(3,4-Dihydroxyphenyl)ethanol, 3,4',5,7-Tetrahydroxyflavone (Kaempferol), (±)-1,2-Dithiolane-3-pentanoic acid, Luteolin, Lycopene, L-Lysine, Neochlorogenic acid, Oleic acid, trans-3,5,4'-Trihydroxystilbene (Resveratrol), 2-(3,4-dihydroxy phenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl]oxymethyl] oxan-2-yl]oxychromen-4-one, Rutin hydrate, Selenol-L-methionine, Thiourea, (+)-α-Tocopherol, Xanthophyll, Alanine and its derivatives, Arginine and its derivatives, Asparagine and its derivatives, Aspartic acid and its derivatives, Cysteine and its derivatives, Glutamine and its derivatives, Glutamic acid and its derivatives, Glycine and its derivatives, Histidine and its derivatives, Isoleucine and its derivatives, Lysine and its derivatives, Methionine and its derivatives, Phenylalanine and its derivatives, Proline and its derivatives, Serine and its derivatives, Threonine and its derivatives, Tryptophan and its derivatives, Tyrosine and its derivatives, Valine and its derivatives, Citric acid (CA), Gentisic acid (GA), Salicylic acid (SA), Erythorbic acid (EA), Phenol, Sodium bisulfite, Butylated hydroxy anisole, Butylated hydroxy toluene, Glutathione, Metabisulfite, Benzyl alcohol, Thymol, Lipoic acid (LA), Thioglycolic acid (TGA), 2,3 Dimercaptopropan-1-ol (BAL), Zinc, Selenium, Albumin, Ethanol, Mannitol, Sucrose, Melatonin, Ebselen, Pyruvic acid, Carboxy-PTIO, Trolox, Uric acid, Edaravone, Beta carotene, NADPH, Lycopene, Lutein, Catalase, Estrogen, Estradiol, Estriol, Ubiquinol, Copper, Quercetin, Cortisone, 2,3-dimercaptosuccinic acid (DMSA), monisoamyl derivative (Mi-ADMSA), Taurine, Dextran, Dextran 40, Dextran 70, PEG 3350, PEG 4000, Polygeline, Gelofusine, PLENVU (polyethylene glycol 3350, sodium sulfate, ascorbic acid, sodium chloride and potassium chloride US FDA 2018 Label), Cyclodextrins, a (alpha)-cyclodextrin, β (beta)-cyclodextrin, and γ (gamma)-cyclodextrin, (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), (2R,3S)-2-(3,4,5-trihydroxyphenyl)-3,4-dihydro-2H-chromene-3,5,7-triol (Gallo-Catechin or GC).

In one aspect, disclosed herein is a radiopharmaceutical composition comprising one or more stabilizing agents that further comprise a first and a second radiolysis stabilizer. In some embodiments, the first and the second radiolysis stabilizer has a molar ratio that is from 1:5 to 5:1. In some embodiments, radiolysis stabilizer is present in the radiopharmaceutical composition at about 0.01 mM to about 5 M. In some embodiments, the stabilizing agent is present in the radiopharmaceutical composition from about 5 mM, 10 mM, 25 mM, 50 mM, or 75 mM to about 80 mM, 100 mM, 125 mM, 150 mM, 175 mM, 200 mM, 250 mM, or 500 mM. In some embodiments, stabilizing agent is present in the radiopharmaceutical composition at about 0.1 mM to about 500 mM. In some embodiments, the stabilizing agent is present in the radiopharmaceutical composition at about 10 mM to about 500 mM. In some embodiments, the stabilizing agent is present in the radiopharmaceutical composition at about 20 mM to about 100 mM. In some embodiments, the radiolysis stabilizer is present in the radiopharmaceutical composition at about 0.0001 wt % to about 10 wt %. In some embodiments, the radiolysis stabilizer is present in the radiopharmaceutical composition at about 0.01 wt % to about 5 wt %, about 0.05 wt % to about 2 wt %, or about 0.1 wt % to about 1 wt %. In some embodiments, the radiolysis stabilizer is present in the radiopharmaceutical composition at a concentration of from about 0.1 to 50 mg/mL. In some embodiments, the volume expander is present in the radiopharmaceutical composition at a concentration of from about 0.001 wt % to 80% wt %.

In one aspect, disclosed herein is a radiopharmaceutical composition comprising one or more stabilizing agent that can comprise a free metal chelator, which is not attached to the targeting ligand. In some embodiments, the free metal chelator is selected from Ethylenediaminetetraacetic acid (EDTA), Diethylenetriaminepentaacetic acid (DTPA), 2-S-(4-Isothiocyanatobenzyl)-1,4,7-triazacyclononane-1,4,7-triacetic acid (NOTA), Triethylenetetramine (TETA), 1, 4, 7, 10, 13-pentaazacyclopentadecane-N, N', N", N"', N"-pentaacetic acid (PEPA), 1,4,8,11-tetraazacyclo tetradecane-1, 4,8,11-tetrapropionic acid (TETPA), triethylenetetraminepentaacetic acid, 2,2',2"-(10-(2,6-dioxotetrahydro-2H-pyran-3-yl)-1,4,7,10-tetraazacyclododecane-1,4,7-triyl)triacetic acid (DOTA-GA), 1,4,7,10-Tetraazacyclododecane-1, 4,7,10-tetra(methylene phosphonic acid (DOTP), Deferoxamine (DFO), N, N-bis(2-hydroxybenzyl)ethylenediamine-N,N-diacetic acid (HBED), 1,4,7,10-Tetraazacyclododecane-1,4,7,10-tetra(methylene phosphonic acid) (DOTP), 6,6'-((1,4,10,13-tetraoxa-7,16-diazacyclooctadecane-7,16-diyl)bis(methylene))dipicolinic acid (Macropa), Meso-2,3-dimercaptosuccinic acid (DMSA), Dimercaptopropane sulfonate (DMPS), Dihydrolipoic acid (DHLA), Lipoic acid (LA), Thioglycolic acid (TGA), 2,3 Dimercaptopropan-1-ol (BAL). In some embodiments, the free metal chelator is EDTA, DTPA, or Macropa. In some embodiments, the free metal chelator is present in the radiopharmaceutical composition at about 0.001 wt % to about 10 wt %. In some embodiments, the free metal chelator is present in the radiopharmaceutical composition at about 0.01 wt % to about 5 wt %, about 0.05 wt % to about 2 wt %, or about 0.1 wt % to about 1 wt %. In some embodiments, the free metal chelator is present in the radiopharmaceutical composition at a concentration of from 0.01 to 50 mg/mL. In some embodiments, the free metal chelator is present in the radiopharmaceutical composition at about 10 mM to about 500 mM.

In one aspect, disclosed herein is a radiopharmaceutical composition comprising one or more stabilizing agent that can comprise one or more pH stabilizers. The pH stabilizers can function as a pH buffer. The one or more pH stabilizers comprise an organic acid, such as an acetic acid, fumaric acid, ascorbic acid, propionic acid, benzene sulfonic acid, carbonic acid, citrate acid, aspartic acid, maleic acid, methane sulfonic acid, or tartaric acid. In some embodiments, the one or more pH stabilizers comprise an inorganic acid, for example, hydrobromic acid, hydrochloric acid, phosphoric acid, boric acid, or sulfuric acid. The one or more pH stabilizers can comprise a base, such as tromethamine (Tris), ammonium hydroxide, diethanolamine, or sodium hydroxide. The one or more pH stabilizers can also comprise an amino acid or a salt thereof. In some embodiments, the amino acid is glycine, lysine, arginine, histidine, or a salt thereof. In another embodiment, the one or more pH stabilizers comprise an alkaline salt, for example, sodium acetate, sodium ascorbate, sodium benzoate, sodium bicarbonate, sodium carbonate, tribasic sodium phosphate acid, dibasic sodium phosphate acid, monobasic sodium phosphate acid, sodium tartrate, sodium lactate, sodium succinate, or disodium succinate. The one or more pH stabilizers can comprise an acid salt, such as ammonium sulfate. In some embodiments, the one or more pH stabilizers comprise Sodium acetate, Sodium ascorbate, Ascorbic acid, Acetic acid, Fumaric acid propionic acid, ascorbic acid, ammonium sulfate, ammonium hydroxide, arginine, aspartic acid, benzene sulfonic acid, sodium benzoate, sodium bicarbonate, boric acid, sodium carbonate, carbonic acid, diethanolamine, citrate acid, hydrobromic acid, glycine, histidine, sodium lactate, (1)-lysine, maleic acid, methane sulfonic acid, phosphate acid, monobasic sodium phosphate acid, tribasic sodium phosphate acid, dibasic sodium phosphate acid, sodium hydroxide, sodium/disodium succinate, sulfuric acid, sodium tartrate, tartaric acid, tromethamine (tris), or a combination thereof. In some embodiments, the one or more pH stabilizers are present in the radiopharmaceutical composition at about 0.001 wt % to about 10 wt %. In some embodiments, one or more pH stabilizers are present in the radiopharmaceutical composition at about 0.01 wt % to about 5 wt %, about 0.05 wt % to about 2 wt %, or about 0.1 wt % to about 1 wt %. In some embodiments, the one or more pH stabilizers are present in the radiopharmaceutical composition at a concentration of from 0.1 to 5 mg/mL. In some embodiments, the one or more pH stabilizers are present in the radiopharmaceutical composition at about 10 mM to about 500 mM. The one or more pH stabilizers can be configured to maintain a pH of the radiopharmaceutical composition at about 4 to about 8. The one or more pH stabilizers can be configured to maintain a pH of the radiopharmaceutical composition at about 5 to about 7. In some embodiments, the pH of the radiopharmaceutical composition is within a range of about 4 to about 8. In some embodiments, the pH of the radiopharmaceutical composition is about 5.5 to about 6.0. The radiopharmaceutical composition can comprise one or more radiolysis stabilizers, one or more free metal chelators, and/or one or more pH stabilizers.

In one aspect, disclosed herein is a radiopharmaceutical composition comprising an aqueous vehicle. The aqueous vehicle can comprise water (e.g., water for injection), saline solution, dextrose in water, dextrose in saline solution, Ringer's solution, or lactated Ringer's solution. The radiopharmaceutical composition can be isotonic. The radiopharmaceutical composition can be a solution or suspension. In some embodiments, the radiopharmaceutical composition is formulated for IV infusion or bolus injection. In some embodiments, the radiopharmaceutical composition further comprises one or more excipients selected from: a tonicity adjusting agent, a preservative, an antimicrobial agent, a solubilizing agent, a suspending agent, and a surfactant.

In one aspect, disclosed herein is a radiopharmaceutical composition comprising a conjugate that further comprises a targeting ligand that covalently links to a metal chelator through a linker. In some embodiments, the targeting ligand is a binding peptide, and the linker is attached to the binding peptide via the N terminus of the peptide. In some embodiments, the targeting ligand is a binding peptide, and the linker is attached to the binding peptide via the C terminus of the peptide. In some embodiments, the targeting ligand is a binding peptide, and the linker is attached to the binding peptide via a non-terminal amino acid of the peptide. The linker can comprise one or more groups selected from: substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In one aspect, disclosed herein is a radiopharmaceutical composition comprising a conjugate that further comprises a radionuclide. The radionuclide can be an alpha particle-emitting radionuclide, such as actinium-225, astatine-211, thorium-227, or radium-223. In some embodiments, the alpha particle-emitting radionuclide is actinium-225. In some embodiments, the actinium-225 is present in the radiopharmaceutical composition that it provides a volumetric radioactivity of about 0.5 to 20 MBq/mL. In some embodiments, the conjugate is $^{225}$Ac-DOTATATE. In another embodiment, the conjugate is $^{225}$Ac-DOTATOC. In some embodiments, the radiopharmaceutical composition retains at least 90 mol % of the initial conjugate after 168 hours at room temperature (25° C.). In some embodiments, the composition retains at least 95 mol % of the initial conjugate after 168 hours at room temperature (25° C.). In some embodiments, the composition retains at least 98 mol % of the initial conjugate after 168 hours at room temperature (25° C.). In some embodiments, the composition retains at least 85 mol %, at least 90 mol %, at least 92 mol %, at least 95 mol %, at least 98 mol % or at least 99 mol % of the initial conjugate after 120 hours at room temperature (25° C.). In some embodiments, the composition retains 95 mol % or more of the initial conjugate after 48 hours, 72 hours, 96 hours, 120 hours, 148 hours, 168 hours, 192 hours, or 216 hours at room temperature (25° C.). In some embodiments, the radionuclide is actinium-225, and wherein the composition contains no more than about 5% free actinium after 168 hours at room temperature (25° C.), compared to the total amount of the initial chelated actinium content in the composition. In some embodiments, the radionuclide is actinium-225, and wherein the composition contains no more than about 2% or about 1% free actinium after 168 hours at room temperature (25° C.), compared to the total amount of the initial chelated actinium content in the composition. In some embodiments, the radionuclide is actinium-225, and wherein the composition contains no more than a total of 5 mol % of free daughter isotopes of actinium-225 after 168 hours at room temperature (25° C.), compared to the total amount of the initial chelated actinium content in the composition. In some embodiments, the radionuclide is actinium-225, and wherein the composition contains no more than a total of 1 mol % of un-chelated daughter isotopes of actinium-225 after 168 hours at room temperature (25° C.), compared to the total amount of the initial chelated actinium content in the composition. In some embodiments, the purity or the molar percentage of the initial conjugate is determined by radio thin layer chromatography (radio-TLC). In some embodiments, the purity or the molar percentage of the initial conjugate is determined by instant thin layer chromatography (iTLC).

In one aspect, the present disclosure relates to a method of making a radiopharmaceutical composition described herein. In some embodiments, the method of making the radiopharmaceutical composition comprises combining a radionuclide (such as $^{225}$Ac) with a pre-labeled conjugate (e.g., DOTATATE or DOTATOC) in the presence of one or more stabilizer agents, wherein the pre-labeled conjugate comprises a targeting ligand and a metal chelator covalently attached to the targeting ligand, thereby producing a mixture comprising a labeled conjugate (e.g., $^{225}$Ac-DOTATATE or $^{225}$Ac-DOTATOC), and optionally combining one or more stabilizing agents to the mixture. In some embodiments, the method of making the radiopharmaceutical composition comprises combining a radionuclide (such as $^{225}$Ac) with a pre-labeled conjugate (e.g., DOTATATE or DOTATOC), wherein the pre-labeled conjugate comprises a targeting ligand and a metal chelator covalently attached to the targeting ligand, thereby producing a labeled conjugate, and combining the one or more stabilizing agents with the labeled conjugate.

In one aspect, the present disclosure relates to a method of treating a disease in a subject in need thereof, comprising administering to the subject the radiopharmaceutical composition described herein. The disease can be a cancer. In some embodiments, the cancer is an SSR-associated cancer, such as an SSTR2-associated cancer. The cancer can be a neuroendocrine cancer, a lymphatic cancer, a pancreatic cancer, a pituitary cancer, a breast cancer, a stomach cancer, medulloblastoma, or neuroblastoma. In some embodiments, the cancer is a neuroendocrine cancer, which can optionally be recurrent. In some embodiments, the neuroendocrine cancer is refractory to a radiotherapy that comprises beta-particle emitting radionuclide. In some embodiments, the subject has received a radiotherapy that comprises beta-particle emitting radionuclide prior to the administering of the radiopharmaceutical composition. The neuroendocrine cancer can also be a neuroendocrine lung cancer or a neuroendocrine pancreatic cancer. In some embodiments, the neuroendocrine cancer is a Carcinoid tumor in the lungs, gastrointestinal tract or thymus, Pancreatic neuroendocrine tumor (e.g., Gastrinoma, Insulinoma, Glucagonoma, VIPoma) Medullary thyroid carcinoma, Merkel cell carcinoma, Pheochromocytoma of the adrenal gland, Adrenal cancer, Small cell carcinoma (such as in the lungs), or Large cell carcinoid tumor (such as in the lungs). In some embodiments, the radiopharmaceutical composition is administered to the subject in an amount equivalent to about 1 kBq/kg to about 0.2 GBq/kg body weight per dose. In some embodiments, the radiopharmaceutical composition is administered to the subject in an amount equivalent to about 5 kBq/kg to about 50,000 kBq/kg body weight per dose. In some embodiments, the radiopharmaceutical composition is administered to the subject in an amount equivalent to about 20 k Bq/kg to about 5,000 kBq/kg body weight per dose. In some embodiments, the radiopharmaceutical composition is administered to the subject in an amount equivalent to about 50 k Bq/kg to about 500 kBq/kg body weight per dose. In some embodiments, the radiopharmaceutical composition is administered to the subject in an amount equivalent to about 50 k Bq/kg to about 200 kBq/kg body weight per dose. In some embodiments, the radiopharmaceutical composition is administered to the subject in an amount equivalent to about 70 kBq/kg to about 150 kBq/kg body weight per dose. In some embodiments, the radiopharmaceutical composition is administered at an 8-week interval. In some embodiments, the radiopharmaceutical composition is administered to achieve a cumulative dose in the subject of about 10,000 kBq to about 100,000 kBq. In some embodiments, the radiopharmaceutical composition is administered to achieve a cumulative dose in the subject of about 40,000 kBq to about 70,000 kBq.

In one aspect, provided herein is a dilution solution comprising one or more stabilizing agents and an aqueous vehicle.

In one aspect, provided herein is a liquid radiopharmaceutical composition comprising: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 80 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, and wherein the radiopharmaceutical composition retains at least 90% of the $^{225}$Ac content as $^{225}$Ac-DOTA-TATE after 120 hours at about 20° C. to about 25° C. as determined by radio thin-layer chromatography (radio-TLC). In one aspect, provided herein is a liquid radiopharmaceutical composition consisting essentially of: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 80 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, and wherein the radiopharmaceutical composition retains at least 90% of the $^{225}$Ac content as $^{225}$Ac-DOTA-TATE after 120 hours at about 20° C. to about 25° C. as determined by radio thin-layer chromatography (radio-TLC). In one aspect, provided herein is a liquid radiopharmaceutical composition consisting of: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 90 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, some embodiments, the composition retains at least 90% of the $^{225}$Ac content as $^{225}$Ac-DOTA-TATE after 168 hours at about 20° C. to about 25° C. In some embodiments, the composition retains at least 90% of the $^{225}$Ac content as $^{225}$Ac-DOTA-TATE after 192 hours at about 20° C. to about 25° C. In some embodiments, the radiopharmaceutical composition is formulated as a unit dose form that contains about 12 mL of the solution, and wherein the liquid radiopharmaceutical composition consists of: (a) $^{225}$Ac-DOTA-TATE present in the radiopharmaceutical composition in an amount of 146-275 µCi in the about 12 mL solution; (b) sodium L-ascorbate present in the radiopharmaceutical composition at a concentration of about 18.5 mg/mL; (c) DTPA, present in the radiopharmaceutical composition at a concentration of about 0.05 mg/mL; and (d) sodium chloride saline solution at a concentration of about 0.9% w/w. In some embodiments, the liquid radiopharmaceutical composition has a pH of about 5.5 to about 7.0. In some embodiments, the radiopharmaceutical composition is formulated for IV infusion.

In one aspect, provided herein is a liquid radiopharmaceutical composition wherein the $^{225}$Ac-DOTA-TATE has a structure illustrated as:

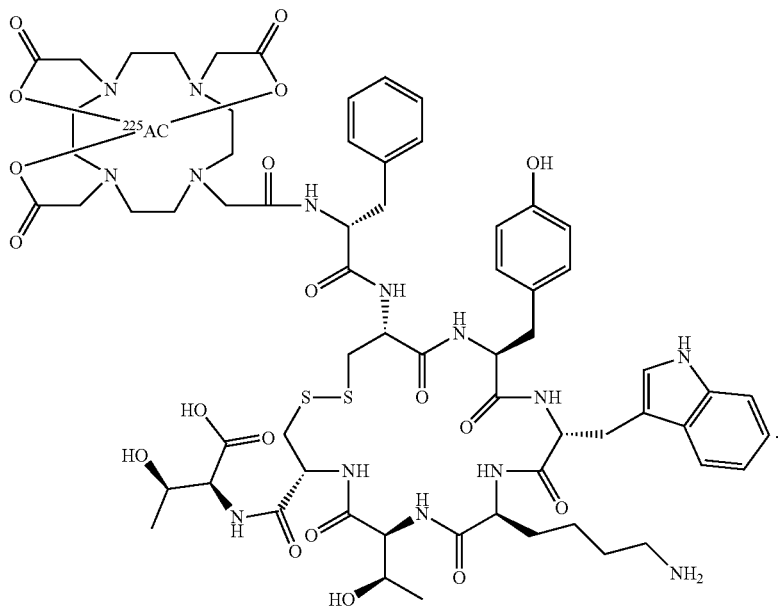

and wherein the radiopharmaceutical composition retains at least 90% of the $^{225}$Ac content as $^{225}$Ac-DOTA-TATE after 120 hours at about 20° C. to about 25° C. as determined by radio thin-layer chromatography (radio-TLC). In some embodiments, the $^{225}$Ac-DOTA-TATE is present in the radiopharmaceutical composition at a concentration equivalent to about 10 mCi/L to about 25 mCi/L. In some embodiments, the $^{225}$Ac-DOTA-TATE is present in the radiopharmaceutical composition at a concentration equivalent to about 12 mCi/L to 23 mCi/L. In some embodiments, the $^{225}$Ac-DOTA-TATE is present in the radiopharmaceutical composition at a concentration equivalent to about 40 µg to about 120 µg of the DOTA-TATE. In some embodiments, the sodium ascorbate is present in the radiopharmaceutical composition at a concentration of about 100 mM. In some embodiments, the DTPA is present in the radiopharmaceutical composition at a concentration of about 0.05 mg/mL. In In one aspect, provided herein is a method of treating a somatostatin receptor-positive (SSTR+) neuroendocrine tumor in a subject in need thereof, comprising administering to the subject an effective amount of a liquid radiopharmaceutical composition, wherein the liquid radiopharmaceutical composition comprises: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 90 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, and wherein the radiopharmaceutical composition retains at least 90% of the $^{225}$Ac content as $^{225}$Ac-DOTA-TATE after 120 hours at about 20° to about 25° C. as determined by radio thin-layer chromatography (radio-TLC).

In one aspect, provided herein is a method of treating a somatostatin receptor-positive (SSTR+) neuroendocrine tumor in a subject in need thereof, comprising administering to the subject an effective amount of a liquid radiopharmaceutical composition, wherein the liquid radiopharmaceutical composition consists essentially of: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 90 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, and wherein the radiopharmaceutical composition retains at least 90% of the $^{225}$Ac content as $^{225}$Ac-DOTA-TATE after 120 hours at about 20° to about 25° C. as determined by radio thin-layer chromatography (radio-TLC).

In one aspect, provided herein is a method of treating a somatostatin receptor-positive (SSTR+) neuroendocrine tumor in a subject in need thereof, comprising administering to the subject an effective amount of a liquid radiopharmaceutical composition, wherein the liquid radiopharmaceutical composition consists of: (a) $^{225}$Ac-DOTA-TATE, wherein the $^{225}$Ac-DOTA-TATE is present in the radiopharmaceutical composition at a concentration equivalent to about 10 mCi/L to about 30 mCi/L; (b) sodium L-ascorbate, wherein the sodium L-ascorbate is present in the radiopharmaceutical composition at a concentration of about 90 mM to about 110 mM; (c) diethylenetriamine pentaacetate (DTPA), wherein the DTPA is present in the radiopharmaceutical composition at a concentration of about 0.04 mg/mL to about 0.06 mg/mL; and (d) an aqueous vehicle, wherein the aqueous vehicle is sodium chloride saline solution at a concentration of about 0.9% w/w; wherein the radiopharmaceutical composition is a solution, and wherein the radiopharmaceutical composition retains at least 90% of the $^{225}$Ac content as $^{225}$Ac-DOTA-TATE after 120 hours at about 20° to about 25° C. as determined by radio thin-layer chromatography (radio-TLC). In some embodiments, the neuroendocrine tumor is gastroenteropancreatic neuroendocrine tumor (GEP-NET). In some embodiments, the subject received $^{177}$Lu-DOTA-TATE or $^{177}$Lu-DOTA-TOC treatment prior to the administrating of the liquid radiopharmaceutical composition. In some embodiments, prior to the administrating of the liquid radiopharmaceutical composition, the subject received $^{177}$Lu-DOTA-TATE or $^{177}$Lu-DOTA-TOC treatment and the tumor has progressed. In some embodiments, the radiopharmaceutical composition is administered to the subject in an amount equivalent to about 60 kBq/kg body weight to 120 kBq/kg body weight per dose. In some embodiments, the radiopharmaceutical composition is administered at an 8-week interval. In some embodiments, the $^{225}$Ac-DOTA-TATE is present in the radiopharmaceutical composition at a concentration equivalent to about 10 mCi/L to about 25 mCi/L.

In one aspect, provided herein is a method of treating a somatostatin receptor-positive (SSTR+) neuroendocrine tumor in a subject in need thereof, comprising administering to the subject an effective amount of a liquid radiopharmaceutical composition, wherein the liquid radiopharmaceutical composition consists of: (a) $^{25}$Ac-DOTA-TATE present in the radiopharmaceutical composition at a concentration equivalent to 10 mCi/L to 25 mCi/L; (b) sodium L-ascorbate present in the radiopharmaceutical composition at a concentration of about 100 mM; (c) DTPA, present in the radiopharmaceutical composition at a concentration of about 0.05 mg/mL; and (d) sodium chloride saline solution at a concentration of about 0.9% w/w.

In one aspect, provided herein is a method of treating a somatostatin receptor-positive (SSTR+) neuroendocrine tumor in a subject in need thereof, comprising administering to the subject an effective amount of a liquid radiopharmaceutical composition, wherein the liquid radiopharmaceutical composition is formulated as a unit dose form that has about 12 mL of the solution, and wherein the liquid radiopharmaceutical composition consists of: (a) $^{225}$Ac-DOTA-TATE present in the radiopharmaceutical composition in an amount of 146-275 µCi in about 12 mL solution; (b) sodium L-ascorbate present in the radiopharmaceutical composition at a concentration of about 18.5 mg/mL; (c) DTPA present in the radiopharmaceutical composition at a concentration of about 0.05 mg/mL; and (d) sodium chloride saline solution at a concentration of about 0.9% w/w.

INCORPORATION BY REFERENCE

All publications, patents, and patent applications mentioned in this specification are herein incorporated by reference for the specific purposes identified herein.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawing (also "figure" and "FIG." herein), of which:

DETAILED DESCRIPTION

Figure 1A:
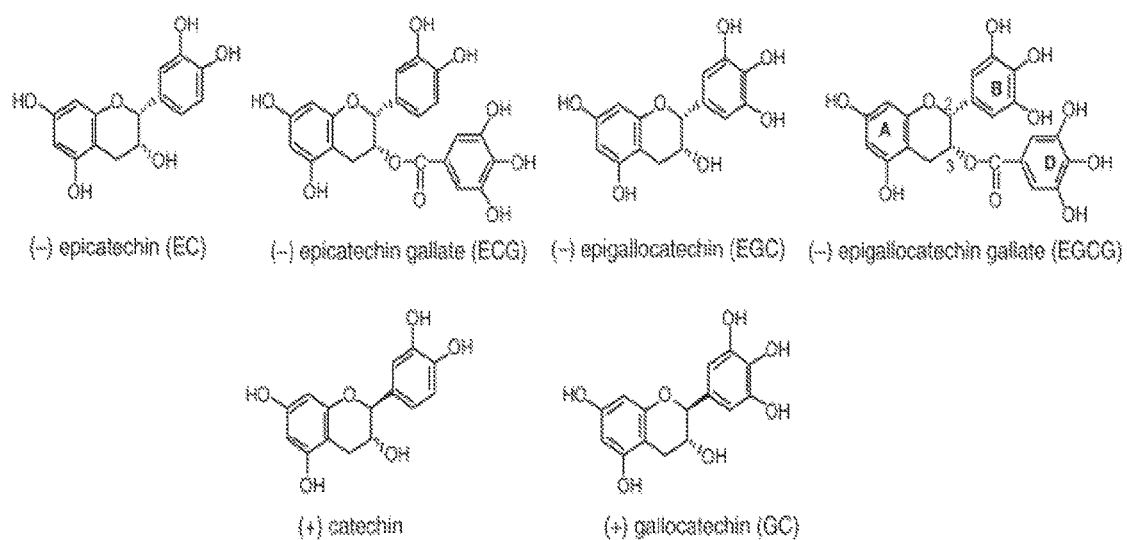
FIG. 1A depicts the structures of exemplary radiolysis stabilizers catechins and their derivatives.
Figure 1B:
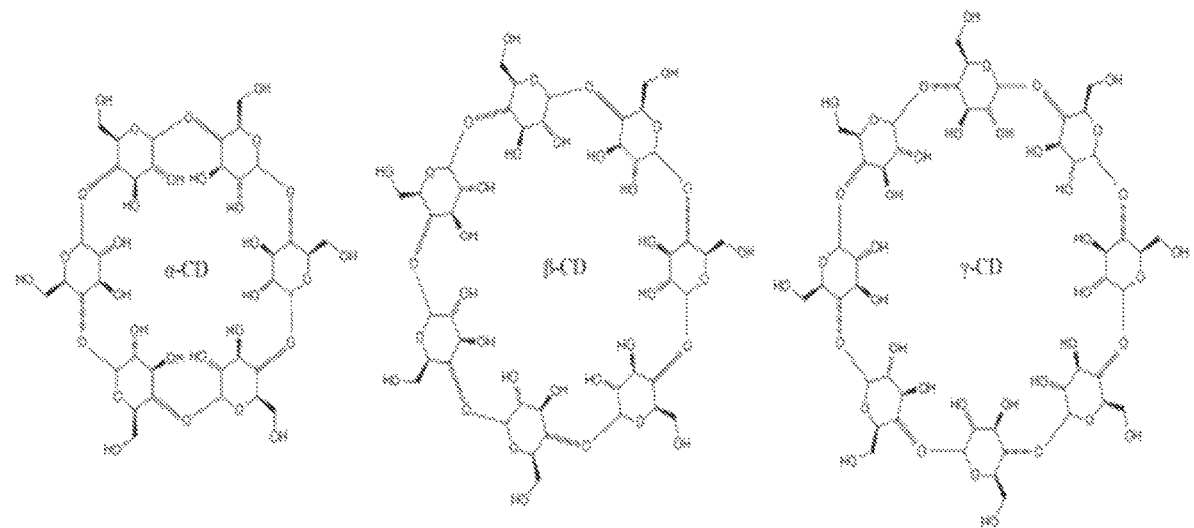
FIG. 1B illustrates the structures of exemplary stabilizing agents cyclodextrin.
Figure 1C:
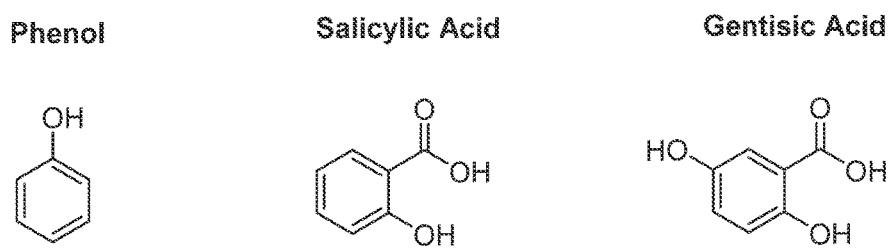
FIG. 1C illustrates the structures of exemplary stabilizing agents (antioxidants)
Figure 1D:
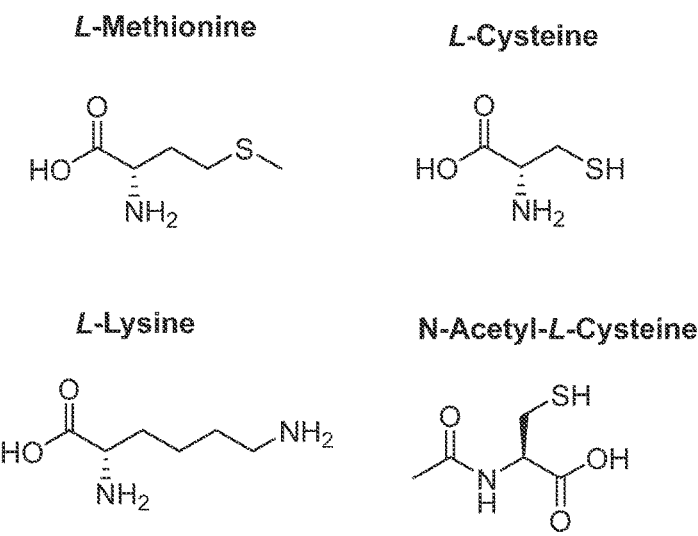
FIG. 1D illustrates the structures of exemplary stabilizing agents (amino acids)
Figure 1E:
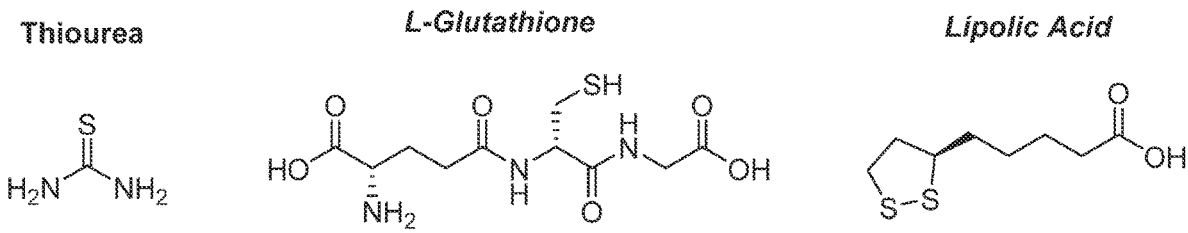
FIG. 1E illustrates the structures of exemplary stabilizing agents.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The section headings used herein are for organizational purposes only and are not to be construed as limiting the subject matter described.

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

I. Definitions

As used in the specification and appended claims, unless specified to the contrary, the following terms have the meaning indicated below.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, within 5-fold, or within 2-fold, of a value.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

"Radiolysis" refers to the decay of radionuclides accompanied by emission of energy in the form of alpha, beta and/or gamma radiations. The energy that goes into the drug-containing formulation can break chemical bonds and can generate reactive chemical species from solvent molecules, which may further decompose the radiopharmaceutical drug directly and/or indirectly.

"Amino" refers to the —$NH_2$ radical.
"Nitro" refers to the —$NO_2$ radical.
"Oxo" refers to the =O radical.
"Imino" refers to the =N—H radical.
"Hydroxy" or "hydroxyl" refers to the —OH radical.
"Alkyl" refers to an optionally substituted straight-chain, or optionally substituted branched-chain saturated hydrocarbon monoradical. An alkyl group can have from one to about twenty carbon atoms, from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a Ci alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, —$NO_2$, or —C≡CH. In some embodiments, the alkyl is optionally substituted with oxo, halogen, —CN, —$CF_3$, —OH, or —OMe. In some embodiments, the alkyl is optionally substituted with halogen.

The term "aryl" refers to a radical comprising at least one aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group comprises a partially reduced cycloalkyl group defined herein (e.g., 1,2-dihydronaphthalene). In some embodiments, an aryl group comprises a fully reduced cycloalkyl group defined herein (e.g., 1,2,3,4-tetrahydronaphthalene). When aryl comprises a cycloalkyl group, the aryl is bonded to the rest of the molecule through an aromatic ring carbon atom. An aryl radical can be a monocyclic or polycyclic (e.g., bicyclic, tricyclic, or tetracyclic) ring system, which may include fused, spiro or bridged ring systems. Unless stated otherwise specifically in the specification, an aryl may be optionally substituted, for example, with halogen, amino, alkylamino, aminoalkyl, nitrile, nitro, hydroxyl, alkyl, alkenyl, alkynyl, haloalkyl, heteroalkyl, alkoxy, aryl, cycloalkyl, heterocycloalkyl, heteroaryl, —$S(O)_2NH$—$C_1$-$C_6$alkyl, and the like. In some embodiments, an aryl is optionally substituted with halogen, methyl, ethyl, —CN, —CF$_3$, —OH, —OMe, —NH$_2$, —NO$_2$, —S(O)$_2$NH$_2$, —S(O)$_2$NHCH$_3$, —S(O)$_2$NHCH$_2$CH$_3$, —S(O)$_2$NHCH(CH$_3$)$_2$, —S(O)$_2$N(CH$_3$)$_2$, or —S(O)$_2$NHC(CH$_3$)$_3$. In some embodiments, an aryl is optionally substituted with halogen, methyl, ethyl, —CN, —CF$_3$, —OH, or —OMe. In some embodiments, the aryl is optionally substituted with halogen. In some embodiments, the aryl is substituted with alkyl, alkenyl, alkynyl, haloalkyl, or heteroalkyl, wherein each alkyl, alkenyl, alkynyl, haloalkyl, heteroalkyl is independently unsubstituted, or substituted with halogen, methyl, ethyl, —CN, —CF$_3$, —OH, —OMe, —NH$_2$, or —NO$_2$.

The term "cycloalkyl" refers to a monocyclic or polycyclic non-aromatic radical, wherein each of the atoms forming the ring (i.e., skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopentyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). A cycloalkyl can comprise a fused, spiro or bridged ring system. In some embodiments, the cycloalkyl comprises a fused ring system. In some embodiments, the cycloalkyl comprises a spiro ring system. In some embodiments, the cycloalkyl comprises a bridged ring system. In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0] octane, bicyclo[4.3.0]nonane, cis-decalin, trans-decalin, bicyclo[2.1.1]hexane, bicyclo[2.2.1] heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$—O—CH$_2$—, —CH$_2$—N(alkyl)-CH$_2$—, —CH$_2$—N(aryl)-CH$_2$—, —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroaryl" refers to a ring system radical comprising carbon atom(s) and one or more ring heteroatoms that selected from the group consisting of nitrogen, oxygen, phosphorous, and sulfur, and at least one aromatic ring. In some embodiments, heteroaryl is monocyclic, bicyclic or polycyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group comprises a partially reduced cycloalkyl or heterocycloalkyl group defined herein (e.g., 7,8-dihydroquinoline). In some embodiments, a heteroaryl group comprises a fully reduced cycloalkyl or heterocycloalkyl group defined herein (e.g., 5,6,7,8-tetrahydroquinoline). When heteroaryl comprises a cycloalkyl or heterocycloalkyl group, the heteroaryl is bonded to the rest of the molecule through a heteroaromatic ring carbon or hetero atom. A heteroaryl radical can be a monocyclic or polycyclic (e.g., bicyclic, tricyclic, or tetracyclic) ring system, which may include fused, spiro or bridged ring systems. Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The term "moiety" refers to a specific segment or functional group of a molecule. Chemical moieties are often recognized chemical entities embedded in or appended to a molecule.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof. As used herein, "treating" includes the concepts of "alleviating", which refers to lessening the frequency of occurrence or recurrence, or the severity, of any symptoms or other ill effects related to a disorder and/or the associated side effects. The term "treating" also encompasses the concept of "managing" which refers to reducing the severity of a particular disease or disorder in a patient or delaying its recurrence, e.g., lengthening the period of remission in a patient who had suffered from the disease. The term "treating" further encompasses the concept of "prevent," "preventing," and "prevention," that is, reducing the probability of developing a disease or condition in a subject, who does not have, but is at risk of or susceptible to developing a disease or condition.

The term "therapeutically effective amount" as used herein to refer to an amount effective at the dosage and duration necessary to achieve the desired therapeutic result. A therapeutically effective amount of the composition may vary depending on factors such as the individual's condition, age, sex, and weight, and the ability of the protein to elicit the desired response of the individual. A therapeutically effective amount can also be an amount that exceeds any toxic or deleterious effect of the composition that would have a beneficial effect on the treatment.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.).

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure. A person of ordinary skill in the art would understand that, while only a single bond is shown, a double bond is intended for those substituents.

The term "optionally substituted" or "substituted" means that the referenced group is optionally substituted with one or more additional group(s) individually and independently selected from D, halogen, —CN, oxo, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from D, halogen, —CN, oxo, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$^2$NH$_2$, —S(=O)$^2$NH(C$_1$-C$_4$alkyl), —S(=O)$^2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —NH(cyclopropyl), —CH$_3$, —CH$_2$CH$_3$, —CF$_3$, —OCH$_3$, and —OCF$_3$. In some embodiments, substituted groups are substituted with one or two of the preceding groups. When indicating the number of substituents, the term "one or more" means from one substituent to the highest possible number of substitutions, i.e. replacement of one hydrogen up to replacement of all hydrogens by substituents.

The term "unsubstituted" means that the specified group bears no substituents.

Certain compounds described herein may exist in tautomeric forms, and all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

The term "peptide" as used herein refers to a compound that includes two or more amino acids. A peptide described herein can comprise one or more unnatural amino acids. The term "peptide" also encompasses peptide mimetics. In the present disclosure, the term "amino acid" is used in its broadest meaning and it embraces not only natural amino acids but also derivatives thereof and artificial amino acids. For example, the term "amino acid" encompasses unnatural amino acids.

As used herein, the term "unnatural amino acid" refers to an amino acid other than the 20 amino acids that occur naturally in protein.

The term "protein" as used herein refers to a polypeptide (i.e., a string of at least 3 amino acids linked to one another by peptide bonds). Proteins can include moieties other than amino acids (e.g., may be glycoproteins, proteoglycans, etc.) and/or can be otherwise processed or modified. A protein can be a complete polypeptide as produced by and/or active in a cell (with or without a signal sequence). In some embodiments, a protein is or comprises a characteristic portion such as a polypeptide as produced by and/or active in a cell. A protein can include more than one polypeptide chain.

The term "peptide mimetic" or "mimetic" refers to biologically active compounds that mimic the biological activity of a peptide or a protein but are no longer entirely peptidic in chemical nature, e.g., they can contain non-peptide bonds (that are, bonds other than amide bonds between amino acids). As used herein, the term peptide mimetic is used in a broader sense to include molecules that are no longer completely peptidic in nature, such as pseudo-peptides, semi-peptides and peptoids. Whether completely or partially non-peptide, peptide mimetics described herein can provide a spatial arrangement of reactive chemical moieties that closely resemble the three-dimensional arrangement of active groups in the subject amino acid sequence or subject molecule on which the peptide mimetic is based. As a result of this similar active-site geometry, the peptide mimetic can have effects on biological systems that are similar to the biological activity of the subject entity.

In some embodiments, the peptide mimetics are substantially similar in both three-dimensional shape and biological activity to the subject amino acid sequence or subject molecule on which the peptide mimetic is based. Examples of methods of structurally modifying a peptide to create a peptide mimetic include the inversion of backbone chiral centers leading to D-amino acid residue structures that may, particularly at the N-terminus, lead to enhanced stability for proteolytical degradation without adversely affecting activity. An example is described in the paper "Tritiated D-alai-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is provided in conformationally restricted thymopentin-like compounds, such as those disclosed in U.S. Pat. No. 4,457,489. A third method is to substitute peptide bonds in the subject entity by pseudopeptide bonds that confer resistance to proteolysis.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, $C_1$-Cx (or $C_1$-x) includes $C_1$-$C_2$, $C_1$-$C_3$ . . . $C_1$-Cx. By way of example only, a group designated as "$C_1$-$C_4$" indicates that there are one to four carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Also, by way of example, $C_0$-$C_2$ alkylene includes a direct bond, —$CH_2$—, and —$CH_2CH_2$— linkages.

The term "cyclized" or "cyclization" as used herein means that two amino acids apart from each other by at least one amino acid bind directly or bind indirectly to each other in one peptide to form a cyclic structure in the molecule. In some cases, the two amino acids bind via a linker or the like.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a companion animal such as a dog or a cat. In one aspect, the mammal is a human.

The term "therapeutically effective amount" as used herein to refer to an amount effective at the dosage to achieve the desired therapeutic result. A therapeutically effective amount of a composition may vary depending on factors such as the individual's condition (e.g., age, sex, and weight), the radiopharmaceutical conjugate, and the method of administration (e.g., oral or parenteral).

II. Technical Overview

Targeted Radiopharmaceutical (TRP) is a new generation of nuclear medicine for cancer treatment or diagnosis. A TRP can selectively deliver high concentration of radionuclide-containing molecules to the target cells such as tumor, and none or very low concentration to the undesired cells like normal tissues. The process can be achieved by engineering the drug molecule with the high-affinity binder (e.g., targeting ligands) linking to the radioactive isotope. The biological targets of those binders are highly expressed on tumor cells, have low or no expression in healthy tissues and organs. When the radioisotope decays, it emits highly energic ionizing radiation in form of alpha, beta, and/or gamma particles. The released energy at the target sites can cause damage or death of the target tissues or be visualized by imaging scanner to achieve therapeutic or diagnostic purposes.

In some traditional radiopharmaceutical formulations, a very high concentration of stabilizer as to radiopharmaceuticals is used. The high concentration can produce unknown biological effects and/or compromise therapeutic efficacy of the drug. Due to the low efficiency of those stabilizers used in the past, significant dilution was needed to slow down the decomposition. As a result, larger volume of dose can require treatment via infusion instead of bolus injection under clinical setting. This is less desired for patients due to the prolonged stay at the infusion center and sometimes hospitalization. One of the major challenges in the production of radiopharmaceutical drugs is to extend the shelf-life of product to allow treatment of patients at remote locations to the manufacturer site. Increasing stability of radiopharmaceutical drug in formulated solution can resolve this challenge.

In some cases, with decay of the parent isotopes, daughter isotopes can be released into the solution. They can be non-radioactive or radioactive. When the daughter ions are radioactive, those non-bonded ions can create non-specific distribution of radioactivity in vivo and generate undesired toxicities. In addition, even if they are not radioactive, they can still bind to the metal chelation moiety on the radiopharmaceutical drug due to their higher affinity. The replacement of their parent ions can chemically cause decomposition of the drug substance. This process can also negatively impact the radiochemical purities overtime. When decay of Actinium-225-DOTA-containing drug starts, the isotope can first decay into Francium-221(I). The recoil energy of the process can be approximately 10000 times higher than any known chemical bond energy. It can cause the daughter ions to escape from their original chelator DOTA. Due to the chemical nature of Francium-221 (I), in some cases, they cannot be recaptured by free DOTA-containing drug. As decay continues, more free daughter ions can enter the solution. Eventually, majority of the decayed daughters can accumulate in the form of stable Bismuth-209 (III). Bismuth (III) can be a much stronger metal to be chelated with DOTA moiety and its competition with the parent drug can lead further dissociation of Ac-225 for its chelator, generate radioactive free metal impurities.

The decay of radionuclides can be accompanied by emission of energy in the form of alpha, beta and/or gamma radiations. The energy can go into the drug-containing solution and can break chemical bonds, generate reactive chemical species from solvent molecules, further decompose the radiopharmaceutical drug directly or indirectly. This process can be referred as radiolysis. Radiolysis can be particularly severer when a concentrated radioactive compound is presented in small volume of the solution. In the case of Actinium-225-DOTA-containing radiopharmaceuticals, Actinium-225 can decay into Francium-221, Astatine-217, Bismuth-213, Thallium-209, Polonium-213, Lead-209, Bismuth-209 in sequence. The decay chain can contain four alpha particle emissions and two beta particle emissions. In addition, Francium-221 and Bismuth-213 can release up to 25% of their decay energy through gamma emission. The ionizing radiation can cause radiolysis of surrounding water molecules particularly produce H· atoms, ·OH radicals, $H_3O^+$ ions and oxidizing agent hydrogen peroxide. These chemical species can be highly reactive. In some cases, they can react with the drug substance, cause degradation of the radioisotope-containing peptide drug, increase radioactive impurity overtime.

Accordingly, provided herein are radiopharmaceutical compositions with improved stability, for example, compositions containing Actinium-225.

In one aspect, the present disclosure relates to radionuclide solution with radioisotopes and its daughter ions. The solution composition can comprise ingredients which stabilize the radioactive drug substance from radiolysis and chemical decomposition. The increased stability of the drug substance can extend shelf-life of radiopharmaceuticals, as such to achieve their wide applications as a drug product for their diagnostic and therapeutic purpose.

In one aspect, the compositions described herein have increased stability of the radiopharmaceutical conjugate. The radiopharmaceutical composition can contain ingredients, such as radiopharmaceutical stabilizers, which stabilize the radioactive drug substance from radiolysis and chemical decomposition. The radiopharmaceuticals stabilizers can comprise reducing agents and/or radical scavengers, such as ascorbic acid to reduce the radiolysis. The composition of the present disclosure can have extended shelf-life. The compositions described herein can comprise one or more stabilizing agents. The stabilizing agents can prevent or delay radiolysis of the radiopharmaceutical conjugate. The stabilizing agents can prevent or delay decomposition of the radiopharmaceutical conjugate. The stabilizing agents can prevent or delay chemical decomposition of the radiopharmaceutical conjugate caused by radioactive decay-generated daughter ions. The stabilizing agents can prevent or delay chemical decomposition of the radiopharmaceutical conjugate caused by pH changes. The stabilizing agents can be added into the composition at a low concentration. The stabilizing agents can be optionally added into the composition at a low concentration. The increased stability of the radiopharmaceutical conjugate can achieve one or more applications. The applications can comprise acting as a drug product for one or more diagnostic purposes. The applications can comprise acting as a drug product for one or more therapeutic purposes. A treatment plan for a patient or subject receiving the radiopharmaceutical compositions described herein can include treatment at remote locations. A treatment plan for a patient or subject receiving the radiopharmaceutical compositions described herein can include a shorter stay at the infusion center or at the hospital.

A radiopharmaceutical conjugate can comprise a radionuclide and a metal chelator. The radionuclide and the metal chelator can be linked by ionic and coordinate bonding. The radionuclides for therapeutic purpose can include Lutetium-177, Actinium-225, Yttrium-90, and Bismuth-213. The radionuclides for diagnostic purpose can include Gallium-68, Copper-64, and Indium-111. The chelator can further bind to a target binder, such as one that has a high-affinity with the target of the radiopharmaceutical conjugate, directly or via a linker covalently. Exemplary metal chelators can include aza-crown ether-based polycarboxylic acid such as 2,2',2'',2'''-(1,4,7,10-Tetraazacyclododecane-1,4,7,10-tetrayl)tetraacetic acid (DOTA), or 1,4,7-Triazacyclononane-1,4,7-triacetic acid (NOTA). The chelation can keep the radionuclide from releasing into surroundings in vitro and/or in vivo.

III. Compositions

In one aspect, the present disclosure provides liquid radiopharmaceutical compositions comprising a radiopharmaceutical conjugate. The conjugate can comprise a targeting ligand. The targeting ligand can be a binding peptide or a chemical group. The conjugate can further comprise a chelator such as a metal chelator. The chelator can be covalently attached to the targeting ligand. The conjugate can further comprise a radionuclide. In some embodiments, the radionuclide is bound to the chelator. The composition can further comprise one or more stabilizing agents. The one or more stabilizing agents are agents that can stabilize the composition or formulation of the radiopharmaceutical conjugates. The one or more stabilizing agents can reduce or delay the decomposition of the radiopharmaceutical conjugates in the composition.

In one aspect, provided herein are liquid radiopharmaceutical compositions comprising $^{225}$Ac-DOTATATE. In one aspect, provided herein are liquid radiopharmaceutical compositions comprising $^{225}$Ac-DOTATOC.

The liquid radiopharmaceutical compositions can comprise pharmaceutically acceptable carriers or diluents. Exemplary pharmaceutically acceptable carriers include solvents (aqueous or non-aqueous), solutions, emulsions, dispersion media, coatings, isotonic and absorption promoting or delaying agents, compatible with pharmaceutical administration. In some embodiments, the liquid radiopharmaceutical compositions described herein are formulated as a solution, emulsion, suspension, syrup or elixir, or the like. The compositions can be aqueous radiopharmaceutical compositions.

The liquid radiopharmaceutical composition can comprise an aqueous vehicle. For example, the aqueous vehicle can comprise water, saline solution, dextrose in water, dextrose in saline solution, Ringer's solution, or lactated Ringer's solution. In some embodiments, the aqueous vehicle is water. In some embodiments, the aqueous vehicle is water for injection. In some embodiments, the aqueous vehicle is 5.0% w/w sodium chloride solution. In some embodiments, the aqueous vehicle is 4.0% w/w sodium chloride solution. In some embodiments, the aqueous vehicle is 3.0% sodium chloride solution. In some embodiments, the aqueous vehicle is 2.0% w/w sodium chloride solution. In some embodiments, the aqueous vehicle is 1.5% w/w sodium chloride solution. In some embodiments, the aqueous vehicle is 1.0% sodium chloride solution. In some embodiments, the aqueous vehicle is 0.9% w/w sodium chloride saline solution. In some embodiments, the aqueous vehicle is 0.5% w/w sodium chloride solution. In some embodiments, the aqueous vehicle is 0.5% to 1.5% w/w sodium chloride solution. In some embodiments, the aqueous vehicle is 0.7% to 1.1% w/w sodium chloride solution. In some embodiments, the aqueous vehicle is saline solution. In some embodiments, the aqueous vehicle is dextrose in water. In some embodiments, the aqueous vehicle is dextrose in saline solution. The compositions can be isotonic. The compositions can be a solution or suspension. In some embodiments, the liquid radiopharmaceutical is formulated as a solution. The compositions can be formulated to be compatible with a particular local or systemic route of administration. The compositions can include carriers, diluents, or excipients suitable for administration by particular routes. The composition can be formulated for IV infusion or bolus injection. In some embodiments, the liquid radiopharmaceutical is formulated for intravenous administration.

Supplementary components or excipients can also be incorporated into the liquid radiopharmaceutical compositions. The composition can further comprise one or more supplementary components or excipients. The supplementary components or excipients can be preservatives, antibacterial, antiviral, antimicrobial and antifungal agents. The supplementary components or excipients can be a tonicity adjusting agent, a solubilizing agent, a suspending agent, and a surfactant.

The liquid radiopharmaceutical compositions described herein can be storage stable for a period of time. In some embodiments, the liquid radiopharmaceutical compositions described herein retain at least 80 mol % of the initial conjugate after 168 hours at room temperature (25° C.). In some embodiments, the compositions retain at least 85 mol % of the initial conjugate after 168 hours at room temperature (25° C.). In some embodiments, the compositions retain at least 90 mol % of the initial conjugate after 168 hours at room temperature (25° C.). In some embodiments, the compositions retain at least 95 mol % of the initial conjugate after 168 hours at room temperature (25° C.). In some embodiments, the compositions described retain at least 98 mol % of the initial conjugate after 168 hours at room temperature (25° C.). In some embodiments, the composition retains at least 85 mol %, at least 90 mol %, at least 92 mol %, at least 95 mol %, at least 98 mol % or at least 99 mol % of the initial conjugate after 120 hours at room temperature (25° C.). In some embodiments, the composition retains at least 85 mol %, at least 90 mol %, at least 92 mol %, at least 95 mol %, at least 98 mol % or at least 99 mol % of the initial conjugate after 96 hours at room temperature (25° C.). In some embodiments, the composition retains at least 85 mol %, at least 90 mol %, at least 92 mol %, at least 95 mol %, at least 98 mol % or at least 99 mol % of the initial conjugate after 48 hours at room temperature (25° C.). In some embodiments, the compositions described herein retain at least 85 mol %, at least 90 mol %, at least 92 mol %, at least 95 mol %, at least 98 mol % or at least 99 mol % of the initial conjugate after 2 weeks at refrigerated condition (about 4° C.). In some embodiments, the compositions described herein retain at least 85 mol %, at least 90 mol %, at least 92 mol %, at least 95 mol %, at least 98 mol % or at least 99 mol % of the initial conjugate after 10 days at refrigerated condition (about 4° C.). In some embodiments, the compositions described herein retain at least 85 mol %, least 90 mol %, at least 92 mol %, at least 95 mol %, at least 98 mol %, at least 99 mol %, or at least 99.5 mol % of the initial conjugate after 168 hours at refrigerated condition (about 4° C.). In some embodiments, the compositions described herein retain at least 85 mol %, at least 90 mol %, at least 92 mol %, at least 95 mol %, at least 98 mol %, at least 99 mol %, or at least 99.5 mol % of the initial conjugate after 96 hours at refrigerated condition (about 4° C.). In some embodiments, the compositions described herein retain at least 85 mol %, at least 90 mol %, at least 92 mol %, at least 95 mol %, at least 98 mol %, at least 99 mol %, or at least 99.5 mol % of the initial conjugate after 48 hours at refrigerated condition (about 4° C.). In some embodiments, the purity or the molar percentage of the conjugate is determined by radio thin layer chromatography (radio-TLC). In some embodiments, the purity or the molar percentage of the conjugate is determined by instant thin layer chromatography (iTLC). In some embodiments, the purity or the molar percentage of the conjugate is determined by measuring the related α-particle emission using radio-TLC.

The liquid radiopharmaceutical compositions described herein can retain an amount of the initial conjugate (such as $^{225}$Ac-DOTA-TATE) after stored for a period of time. In some embodiments, the radiopharmaceutical composition retains 95 mol % or more of the initial conjugate after 48 hours, 72 hours, 96 hours, 120 hours, 148 hours, 168 hours, 192 hours, or 216 hours at room temperature (25° C.). In some embodiments, the radiopharmaceutical composition retains 95 mol % or more of the initial conjugate after 96 hours at room temperature (25° C.). In some embodiments, the radiopharmaceutical composition retains 95 mol % or more of the initial conjugate after 120 hours at room temperature (25° C.). In some embodiments, the radiopharmaceutical composition retains 95 mol % or more of the initial conjugate after 148 hours at room temperature (25° C.). In some embodiments, the radiopharmaceutical composition retains 95 mol % or more of the initial conjugate after 168 hours at room temperature (25° C.). In some embodiments, the radiopharmaceutical composition retains 95 mol % or more of the initial conjugate after 192 hours at room temperature (25° C.). In some embodiments, the purity or the molar percentage of the conjugate is determined by instant thin-layer chromatography (iTLC). In some embodiments, the purity or the molar percentage of the conjugate is determined by radio thin-layer chromatography (radio-TLC).

The liquid radiopharmaceutical compositions described herein can contain a small amount of the unchelated and un-conjugated radionuclide after stored for a period of time. In some embodiments, the liquid radiopharmaceutical compositions described herein contain a small amount of free actinium-225 and actinium-225 present in a fragment of the conjugate $^{225}$Ac-DOTA-TATE (e.g., as $^{225}$Ac-DOTA fragment) after being stored for a period of time. For example, see Example 3. A total content of the radionuclide such as actinium-225 in the radiopharmaceutical composition can also decrease over time due to the decay of the radionuclide. In some embodiments, the liquid radiopharmaceutical compositions comprise a conjugate that comprises actinium-225. In some embodiments, a radiopharmaceutical composition comprising actinium-225 conjugates contains no more than about 20% free actinium-225 after 120 hours at about 20° C. to 25° C., compared to the total amount of the actinium-225 content in the composition (at that time). In some embodiments, a radiopharmaceutical composition comprising actinium-225 conjugates contains no more than about 10% free actinium-225 after 120 hours at about 20° C. to 25° C., compared to the total amount of the actinium-225 content in the composition. In some embodiments, a radiopharmaceutical composition comprising actinium-225 conjugates contains no more than about 5% free actinium-225 after 120 hours at about 20° C. to 25° C., compared to the total amount of the actinium-225 content in the composition. In some embodiments, a radiopharmaceutical composition comprising actinium-225 conjugates contains no more than about 2% free actinium-225 after 120 hours at about 20° C. to 25° C., compared to the total amount of the actinium-225 content in the composition. In some embodiments, a radiopharmaceutical composition comprising actinium-225 conjugates contains no more than about 1% free actinium-225 after 120 hours at about 20° C. to 25° C., compared to the total amount of the actinium-225 content in the composition.

In some embodiments, after being stored for 120 hours at about 20° C. to about 25° C., at least 90 mol % of the $^{225}$Ac (i.e., actinium-225) content in the liquid radiopharmaceutical composition (at that time) is present as $^{225}$Ac-DOTA-TATE. In some embodiments, after being stored for 120 hours at about 20° C. to about 25° C., at least 95 mol % of the $^{225}$Ac (i.e., actinium-225) content in the liquid radiopharmaceutical composition is present as $^{225}$Ac-DOTA-TATE. In some embodiments, after being stored for 120 hours at about 20° C. to about 25° C., at least 98 mol % of the $^{225}$Ac (i.e., actinium-225) content in the liquid radiopharmaceutical composition is present as $^{225}$Ac-DOTA-TATE. In some embodiments, after being stored for 120 hours at about 20° C. to about 25° C., at least 99 mol % of the $^{225}$Ac (i.e., actinium-225) content in the liquid radiopharmaceutical composition is present as $^{225}$Ac-DOTA-TATE. In some embodiments, after being stored for 144 hours at about 20° C. to about 25° C., at least 90 mol % of the $^{225}$Ac (i.e., actinium-225) content in the liquid radiopharmaceutical composition (at that time) is present as $^{225}$Ac-DOTA-TATE. In some embodiments, after being stored for 168 hours at about 20° C. to about 25° C., at least 90 mol % of the $^{225}$Ac (i.e., actinium-225) content in the liquid radiopharmaceutical composition (at that time) is present as $^{225}$Ac-DOTA-TATE. In some embodiments, after being stored for 192 hours at about 20° C. to about 25° C., at least 90 mol % of the $^{225}$Ac (i.e., actinium-225) content in the liquid radiopharmaceutical composition (at that time) is present as $^{225}$Ac-DOTA-TATE.

In some embodiments, a radiopharmaceutical composition comprising actinium-225 conjugates contains no more than a combined amount of about 20% of free $^{225}$Ac and $^{225}$Ac present in a fragment of the conjugate (e.g., as $^{225}$Ac-DOTA fragment) after 120 hours at about 20° C. to 25° C., compared to the total amount of the $^{225}$Ac content in the composition. In some embodiments, a radiopharmaceutical composition comprising actinium-225 conjugates contains no more than a combined amount of about 15% of free $^{225}$Ac and $^{225}$Ac present in a fragment of the conjugate (e.g., as $^{225}$Ac-DOTA fragment) after 120 hours at about 20° C. to 25° C., compared to the total amount of the $^{225}$Ac content in the composition. In some embodiments, a radiopharmaceutical composition comprising actinium-225 conjugates contains no more than a combined amount of about 10% of free $^{225}$Ac and $^{225}$Ac present in a fragment of the conjugate (e.g., as $^{225}$Ac-DOTA fragment) after 120 hours at about 20° C. to 25° C., compared to the total amount of the $^{225}$Ac content in the composition. In some embodiments, a radiopharmaceutical composition comprising actinium-225 conjugates contains no more than a combined amount of about 10% of free $^{225}$Ac and $^{225}$Ac present in a fragment of the conjugate (e.g., as $^{225}$Ac-DOTA fragment) after 120 hours at about 20° C. to 25° C., compared to the total amount of the $^{225}$Ac content in the composition. In some embodiments, a radiopharmaceutical composition comprising actinium-225 conjugates contains no more than a combined amount of about 5% of free $^{225}$Ac and $^{225}$Ac present in a fragment of the conjugate (e.g., as $^{225}$Ac-DOTA fragment) after 120 hours at about 20° C. to 25° C., compared to the total amount of the $^{225}$Ac content in the composition. The total amount of the $^{225}$Ac content in a composition can decrease overtime as the radionuclide actinium-225 naturally decays. In some embodiments, a radiopharmaceutical composition comprising actinium-225 conjugates contains no more than a combined amount of about 10% of free $^{225}$Ac and $^{225}$Ac present in a fragment of the conjugate (e.g., as $^{225}$Ac-DOTA fragment) after 144 hours at about 20° C. to 25° C., compared to the total amount of the $^{225}$Ac content in the composition. In some embodiments, a radiopharmaceutical composition comprising actinium-225 conjugates contains no more than a combined amount of about 10% of free $^{225}$Ac and $^{225}$Ac present in a fragment of the conjugate (e.g., as $^{225}$Ac-DOTA fragment) after 168 hours at about 20° C. to 25° C., compared to the total amount of the $^{225}$Ac content in the composition. In some embodiments, a radiopharmaceutical composition comprising actinium-225 conjugates contains no more than a combined amount of about 10% of free $^{225}$Ac and $^{225}$Ac present in a fragment of the conjugate (e.g., as $^{225}$Ac-DOTA fragment) after 192 hours at about 20° C. to 25° C., compared to the total amount of the $^{225}$Ac content in the composition. In some embodiments, the amount of $^{225}$Ac is determined by radio-TLC.)

In some embodiments, a radiopharmaceutical composition described herein retains at least 90% of the $^{225}$Ac (i.e., actinium-225) content in the liquid radiopharmaceutical composition as $^{225}$Ac-DOTA-TATE after 120 hours at about 20° C. to 25° C. as determined by radio-TLC. In some embodiments, a radiopharmaceutical composition described herein retains at least 95% of the $^{225}$Ac (i.e., actinium-225) content in the liquid radiopharmaceutical composition as $^{225}$Ac-DOTA-TATE after 120 hours at about 20° C. to 25° C. as determined by radio-TLC. In some embodiments, a radiopharmaceutical composition described herein retains at least 98% of the $^{225}$Ac (i.e., actinium-225) content in the liquid radiopharmaceutical composition as $^{225}$Ac-DOTA-TATE after 120 hours at about 20° C. to 25° C. as determined by radio-TLC. In some embodiments, a radiopharmaceutical composition described herein retains at least 99% of the $^{225}$Ac (i.e., actinium-225) content in the liquid radiopharmaceutical composition as $^{225}$Ac-DOTA-TATE after 120 hours at about 20° C. to 25° C. as determined by radio-TLC. In some embodiments, a radiopharmaceutical composition described herein retains at least 90% of the $^{225}$Ac (i.e., actinium-225) content in the liquid radiopharmaceutical composition as $^{225}$Ac-DOTA-TATE after 144 hours at about 20° C. to 25° C. as determined by radio-TLC. In some embodiments, a radiopharmaceutical composition described herein retains at least 90% of the $^{225}$Ac (i.e., actinium-225) content in the liquid radiopharmaceutical composition as $^{225}$Ac-DOTA-TATE after 168 hours at about 20° C. to 25° C. as determined by radio-TLC. In some embodiments, a radiopharmaceutical composition described herein retains at least 90% of the $^{225}$Ac (i.e., actinium-225) content in the liquid radiopharmaceutical composition as $^{225}$Ac-DOTA-TATE after 192 hours at about 20° C. to 25° C. as determined by radio-TLC.

In some embodiments, a radiopharmaceutical composition comprising actinium-225 conjugates contains no more than about 20% free actinium after 168 hours at room temperature (25° C.), compared to the total amount of the initial chelated actinium content in the composition. In some embodiments, a radiopharmaceutical composition comprising actinium-225 conjugates contains no more than about 10% free actinium after 168 hours at room temperature (25° C.), compared to the total amount of the initial chelated actinium content in the composition. In some embodiments, a radiopharmaceutical composition comprising actinium-225 conjugates contains no more than about 5% free actinium after 168 hours at room temperature (25° C.), compared to the total amount of the initial chelated actinium content in the composition. In some embodiments, a radiopharmaceutical composition comprising actinium-225 conjugates contains no more than about 3% free actinium after 168 hours at room temperature (25° C.), compared to the total amount of the initial chelated actinium content in the composition. In some embodiments, a radiopharmaceutical composition comprising actinium-225 conjugates contains no more than about 2% free actinium after 168 hours at room temperature (25° C.), compared to the total amount of the initial chelated actinium content in the composition. In some embodiments, a radiopharmaceutical composition comprising actinium-225 conjugates contains no more than about 1% free actinium after 168 hours at room temperature (25° C.), compared to the total amount of the initial chelated actinium content in the composition. In some embodiments, a radiopharmaceutical composition comprising actinium-225 conjugates contains no more than about a total of 20 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 15 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 10 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 5 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 3 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 2 mol % of free daughter isotopes of actinium-225 after 168 hours at room temperature (25° C.), compared to the total amount of the initial chelated actinium content in the composition. In some embodiments, a radiopharmaceutical composition comprising actinium-225 conjugates contains no more than about a total of 1 mol % of free daughter isotopes of actinium-225 after 168 hours at room temperature (25° C.), compared to the total amount of the initial chelated actinium content in the composition. In some embodiments, the purity or the molar percentage of the conjugate is determined by radio thin layer chromatography (radio-TLC).

Stabilizing Agents

In one aspect, disclosed herein are radiopharmaceutical compositions with improved stability. Pharmaceutical compositions described herein can comprise one or more stabilizing agents. In one aspect, provided herein are solutions that comprise one or more stabilizing agents for use in a radiopharmaceutical composition. In some embodiments, the solutions that comprise one or more stabilizing agents are dilution solutions. The one or more stabilizing agents can reduce, prevent, or delay decomposition of the radiopharmaceutical. The decomposition can comprise radiolysis-caused decomposition of the radiopharmaceuticals. The one or more stabilizing agents can reduce, prevent, or delay the decay of radionuclides.

Radiolysis Stabilizer

The one or more stabilizing agents of the herein described pharmaceutical composition can comprise a radiolysis stabilizer. The one or more stabilizing agents can comprise two or more radiolysis stabilizers. The one or more stabilizing agents can comprise a first and a second radiolysis stabilizer. The radiolysis stabilizer can be an amino acid or a peptide or a derivative thereof, a vitamin or a derivative thereof, a lipid or a derivative thereof, a carbohydrate or a derivative thereof, a volume expander or an antioxidant.

The molar ratio of the first and the second radiolysis stabilizer can be from 1:100,000 to 100,000, from 1:1,000 to 1,000:1, from 1:100 to 100:1, from 1:20 to 20:1, from 1:10 to 10:1, and from 1:5 to 5:1. The molar ratio of the first and the second radiolysis stabilizer can be from 1:5 to 5:1. The radiolysis stabilizer can be present in the radiopharmaceutical composition at a concentration of from about 1 µM, 10 µM, 0.1 mM, 1 mM, 5 mM, 10 mM, 25 mM, 50 mM, or 75 mM to about 80 mM, 100 mM, 125 mM, 150 mM, 175 mM, 200 mM, 250 mM, 500 mM, 1 M, 2 M, 3 M, 4 M, 5 M. The radiolysis stabilizer can be present in the radiopharmaceutical composition at a concentration of from about 1 µM to 5 M. The radiolysis stabilizer can be present in the radiopharmaceutical composition at a concentration of from about 10 µM to 1 M. The radiolysis stabilizer can be present in the radiopharmaceutical composition at a concentration of from about 0.1 mM to 500 mM. The radiolysis stabilizer can be present in the radiopharmaceutical composition at a concentration of from about 10 mM to 500 mM. The radiolysis stabilizer can be present in the radiopharmaceutical composition at a concentration of from about 20 mM to 100 mM. The radiolysis stabilizer can be present in the radiopharmaceutical composition at a concentration of from about 25 mM to 75 mM. The radiolysis stabilizer can be present in the radiopharmaceutical composition at about 0.001 wt % to about 10 wt %. The radiolysis stabilizer can be present in the radiopharmaceutical composition at about 0.0001 wt % to about 20 wt %, 0.001 wt % to about 10 wt %, 0.01 wt % to about 5 wt %, about 0.05 wt % to about 2 wt %, or about 0.1 wt % to about 1 wt %. The radiolysis stabilizer can be present in the radiopharmaceutical composition at about 0.01 wt % to about 5 wt %. The radiolysis stabilizer can be present in the radiopharmaceutical composition at about 1 wt % to about 10 wt %, about 3 wt % to about 7 wt %, about 4 wt % to about 6 wt %, or about 2 wt % to about 15 wt %. The radiolysis stabilizer can be present in the radiopharmaceutical composition at about 5 wt %. The radiolysis stabilizer can be present in the radiopharmaceutical composition at about 0.05 wt % to about 2 wt %. The radiolysis stabilizer can be present in the radiopharmaceutical composition at about 0.1 wt % to about 1 wt %. The radiolysis stabilizer can also be present in the radiopharmaceutical composition at a concentration of from 0.0001 to 5,000 mg/mL. The radiolysis stabilizer can also be present in the radiopharmaceutical composition at a concentration of from 0.1 to 500 mg/mL. The radiolysis stabilizer can also be present in the radiopharmaceutical composition at a concentration of from 0.01 to 50 mg/mL. The radiolysis stabilizer can also be present in the radiopharmaceutical composition at a concentration of from 0.1 to 5 mg/mL. The radiolysis stabilizer can also be present in the radiopharmaceutical composition at a concentration of from 0.5 to 2 mg/mL. In some embodiments, the radiolysis stabilizer is dextran (such as Dextran 40).

The radiolysis stabilizers can comprise an amino acid or a derivative thereof. The radiolysis stabilizers can comprise a peptide or a derivative thereof. The amino acid or a derivative thereof can be a natural amino acid or an unnatural amino acid. The amino acid can act to scavenge chemically active ingredients generated by radiolysis. The amino acid can contain an amino group. The amino acid can comprise optionally an extra reducing heteroatom, such as L-methionine, L-Cysteine, or L-Lysine. The peptide or a derivative thereof can comprise two or more amino acids. The peptide can comprise 2 to 50 amino acids. The peptide can comprise 2 to 30 amino acids. The peptide can comprise 2 to 15 amino acids. The peptide can comprise 2 to 7 amino acids. The peptide can comprise 2 to 4 amino acids. The peptide can comprise 3 amino acids. The amino acid can be an essential amino acid. The amino acid can be a nonessential amino acid. The amino acid can be an aliphatic amino acid. The amino acid can be an aromatic amino acid. The amino acid can be an acidic amino acid. The amino acid can be a basic amino acid. The amino acid can be a hydroxylic amino acid. The amino acid can be a sulfur-containing amino acid. The amino acid can be an amidic amino acid. The amino acid, its derivative, or peptide can be N-Acetyl-L-cysteine, Glutathione, L-Lysine, Selenol-L-methionine, Glutathione, Albumin, Melatonin, Taurine, Alanine, Arginine, Asparagine, Aspartic acid, Cysteine, Glutamine, Glutamic acid, Glycine, Histidine, Isoleucine, Lysine, Methionine, Phenylalanine, Proline, Serine, Threonine, Tryptophan, Tyrosine, Valine, and/or derivatives thereof. The amino acid can be a methionine. The amino acid derivative, such as N-Acetyl-L-cysteine, can have higher solubilities. The radiolysis stabilizer, such as Thiourea, L-Glutathione, and Lipoic Acid, can comprise an organic sulfur. The organic sulfur can optionally be oxidized to a higher oxidation state and coordinate to free heavy metal ions in a solution.

The radiolysis stabilizers can comprise an antioxidant (or reducing agent or radical scavengers). The radiolysis stabilizers can comprise one or more antioxidants. The antioxidant can comprise a flavonoid or a derivative thereof. The flavonoid can be polyphenol compounds that comprise multiple phenol units. A flavonoid can comprise a 15-carbon structure. The 15-carbon structure can further comprise two phenyl rings and a heterocyclic ring. The flavonoid can comprise bioflavonoids, isoflavonoids, or neoflavonoids. The flavonoid can comprise a catechin or a derivative thereof, such as the compounds illustrated in FIG. 1, (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), (−)-cis-3,3',4',5,7-Pentahydroxyflavane (Epi-Catechin or EC), 3,4,5-Trihydroxybenzoic acid (Gallic acid), (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4,5-trihydroxyphenyl)-3,4-dihydro-2H-chromene-3,5,7-triol or Epigallo-Catechin (EGC), or (2R,3S)-2-(3,4,5-trihydroxyphenyl)-3,4-dihydro-2H-chromene-3,5,7-triol (Gallo-Catechin or GC). The catechins can be administered in human from 1 mg/kg to 50 mg/kg, from 5 mg/kg to 40 mg/kg, from 10 mg/kg to 40 mg/kg, from 20 mg/kg to 35 mg/kg. The flavonoid can comprise (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), 3,3',4',5,5',7-Hexahydroxyflavylium chloride, (−)-cis-3,3',4',5,7-Pentahydroxyflavane (Epi-Catechin or EC), 7-Hydroxy-3-(4'-methoxyphenyl)-4H-benzopyran-4-one, 3,4,5-Trihydroxybenzoic acid (Gallic acid), 3,4',5,7-Tetrahydroxyflavone (Kaempferol), Luteolin, 2-(3,4-dihydroxyphenyl)-5,7-dihydroxy-3-[(2S,3R,4S,5S,6R)-3,4,5-trihydroxy-6-[[(2R,3R,4R,5R,6 S)-3,4,5-trihydroxy-6-methyloxan-2-yl]oxymethyl]oxan-2-yl] oxychromen-4-one (Rutin hydrate), Quercetin, (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3,4-dihydro-2H-chromen-3-yl] 3,4,5-trihydroxybenzoate, Epi-Catechin Gallate (ECG), (2R,3R)-2-(3,4,5-trihydroxyphenyl)-3,4-dihydro-2H-chromene-3,5,7-triol (Epigallo-Catechin or EGC), or (2R,3S)-2-(3,4,5-trihydroxyphenyl)-3,4-dihydro-2H-chromene-3,5,7-triol (Gallo-Catechin or GC), or a combination thereof. In some embodiments, the antioxidant is a carotenoid or a derivative thereof. The carotenoid can be a fat-soluble pigment, such as yellow, orange, or red pigments. The carotenoid can be all-trans-Fucoxanthin, Lycopene, Xanthophyll, Beta carotene, Lycopene, or Lutein.

In some embodiment, a herein described pharmaceutical composition comprises an antioxidant that is N-acetyl cysteine, L-Ascorbic acid, N-tert-Butyl-α-phenylnitrone, 3-(3,4-Dihydroxyphenyl)-2-propenoic acid (Caffeic Acid), β-Carotene, Provitamin A, (2S,3R)-2-(3,4-Dihydroxyphenyl)-3,4-dihydro-1 (2H)-benzopyran-3,5,7-triol 3-(3,4,5-trihydroxybenzoate ((−) Catechin gallate or CG), 1,4,5-Trihydroxycyclohexanecarboxylic acid, trans-4-Hydroxycinnamic acid (p-Coumaric acid), 3,3',4',5,5',7-Hexahydroxyflavylium chloride, Thiocytic Acid (Dihydrolipoic Acid, DHLA), 4,4',5,5',6,6'-Hexahydroxydiphenic acid 2,6,2',6'-dilactone (Ellagic acid), (−)-cis-3,3',4',5,7-Pentahydroxyflavane (Epi-Catechin or EC), 2-Methoxy-4-(2-propenyl) phenol, trans-4-Hydroxy-3-methoxycinnamic acid (Ferulic acid), 7-Hydroxy-3-(4'-methoxyphenyl)-4H-benzopyran-4-one, all-trans-Fucoxanthin, 3,4,5-Trihydroxybenzoic acid (Gallic acid), (2S,3R)-2-(3,4,5-Trihydroxyphenyl)-3,4-dihydro-1 (2H)-benzopyran-3,5,7-triol ((−)-Gallocatechin), Glutathione, 2-(3,4-Dihydroxyphenyl)ethanol, 3,4',5,7-Tetrahydroxyflavone (Kaempferol), (±)-1,2-Dithiolane-3-pentanoic acid, Luteolin, Lycopene, L-Lysine, Neochlorogenic acid, Oleic acid, trans-3,5,4'-Trihydroxystilbene (Resveratrol), 2-(3,4-dihydroxy phenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl]oxy methyl]oxan-2-yl]oxychromen-4-one, Rutin hydrate, Selenol-L-methionine, Thiourea, (+)-α-Tocopherol, Xanthophyll, Citric acid (CA), Gentisic acid (GA), Salicylic acid (SA), Erythorbic acid (EA), Phenol, Sodium bisulfite, Butylated hydroxy anisole, Butylated hydroxy toluene, Metabisulfite, Benzyl alcohol, Thymol, Lipoic acid (LA), Thioglycolic acid (TGA), 2,3 Dimercaptopropan-1-ol (BAL), Zinc, Selenium, Albumin, Ethanol, Mannitol, Sucrose, Melatonin, Ebselen, Pyruvic acid, Carboxy-PTIO, Trolox, Ebselen, Uric acid, Edaravone, Beta carotene, NADPH, Lycopene, Lutein, Catalase, Estrogen, Estradiol, Estriol, Ubiquinol, Copper, Quercetin, Cortisone, Taurine, (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl] 3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), (2R,3S)-2-(3,4,5-trihydroxyphenyl)-3,4-dihydro-2H-chromene-3,5,7-triol (Gallo-Catechin or GC), (−)-cis-2-(3,4,5-Trihydroxyphenyl)-3,4-dihydro-1(2H)-benzopyran-3,5,7-triol 3-gallate ((−)-Epigalocatechin-3-O-Gallate), 5-Aminolevulibic Acid hydrate, Ploysorbate 80, Garlic Acid, Sodium L-Ascorbate, Hyaluronic Acid, Dextran 60-90, Selenol, and LysaKare. or a combination thereof. Exemplary antioxidants of the present disclosure are further described in Table 1.

TABLE 1

| Exemplary Antioxidants | |
|---|---|
| N-Acetyl-L-cysteine | Benzyl alcohol |
| L-Ascorbic acid | Thymol |
| N-tert-Butyl-α-phenylnitrone | Lipoic acid (LA) |
| 3-(3,4-Dihydroxyphenyl)-2-propenoic acid (Caffeic Acid) | Thioglycolic acid (TGA) |
| β-Carotene, Provitamin A | 2,3 Dimercaptopropan-1-ol (BAL) |
| (2S,3R)-2-(3,4-Dihydroxyphenyl)-3,4-dihydro-1(2H)-benzopyran-3,5,7-triol 3-(3,4,5-trihydroxybenzoate ((-) Catechin gallate) (from green tea) | Zinc |

TABLE 1-continued

Exemplary Antioxidants

| | |
|---|---|
| 1,4,5-Trihydroxycyclohexanecarboxylic acid | Selenium |
| trans-4-Hydroxycinnamic acid (p-Coumaric acid) | Albumin |
| 3,3',4',5,5',7-Hexahydroxyflavylium chloride | Ethanol |
| Thiocytic Acid (Dihydrolipoic Acid, DHLA) | Mannitol |
| 4,4',5,5',6,6'-Hexahydroxydiphenic acid 2,6,2',6'-dilactone (Ellagic acid) | Sucrose |
| (−)-cis-3,3',4',5,7-Pentahydroxyflavane (from green tea) | Melatonin |
| 2-Methoxy-4-(2-propenyl) phenol | Ebselen |
| trans-4-Hydroxy-3-methoxycinnamic acid (Ferulic acid) | Pyruvic acid |
| 7-Hydroxy-3-(4'-methoxyphenyl)-4H-benzopyran-4-one | 2-(4-Carboxyphenyl)-4,5-dihydro-4,4,5,5-tetramethyl-1H-imidazol-1-yloxy-3-oxide potassium salt, 2-(4-Carboxyphenyl)-4,4,5,5-tetramethylimidazoline-1-oxyl-3-oxide (Carboxy-PTIO) Salt |
| all-trans-Fucoxanthin | Trolox |
| 3,4,5-Trihydroxybenzoic acid (Gallic acid) | Ebselen |
| (2S,3R)-2-(3,4,5-Trihydroxyphenyl)-3,4-dihydro-1(2H)-benzopyran-3,5,7-triol ((−)-Gallocatechin)(from green tea) | Uric acid |
| Glutathione | Edaravone |
| 2-(3,4-Dihydroxyphenyl)ethanol | Beta carotene |
| 3,4',5,7-Tetrahydroxyflavone (Kaempferol) | Nicotinamide adenine dinucleotide phosphate (NADPH) |
| (±)-1,2-Dithiolane-3-pentanoic acid | Lycopene |
| Luteolin | Lutein |
| Lycopene (from tomato) | Catalase |
| Neochlorogenic acid | Estrogen |
| Oleic acid | Estradiol |
| trans-3,5,4'-Trihydroxystilbene (Resveratrol) | Estriol |
| 2-(3,4-dihydroxyphenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl]oxymethyl]oxan-2-yl]oxychromen-4-one;hydrateRutin hydrate | Ubiquinol |
| L-methionine | Copper |
| Thiourea | Quercetin |
| (+)-α-Tocopherol | Cortisone |
| Xanthophyll | 2,3-dimercaptosuccinic acid (DMSA) or monisoamyl derivative (MiADMSA) |
| Natural L-amino acids: Alanine, Arginine, Asparagine, Aspartic acid, Cysteine, Glutamine, Glutamic acid, Glycine, Histidine, Isoleucine, Lysine, Methionine, Phenylalanine, Proline, Serine, Threonine, Tryptophan, Tyrosine, Valine, and their derivatives | Taurine |
| Citric acid (CA) | Dextran 40 |
| Gentisic acid (GA) | Dextran 70 |
| Salicylic acid (SA) | PEG 3350 |
| Erythorbic acid (EA) | PEG 4000 |
| Phenol | Polygeline |
| Sodium bisulfite | Gelofusine |
| Butylated hydroxy anisole | PLENVU (polyethylene glycol 3350, sodium sulfate, ascorbic acid, sodium chloride and potassium chloride) |
| Butylated hydroxy toluene | Cyclodextrins |
| Glutathione | Metabisulfite |
| PEG 400 | PEG 1000 |
| PEG (e.g., PEG having a number average molecular weight of about 200-8000) | (−)-Epigallocatechin-3-O-Gallate |
| 5-Aminolevulibic Acid hydrate | Ploysorbate 80 |
| Garlic Acid | Sodium L-Ascorbate |
| Hyaluronic Acid | Dextran 60-90 |
| Selenol | LysaKare |

In some embodiments, the radiolysis stabilizers comprise a salt, an ester, an amide, an enantiomer, or an acetylation derivative of a compound of Table 1, or a combination thereof.

The radiolysis stabilizers can comprise a vitamin or a derivative thereof. The radiolysis stabilizers can comprise one or more vitamins or derivatives thereof. The vitamin or a derivative thereof can be L-Ascorbic acid, β-Carotene, Provitamin A, (+)-α-Tocopherol, Erythorbic acid (EA), Trolox, or Lutein.

The radiolysis stabilizers can comprise a fatty acid or a derivative thereof. The radiolysis stabilizers can comprise one or more lipids. The lipids can be fatty acids or derivatives thereof. In some embodiments, the fatty acid is a saturated fatty acid. In some embodiments, the fatty acid is an unsaturated fatty acid. The fatty acid can comprise a mono-unsaturated fatty acid. The fatty acid can comprise a poly-unsaturated fatty acid. The fatty acid can comprise a trans-fat. The fatty acid can comprise a $C_3$ to $C_{40}$ fatty acid, $C_6$ to $C_{30}$ fatty acid, $C_6$ to $C_{20}$ fatty acid, and $C_6$ to $C_{10}$ fatty acid. In some embodiments, the fatty acid is a $C_6$ to $C_{30}$ fatty acid. The fatty acid can comprise a saturated or unsaturated $C_6$ to $C_{30}$ fatty acid. The fatty acid can comprise a saturated or unsaturated $C_{19}$ to $C_{20}$ fatty acid. The fatty acid can comprise a saturated or unsaturated $C_{12}$ to $C_{26}$ fatty acid. The fatty acid can comprise oleic acid, Myristoleic acid, Palmitoleic acid, Sapienic acid, Elaidic acid, Vaccenic acid, or Linoleic acid, α-Linolenic acid, or a combination thereof.

In some embodiments, the radiolysis stabilizers comprise a lipid that is a steroid or a derivative thereof. The steroid can be a corticosteroid, such as Estrogen, Estradiol, Estriol, or Cortisone. The steroid can have four carbon rings. The steroid can be Estrogen, Estradiol, Estriol, or Cortisone.

The radiolysis stabilizers can comprise a volume expander. In some embodiments, the volume expander can expand the volume of a liquid, such as human blood volume. The volume expander can serve as an absorptive radio-protectant. The volume expander can mimic human serum albumin. The volume expander can comprise human albumin. The volume expander can comprise polymers, such as polyethylene glycol (PEG), a glucose polymer, or polymer mixtures. A glucose polymer can be a Dextran or a saccharide, such as an oligosaccharide. The glucose polymer can have a number average molecular weight from 1 kDa to 40,000,000 kDa, from 5 kDa to 1,000,000 kDa, from 10KDa to 500,000 kDa, from 15 kDa to 1,000 kDa, from 20 kDa to 100 kDa, or from 30 kDa to 50 kDa. The glucose polymer can have an average molecular of about 20-60 kDa, e.g., about 40 kDa. The glucose polymer can be linear or cyclic. The cyclic form glucose polymer can be cyclic oligosaccharides, such as cyclodextrins. The cyclodextrins can comprise a macrocyclic ring of glucose subunits joined by α-1,4 glycosidic bonds. The macrocyclic ring can comprise 6 to 8 glucose subunits, such as, α (alpha)-cyclodextrin, β (beta)-cyclodextrin, and γ (gamma)-cyclodextrin. The polymer mixture, such as an artificial colloid, can comprise the glucose polymer from 0.001 wt % to 80% wt %. The polymer mixture can comprise the glucose polymer from 0.1 wt % to 50% wt %. The polymer mixture can comprise the glucose polymer from 1 wt % to 20% wt %. The polymer mixture can be a mixture comprise the glucose polymer from 5 wt % to 15% wt %. The polymer mixture can comprise from 0.1% wt to 15% wt glucose polymer, or from 1% wt to 10% glucose polymer. The Dextran can be Dextran 40 and Dextran 70. The Dextran can have a number average molecular weight of about 5 to 100 kDa. The Dextran can have a number average molecular weight of about 40 to 70 kDa. The Dextran can have a number average molecular weight of 40, 60, or 70 kDa. Dextran 40 can be provided as a Dextran 40 mixture, such as a 10% Dextran 40 solution in 0.9% sodium chloride in an infusion bag. The Dextran 40 mixture can comprise from 0.1% wt to 15% wt Dextran 40, or from 1% wt to 10% Dextran 40. The Dextran 40 mixture can have a total osmolality from 300 mOsmol/L to 450 mOsmol/L. The Dextran 40 mixture can have a total osmolality from 350 mOsmol/L to 420 mOsmol/L. The Dextran 40 mixture can have a total osmolality from 380 mOsmol/L to 400 mOsmol/L. The Dextran 40 mixture can have a total osmolality of 390 mOsmol/L. The polymer can be a Polyethylene glycol (PEG), such as PEG 4000, PEG 3350. In some embodiments, the PEG has a number average molecular weight of about 200 to 20,000, 1000 to 10,000, 2000 to 8000, 3000 to about 5000, or 3000 to 4000. The polymer mixture can comprise PEG, such as PLENVU, a combination of PEG 3350, sodium ascorbate, sodium sulfate, ascorbic acid, sodium chloride and potassium chloride. The polymer can be a gelatin or a modified gelatin, such as polygeline and succinylated gelatin. The polygeline can have a number average molecular weight from 5 kDa to 50 kDa, from 10 kDa to 45 kDa, from 20KDa to 50 kDa, from 30 kDa to 40 kDa. The polygeline can have an average molecular of 35 kDa. The polymer mixture can be a mixture containing polygeline. A mixture comprising polygeline, such as Haemaccel, can also contain calcium chloride, potassium chloride and or sodium chloride. The polymer mixture can comprise modified fluid gelatin, such as succinylated gelatin. The polymer mixture can be a solution, such as Gelofusine. Gelofusine can comprise 4% w/v succinylated gelatin.

The radiolysis stabilizers can comprise a carbohydrate or a derivative thereof. The carbohydrate can be a saccharide. The saccharide can be a monosaccharide. The saccharide can be a disaccharide, an oligosaccharide, or a polysaccharide. Exemplary disaccharides include a mannitol and a sucrose. The polysaccharide can be a Dextran such as Dextran 40 and Dextran 70. The Dextran can have a molecular weight of about 10-200, 20-100, 30-50, or 40-70 kDa. The polysaccharide can have a number average molecular weight from 5 kDa to 1,000,000 kDa, from 10KDa to 500,000 kDa, from 15 kDa to 1,000 kDa, from 20 kDa to 100 kDa, or from 30 kDa to 80 kDa. The oligosaccharide can be a cyclic oligosaccharide, such as cyclodextrin. The cyclodextrin can comprise a macrocyclic ring of glucose subunits joined by α-1,4 glycosidic bonds. The macrocyclic ring can comprise 6 to 8 glucose subunits, such as, α (alpha)-cyclodextrin, β (beta)-cyclodextrin, and γ (gamma)-cyclodextrin. The polysaccharide can be a Dextran. The carbohydrate can be Mannitol, Sucrose, Dextran (e.g., Dextran 40, Dextran 70), or Cyclodextrins (α-cyclodextrin, O-cyclodextrin, or γ-cyclodextrin), such as 2-Hydroxypropyl-O-cyclodextrin (HP-β-CD) or sulfobutylether-O-Cyclodextrin (SEB-β-CD).

Free Metal Chelator

The one or more stabilizing agents can comprise a free metal chelator. The one or more stabilizing agents can comprise two or more free metal chelators. In some embodiments, the free metal chelator is not attached to the targeting ligand. The one or more stabilizing agents can comprise a first and a second free metal chelator. In some embodiments, the molar ratio of the first and the second free metal chelator is from 1:100,000 to 100,000:1, from 1:1,000 to 1,000:1, from 1:100 to 100:1, from 1:20 to 20:1, from 1:10 to 10:1, and from 1:5 to 5:1. In some embodiments, the molar ratio of the first and the second free metal chelator is from 1:5 to 5:1. The free metal chelator can be present in the radiopharmaceutical composition at about 0.001 wt % to about 10 wt %. The free metal chelator can be present in the radiopharmaceutical composition at about 0.0001 wt % to about 20 wt %, 0.001 wt % to about 10 wt %, 0.01 wt % to about 5 wt %, about 0.05 wt % to about 2 wt %, or about 0.1 wt % to about 1 wt %. The free metal chelator can be present in the radiopharmaceutical composition at about 0.01 wt % to about 5 wt %. The free metal chelator can be present in the radiopharmaceutical composition at about 0.05 wt % to about 2 wt %. The free metal chelator can be present in the radiopharmaceutical composition at about 0.1 wt % to about 1 wt %. The free metal chelator can also be present in the radiopharmaceutical composition at a concentration of from 0.0001 to 5,000 mg/mL. The free metal chelator can also be present in the radiopharmaceutical composition at a concentration of from 0.1 to 500 mg/mL. The free metal chelator can also be present in the radiopharmaceutical composition at a concentration of from 0.01 to 50 mg/mL. The free metal chelator can also be present in the radiopharmaceutical composition at a concentration of from 0.1 to 5 mg/mL. The free metal chelator can also be present in the radiopharmaceutical composition at a concentration of from 0.5 to 2 mg/mL.

The free metal chelator can be a linear or cyclic. The linear free metal chelator, such as Ethylenediaminetetraacetic acid (EDTA) and Diethylenetriaminepentaacetic acid (DTPA), can be a heavy metal poisoning antidote or a free heavy metal scavenger. The DTPA can be present in the radiopharmaceutical composition at a concentration from 0.001 mg/mL to 2.5 mg/mL, from 0.01 mg/mL to 5 mg/mL, from 0.02 mg/mL to 3 mg/mL, from 0.04 mg/mL to 1 mg/mL, or from 0.05 mg/mL to 0.1 mg/mL. In some embodiments, the free metal chelator (such as DTPA) is present in the radiopharmaceutical composition at a concentration of about 0.05 mg/mL. In some embodiments, the free metal chelator (such as DTPA) is present in the radiopharmaceutical composition at a concentration of about 0.01 to 0.1 mg/mL. In some embodiments, the free metal chelator (such as DTPA) is present in the radiopharmaceutical composition at a concentration of about 0.02 to 0.07 mg/mL. In some embodiments, the free metal chelator is DTPA and is present in the radiopharmaceutical composition at a concentration from 0.01 mg/mL to 5 mL/mL. In some embodiments, the free metal chelator is DTPA and is present in the radiopharmaceutical composition at a concentration from 0.02 mg/mL to 2.5 mg/mL. In some embodiments, the free metal chelator is DTPA and is present in the radiopharmaceutical composition at a concentration from 0.04 mg/mL to 1 mg/mL. In some embodiments, the free metal chelator is DTPA and is present in the radiopharmaceutical composition at a concentration from 0.01 to 0.25 mg/mL. In some embodiments, the free metal chelator is DTPA and is present in the radiopharmaceutical composition at a concentration from 0.02 to 0.125 mg/mL. In some embodiments, the free metal chelator is DTPA and is present in the radiopharmaceutical composition at a concentration from 0.04 to 0.06 mg/mL. In some embodiments, the free metal chelator is DTPA and is present in the radiopharmaceutical composition at a concentration of 0.05 mg/mL. The free metal chelator can also prevent potential hepatoxicity caused by free radioactive metal ion when administered into a subject, such as a human subject. The cyclic free metal chelator can be a macrocyclic free metal chelator, such as 1,4,7-Triazacyclononane-1,4,7-triacetic acid (NOTA) 2,2',2'',2'''-(1,4,7,10-Tetraazacyclododecane-1,4,7,10-tetrayl)tetraacetic acid (DOTA). The macrocyclic free metal chelator can have strong chelation ability and used in lower concentration. The free metal chelator can comprise Ethylenediaminetetraacetic acid (EDTA), Diethylenetriaminepentaacetic acid (DTPA), 2-S-(4-Isothiocyanatobenzyl)-1,4,7-triazacyclononane-1,4,7-triacetic acid (NOTA), Triethylenetetramine (TETA), 1, 4, 7, 10, 13-pentaazacyclopentadecane-N, N', N'', N''', N''''-pentaacetic acid (PEPA), TETPA, 2,2',2''-(10-(2,6-dioxotetrahydro-2H-pyran-3-yl)-1,4,7,10-tetraazacyclododecane-1,4,7-triyl)triacetic acid (DOTA-GA), 1,4,7,10-Tetraazacyclododecane-1,4,7,10-tetra(methylene phosphonic acid (DOTP), Deferoxamine (DFO), N, N-bis (2-hydroxybenzyl)ethylenediamine-N,N-diacetic acid (HBED), 1,4,7,10-Tetraazacyclododecane-1,4,7,10-tetra (methylene phosphonic acid) (DOTP), 6,6'-((1,4,10,13-tetraoxa-7,16-diazacyclooctadecane-7,16-diyl)bis(methylene)) dipicolinic acid (Macropa), Meso-2,3-dimercaptosuccinic acid (DMSA), Dimercaptopropane sulfonate (DMPS), Dihydrolipoic acid (DHLA), Lipoic acid (LA), Thioglycolic acid (TGA), 2,3 Dimercaptopropan-1-ol (BAL), or a combination thereof. The free metal chelator can comprise EDTA, DTPA, or Macropa. Exemplary free metal chelators of the present disclosure are further described in Table 2.

TABLE 2

Exemplary Free Metal Chelators

| | |
|---|---|
| Ethylenediaminetetraacetic acid (EDTA) | N,N-bis(2-hydroxybenzyl)ethylenediamine-N,N-diacetic acid (HBED) |
| Diethylenetriaminepentaacetic acid (DTPA) | 1,4,7,10-Tetraazacyclododecane-1,4,7,10-tetra(methylene phosphonic acid) (DOTP) |
| 1,4,7-Triazacyclononane-1,4,7-triacetic acid (NOTA) | 6,6'-((1,4,10,13-tetraoxa-7,16-diazacyclooctadecane-7,16-diyl)bis(methylene))dipicolinic acid (Macropa) |
| 2,2',2'',2'''-(1,4,7,10-Tetraazacyclododecane-1,4,7,10-tetrayl)tetraacetic acid (DOTA) | Meso-2,3-dimercaptosuccinic acid (DMSA) |
| Triethylenetetramine (TETA) | Dimercaptopropane sulfonate (DMPS) |
| 1,4,7,10,13-pentaazacyclopentadecane-N,N',N'',N''',N''''-pentaacetic acid (PEPA) | Dihydrolipoic acid (DHLA) |
| TETPA | Lipoic acid (LA) |
| 2,2',2''-(10-(2,6-dioxotetrahydro-2H-pyran-3-yl)-1,4,7,10-tetraazacyclododecane-1,4,7-triyl)triacetic acid (DOTA-GA) | Thioglycolic acid (TGA) |
| 1,4,7,10-Tetraazacyclododecane-1,4,7,10-tetra(methylene phosphonic acid (DOTP) | 2,3 Dimercaptopropan-1-ol (BAL) |
| Deferoxamine (DFO) | | pH Stabilizer

In some embodiments, stabilities of the described radiopharmaceutical compositions can vary at different pH values. When pH fails out of certain range, leakage of the radioactive metal may also affect radiochemical purity of the formulated dose and shorten its shelf-life. Accordingly, in some embodiments, the one or more stabilizing agents can comprise pH stabling buffers in addition to the radiolysis protectants and/or free metal chelating agents. Exemplary pH stabilizers include sodium acetate/acetic acid and sodium L-ascorbate/L-ascorbic acid aqueous buffer.

The one or more stabilizing agents can comprise one or more pH stabilizers. The one or more pH stabilizers can function as a pH buffer. The one or more pH stabilizer can function as a pH buffer. The one or more pH stabilizer can comprise an organic acid. The organic acid can comprise an acetic acid, fumaric acid, ascorbic acid, propionic acid, benzene sulfonic acid, carbonic acid, citrate acid, aspartic acid, maleic acid, methane sulfonic acid, or tartaric acid. The one or more pH stabilizer can comprise an inorganic acid, which can further comprise a hydrobromic acid, hydrochloric acid, phosphoric acid, boric acid, or sulfuric acid. The one or more pH stabilizer can comprise a base. The base can comprise tromethamine (Tris), ammonium hydroxide, diethanolamine, or sodium hydroxide. The one or more pH stabilizers can comprise an amino acid or a salt thereof. The one or more pH stabilizers can comprise glycine, lysine, arginine, histidine, or a salt thereof. The one or more pH stabilizers can comprise an alkaline salt. The alkaline salt can comprise sodium acetate, sodium ascorbate, sodium benzoate, sodium bicarbonate, sodium carbonate, tribasic sodium phosphate acid, dibasic sodium phosphate acid, monobasic sodium phosphate acid, sodium tartrate, sodium lactate, sodium succinate, or disodium succinate. The sodium ascorbate be present in the radiopharmaceutical composition at a concentration of from about 50 mM to 200 mM. The one or more pH stabilizers can comprise an acid salt. The acid salt can be ammonium sulfate. The one or more pH stabilizers can comprise Sodium acetate, Sodium ascorbate, Ascorbic acid, Acetic acid, Fumaric acid propionic acid, ascorbic acid, ammonium sulfate, ammonium hydroxide, arginine, aspartic acid, benzene sulfonic acid, sodium benzoate, sodium bicarbonate, boric acid, sodium carbonate, carbonic acid, diethanolamine, citrate acid, hydrobromic acid, glycine, histidine, sodium lactate, (1)-lysine, maleic acid, methane sulfonic acid, phosphate acid, monobasic sodium phosphate acid, tribasic sodium phosphate acid, dibasic sodium phosphate acid, sodium hydroxide, sodium/disodium succinate, sulfuric acid, sodium tartrate, tartaric acid, tromethamine (tris), or a combination thereof. Exemplary pH stabilizers of the present disclosure are further described in Table 3.

TABLE 3

Exemplary pH Stabilizers

| | |
|---|---|
| Sodium acetate | Citrate acid |
| Acetic acid | Hydrobromic acid |
| Sodium L-ascorbate | Glycine |
| L-Ascorbic acid | Histidine |
| Fumaric acid | Sodium lactate |
| Propionic acid | (L)-Lysine |
| Ammonium sulfate | Maleic acid |
| Ammonium hydroxide | Methane sulfonic acid |
| Arginine | Phosphate acid |
| Aspartic acid | Monobasic sodium phosphate acid |
| Benzene sulfonic acid | Tribasic sodium phosphate acid |
| Sodium benzoate | Dibasic sodium phosphate acid |
| Sodium bicarbonate | Sodium hydroxide |
| Boric acid | Sodium/disodium succinate |
| Sodium carbonate, | Sulfuric acid |
| Carbon dioxide | Sodium tartrate |
| Diethanolamine | Tartaric acid |
| Tromethamine (Tris) | |

In some embodiments, the pH stabilizers can reduce the pH changes and maintain the radiopharmaceutical purity, which reduces the decomposition of the conjugate and thereby extending the shelf-life of the radiopharmaceutical compositions described herein. The one or more stabilizing agents can comprise a pH stabilizer. The one or more stabilizing agents can comprise two or more pH stabilizers. The one or more stabilizing agents can comprise a first and a second pH stabilizers. In some embodiments, the molar ratio of the first and the second pH stabilizer is from 1:100,000 to 100,000:1, from 1:1,000 to 1,000:1, from 1:100 to 100:1, from 1:20 to 20:1, from 1:10 to 10:1, and from 1:5 to 5:1. In some embodiments, the molar ratio of the first and the second pH stabilizer is from 1:5 to 5:1. The pH stabilizer can be present in the radiopharmaceutical composition at about 0.001 wt % to about 10 wt %. The pH stabilizer can be present in the radiopharmaceutical composition at about 0.0001 wt % to about 20 wt %, 0.001 wt % to about 10 wt %, 0.01 wt % to about 5 wt %, about 0.05 wt % to about 2 wt %, or about 0.1 wt % to about 1 wt %. The pH stabilizer can be present in the radiopharmaceutical composition at about 0.01 wt % to about 5 wt %. The pH stabilizer can be present in the radiopharmaceutical composition at about 0.05 wt % to about 2 wt %. The pH stabilizer can be present in the radiopharmaceutical composition at about 0.1 wt % to about 1 wt %. The pH stabilizer can also be present in the radiopharmaceutical composition at a concentration of from about 1 µM, 10 µM, 0.1 mM, 1 mM, 5 mM, 10 mM, 25 mM, 50 mM, or 75 mM to about 80 mM, 100 mM, 125 mM, 150 mM, 175 mM, 200 mM, 250 mM, 500 mM, 1 M, 2 M, 3 M, 4 M, or 5 M. The pH stabilizer can be present in the radiopharmaceutical composition at a concentration of from about 1 µM to 5 M. The pH stabilizer can be present in the radiopharmaceutical composition at a concentration of from about 10 µM to 1 M. The pH stabilizer can be present in the radiopharmaceutical composition at a concentration of from about 0.1 mM to 500 mM. The pH stabilizer can be present in the radiopharmaceutical composition at a concentration of from about 10 mM to 500 mM. The pH stabilizer can be present in the radiopharmaceutical composition at a concentration of from about 50 mM to 250 mM. The pH stabilizer can be present in the radiopharmaceutical composition at a concentration of from about 80 mM to 200 mM. The pH stabilizer can be present in the radiopharmaceutical composition at a concentration of from about 80 mM to 120 mM. The pH stabilizer can also be present in the radiopharmaceutical composition at a concentration of from 0.0001 to 5,000 mg/mL. The pH stabilizer can also be present in the radiopharmaceutical composition at a concentration of from 0.1 to 500 mg/mL. The pH stabilizer can also be present in the radiopharmaceutical composition at a concentration of from 0.01 to 50 mg/mL. The pH stabilizer can also be present in the radiopharmaceutical composition at a concentration of from 0.1 to 5 mg/mL. The pH stabilizer can also be present in the radiopharmaceutical composition at a concentration of from 0.5 to 2 mg/mL. In some embodiments, the pH stabilizer comprises sodium L-ascorbate. In some embodiments, the pH stabilizer comprises sodium ascorbate (e.g., sodium L-ascorbate) and is present in the radiopharmaceutical composition at a concentration of 1 mM to 10 M. In some embodiments, the pH stabilizer comprises sodium L-ascorbate and is present in the radiopharmaceutical composition at a concentration of 10 mM to 1 M. In some embodiments, the pH stabilizer comprises sodium L-ascorbate and is present in the radiopharmaceutical composition at a concentration of 20 mM to 500 mM. In some embodiments, the pH stabilizer comprises sodium L-ascorbate and is present in the radiopharmaceutical composition at a concentration of 40 mM to 250 mM. In some embodiments, the pH stabilizer comprises sodium L-ascorbate and is present in the radiopharmaceutical composition at a concentration of 80 mM to 125 mM. In some embodiments, the pH stabilizer comprises sodium L-ascorbate and is present in the radiopharmaceutical composition at a concentration of 90 mM to 110 mM. In some embodiments, the pH stabilizer comprises sodium L-ascorbate and is present in the radiopharmaceutical composition at a concentration of 100 mM.

In some embodiments, the sodium ascorbate is present in the radiopharmaceutical composition at a concentration of 1 mM to 10 M. In some embodiments, the sodium ascorbate is present in the radiopharmaceutical composition at a concentration of 10 mM to 1 M. In some embodiments, the sodium ascorbate is present in the radiopharmaceutical composition at a concentration of 20 mM to 500 mM. In some embodiments, the sodium ascorbate is present in the radiopharmaceutical composition at a concentration of 40 mM to 250 mM. In some embodiments, the sodium ascorbate is present in the radiopharmaceutical composition at a concentration of 80 mM to 125 mM. In some embodiments, the sodium ascorbate is present in the radiopharmaceutical composition at a concentration of 90 mM to 110 mM. In some embodiments, the sodium ascorbate is present in the radiopharmaceutical composition at a concentration of about 100 mM. In some embodiments, the sodium ascorbate is present in the radiopharmaceutical composition at a concentration of about 1 mg/mL to 100 mg/mL. In some embodiments, the sodium ascorbate is present in the radiopharmaceutical composition at a concentration of about 5 mg/mL to 50 mg/mL. In some embodiments, the sodium ascorbate is present in the radiopharmaceutical composition at a concentration of about 10 mg/mL to 30 mg/mL. In some embodiments, the sodium ascorbate is present in the radiopharmaceutical composition at a concentration of 18.5±4.63 mg/mL. In some embodiments, the sodium ascorbate is present in the radiopharmaceutical composition at a concentration of 18.5±5 mg/mL. In some embodiments, the sodium ascorbate is present in the radiopharmaceutical composition at a concentration of 18.5±10 mg/mL. In some embodiments, the sodium ascorbate is present in the radiopharmaceutical composition at a concentration of about 18.5 mg/mL. In some embodiments, the sodium ascorbate is sodium L-ascorbate.

Radiopharmaceutical compositions described herein can have a suitable pH value. The one or more pH stabilizers can be configured to maintain a pH of the radiopharmaceutical composition at about 3 to about 9, about 4 to about 8, or about 5 to about 7. The pH of the radiopharmaceutical composition can be within a range of about 3 to about 9. The pH of the radiopharmaceutical composition can be within a range of about 4 to about 8. The pH of the radiopharmaceutical composition can be within a range of about 5 to about 7. In some embodiments, the pH of the radiopharmaceutical composition is from about 4.0 to about 9.0, from about 4.5 to about 8.5, from about 5.0 to about 8.0, from about 5.5 to about 7.75, from about 6.0 to about 7.5, from about 6.5 to about 7.25, from 6.75 to about 7.25. The pH of the radiopharmaceutical composition can be about 4.0 to about 9.0. The pH of the radiopharmaceutical composition can be about 4.5 to about 8.5. The pH of the radiopharmaceutical composition can be about 5.0 to about 8.0. The pH of the radiopharmaceutical composition can be about 5.0 to about 7.0. The pH of the radiopharmaceutical composition can be about 5.5 to about 6.5. The pH of the radiopharmaceutical composition can be about 5.5 to about 6. The pH of the radiopharmaceutical composition can be about 5.6 to about 5.8. The pH of the radiopharmaceutical composition can be about 5.75 to about 5.85. The pH of the radiopharmaceutical composition can be about 5.5 to about 7.75. The pH of the radiopharmaceutical composition can be about 6.0 to about 7.5. The pH of the radiopharmaceutical composition can be about 6.5 to about 7.25. The pH of the radiopharmaceutical composition can be about 6.75 to about 7.25. In some embodiments, the pH of the radiopharmaceutical composition is about 7. In some embodiments, the pH of the radiopharmaceutical composition is about 5.5. In some embodiments, the pH of the radiopharmaceutical composition is about 5.6. In some embodiments, the pH of the radiopharmaceutical composition is about 5.7. In some embodiments, the pH of the radiopharmaceutical composition is about 5.8. In some embodiments, the pH of the radiopharmaceutical composition is about 5.9. In some embodiments, the pH of the radiopharmaceutical composition is about 6. In some embodiments, the pH of the radiopharmaceutical composition is about 6.1. In some embodiments, the pH of the radiopharmaceutical composition is about 6.2.

The radiopharmaceutical composition can comprise one or more radiolysis stabilizers, one or more free metal chelators, and/or one or more pH stabilizers. The radiopharmaceutical composition can comprise one or more radiolysis stabilizers. The radiopharmaceutical composition can comprise one or more free metal chelators. The radiopharmaceutical composition can comprise one or more pH stabilizers.

In some embodiments, a radiopharmaceutical composition described herein comprises: (a) a conjugate (e.g., $^{225}$Ac-DOTA-TATE or $^{225}$Ac-DOTA-TOC), wherein the conjugate is present in the radiopharmaceutical composition at a concentration equivalent to about 10 to 45 mCi/L (e.g., 30 mCi/L); (b) a pH stabilizer, wherein the pH stabilizer is present in the radiopharmaceutical composition at a concentration of about 80 to about 120 mM; (c) optionally a radiolysis stabilizer, wherein the radiolysis stabilizer is present in the radiopharmaceutical composition at concentration of about 1 wt % to about 10 wt %; (d) a free metal chelator, therein the free metal chelator is present in the radiopharmaceutical composition at concentration of about 0.01 mg/mL to about 1 mg/mL; and (e) an aqueous vehicle. In some embodiments, the conjugate is present in the radiopharmaceutical composition at a concentration equivalent to about 15 to 45 mCi/L. In some embodiments, the conjugate is present in the radiopharmaceutical composition at a concentration equivalent to about 10 to 35 mCi/L. In some embodiments, the conjugate is present in the radiopharmaceutical composition at a concentration equivalent to about 10 to 25 mCi/L. In some embodiments, the conjugate is present in the radiopharmaceutical composition at a concentration equivalent to about 12 to 23 mCi/L. In some embodiments, a radiopharmaceutical composition described herein comprises: (a) a conjugate (e.g., $^{225}$Ac-DOTA-TATE or $^{225}$Ac-DOTA-TOC), wherein the conjugate is present in the radiopharmaceutical composition at a concentration equivalent to about 10 to 45 mCi/L; (b) a pH stabilizer, wherein the pH stabilizer is sodium L-ascorbate and is present in the radiopharmaceutical composition at a concentration of about 80 to about 120 mM; (c) optionally a radiolysis stabilizer, wherein the radiolysis stabilizer is Dextran 40 and is present in the radiopharmaceutical composition at a concentration of about 1 wt % to about 10 wt %; (d) a free metal chelator, wherein the free metal chelator is DTPA and is present in the radiopharmaceutical composition at a concentration of about 0.01 mg/mL to about 1 mg/mL; and (e) an aqueous vehicle, wherein the aqueous vehicle is saline solution. In some embodiments, the conjugate is present in the radiopharmaceutical composition at a concentration equivalent to about 15 to 45 mCi/L. In some embodiments, the radiopharmaceutical composition comprises (a) the conjugate, wherein the conjugate is present in the radiopharmaceutical composition at a concentration equivalent to about 25 to 35 mCi/L; (b) a pH stabilizer, wherein the pH stabilizer is sodium L-ascorbate and is present in the radiopharmaceutical composition at a concentration of about 90-110 mM; (c) a radiolysis stabilizer, wherein the radiolysis stabilizer is Dextran 40 and is present in the radiopharmaceutical composition at a concentration of about 4-6 wt %; (d) a free metal chelator, wherein the free metal chelator is DTPA and is present in the radiopharmaceutical composition at a concentration of about 0.01-0.03 mg/mL; and (e) an aqueous vehicle, wherein the aqueous vehicle is sodium chloride saline solution at a concentration of about 0.9% w/w. In some embodiments, the radiopharmaceutical composition comprises (a) the conjugate, wherein the conjugate is present in the radiopharmaceutical composition at a concentration equivalent to about 10 to 25 mCi/L; (b) a pH stabilizer, wherein the pH stabilizer is sodium L-ascorbate and is present in the radiopharmaceutical composition at a concentration of about 90-110 mM; (c) a radiolysis stabilizer, wherein the radiolysis stabilizer is Dextran 40 and is present in the radiopharmaceutical composition at a concentration of about 4-6 wt %; (d) a free metal chelator, wherein the free metal chelator is DTPA and is present in the radiopharmaceutical composition at a concentration of about 0.01-0.03 mg/mL; and (e) an aqueous vehicle, wherein the aqueous vehicle is sodium chloride saline solution at a concentration of about 0.9% w/w. In some embodiments, the radiopharmaceutical composition comprises (a) the conjugate, wherein the conjugate is present in the radiopharmaceutical composition at a concentration equivalent to about 25 to 35 mCi/L; (b) a pH stabilizer, wherein the pH stabilizer is sodium L-ascorbate and is present in the radiopharmaceutical composition at a concentration of about 90-110 mM; (c) a free metal chelator, wherein the free metal chelator is DTPA and is present in the radiopharmaceutical composition at a concentration of about 0.04-0.06 mg/mL; and (d) an aqueous vehicle, wherein the aqueous vehicle is sodium chloride saline solution at a concentration of about 0.9% w/w. In some embodiments, the radiopharmaceutical composition comprises (a) the conjugate, wherein the conjugate is present in the radiopharmaceutical composition at a concentration equivalent to about 10 to 25 mCi/L; (b) a pH stabilizer, wherein the pH stabilizer is sodium L-ascorbate and is present in the radiopharmaceutical composition at a concentration of about 90-110 mM; (c) a free metal chelator, wherein the free metal chelator is DTPA and is present in the radiopharmaceutical composition at a concentration of about 0.04-0.06 mg/mL; and (d) an aqueous vehicle, wherein the aqueous vehicle is sodium chloride saline solution at a concentration of about 0.9% w/w.

Additional Excipients

Radiopharmaceutical compositions described herein can comprise additional excipients. In some embodiments, the additional excipients include excipients suitable for a formulation configured for intravenous administration.

In some embodiments, the radiopharmaceutical composition described herein comprises a surfactant. "Surfactants" can be defined as surface-active amphiphilic compounds such as block co-polymers. They can be referred to as wetting agents. Non-limiting examples of surfactants include a poloxamer (e.g., poloxamer 188), sodium lauryl sulfate, Desoxycholate sodium, Egg yolk phospholipid, Gelatin, Hydrolyzed Lecithin, Polyoxyethylated fatty acid, Polysorbate 80 (Tween 80), Polysorbate 20 (Tween 20), PEG 40 castor oil (polyoxyl 40 castor oil, castor oil POE-40, Croduret 40, polyoxyethylene 40 castor oil, Protachem CA-40), PEG 60 castor oil (Cremophor RH 60, hydrogenated castor oil POE-60, Protachem CAH-60), Poloxamer 188 (Pluronic F68), Povidone (Polyvinyl pyrrolidone, Crosspovidone), Sodium dodecyl sulfate (Na lauryl sulfate), Aluminum monostearate, Sorbitol, and Triton X-100 (Octoxynol-9).

The surfactant used in the present disclosure can comprise a non-ionic surfactant. A non-ionic surfactant has no charged groups in its head. Exemplary nonionic surfactants include, without limitation, fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), and polyethoxylated tallow amine (POEA). In some embodiments, the surfactant is a non-ionic surfactant that comprises polyethylene glycol. In some embodiments, the surfactant is a block copolymer of polyethylene glycol and polypropylene glycol.

In some embodiments, the non-ionic surfactant has a number average molecular weight of from about from about 1000 to about 100,000 Da, 2000 to about 20,000 Da, from about 4000 to about 15,000 Da, from about 6000 to about 12,000 Da, or from about 7000 to about 10,000 Da. In some embodiments, the non-ionic surfactant has a number average molecular weight of from about 7000 to about 10,000 Da. In some embodiments, the non-ionic surfactant has an ethylene glycol content of from about 30 wt % to about 99 wt %, from about 50 wt % to about 95 wt %, from about 60 wt % to about 95 wt %, from about 75 wt % to about 90 wt %, or from about 80 wt % to about 85 wt %. In some embodiments, the non-ionic surfactant has an ethylene glycol content of from about 80 wt % to about 85 wt %.

The surfactant used in the present disclosure can comprise a cationic surfactant. Cationic surfactants include pH-dependent primary, secondary, or tertiary amines such as octenidine dihydrochloride; and permanently charged quaternary ammonium salts such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB).

The surfactant used in the present disclosure can comprise an anionic surfactant. Anionic surfactants contain anionic functional groups at their head, such as sulfate, sulfonate, phosphate, and carboxylates. Exemplary anionic surfactants include, but are not limited to, ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), sodium myreth sulfate, docusate (dioctyl sodium sulfosuccinate), perfluorooctanesulfonate (PFOS), perfluorobutanesulfonate, alkyl-aryl ether phosphates, and alkyl ether phosphates.

The surfactant used in the present disclosure can be a zwitterionic surfactant. Zwitterionic (amphoteric) surfactants refer to those having cationic and anionic centers attached to the same molecule. Exemplary zwitterionic surfactants include, without limitation, phospholipids phosphatidylserine, phosphatidylethanolamine, phosphatidylcholine, and sphingomyelins.)

In some embodiments of the present disclosure, the concentration of a surfactant described herein in the described liquid pharmaceutical composition is 0.1% to 15% by weight. In some embodiments, the concentration of the surfactant is 0.5%-8% by weight in the liquid pharmaceutical composition. In some embodiments, the concentration of the surfactant is 0.5%-6% by weight in the liquid pharmaceutical composition. In some embodiments, the concentration of the surfactant is 0.25%-8% by weight in the liquid pharmaceutical composition. In some embodiments, the concentration of the surfactant is 0.75%-8% by weight in the liquid pharmaceutical composition. In some embodiments, the concentration of the surfactant is 0.5%-5% by weight in the liquid pharmaceutical composition. In some embodiments, the concentration of the surfactant is 0.75%-10% by weight in the liquid pharmaceutical composition. In some embodiments, the concentration of the surfactant is 0.75%-6% by weight in the liquid pharmaceutical composition. In some embodiments, the concentration of the surfactant is 0.75%-4% by weight in the liquid pharmaceutical composition. In some embodiments, the concentration of the surfactant is 1%-4% by weight in the liquid pharmaceutical composition. In some embodiments, the concentration of the surfactant is 1%-6% by weight in the liquid pharmaceutical composition. In some embodiments, the concentration of the surfactant is 5%-10% by weight in the liquid pharmaceutical composition. In some embodiments, the concentration of the surfactant is 5%-15% by weight in the liquid pharmaceutical composition. In some embodiments, the concentration of the surfactant is 10%-25% by weight in the liquid pharmaceutical composition.

In some embodiments, the radiopharmaceutical composition described herein comprises a tonicity adjusting agent. Exemplary tonicity adjusting agents include dextrose, glycerin, mannitol, potassium chloride and sodium chloride.

In some embodiments, the radiopharmaceutical composition described herein comprises a special additive. In some embodiments, the special additive comprises Acetyl tryptophan, Aluminum hydroxide, Aluminum phosphate, Aluminum potassium sulfate, Amino acids (leucine, isoleucine, lysine (as acetate or HCl salt), valine, phenylalanine, threonine, tryptophan, alanine, aspartic acid, glutamic acid, proline, serine, tyrosine, taurine), ε-Aminocaproic acid, Calcium D-saccharate, Caprylate sodium, 8-Chlorotheophylline, Creatine, Creatinine, Cholesterol, Cholesteryl sulfate sodium, Cyclohexanedione dioxime, Diethanolamine, Distearyl phosphatidylcholine, Distearyl phosphatidylglycerol, L-alpha-dimyristoylphosphatidylcholine, L-alpha-dimyristoylphosphatidylglycerol, Dioleoylphosphatidylcholine (DOPC), Dipalmitoylphosphatidylglycerol (DPPG), (R)-hexadecanoic acid, 1-Rphosphonoxy)methyl1-1,2-ethanediyl ester, monosodium salt (DPPA), (R)-4-hydroxy-N,N,N-trimethyl-10-oxo-7-[(loxohexadecyl)oxy]-3,4,9-trioxa-4-phosphapentacosan-1-aminium, 4-oxide, inner salt (DPPC), (R)-[6-hydroxy-6-oxido-9-[(1-oxohexadecyl)oxy]-5,7,11-trioxa-2aza-6-phosphahexacos-1-yl]-ω-methoxypoly(ox-1,2-ethanediyl), monosodium salt (MPEG5000 DPPE), MPEG-distearoyl phosphoethanolamine, Ethyl lactate, Ethylenediamine, L-Glutamate sodium, Hyaluronate sodium, Hydrogenated soy phosphatidylcholine, Iron ammonium citrate, Lactic acid, D,L-lactic and glycolic acid copolymer, Meglumine, Methyl boronic acid, Niacinamide, Paraben methyl, Phosphatidylglycerol, egg (EPG), Potassium sodium tartrate, Protamine (as sulfate), Simethicone, Saccharin sodium, Sodium D-gluconate, Sodium hypochlorite, Sodium sulfate, Stannous chloride, Sulfosalicylate disodium, Tin chloride (stannous and stannic), Tri-n-butyl phosphate, Tricaprylin, Triolein, von Willebrand factor, Zinc, Zinc acetate, Zinc carbonate, Zinc oxide, or a combination thereof.

In some embodiments, the radiopharmaceutical composition described herein comprises a suspending agent. Non-limiting examples of suspending agents include Carboxy methyl cellulose (CMC), Croscarmellose sodium, sodium CMC, xanthan gum, hydroxyl ethyl cellulose (HEC), hydroxyl propyl methyl cellulose (HPMC), and Avicel CL-611. Further exemplary suspending agents include carboxymethylcellulose (sodium and other salts), carboxyvinyl copolymers, carboxymethyl hydroxyethylcellulose, cellulose, such as microcrystalline cellulose, combinations of microcrystalline cellulose with sodium carboxymethylcellulose (such as Avicel RC-501, RC-581, RC-591, and CL-611), hydrophobically modified hydroxyethyl cellulose, hydroxyethyl cellulose, hydroxypropyl guar, hydroxypropyl methylcellulose (such as Benecel K750® or Benecel K1500®), hydroxypropyl cellulose, methyl cellulose, natural gums and their derivatives, xanthan gum, guar gum, gum Arabic, partially and fully hydrolyzed polyvinyl alcohols, partially neutralized polyacrylic acid, polyalkylene glycol, polysaccharide gums, polyvinylpyrrolidone and derivatives thereof, starch and its derivatives, vinylpyrrolidone homo- and copolymers, water-soluble cellulose ethers, and the mixtures thereof.

These compositions can be sterilized by conventional sterilization techniques. The resulting aqueous solutions may be packaged for use or filtered under aseptic conditions and lyophilized. The lyophilized preparation can be combined with a sterile aqueous solution prior to administration. The compositions can contain pharmaceutically acceptable auxiliary substances as appropriate to approximate physiological conditions, such as tonicity adjusting agents and the like, for example, sodium acetate, sodium lactate, sodium chloride, potassium chloride, calcium chloride, sodium lactate, sorbitan monolaurate, triethanolamine oleate, etc. Pharmaceutical compositions can be selected according to their physical characteristic, including, but not limited to fluid volumes, viscosities and other parameters in accordance with the particular mode of administration selected.

Conjugate

In one aspect, provided herein is a radiopharmaceutical composition comprising a conjugate or pharmaceutically acceptable salts or solvates thereof described herein. The radiopharmaceutical composition can further comprise a pharmaceutically acceptable carrier such as an aqueous vehicle. Normal saline can be employed as the pharmaceutically acceptable carrier. Other suitable carriers or aqueous vehicles can include, e.g., water, buffered water, 0.9% isotonic saline, 0.4% saline, 0.3% glycine, and the like, including glycoproteins for enhanced stability, such as albumin, lipoprotein, globulin, etc. In some embodiments, the aqueous vehicle is water for injection. In some embodiments, the aqueous vehicle is 0.9% w/w sodium chloride saline solution.

The amount of conjugates administered can depend upon the particular targeting moiety used, the disease state being treated, the therapeutic agent being delivered, and the judgment of the clinician.

The concentration of the conjugates or pharmaceutically acceptable salts or solvates thereof described herein in the pharmaceutical formulations can vary. In some embodiments, the conjugate is present in the pharmaceutical composition from about 0.05% to about 1% by weight, about 1% to about 2% by weight, about 2% to about 5% by weight, about 5% to about 10% by weight, about 10% to about 30% by weight, about 30% to about 50% by weight, about 50% to about 75% by weight, or about 75% to about 99% by weight.

In some embodiments, the conjugate is present in the pharmaceutical composition in an amount that provides a radioactivity of about 0.5 to about 1000 µCi/ml. In some embodiments, the conjugate is present in the pharmaceutical composition in an amount that provides a radioactivity of about 1 to about 15 µCi/ml, about 2 to about 20 µCi/ml, about 5 to about 50 µCi/ml, about 10 to about 100 µCi/ml, about 20 to about 200 µCi/ml, about 50 to about 500 µCi/ml, about 100 to about 250 µCi/ml, about 5 to about 25 µCi/ml, about 10 to about 30 µCi/ml, or about 5 to about 15 µCi/ml. In some embodiments, the conjugate is present in the radiopharmaceutical composition at a concentration equivalent to about 15 to 45 µCi/mL. In some embodiments, the conjugate is present in the radiopharmaceutical composition at a concentration equivalent to about 10 to 35 µCi/mL. In some embodiments, the conjugate is present in the radiopharmaceutical composition at a concentration equivalent to about 10 to 25 μCi/mL. In some embodiments, the conjugate is present in the radiopharmaceutical composition at a concentration equivalent to about 12 to 23 μCi/mL. In some embodiments, the conjugate is present in the pharmaceutical composition in an amount that provides a radioactivity of at most about 5, 10, 15, 50, 75, 100, 200, or 500 μCi/ml. In some embodiments, the conjugate is present in the pharmaceutical composition in an amount that provides a radioactivity of at most about 15 μCi/ml. In some embodiments, the conjugate is present in the pharmaceutical composition in an amount that provides a radioactivity of about 1 to 15 μCi/ml. In some embodiments, the conjugate is present in the pharmaceutical composition in an amount that provides a radioactivity of at most about 35 μCi/ml. In some embodiments, the conjugate is present in the pharmaceutical composition in an amount that provides a radioactivity of about 1 to 35 μCi/ml. In some embodiments, the conjugate is present in the pharmaceutical composition in an amount that provides a radioactivity of at least about 1, 2, 3, 4, 5, 6, 7, 8, 9, 10, 11, 12, 13, 14, 15, 16, 17, 18, 19, 20, 25, 30, or 50 μCi/ml.

A composition described herein can comprise a conjugate, or a pharmaceutically acceptable salt or solvate thereof, that comprises actinium-225. In some embodiments, actinium-225 is present in a herein-described radiopharmaceutical composition that it provides a volumetric radioactivity of about 0.005 to 1000 MBq/mL. In some embodiments, the actinium-225 is present in a herein-described radiopharmaceutical composition that it provides a volumetric radioactivity of about 0.5 to 20 MBq/mL. In some embodiments, the actinium-225 is present in a herein-described radiopharmaceutical composition that it provides a volumetric radioactivity of about 0.4 to 20 MBq/mL. In some embodiments, the actinium-225 is present in a herein-described radiopharmaceutical composition that it provides a volumetric radioactivity of about 0.2 to 5 MBq/mL. In some embodiments, the actinium-225 is present in a herein-described radiopharmaceutical composition that it provides a volumetric radioactivity of about 0.4 to 1 MBq/mL. In some embodiments, actinium-225 is present in a herein-described radiopharmaceutical composition that it provides a volumetric radioactivity of about 0.1 to 100 MBq/mL. In some embodiments, actinium-225 is present in a herein-described radiopharmaceutical composition that it provides a volumetric radioactivity of about 0.1 to 100, about 0.1 to 50, about 0.1 to 25, about 0.1 to 10, about 0.1 to 5, about 1 to 100, about 0.5 to 10, about 0.5 to 50, about 10 to 100, about 10 to 50, about 10 to 20, about 1 to 10, or about 1 to 20 MBq/mL. In some embodiments, actinium-225 is present in a herein-described radiopharmaceutical composition that it provides a volumetric radioactivity of about 0.1, 0.5, 1, 2, 3, 4, 5, 6, 7, 8, 9, 10, 11, 12, 13, 14, 15, 16, 17, 18, 19, 20, 21, 22, 23, 24, 25 or 30 MBq/mL. In some embodiments, actinium-225 is present in a herein-described radiopharmaceutical composition that it provides a volumetric radioactivity of at least about 0.001, 0.01, 0.1, 0.5, 1, 2, 3, 4, 5, 6, 7, 8, 9, 10, 11, 12, 13, 14, 15, 16, 17, 18, 19, 20, 21, 22, 23, 24, or 25 MBq/mL. In some embodiments, actinium-225 is present in a herein-described radiopharmaceutical composition that it provides a volumetric radioactivity of at most about 0.5, 1, 2, 3, 4, 5, 6, 7, 8, 9, 10, 11, 12, 13, 14, 15, 16, 17, 18, 19, 20, 21, 22, 23, 24, 25, 30, 40 or 50 MBq/mL. In some embodiments, a composition described herein has a total DOTA-TATE peptide concentration of ≤11.5 μg/mL (including e.g., unlabeled DOTATATE, $^{225}$Ac-DOTATATE, and metal-DOTATATE species). In some embodiments, a composition described herein has a total DOTA-TATE peptide concentration of at most about 5, 6, 7, 8, 9, 10, 11, 12, 13, 14, 15, 16, 17, 18, 19, 20 or 50 μg/mL. In some embodiments, a composition described herein has a total DOTA-TATE peptide concentration of at least about 0.5, 1, 2, 3, 4, 5, 6, 7, 8, 9, 10, 11, 12, 13, 14, 15, 16, 17, 18, 19, or 20 μg/mL.

The composition described herein can comprise a conjugate, or a pharmaceutically acceptable salt or solvate thereof, and a pharmaceutically acceptable excipient or carrier. The conjugate as described can be substantially pure, in that it contains less than about 10%, less than about 5%, or less than about 1%, or less than about 0.1% by weight, of other organic small molecules, such as unreacted intermediates or synthesis by-products that are created, for example, in one or more of the steps of a synthesis method. The conjugate can be $^{225}$Ac-DOTA-TATE or $^{225}$Ac-DOTA-TOC. The conjugate can be $^{225}$Ac-DOTA-TATE. The conjugate can be $^{225}$Ac-DOTA-TOC.

$^{225}$Ac-DOTA-TATE can be illustrated as having the following structure:

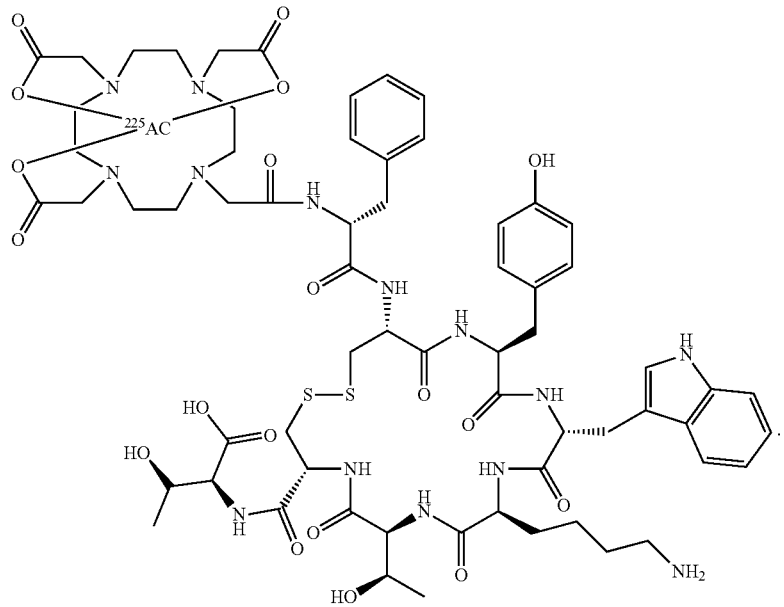

The IUPAC Name for $^{225}$Ac-DOTA-TATE is: (2,2',2''-(10-(2-4(R)-1-(((4R,7S,10S,13R,16S,19R)-13-((1H-indol-3-yl)methyl)-10-(4-aminobutyl)-4-(((1S,2R)-1-carboxy-2-hydroxypropyl)carbamoyl)-16-(4-hydroxybenzyl)-7-((R)-1-hydroxyethyl)-6,9,12,15,18-pentaoxo-1,2-dithia-5,8,11,14,17-pentaazacycloicosan-19-yl)amino)-1-oxo-3-phenylpropan-2-yl)amino)-2-oxoethyl)-1,4,7,10-tetraazacyclododecane-1,4,7-triyl)triacetate; actinium-225 (3+)).

In some embodiments, provided herein is a pharmaceutical composition comprising a conjugate that is

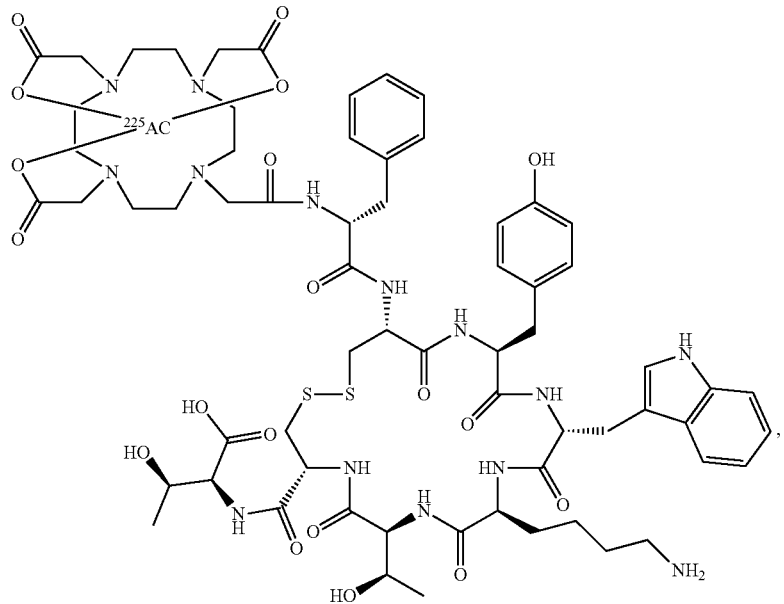

and one or more stabilizing agents.

In some embodiments, provided herein is a pharmaceutical composition comprising a conjugate that has a structure of

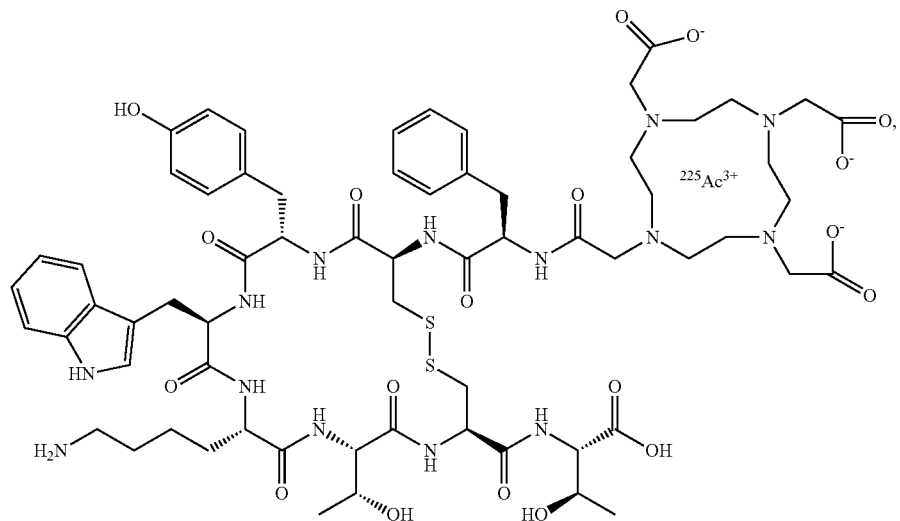

and one or more stabilizing agents. In some embodiments, provided herein is a pharmaceutical composition comprising a conjugate that has a structure of

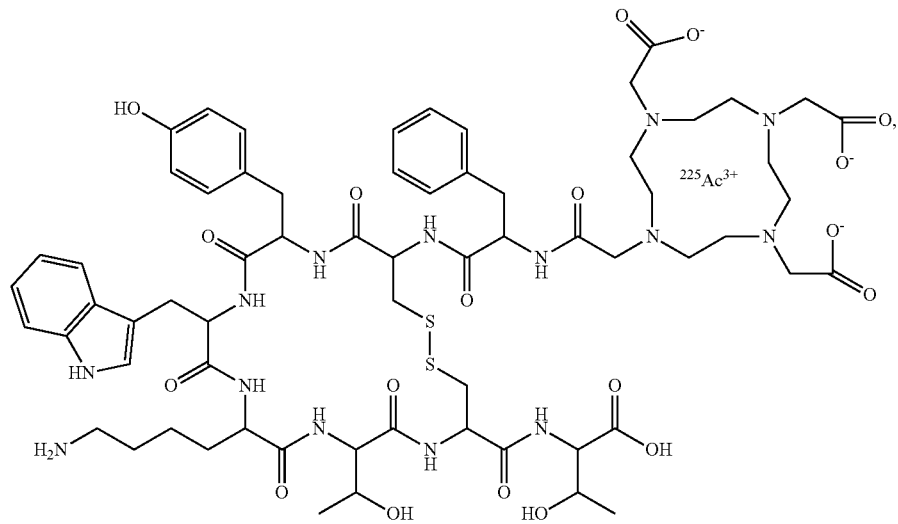

and one or more stabilizing agents. It is understood that the chelation between $^{225}$Ac and the metal chelator is not shown in the above two structures. In some embodiments, for example in acidic aqueous conditions, the radionuclide actinium-225 exists in a salt form, e.g., as $^{225}$Ac$^{3+}$. In some embodiments, the conjugate is in a salt form. In some embodiments, the conjugate is an acetate salt. In some embodiments, provided herein is a pharmaceutical composition comprising a conjugate that is

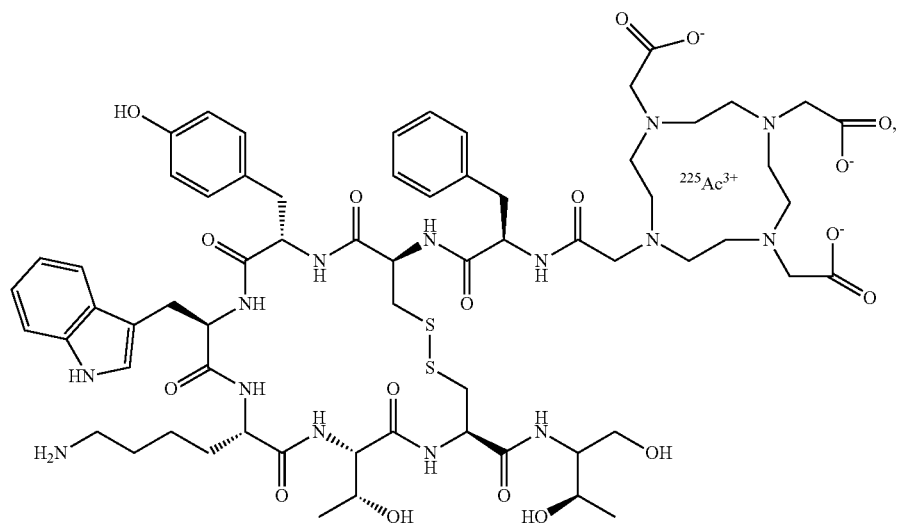

and one or more stabilizing agents. In some embodiments, provided herein is a pharmaceutical composition comprising a conjugate that is agonist of the SSR. The antagonist of the SSR can comprise a competitive antagonist of the SSR. The targeting ligand can comprise an allosteric modulator of the SSR. The

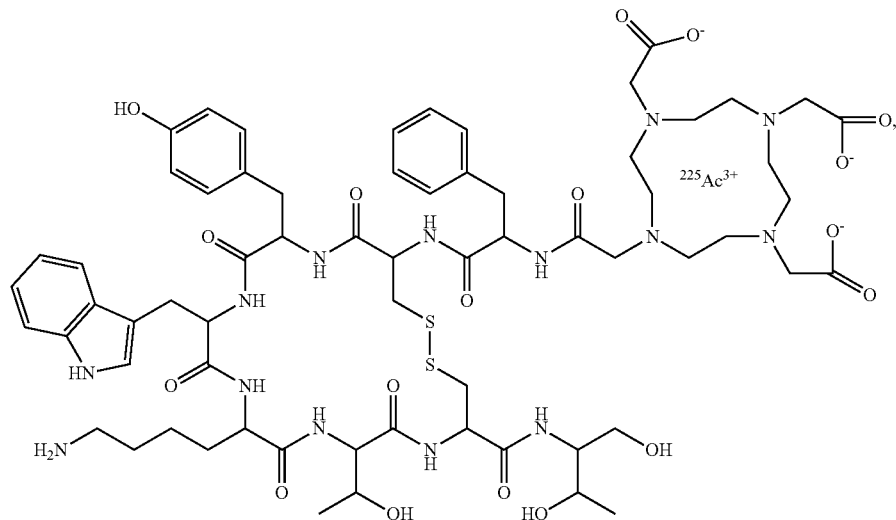

and one or more stabilizing agents. It is understood that the chelation between $^{225}$Ac and the metal chelator is not shown in the above two structures. In some embodiments, for example in acidic aqueous conditions, the radionuclide actinium-225 exists in a salt form, e.g., as $^{225}$Ac$^{3+}$. In some embodiments, the conjugate is in a salt form. In some embodiments, the conjugate is an acetate salt. A person of ordinary skill would appreciate that the dissociation of an acid can depend on the pH value of the environment and its pK value. Accordingly, in some embodiments, a conjugate described herein can exist in a completely ionized, partially ionized or non-ionized form.

Targeting Ligand

In one aspect, provided herein is a radiopharmaceutical composition comprising a conjugate or pharmaceutically acceptable salts or solvates thereof. In some embodiments, the conjugate described herein comprises a targeting ligand and a metal chelator.

The targeting ligand described herein can bind to one or more target within a subject's system or an in vitro system. The targeting ligand can target a protein, a receptor on a cell, or other chemical moiety that can perform signaling functions within the subject's system. The targeting ligand can bind to a receptor on the surface of a cell within the subject's system. In some embodiments, the targeting ligand binds to a somatostatin receptor (SSR). An SSR can be a mammalian SSR. A mammalian SSR can be a human SSR. A human SSR can comprise somatostatin receptor type 1 (SSTR1), somatostatin receptor type 2 (SSTR2), somatostatin receptor type 3 (SSTR3), somatostatin receptor type 4 (SSTR4), and/or somatostatin receptor type 5 (SSTR5). An SSR can be a human somatostatin receptor type 2 (SSTR2). In some embodiments, the targeting ligand binds to a human somatostatin receptor type 2 (SSTR2). The targeting ligand can comprise a peptide and/or a small molecule compound. The targeting ligand can comprise an agonist of the SSR. The targeting ligand can comprise an antagonist of the SSR. The agonist of the SSR can comprise a partial agonist of the SSR. The agonist of the SSR can comprise a full agonist of the SSR. The agonist of the SSR can comprise an inverse allosteric modulator of the SSR can be an allosteric agonist of SSR. The allosteric modulator of the SSR can be an allosteric antagonist of SSR.

The targeting ligand described herein can comprise one or more peptides, which can be the same or different. The peptide can be linear or cyclic. The peptide can be monocyclic. The peptide can comprise a binding peptide. The binding peptide can bind to one or more target within a subject's system or an in vitro system. The binding peptide can bind to a somatostatin receptor (SSR). The binding peptide can bind to a somatostatin receptor type 1 (SSTR1), somatostatin receptor type 2 (SSTR2), somatostatin receptor type 3 (SSTR3), somatostatin receptor type 4 (SSTR4), and/or somatostatin receptor type 5 (SSTR5). The binding peptide can bind to a somatostatin receptor type 2 (SSTR2). The binding peptide can bind to a human somatostatin receptor type 2 (SSTR2).

The peptide can comprise any suitable number of amino acid residues. The peptide can comprise from 4 to 50, 5 to 40, 6 to 30, 7 to 20, or 8 to 10 amino acid residues. The peptide can comprise from 6 to 14 amino acid residues. The peptide can comprise from 6 to 10 amino acid residues. The peptide can comprise from 7 to 9 amino acid residues. The peptide can comprise 8 to 9 amino acid residues. The peptide can comprise 14 amino acid residues. The peptide can comprise 13 amino acid residues. The peptide can comprise 12 amino acid residues. The peptide can comprise 11 amino acid residues. The peptide can comprise 10 amino acid residues. The peptide can comprise 9 amino acid residues. The peptide can comprise 8 amino acid residues. The peptide can comprise 7 amino acid residues. The peptide can comprise 6 amino acid residues. The peptide can consist of 10 amino acid residues. The peptide can consist of 14 amino acid residues. The peptide can consist of 13 amino acid residues. The peptide can consist of 12 amino acid residues. The peptide can consist of 11 amino acid residues. The peptide can consist of 10 amino acid residues. The peptide can consist of 9 amino acid residues. The peptide can consist of 8 amino acid residues. The peptide can consist of 7 amino acid residues. The peptide can consist of 6 amino acid residues. The conjugate can comprise a monocyclic peptide of 6, 7, 8, 9, 10, 11, 12, 13, or 14 amino acid residues. The amino acid residues described herein can be modified to remove or add one or more functional groups.

A targeting ligand described herein can be a cyclized peptide. Cyclization can be achieved via a single disulfide bond or via a peptide bond, alkyl bond, alkenyl bond, ester bond, thioester bond, ether bond, thioether bond, phosphate ether bond, azo bond, C—S—C bond, C—N—C bond, CN—C bond, C=N—O bond, amide bond, lactam bridge, carbamoyl bond, urea bond, thiourea bond, amine bond, thioamide bond, or the like, but not limited to them. The peptide can comprise a cyclic peptide that is cyclized by a peptide bond. A cyclization of a peptide can stabilize the peptide structure and thereby enhance affinity for a target. The cyclization can occur between the N- and C-terminus, or it can occur between a terminal amino acid and a non-terminal amino acid. The cyclization can occur between two non-terminal amino acids. The peptide can be cyclized via one or more cysteines. The peptide can comprise a cysteine at the C-terminus. The peptide can comprise a cysteine at the N-terminus. The cyclization can occur via a disulfide bond between cysteines or between cysteine and another thiol group-bearing residue.

Exemplary targeting ligands include BMS-753493, Somatostatins or somatotropin release inhibiting factor (SRIF), SRIF-14, SRIF-28, Octreotide, Octreotate, Lanreotide, Pasireotide, JR-11, L-779,976, BIM-23120, Satoreotide, depreotide, 18F-KYNDRLPLYISNP (SEQ ID NO: 103), CaIX-P1, and FAP-2286. The targeting ligand can comprise octreotate, octreotide, D-Phe1-cyclo(Cys2-Tyr3-D-Trp4-Lys5-Thr6-Cys7)Thr8 (SEQ ID NO: 97) (tyr3-octreotate or TATE), D-Phe1-cyclo(Cys2-Tyr3-D-Trp4-Lys5-Thr6-Cys7)Thr(ol)8 (SEQ ID NO: 98) (Phe1-Tyr3octreotide, edotreotide, or TOC), D-Phe1-cyclo(Cys2-Phe3-D-Trp4-Lys5-Thr6-Cys7)Thr(ol)8 (SEQ ID NO: 99) (OC), D-Phe1-cyclo(Cys2-1-Nal-D-Trp4-Lys5-Thr6-Cys7)Thr(ol)8 (SEQ ID NO: 100) (NOC), p-Cl-Phe-cyclo(D-Cys-Aph(Hor)-D-Aph(Cbm)-Lys-Thr-Cys)D-Tyr-NH$_2$) (SEQ ID NO: 101) (JR11), or p-Cl-Phe-cyclo(D-Cys-Tyr-D-Aph(Cbm)-Lys-Thr-Cys)-D-Tyr-NH$_2$ (SEQ ID NO: 102) (LM3). The targeting ligand can be tyr3-octreotate, edotreotide, octreotate, or octreotide. The targeting ligand can be tyr3-octreotate.

The binding peptide can comprise an amino acid sequence with at least 70% identity to a sequence selected from SEQ IDs 1 to 96. The binding peptide can comprise an amino acid sequence with at least 75% identity to a sequence selected from SEQ IDs 1 to 96. The binding peptide can comprise an amino acid sequence with at least 80% identity to a sequence selected from SEQ IDs 1 to 96. The binding peptide can comprise an amino acid sequence with at least 85% identity to a sequence selected from SEQ IDs 1 to 96. The binding peptide can comprise an amino acid sequence with at least 85% identity to a sequence selected from SEQ IDs 1 to 96. The binding peptide can comprise an amino acid sequence with at least 90% identity to a sequence selected from SEQ IDs 1 to 96. The binding peptide can comprise an amino acid sequence with at least 95% identity to a sequence selected from SEQ IDs 1 to 96. The binding peptide can comprise an amino acid sequence with at least 98% identity to a sequence selected from SEQ IDs 1 to 96. The binding peptide can comprise an amino acid sequence with at least 99% identity to a sequence selected from SEQ IDs 1 to 96. The binding peptide can comprise an amino acid sequence an amino acid sequence selected from SEQ IDs 1 to 96, as listed in Table 4.

TABLE 4

Sequence ID List

| SEQ ID | Sequences |
|---|---|
| 1 | H-$^D$Phe-c[Cys-Tyr-$^D$Trp-Lys-Val-Cys]-Trp-OH |
| 2 | H-$^D$3Pal-c[Cys-Tyr-$^D$Trp-Lys-Val-Cys]-Thr-OH |
| 3 | H-$^D$Phe-c[Cys-Phe-$^D$Trp-Lys-Thr-Cys]-Thr[ol] |
| 4 | H-Nal-c[$^D$Cys-3Pal-$^D$Trp-Lys-Ala-Cys]-Nal-OH |
| 5 | H-Nal-c[$^D$Cys-3Pal-$^D$Trp-Lys-Gly-Cys]-Nal-OH |
| 6 | H-Nal-c[$^D$Cys-3Pal-$^D$Trp-Lys-Ile-Cys]-Nal-OH |
| 7 | H-Nal-c[$^D$Cys-3Pal-$^D$Trp-Lys-Leu-Cys]-Nal-OH |
| 8 | H-Nal-c[$^D$Cys-3Pal-$^D$Trp-Lys-Val-Cys]-Nal-OH |
| 9 | H-c[Cys-Lys-Phe-Phe-$^D$Trp-Amp-Thr-Phe-Thr-Ser-Cys]-OH |
| 10 | H-Ser-Ala-Asn-Ser-Asn-Pro-Ala-Met-Ala-Pro-Arg-Glu-Arg-Lys-Ala-Gly-c[Cys-Lys-Asn-Phe-Phe-Trp-Lys-Thr-Phe-Thr-Ser-Cys]-OH |
| 11 | H-c[Cys-Phe-Phe-Trp-Lys-Thr-Phe-Cys]-OH (OLT-8) |
| 12 | H-c[Cys-Phe-Phe-$^D$Trp-Lys-Thr-Phe-Cys]-OH (O$^D$T-8) |
| 13 | H-c[Cys-$^L$Agl(N$^\beta$Me,benzoyl)-Phe-$^D$Trp-Lys-Thr-Phe-Cys]-OH |
| 14 | H-c[Cys-$^D$Agl(N$^\beta$Me,benzoyl)-Phe-$^D$Trp-Lys-Thr-Phe-Cys]-OH |
| 15 | H-c[Cys-Phe-$^L$Agl(N$^\beta$Me,benzoyl)-Trp-Lys-Thr-Phe-Cys]-OH |
| 16 | H-c[Cys-Phe-$^D$Agl(N$^\beta$Me,benzoyl)-Trp-Lys-Thr-Phe-Cys]-OH |

TABLE 4-continued

Sequence ID List

| SEQ ID | Sequences |
|---|---|
| 17 | H-c[Cys-Phe-$^L$Agl(N$^\beta$Me,benzoyl)-$^D$Trp-Lys-Thr-Phe-Cys]-OH |
| 18 | H-c[Cys-Phe-$^D$Agl(N$^\beta$Me,benzoyl)-$^D$Trp-Lys-Thr-Phe-Cys]-OH |
| 19 | H-c[$^D$Cys-Phe-$^L$Agl(N$^\beta$Me,benzoyl)-$^D$Trp-Lys-Thr-Phe-Cys]-OH |
| 20 | H-c[$^D$Cys-Phe-$^D$Agl(N$^\beta$Me,benzoyl)-$^D$Trp-Lys-Thr-Phe-Cys]-OH |
| 21 | H-Tyr-c[Cys-Phe-$^L$Agl(N$^\beta$Me,benzoyl)-Trp-Lys-Thr-Phe-Cys]-OH |
| 22 | H-Tyr-c[Cys-Phe-$^D$Agl(N$^\beta$Me,benzoyl)-Trp-Lys-Thr-Phe-Cys]-OH |
| 23 | H-Tyr-c[Cys-Phe-$^L$Agl(N$^\beta$Me,benzoyl)-$^D$Trp-Lys-Thr-Phe-Cys]-OH |
| 24 | H-Tyr-c[Cys-Phe-$^D$Agl(N$^\beta$Me,benzoyl)-$^D$Trp-Lys-Thr-Phe-Cys]-OH |
| 25 | H-c[Cys-Phe-Phe-$^D$Trp-$^L$Agl($^\beta$Ala)-Thr-Phe-Cys]-OH |
| 26 | H-c[Cys-Phe-Phe-$^D$Trp-$^D$Agl($^\beta$Ala)-Thr-Phe-Cys]-OH |
| 27 | H-c[Cys-Phe-Phe-$^D$Trp-$^L$Agl(N$^\beta$Me,$^\beta$Ala)-Thr-Phe-Cys]-OH |
| 28 | H-c[Cys-Phe-Phe-$^D$Trp-$^D$Agl(N$^\beta$Me,$^\beta$Ala)-Thr-Phe-Cys]-OH |
| 29 | H-c[Cys-Phe-Phe-$^D$Trp-Lys-$^L$Agl-(N$^\beta$Me,HO-Ac)-Phe-Cys]-OH |
| 30 | H-c[Cys-Phe-Phe-$^D$Trp-Lys-$^D$Agl-(N$^\beta$Me,HO-Ac)-Phe-Cys]-OH |
| 31 | H-c[Cys-Phe-Phe-$^D$Trp-Lys-Thr-$^L$Agl(N$^\beta$Me,benzoyl)-Cys]-OH |
| 32 | H-c[Cys-Phe-Phe-$^D$Trp-Lys-Thr-$^L$Agl(N$^\beta$Me,benzoyl)-Cys]-OH |
| 33 | H-c[Cys-Phe-Phe-$^D$Trp-Lys-Thr-Tyr-Cys]-OH |
| 34 | H-c[Cys-Phe-Phe-Trp-Lys-Thr-Tyr-Cys]-OH |
| 35 | H-c[Cys-Phe-Xle-Trp-Lys-Thr-Phe-Cys]-OH |
| 36 | H-c[Cys-Phe-Tyr-$^D$Trp-Lys-Thr-Phe-Cys]-OH |
| 37 | H-c[Cys-Phe-Tyr-Trp-Lys-Thr-Phe-Cys]-OH |
| 38 | H-Tyr-c[Cys-Phe-Ala-$^D$Trp-Lys-Thr-Phe-Cys]-OH |
| 39 | H-Tyr-c[Cys-Phe-Ala-Trp-Lys-Thr-Phe-Cys]-OH |
| 40 | H-Tyr-c[Cys-Phe-Phe-Trp-Lys-Thr-Phe-Cys]-OH |
| 41 | H-Tyr-c[Cys-Phe-Xle-Trp-Lys-Thr-Phe-Cys]-OH |
| 42 | H-Ala-Gly-c[Cys-Lys-Asn-Phe-Phe-Trp-Lys-Thr-Phe-Thr-Ser-Cys]-OH |
| 43 | H-c[Cys-Phe-Ala-$^D$Trp-Lys-Thr-Ala-Cys]-OH |
| 44 | H-c[Cys-Phe-Ala-$^D$Trp-Lys-Thr-Phe-Cys]-OH |
| 45 | H-c[Cys-Phe-Phe-$^D$Trp-Lys-Thr-Phe-Cys]-OH |
| 46 | H-c[Cys-Phe-Phe-Trp-Lys-Thr-Phe-Cys]-OH |
| 47 | H-N(Me)-c[Cys-Lys-Phe-Phe-$^D$Nal-Amp-Thr-Phe-Thr-Ser-Cys]-OH |
| 48 | H-N(Me)-c[Cys-Lys-Phe-Phe-$^D$Trp-Amp-Thr-Phe-Thr-Ser-Cys]-OH |
| 49 | H-N(Me)-c[Cys-Lys-Phe-Phe-$^D$Trp-Amp(NMe)-Thr-Phe-Thr-Ser-Cys]-OH |
| 50 | H-c[Cys-Lys-Phe-Phe-$^D$Nal-Amp-Thr-Phe-Thr-Ser-Cys]-OH |
| 51 | H-c[Cys-Lys-Phe-Phe-$^D$Trp-Lys-Thr-Tyr-Thr-Ser-Cys]-OH |
| 52 | H-c[Cys-Lys-Phe-Phe-Trp-3Pal-Thr-Tyr-Thr-Ser-Cys]-OH |
| 53 | H-c[Cys-Phe-$^D$Trp-Lys-Thr-Phe-Cys]-OH |
| 54 | H-c[Cys-Phe-Phe-$^D$Trp-Lys-Phe-Cys]-OH |

TABLE 4-continued

Sequence ID List

| SEQ ID | Sequences |
|---|---|
| 55 | H-c[Cys-Phe-Phe-$^D$Trp-Lys-Thr-Cys]-OH |
| 56 | H-c[Cys-Phe-Phe-$^D$Trp-Lys-Thr-Phe-Thr-Cys]-OH |
| 57 | H-c[Cys-Phe-Phe-$^D$Trp-Lys-Thr-Phe-Thr-Cys]-OH |
| 58 | H-c[Cys-Lys-Phe-Phe-$^D$Trp-3Pal-Thr-Phe-Cys]-OH |
| 59 | H-c[Cys-Lys-Phe-Phe-$^D$Trp-Lys-Thr-Phe-Cys]-OH |
| 60 | H-c[Cys-Asn-Phe-Phe-$^D$Trp-Lys-Thr-Phe-Cys]-OH |
| 61 | H-c[Cys-Asn-Phe-Phe-$^D$Trp-Lys-Thr-Phe-Thr-Cys]-OH |
| 62 | H-Tyr-c[Cys-Phe-$^D$Trp-Lys-Thr-Phe-Cys]-OH |
| 63 | H-Tyr-c[Cys-Lys-Phe-$^D$Trp-3Pal-Thr-Phe-Thr-Cys]-OH |
| 64 | H-Tyr-c[Cys-Lys-Glu2-Phe-$^D$Trp-3Pal-Thr-Phe-Lys2-Ser-Cys]-OH |
| 65 | H-Tyr-c[Cys-Lys-Phe-Glu2-Phe-$^D$Trp-3Pal-Thr-Phe-Lys2-Ser-Cys]-OH |
| 66 | H-c[Cys-Phe-4Aph-Trp-Lys-Thr-Phe-Cys]-OH |
| 67 | H-c[Cys-Phe-4Aph-$^D$Trp-Lys-Thr-Phe-Cys]-OH |
| 68 | H-N(Cbm)-c[Cys-Phe-4Aph-Trp-Lys-Thr-Phe-Cys]-OH |
| 69 | H-N(Cbm)-c[Cys-Phe-4Aph-$^D$-Trp-Lys-Thr-Phe-Cys]-OH |
| 70 | H-c[Cys-Phe-4Aph-2Nal-Lys-Thr-Phe-Cys]-OH |
| 71 | H-Tyr-c[Cys-Phe-4Aph-Trp-Lys-Thr-Phe-Cys]-OH |
| 72 | H-Tyr-c[Cys-Phe-4Aph-$^D$-Trp-Lys-Thr-Phe-Cys]-OH |
| 73 | H-N(Cbm)-Tyr-c[Cys-Phe-4Aph-Trp-Lys-Thr-Phe-Cys]-OH |
| 74 | H-c[Cys-Phe-4Aph-Trp-Lys-Thr-Tyr-Cys]-OH |
| 75 | H-N(Cbm)-c[Cys-Phe-4Aph-Trp-Lys-Thr-Tyr-Cys]-OH |
| 76 | H-c[Cys-Phe-Ala-Trp-Lys-Thr-Phe-Cys]-OH |
| 77 | H-Tyr-c[Cys-Phe-Ala-Trp-Lys-Thr-Phe-Cys]-OH |
| 78 | H-Tyr-c[Cys-Phe-Ala-$^D$-Trp-Lys-Thr-Phe-Cys]-OH |
| 79 | H-Tyr-c[Cys-Phe-4Amp-Trp-Lys-Thr-Phe-Cys]-OH |
| 80 | H-c[$^D$Cys-Phe-Tyr-threo-(2R,3S)C$^\beta$Me-2Nal-Lys-Thr-Phe-Cys]-OH |
| 81 | H-c[Cys-Phe-Tyr-threo-(2R,3S)C$^\beta$Me-2Nal-Lys-Thr-Phe-Cys]-OH |
| 82 | H-N(Cbm)-c[Cys-Phe-4Aph-$^D$-Trp-Lys-Thr-Tyr-Cys]-OH |
| 83 | H-c[Cys-Phe-Val-$^D$Trp-Lys-Thr-Phe-Cys]-OH |
| 84 | H-c[Cys-Phe-Ala-Trp-Lys-Thr-Ala-Cys]-OH |
| 85 | H-c[Cys-Phe-Ala-$^D$Trp-Lys-Thr-Ala-Cys]-OH |
| 86 | H-c[Cys-Phe-Ala-Trp-Lys-Thr-Phe-Cys]-OH |
| 87 | H-GABA-c[Cys-Phe-Ala-Trp-Lys-Thr-Phe-Cys]-OH |
| 88 | H-c[Cys-Phe-Ala-Trp-Lys-Thr-Val-Cys]-OH |
| 89 | H-c[Cys-Phe-Val-Trp-Lys-Thr-Val-Cys]-OH |
| 90 | H-c[Cys-Phe-Ala-Trp-Lys-Thr-Gly-Cys]-OH |
| 91 | H-Phe-c[Cys-Phe-Ala-Trp-Lys-Thr-Phe-Cys]-OH |
| 92 | H-N(Cbm)-Tyr-c[Cys-Phe-Ala-Trp-Lys-Thr-Phe-Cys]-OH |

TABLE 4-continued

Sequence ID List

| SEQ ID | Sequences |
|---|---|
| 93 | H-N(Cbm)-Tyr-c[Cys-Phe-Amp-Trp-Lys-Thr-Phe-Cys]-OH |
| 94 | H-Tyr-c[Cys-Phe-4Iamp-Trp-Lys-Thr-Phe-Cys]-OH |
| 95 | H-c[$^D$Cys-Phe-Tyr-threo-(2S,3R)C$^\beta$Me-2Nal-Lys-Thr-Phe-Cys]-OH |
| 96 | H-c[Cys-Phe-Tyr-threo-(2S,3R)C$^\beta$Me-2Nal-Lys-Thr-Phe-Cys]-OH |

Figure 18A:
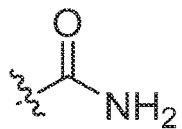
FIG. 18A and FIG. 18B illustrate the abbreviations and modification of amino acids.
Figure 18A:
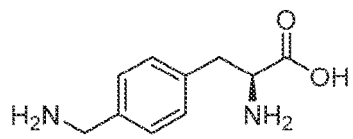
Figure 18A:
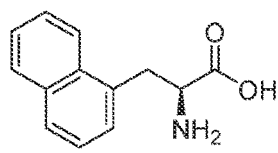
Figure 18A:
Figure 18A:
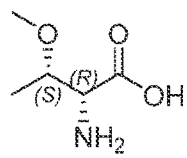
Figure 18A:
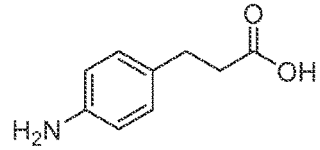
Figure 18A:
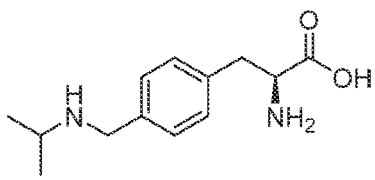
Figure 18A:
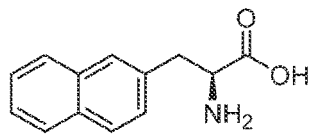
Figure 18A:
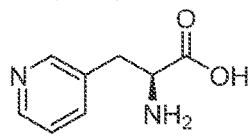
Figure 18A:
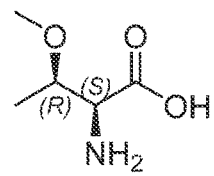
Figure 18B:
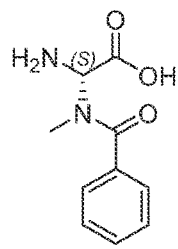
Figure 18B:
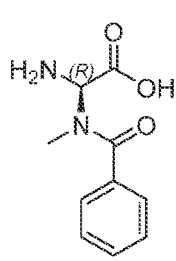
Figure 18B:
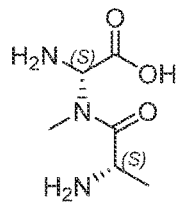
Figure 18B:
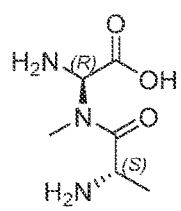
Figure 18B:
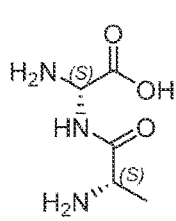
Figure 18B:
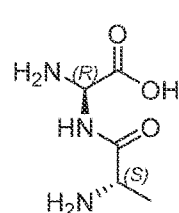
Figure 18B:
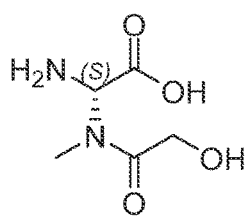
Figure 18B:
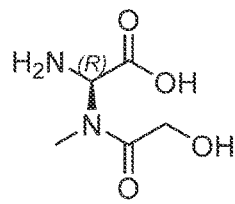

Exemplary abbreviations and modifications in Table 4 are illustrated in FIG. 18A and FIG. 18B.

Figure 2A:
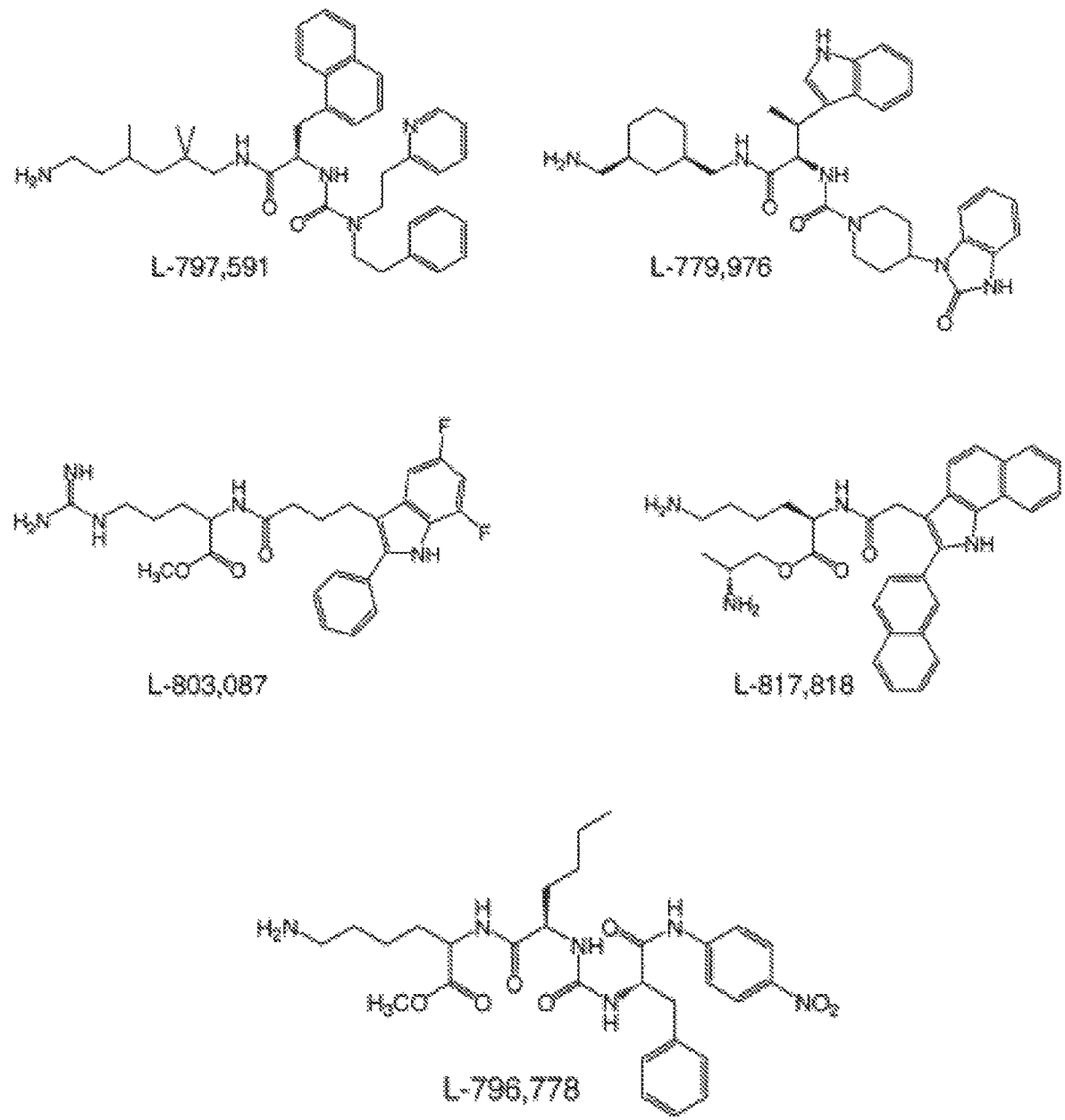
FIG. 2A illustrates the structures of exemplary small molecule targeting ligands.
Figure 2B:
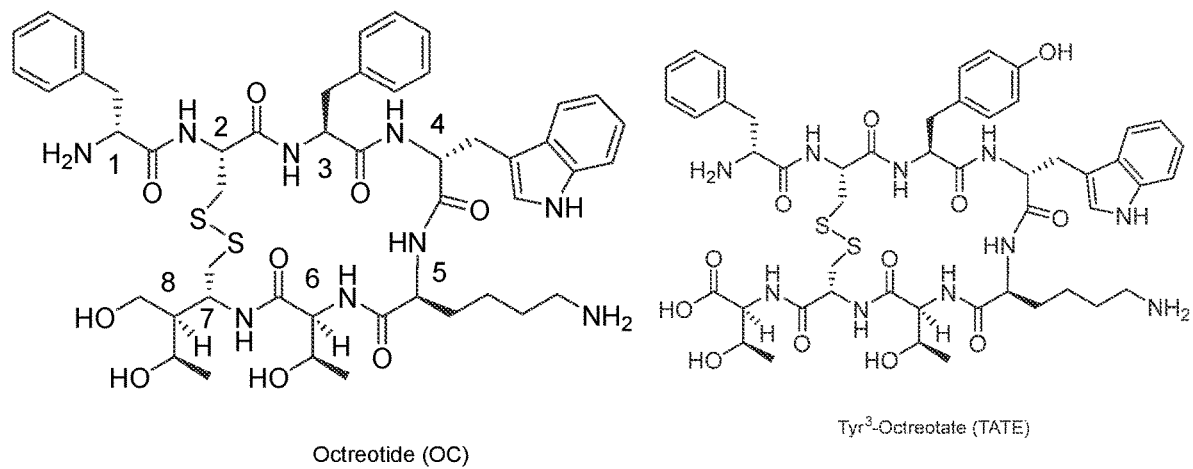
FIG. 2B illustrates the structures of exemplary binding peptide.
Figure 2B:
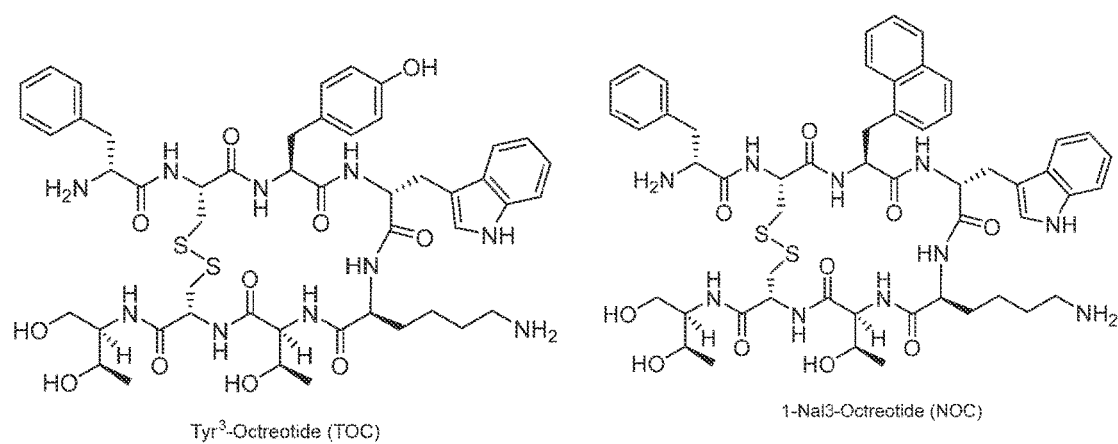
Figure 3:
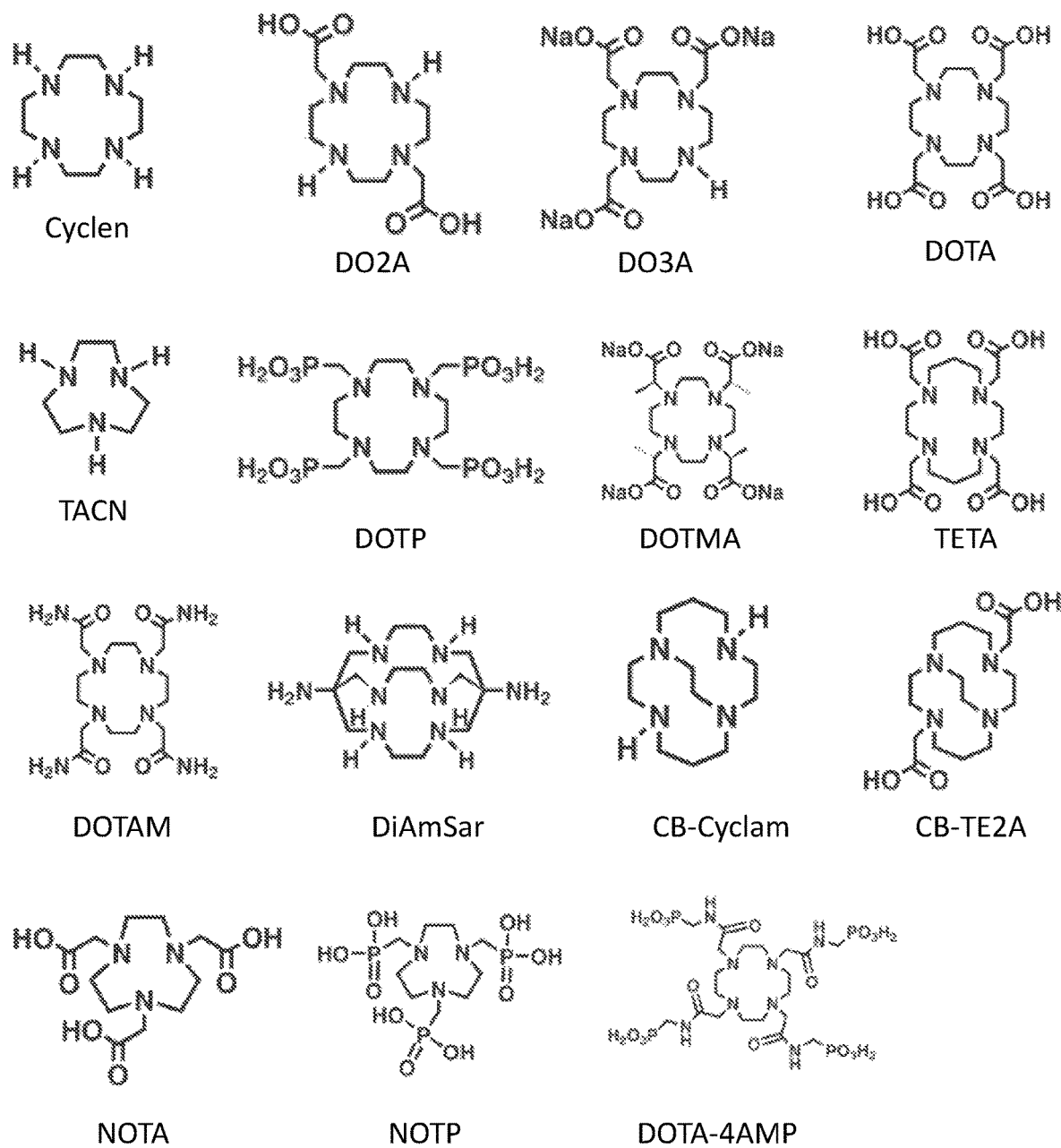
FIG. 3-FIG. 17 depict the structures of representative metal chelators.
Figure 4:
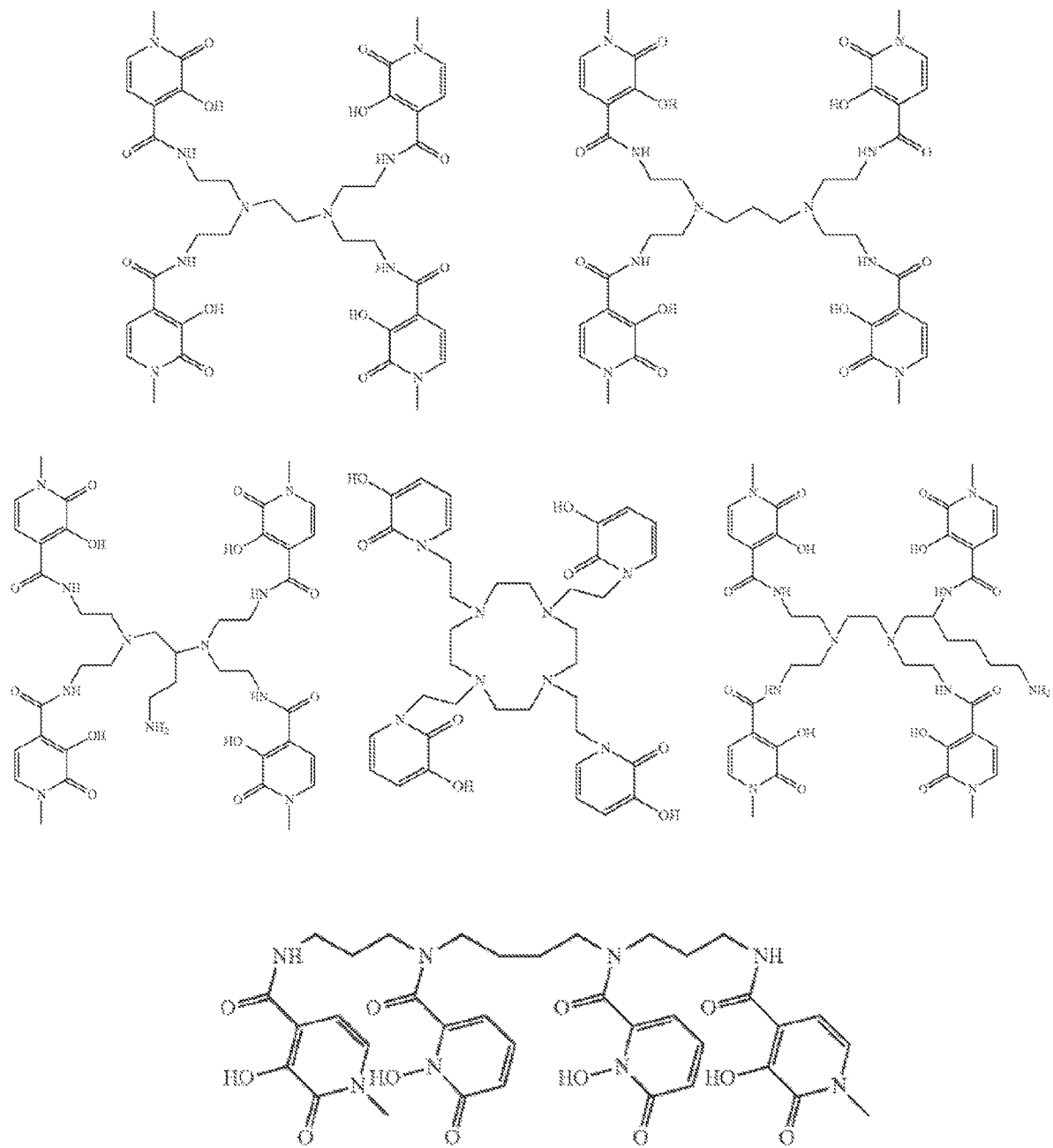
Figure 5:
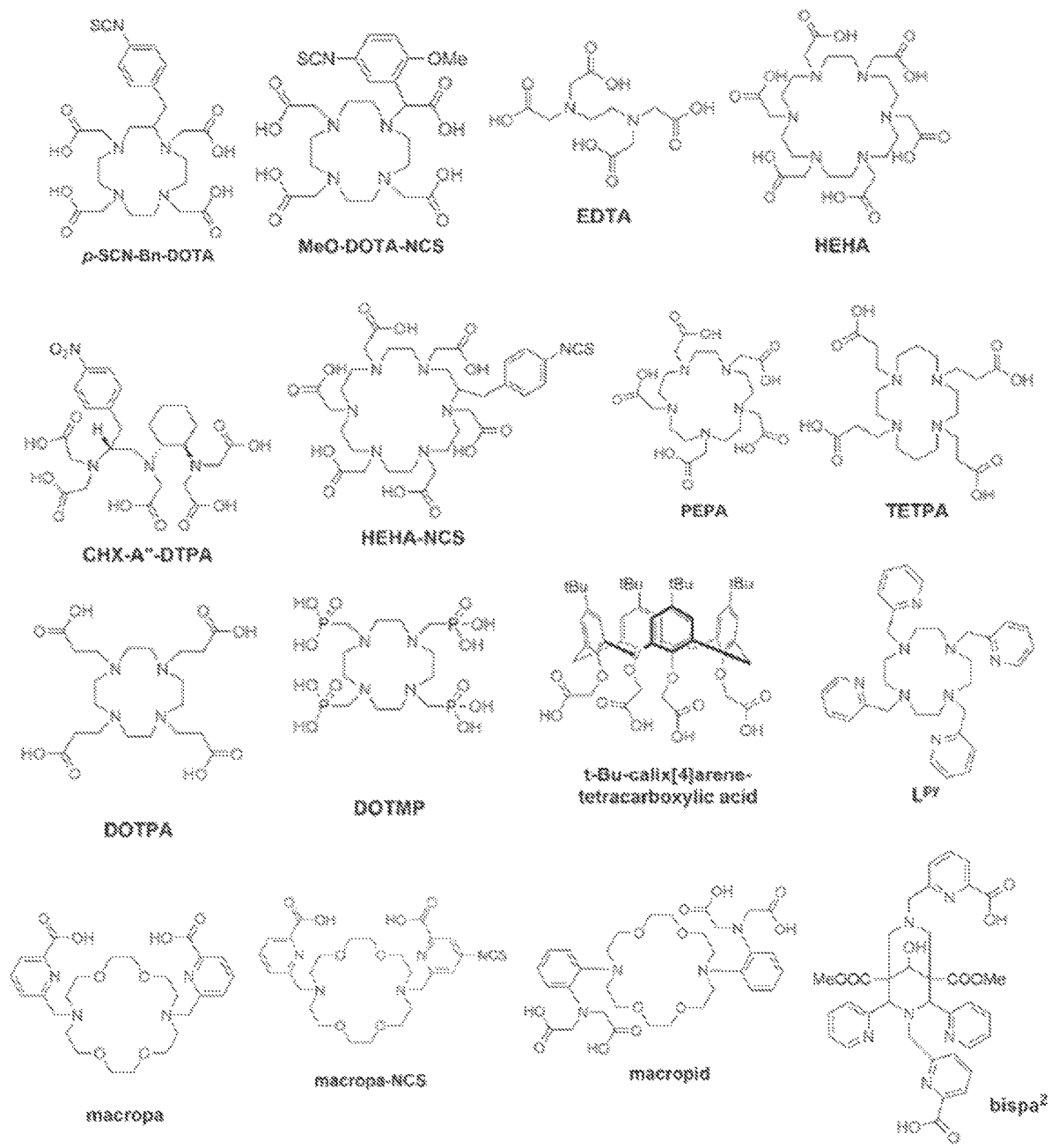
Figure 6:
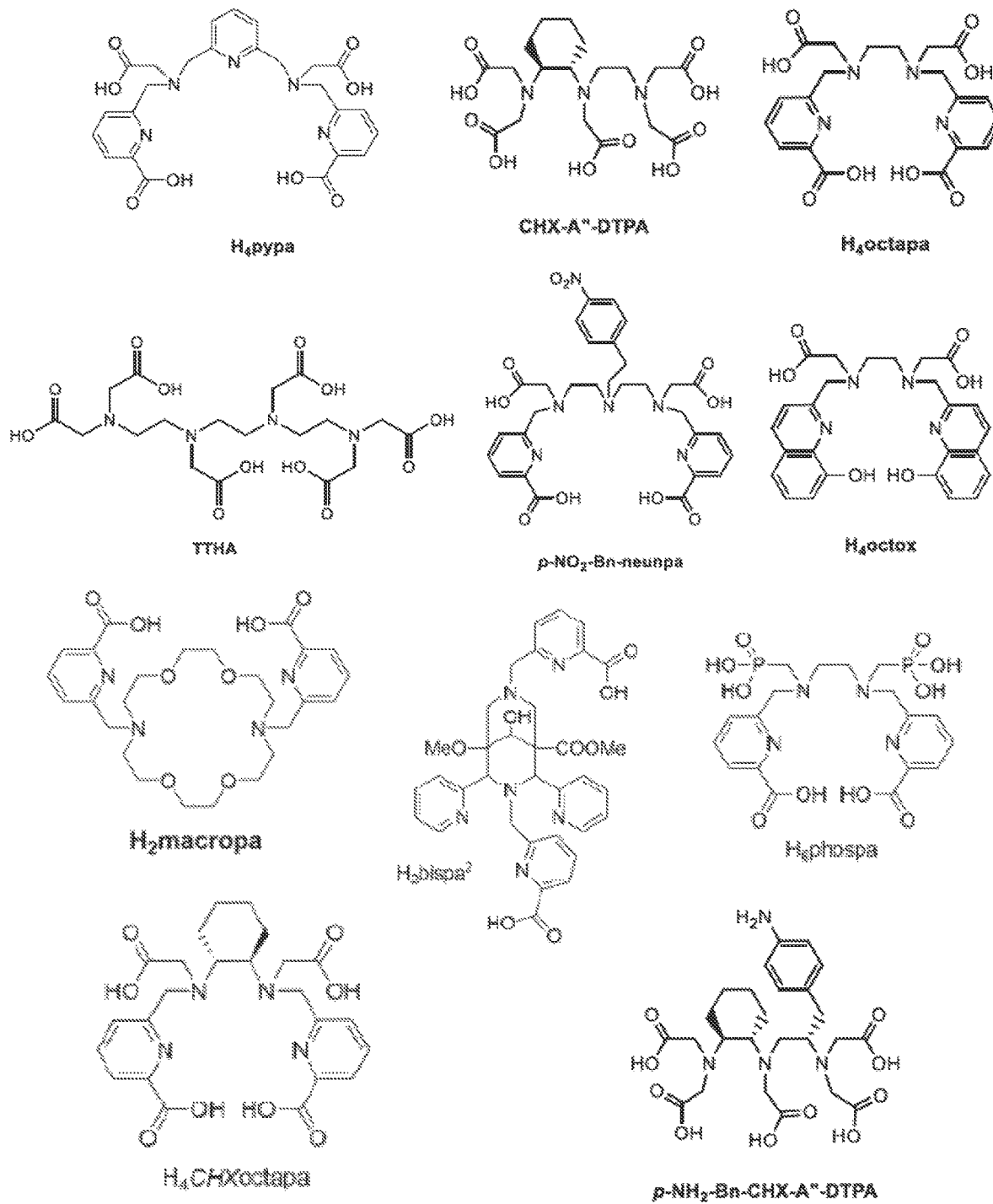
Figure 7:
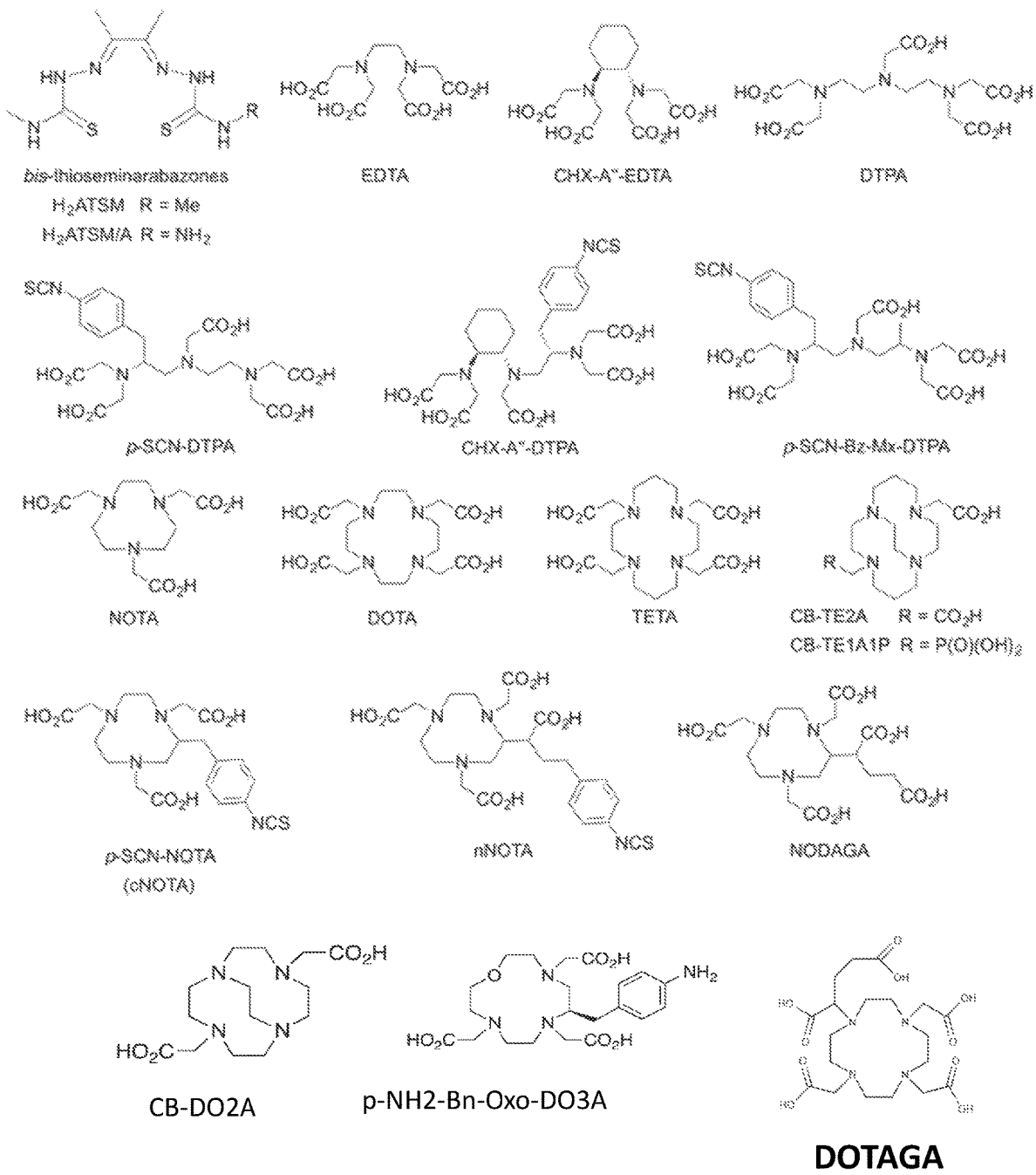
Figure 8:
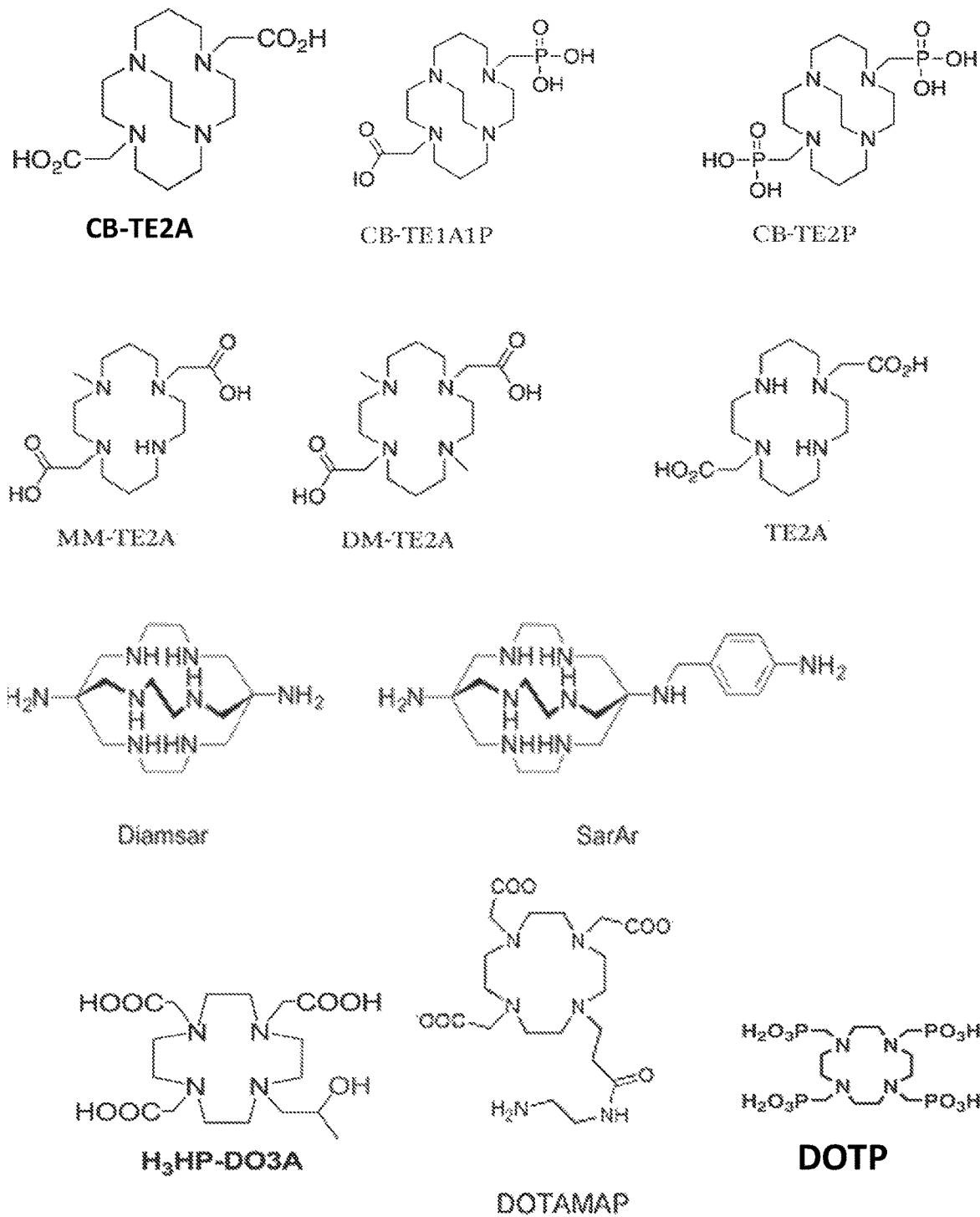
Figure 9:
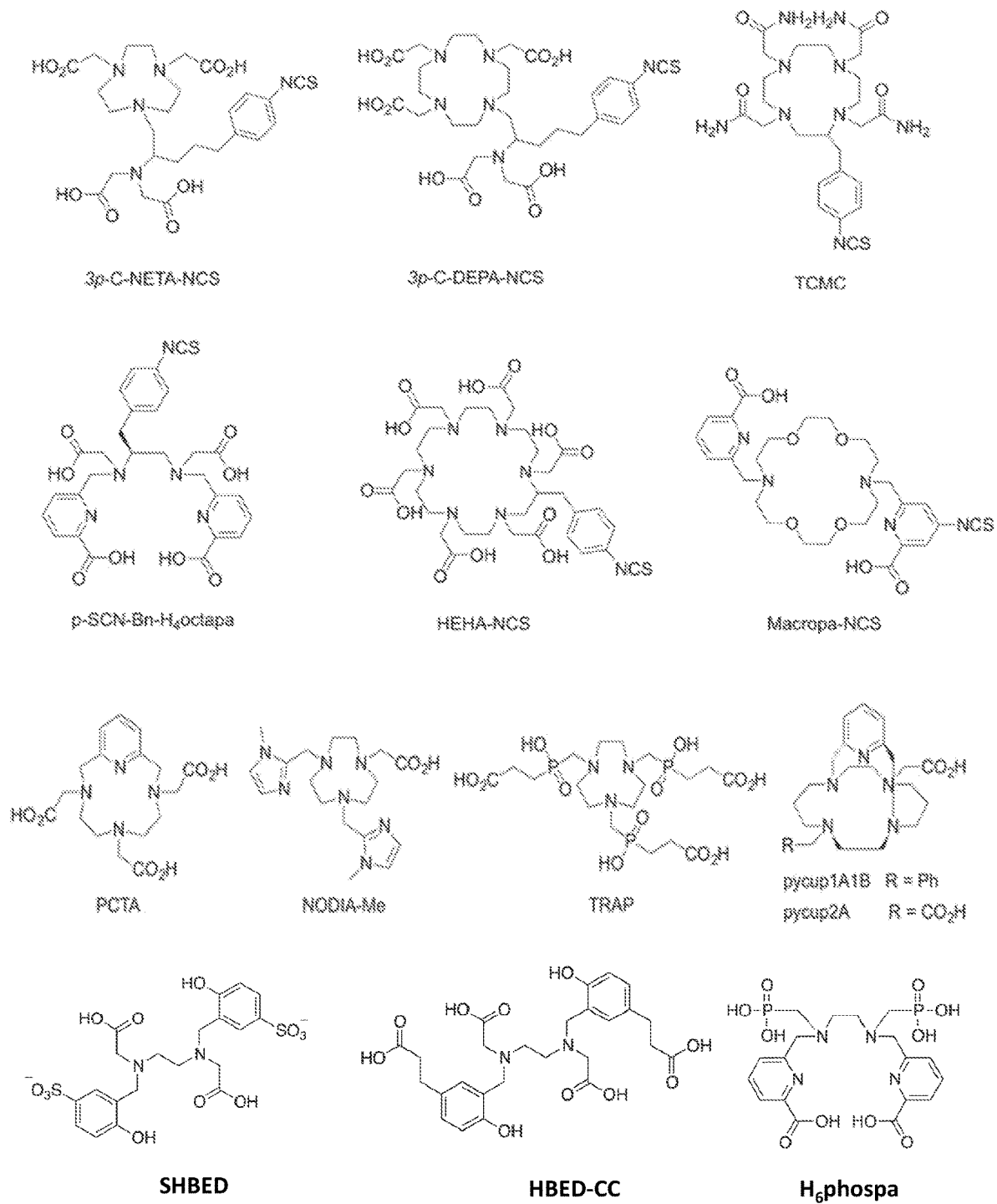
Figure 10:
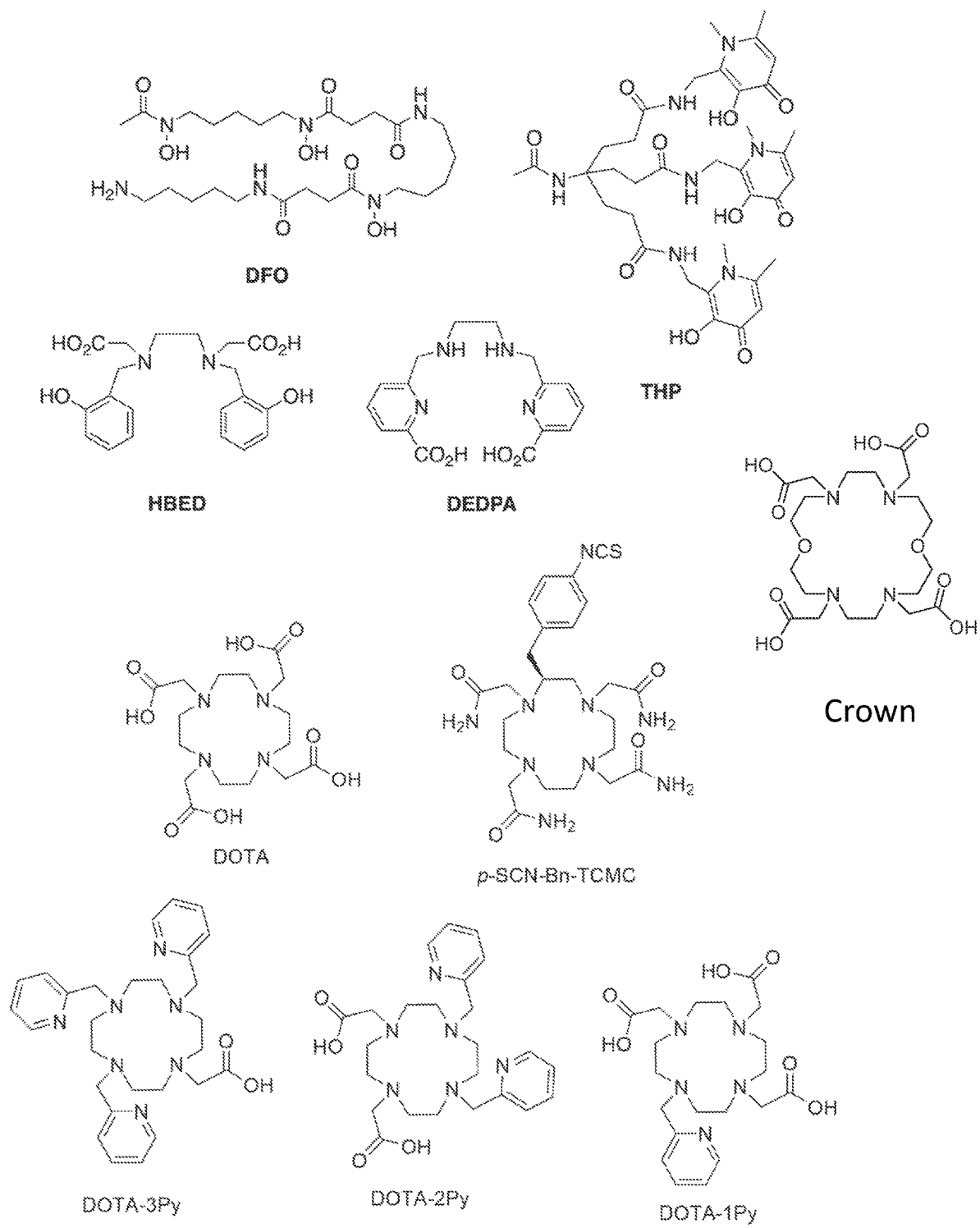
Figure 11:
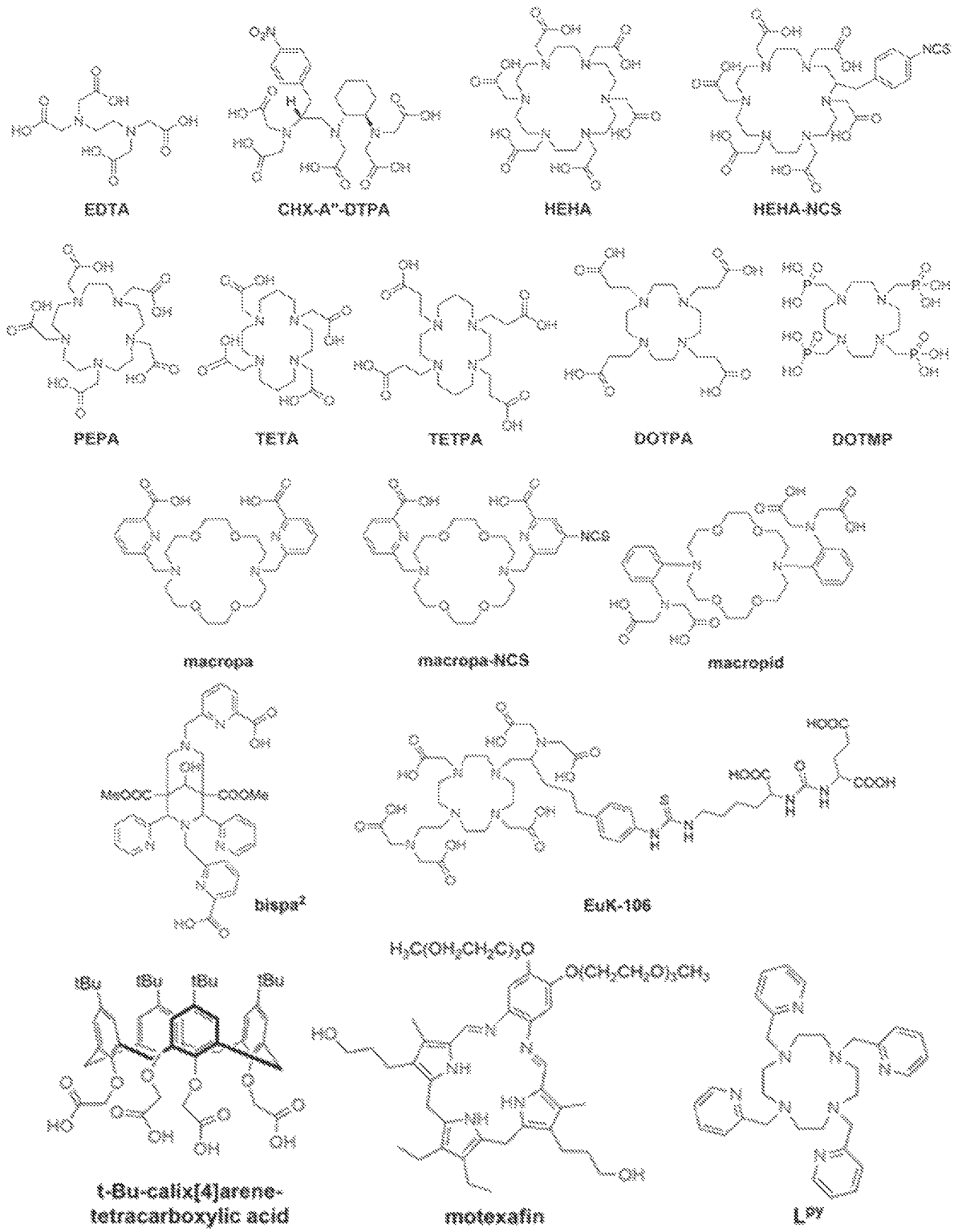
Figure 12:
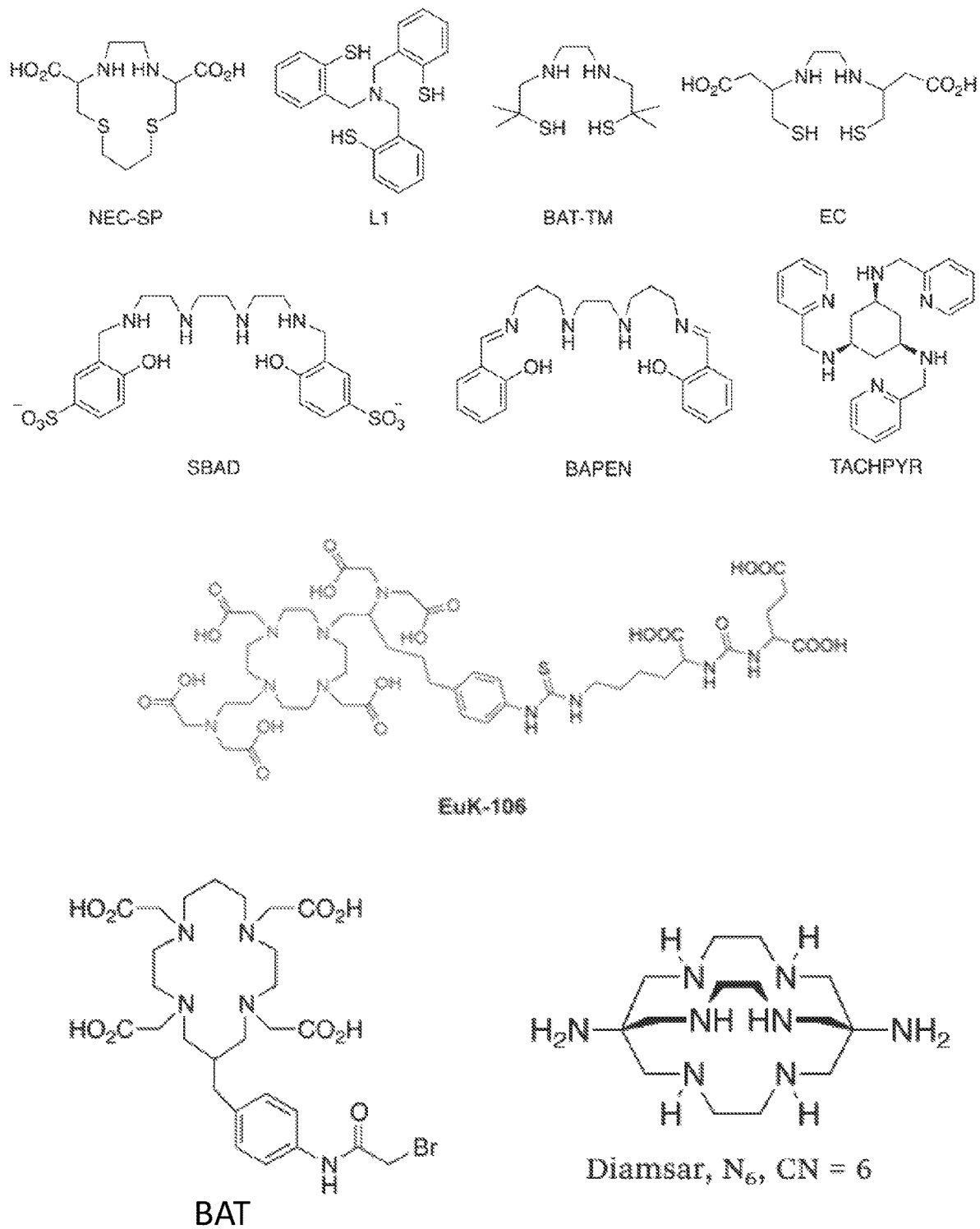
Figure 13:
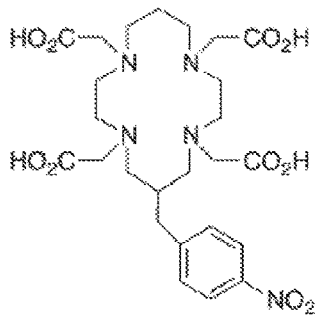
Figure 13:
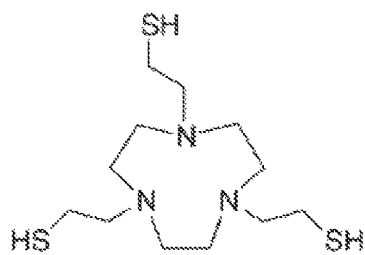
Figure 13:
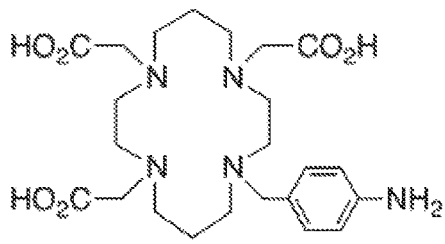
Figure 13:
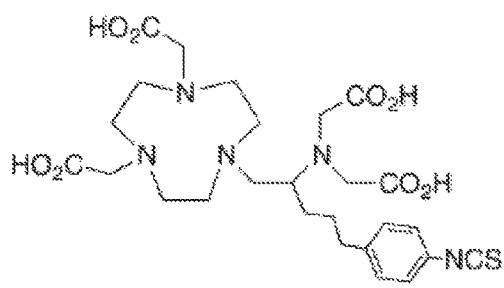
Figure 13:
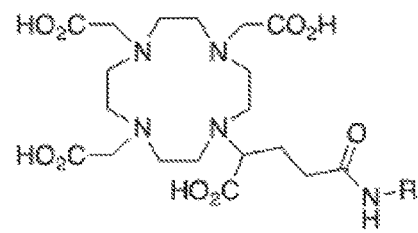
Figure 13:
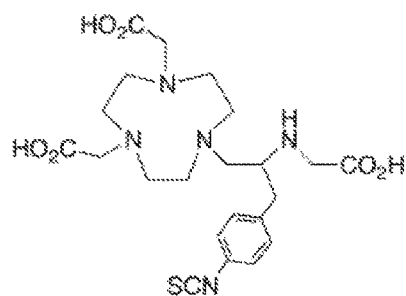
Figure 13:
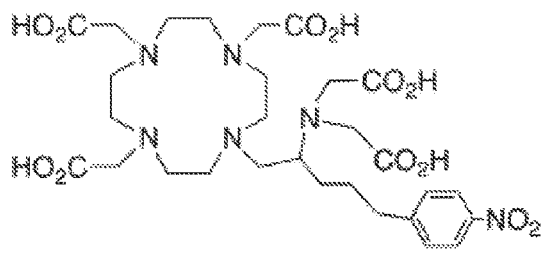
Figure 13:
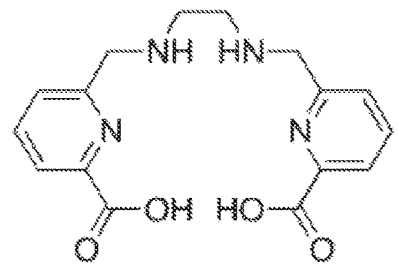
Figure 14:
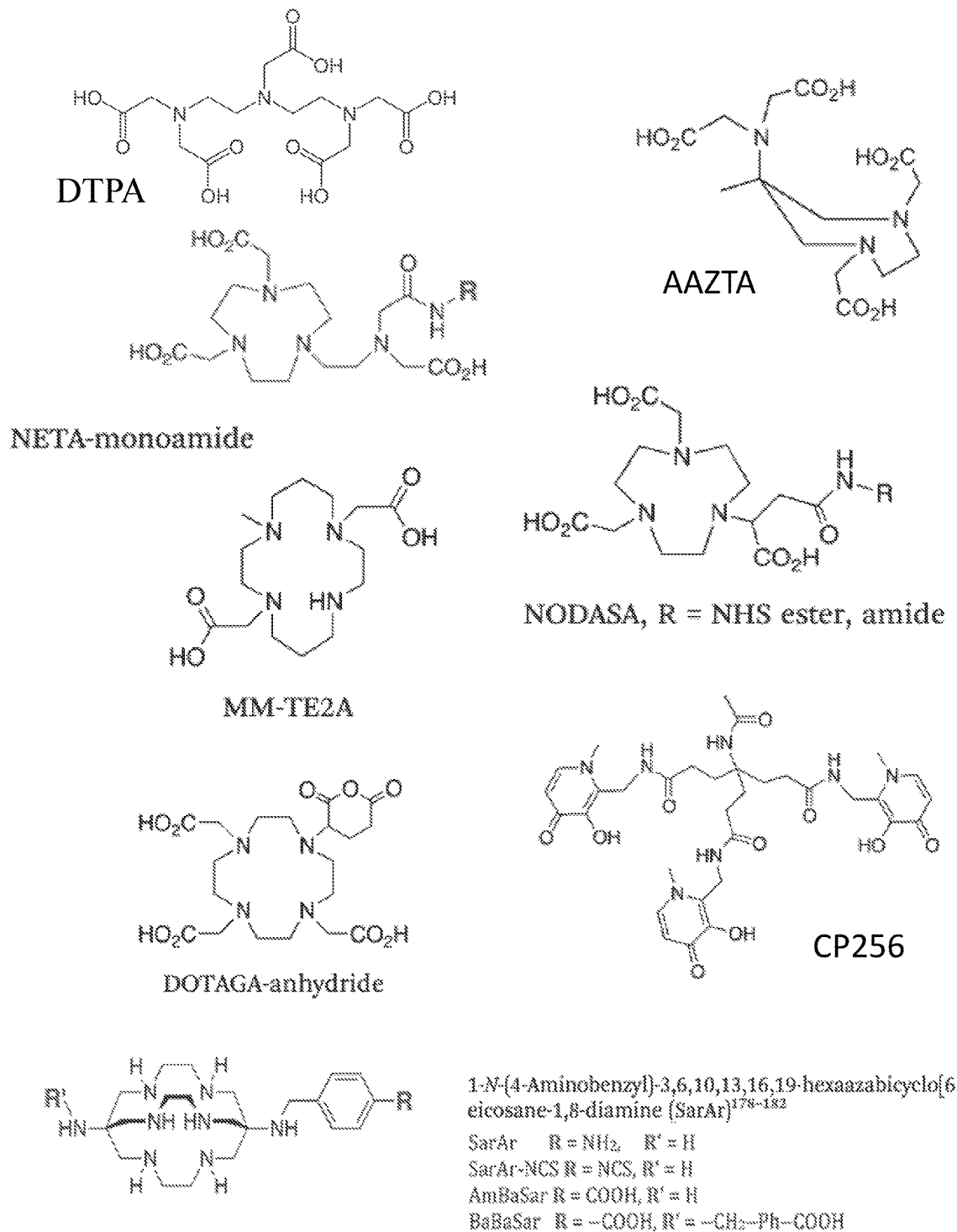
Figure 15:
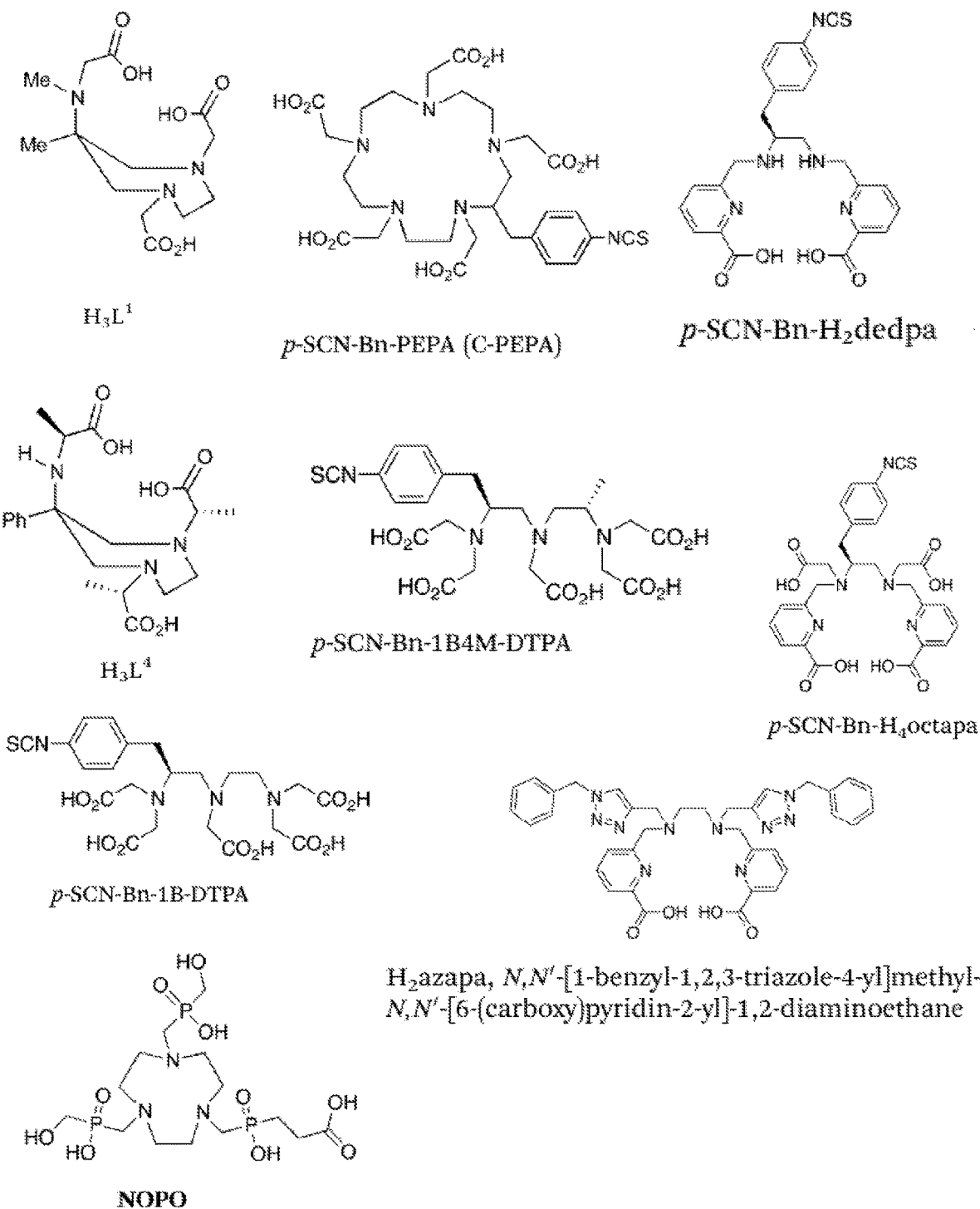
Figure 16:
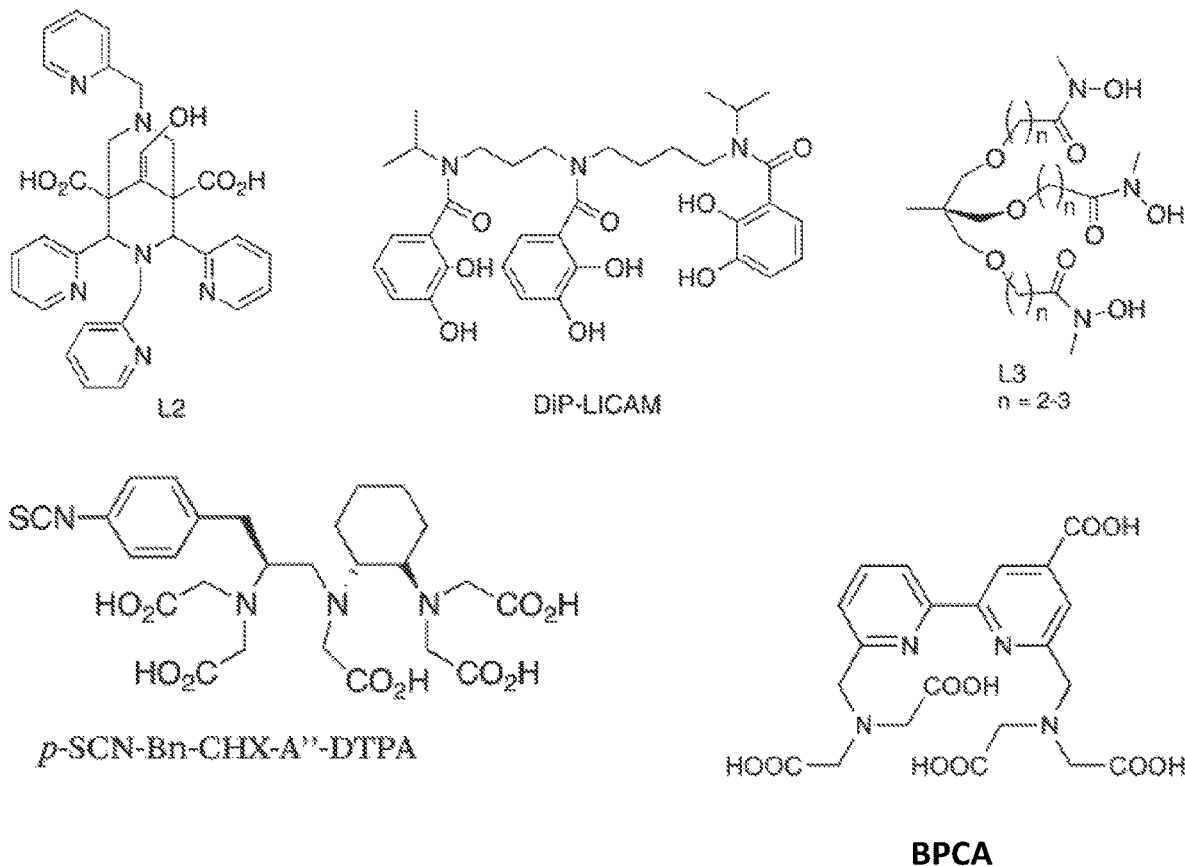
Figure 17:
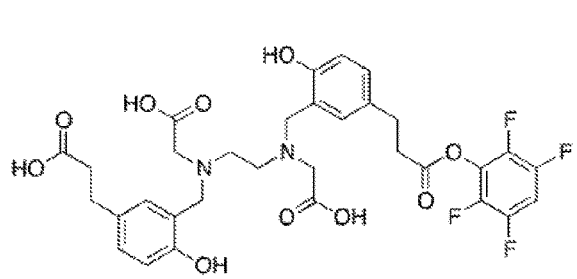
Figure 17:
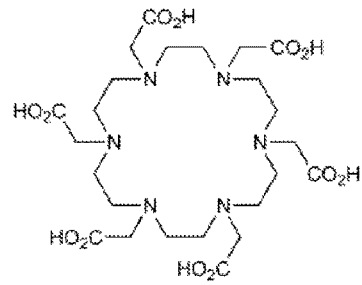
Figure 17:
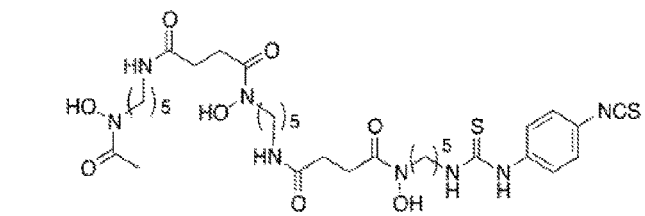
Figure 17:
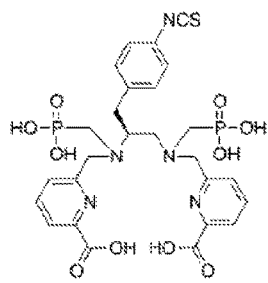
Figure 17:
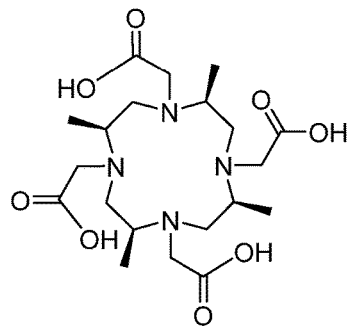
Figure 17:
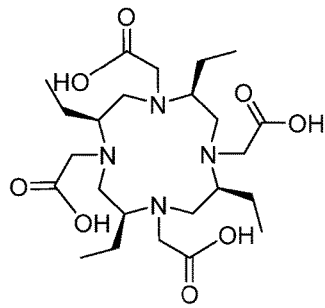

The targeting ligands can further comprise small molecule compounds. Such small molecule compounds can comprise L-797,591, L-779,976, L-796,778, L-803,087, or L-817,818, the structures of which are illustrated in FIG. 2A The targeting ligand can have a binding affinity to a human SSR that is not more than about 1 mM, by half maximal inhibitory concentration ($IC_{50}$). The targeting ligand can have a binding affinity to a human SSR that is not more than about 1000 nM, by half maximal inhibitory concentration ($IC_{50}$). The targeting ligand can have a binding affinity to a human SSR that is not more than about 500 nM, by half maximal inhibitory concentration ($IC_{50}$). The targeting ligand can have a binding affinity to a human SSR that is not more than about 250 nM, by half maximal inhibitory concentration ($IC_{50}$). The targeting ligand can have a binding affinity to a human SSR that is not more than about 200 nM, by half maximal inhibitory concentration ($IC_{50}$). The targeting ligand can have a binding affinity to a human SSR that is not more than about 150 nM, by half maximal inhibitory concentration ($IC_{50}$). The targeting ligand can have a binding affinity to a human SSR that is not more than about 100 nM, by half maximal inhibitory concentration ($IC_{50}$). The targeting ligand can have a binding affinity to a human SSR that is not more than about 75 nM, by half maximal inhibitory concentration ($IC_{50}$). The targeting ligand can have a binding affinity to a human SSR that is not more than about 50 nM, by half maximal inhibitory concentration ($IC_{50}$). The targeting ligand can have a binding affinity to a human SSR that is not more than about 25 nM, by half maximal inhibitory concentration ($IC_{50}$). The targeting ligand can have a binding affinity to a human SSR that is not more than about 10 nM, by half maximal inhibitory concentration ($IC_{50}$). The targeting ligand can have a binding affinity to a human SSR that is not more than about 5 nM, by half maximal inhibitory concentration ($IC_{50}$). The targeting ligand can have a binding affinity to a human SSR that is not more than about 2 nM, by half maximal inhibitory concentration ($IC_{50}$). The targeting ligand can comprise a monocyclic peptide or peptide mimics or derivatives thereof.

Radionuclide

In one aspect, described herein are conjugates that comprise a radionuclide. Exemplary radionuclides include, but are not limited to, astatine-211, astatine-217, actinium-225, americium-243, radium-223, lead-212, lead-203, copper-64, copper-67, copper-60, copper-61, copper-62, bismuth-212, bismuth-213, gallium-68, gallium-67, dysprosium-154, gadolinium-148, gadolinium-153, samarium-146, samarium-147, samarium-153, terbium-149, thorium-227, thorium-229, iron-59, yttrium-86, indium-111, holmium-166, technetium-94, technetium-99m, yttrium-90, lutetium-177, terbium-161, rhenium-186, rhenium-188, cobalt-55, scandium-43, scandium-44, scandium-47, dysprosium-166, fluorine-18, or iodine-131.

Generally, the type of radionuclide used in a therapeutic radiopharmaceutical can be tailored to the specific type of cancer, the type of targeting moiety, etc. Radionuclides that undergo α-decay produce particles composed of two neutrons and two protons, and radionuclides that undergo β-decay emit energetic electrons from their nuclei. Some radionuclides can also emit Auger. In some embodiments, the conjugate comprises an alpha particle-emitting radionuclide. Alpha radiation can cause direct, irreparable double-strand DNA breaks compared with gamma and beta radiation, which can cause single-stranded breaks via indirect DNA damage. The range of these particles in tissue and the half-life of the radionuclide can also be considered in designing the radiopharmaceutical conjugate. Tables 5A and 5B below illustrate some properties of exemplary radionuclides.

TABLE 5A

Exemplary radionuclides

| Nuclide | Emission | Half-life (days) |
|---|---|---|
| Actinium-225 (Ac-225) | α | about 9.92 |
| Lutetium (Lu-177) | β | about 6.646 |
| Radium-223 | α | about 11.4 |
| Radium-224 | α | About 3.63 |
| Astatine-211 | α | about 0.3 |
| Yttrium-90 | β | about 2.7 |
| Iodine-131 | β | about 8 |
| Samarium-153 | β | about 1.9 |
| Lead-212 | β | about 0.4 |
| Bismuth-212 | α | about 0.04 |
| Thorium-227 | α | about 18.7 |
| Terbium-149 | α | about 0.17 |

TABLE 5B

Exemplary radionuclides

| Nuclide | Half-life |
|---|---|
| Lutetium-177 (Lu-177) | about 6.646 days |
| Indium-111 (In-111) | about 2.8 days |
| Gallium-68 (Ga-68) | about 68 minutes |
| Copper-64 (Cu-64) | about 12.7 hours |
| Zirconium-89 (Zr-89) | about 78.4 hours |

In some embodiments, a conjugate described herein comprises one or more independent radionuclides. In some embodiments, the conjugate comprises two radionuclides. In some embodiments, each of the one or more radionuclides is bound to a metal chelator of the conjugate. In some embodiments, two radionuclides of a conjugate are bound to the same metal chelator. In some embodiments, two radionuclides of a conjugate are bound to two independent metal chelators. In some embodiments, each of the one or more radionuclides is an alpha particle-emitting radionuclide.

In some embodiments, a conjugate described herein comprises an alpha particle-emitting radionuclide. In some embodiments, the alpha particle-emitting radionuclide is actinium-225 ($^{225}$Ac), astatine-211 ($^{211}$At), radium-223 ($^{223}$Ra), radium-224 ($^{224}$Ra) bismuth-213 ($^{213}$Bi), Terbium-149 ($^{149}$Th), or thorium-227 ($^{227}$Th). In some embodiments, the alpha particle-emitting radionuclide is $^{225}$Ac. In some embodiments, the alpha particle-emitting radionuclide is $^{213}$Bi. In some embodiments, the alpha particle-emitting radionuclide is $^{212}$Bi. In some embodiments, the alpha particle-emitting radionuclide is $^{212}$Pb. In some embodiments, the alpha particle-emitting radionuclide is $^{224}$Ra. In some embodiments, the alpha particle-emitting radionuclide is $^{223}$Ra. In some embodiments, the alpha particle-emitting radionuclide is $^{227}$Th. In some embodiments, the alpha particle-emitting radionuclide is $^{211}$At. In some embodiments, the alpha particle-emitting radionuclide is $^{149}$Tb. In some embodiments, the radionuclide is Zirconium-89 ($^{89}$Zr). In some embodiments, a conjugate described herein comprises a radionuclide selected from $^{67}$Cu, $^{64}$Cu, $^{89}$Zr, $^{90}$Y, $^{109}$Pd, $^{111}$Ag, $^{149}$Pm, $^{153}$Sm, $^{166}$Ho, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{123}$I, $^{131}$I, $^{160}$Gd, $^{148}$Nd, $^{89}$Sr, and $^{211}$At. In some embodiments, the radionuclide is $^{225}$Ac. In some embodiments, the radionuclide is a decay daughter of $^{225}$Ac such as $^{221}$Fr, $^{217}$At, $^{213}$Bi, $^{213}$Po, $^{209}$Tl, $^{209}$Pb, or $^{209}$Bi. In some embodiments, the conjugate comprises two $^{225}$Ac radionuclides. In some embodiments, the radionuclide is $^{177}$Lu. In some embodiments, the conjugate comprises two $^{177}$Lu radionuclides.

In some embodiments, the conjugate comprises an alpha particle-emitting radionuclide bound to the metal chelator. In some embodiments, the alpha particle-emitting radionuclide is actinium-225, astatine-211, thorium-227, or radium-223. In some embodiments, the alpha particle-emitting radionuclide is actinium-225.

In some embodiments, the conjugate comprises a beta particle-emitting radionuclide bound to the metal chelator. In some embodiments, the beta particle emitting radionuclide is zirconium-89, yttrium-90, iodine-131, samarium-153, lutetium-177, or lead-212.

In some embodiments, the conjugate comprises a gamma particle emitting radionuclide. In some embodiments, the gamma particle emitting radionuclide is indium-111.

In some embodiments, conjugates described herein do not contain any radionuclide, i.e., a cold conjugate. For example, in some cases, a radionuclide can be replaced with a surrogate (e.g., $^{225}$Ac replaced with lanthanum) for testing and experimental purposes.

Metal Chelator

In one aspect, described herein are conjugates that comprise a metal chelator that is configured to bind with a radionuclide. The metal chelator can refer to a moiety of the conjugate that is configured to bind with a radionuclide. In some embodiments, a conjugate described herein comprises two or more independent metal chelators, e.g., 2, 3, 4, 5, or more metal chelators. In some embodiments, a conjugate described herein comprises two metal chelators, which can be the same or different. The metal chelator can be attached to the linker or the targeting ligand through any suitable group/atom of the chelator.

In some embodiments, the metal chelator is capable of binding a radioactive atom. The binding can be direct, e.g., the metal chelator can make hydrogen bonds or electrostatic interactions with the radioactive atom. The binding can also be indirect, e.g., the metal chelator binds to a molecule that comprises a radioactive atom. In some embodiments, the metal chelator comprises, or is, a macrocycle. In some embodiments, the metal chelator comprises, or is, DOTA or NOTA. In some embodiments, the metal chelator comprises a macrocycle, e.g., a macrocycle comprising an O and/or a N, DOTA, NOTA, one or more amines, one or more ethers, one or more carboxylic acids, EDTA, DTPA, TETA, DO3A, PCTA, or desferrioxamine.

In some embodiments, the metal chelator comprises a plurality of amines. In some embodiments, the metal chelator includes 4 or more N, 4 or more carboxylic acid groups, or a combination thereof. In some embodiments, the metal chelator does not comprise S. In some embodiments, the metal chelator comprises a ring. In some embodiments, the ring comprises an O and/or an N. In some embodiments, the metal chelator is a ring that includes 3 or more N, 3 or more carboxylic acid groups, or a combination thereof. In some embodiments, the metal chelator is poly polydentate.

In some embodiments, a metal chelator described herein comprises a cyclic chelating agent. Exemplary cyclic chelating agents include, but are not limited to, AAZTA, BAT, BAT-TM, Crown, Cyclen, DO2A, CB-DO2A, DO3A, H3HP-DO3A, Oxo-DO3A, p-NH$_2$-Bn-Oxo-DO3A, DOTA, DOTA-3py, DOTA-PA, DOTA-GA, DOTA-4AMP, DOTA-2py, DOTA-1py, p-SCN-Bn-DOTA, CHX-A"-EDTA, MeO-DOTA-NCS EDTA, DOTAMAP, DOTAGA, DOTAGA-anhydride, DOTMA, DOTASA, DOTAM, DOTP, CB-Cyclam, TE2A, CB-TE2A, CB-TE2P, DM-TE2A, MM-TE2A, NOTA, NOTP, HEHA, HEHA-NCS, p-SCN-Bn-HEHA, DTPA, CHX-A"-DTPA, p-NH$_2$-Bn-CHX-A"-DTPA, p-SCN-DTPA, p-SCN-Bz-Mx-DTPA, 1B4M-DTPA, p-SCN-Bn1B-DTPA, p-SCN-Bn-1B4M-DTPA, p-SCN-Bn-CHX-A"-DTPA, PEPA, p-SCN-Bn-PEPA, TETPA, DOTPA, DOTMP, DOTPM, t-Bu-calix[4]arene-tetracarboxylic acid, macropa, macropa-NCS, macropid, H$_3$L$^1$, H$_3$L$^4$, H2azapa, H5decapa, bispa2, H4pypa, H4octapa, H4CHXoctapa, p-SCN-Bn-H4octapa, p-SCN-Bn-H4octapa, TTHA, p-NO$_2$-Bn-neunpa, H4octox, H2macropa, H2bispa2, H4phospa, H6phospa, p-SCN-Bn-H6phospa, TETA, p-NO$_2$-Bn-TETA, TRAP, TPA, HBED, SHBED, HBED-CC, (HBED-CC)TFP, DMSA, DMPS, DHLA, lipoic acid, TGA, BAL, Bis-thioseminarabazones, p-SCN-NOTA, nNOTA, NODAGA, CB-TE1A1P, 3P-C-NETA-NCS, 3p-C-DEPA, 3P-C-DEPA-NCS, TCMC, PCTA, NODIA-Me, TACN, pycup1A1B, pycup2A, THP, DEDPA, H2DEDPA, p-SCN-Bn-H2DEDPA, p-SCN-Bn-TCMC, motexafin, NTA, NOC, 3p-C-NETA, p-NH$_2$-Bn-TE3A, SarAr, DiAm-Sar, SarAr-NCS, AmBaSar, BaBaSar, TACN-TM, CP256, C-NE3TA, C-NE3TA-NCS, NODASA, NETA-monoamide, C-NETA, NOPO, BPCA, p-SCN-Bn-DFO, DFO-ChX-Mal, DFO, DFO-IAC, DFO-BAC, DiP-LICAM, EC, SBAD, BAPEN, TACHPYR, NEC-SP, L$^{py}$, L1, L2, L3, and EuK-106.

In some embodiments, the metal chelator is DO3A. In some embodiments, the metal chelator is PEPA. In some embodiments, the metal chelator is EDTA. In some embodiments, the metal chelator is CHX-A"-DTPA. In some embodiments, the metal chelator is HEHA. In some embodiments, the metal chelator is DOTMP. In some embodiments, the metal chelator is t-Bu-calix[4]arene-tetracarboxylic acid. In some embodiments, the metal chelator is macropa. In some embodiments, the metal chelator is macropa-NCS. In some embodiments, the metal chelator is H4py4pa. In some embodiments, the metal chelator is H4octapa. In some embodiments, the metal chelator is H4CHXoctapa. In some embodiments, the metal chelator is DOTP. In some embodiments, the metal chelator is crown.

In some embodiments, the metal chelator is DOTA. In some embodiments, the metal chelator is a chiral derivative of DOTA. Exemplary chiral DOTA chelators are described in Dai et al., Nature Communications (2018) 9:857. In some embodiments, the metal chelator is 2,2',2",2'''-((2S,5S,8S,11S)-2,5,8,11-tetramethyl-1,4,7,10-tetraazacyclododecane-1,4,7,10-tetrayl)tetraacetic acid. In some embodiments, the metal chelator has a structure of

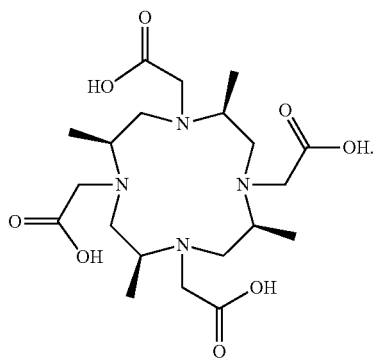 [SMILES: C[C@H]1CN(CC(=O)O)[C@@H](C)CN(CC(=O)O)[C@@H](C)CN(CC(=O)O)[C@@H](C)CN1CC(=O)O]

In some embodiments, the metal chelator is 2,2',2",2'''-((2S,5S,8S,11S)-2,5,8,11-tetraethyl-1,4,7,10-tetraazacyclododecane-1,4,7,10-tetrayl)tetraacetic acid. In some embodiments, the metal chelator has a structure of

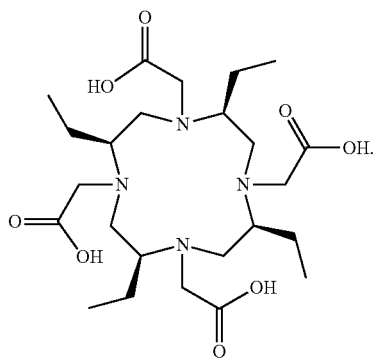 [SMILES: CC[C@H]1CN(CC(=O)O)[C@@H](CC)CN(CC(=O)O)[C@@H](CC)CN(CC(=O)O)[C@@H](CC)CN1CC(=O)O]

In some embodiments, the conjugate comprises DOTA. In some embodiments, the conjugate comprises a DOTA derivative such as p-SCN-Bn-DOTA and MeO-DOTA-NCS. In some embodiments, the conjugate comprises two independent metal chelators, and at least one or both are DOTA. The structures of some exemplary metal chelators are illustrated in FIGS. 3-17 (without showing the attachment points). Exemplary metal chelators are further described in WO2012/174136; US20130183235A1; US20120219495A1; Ramogidaand et al., EJNMMI radiopharm. chem. 4, 21 (2019); Thiele et al., Cancer Biotherapy and Radiopharmaceuticals 2018; Li et al., Bioconjugate Chem. 2019, 30, 5, 1539-1553; and Baranyai et al., Eur. J. Inorg. Chem. 36-56 (2020), each of which is incorporated by reference in its entirety.

Linker

Chemical scaffold, covalently joining pharmacophore and metal-chelator in a targeted radiopharmaceutical, can be referred to as a linker. Incorporating a well-designed inker to a drug molecule can further boost affinity towards its biological target, accelerate internalization into the targeted tissues, and optimize the pharmacokinetic properties. Diverse chemical moieties can be used to construct the linkers. By changing their physio-chemical characters, the desired in vivo characters (i.e. absorption, distribution, metabolism, and excretion of the drug molecules) can be achieved. In some embodiments, physio-chemical characters of the conjugates can be adjusted by the linkers, for example, when it is difficult to change pharmacophore and metal-chelating portions without sacrificing the biological affinity or metal-binding ability. A conjugate described herein can comprise one or more linkers. The targeting ligand can be covalently linked to the metal chelator through a linker. The linker can covalently attach the targeting ligand with the metal chelator. The targeting ligand can also attach directly to the metal chelator without a linker. 10161J A linker can comprise one or more amino acid residues. The linker can comprise 1 to 3, 1 to 5, 1 to 10, 5 to 10, or 5 to 20 amino acid residues. The linker can comprise 1, 2, 3, 4, 5, 6, 7, 8, 9, or 10 amino acid residues. The linker can comprise 1 to 5 amino acid residues. For example, the linker can comprise one or more lysine (K) residues such as K, KK, or KKK sequences. The linker can comprise a lysine or a derivative thereof. The linker can comprise a lysine. The linker can comprise one or more amino acids that are unnatural amino acids.

A herein-described linker can attach to the N-terminus of the peptide, the C-terminus of the peptide, or a non-terminal amino acid of the peptide, or it can attach to the peptide through a combination of the above. In some embodiments, the linker is attached to the peptide via its N-terminus. In some embodiments, the linker is attached to the peptide via its C-terminus. In some embodiments, the linker is attached to the peptide via a non-terminal amino acid. The linker can be bonded to the peptide, the metal chelator, or both, for example, through a chemically reactive group. Exemplary chemically reactive groups include, but are not limited to, a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound to the peptide can be a natural or unnatural amino acid of the peptide and/or it can be introduced into the peptide, e.g., by DNA recombinant technology (e.g., by introducing a cysteine or protease cleavage site in the amino acid sequence) or by protein biochemistry (e.g., reduction, pH adjustment or proteolysis). Exemplary methods for attaching the linker includes carbodiimide reaction, reactions using bifunctional agents such as dialdehydes or imidoesters, Schiff base reaction, Suzuki-Miyaura cross-coupling reactions, Isothiocyanates as coupling agents, and click chemistry.

The linker can have a prescribed length thereby linking the metal chelator (and optionally radionuclide) and the peptide while allowing an appropriate distance therebetween. In some embodiments, the linker has 1 to 100 atoms, 1 to 60 atoms, 1 to 30 atoms, 1 to 15 atoms, 1 to 10 atoms, 1 to 5, or 2 to 20 atoms in length. In some embodiments, the linker has 1 to 10 atoms in length.

The linker can comprise flexible and/or rigid regions. Exemplary flexible linker regions include those comprising Gly and Ser residues ("GS" linker), glycine residues, alkylene chain, PEG chain, etc. Exemplary rigid linker regions include those comprising alpha helix-forming sequences (e.g., EAAAK (SEQ ID NO: 104)), proline-rich sequences, and regions rich in double and/or triple bonds.

In some embodiments, the linker comprises a click chemistry residue. The linker can be attached to the peptide, to the metal chelator, or both via click chemistry, thereby forming a click chemistry residue. For example, the peptide can comprise an azide group (at N- or C-terminus or at a non-terminal amino acid) that reacts with an alkyne moiety of the linker. For another example, the peptide can comprise an alkyne group (at N- or C-terminus or at a non-terminal amino acid) that reacts with an azide of the linker. The metal chelator and the linker can be attached similarly. In some embodiments, the linker comprises an azide moiety, an alkyne moiety, or both.

A linker described herein can comprise one or more motifs. One or more of the motifs can be connected via click chemistry such that they can be clicked in/out of the linker. Each of the motifs in a linker can have independent functions. For example, a linker can comprise a motif that functions to adjust plasma half-life and/or a motif that functions as a spacer between the peptide and metal chelator.

In some embodiments, the linker has a structure of

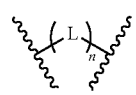

Formula (I)

wherein each L is independently —O—, —NR$^L$—, —N(R$^L$)$_2$$^+$—, —OP(=O)(OR$^L$)O—, —S—, —S(=O)—, —S(=O)$_2$—, =CH—, —C(=O)—, —C(=O)O—, —OC(=O)—, —OC(=O)O—, —OC(=O)NR$^L$—, —NR$^L$C(=O)O—, —CR$^L$=N—, —N=CR$^L$, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_{30}$ alkylene, substituted or unsubstituted $C_2$-$C_{30}$ alkenylene, substituted or unsubstituted $C_2$-$C_{30}$ alkynylene, substituted or unsubstituted $C_1$-$C_{30}$ heteroalkylene, —($C_1$-$C_{30}$ alkylene)-O—, —O—($C_1$-$C_{30}$ alkylene)-, —($C_1$-$C_{30}$ alkylene)-NR$^L$—, —NR$^L$—($C_1$-$C_{30}$ alkylene)-, —($C_1$-$C_{30}$ alkylene)-N(R$^L$)$_2$$^+$—, —N(R$^L$)$_2$$^+$—($C_1$-$C_{30}$ alkylene)-, or a click chemistry residue; and each R$^L$ is independently hydrogen, substituted or unsubstituted $C_1$-$C_4$ alkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; and n is 1, 2, 3, 4, 5, 6, 7, 8, 9, 10, 11, 12, 13, 14, or 15.

Isomers/Stereoisomers

In some embodiments, the compounds described herein exist as geometric isomers. In some embodiments, the compounds described herein possess one or more double bonds. The compounds presented herein include cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Tautomers

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

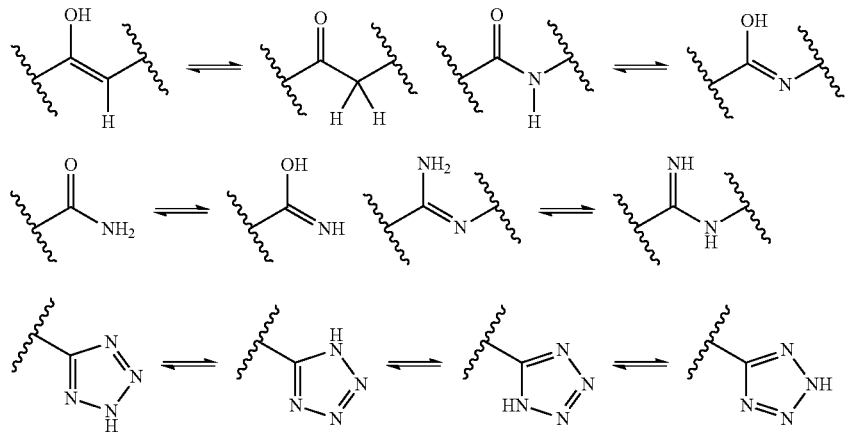

-continued

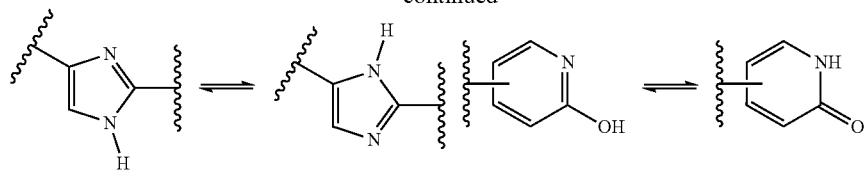

In some instances, the compounds disclosed herein exist in tautomeric forms. The structures of said compounds are illustrated in the one tautomeric form for clarity. The alternative tautomeric forms are expressly included in this disclosure.

Labeled Compounds.

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are notable for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts.

In some embodiments, the compounds described herein exist as their pharmaceutically acceptable salts. In some embodiments, the compounds disclosed herein include their pharmaceutically acceptable salts. As used herein, a "pharmaceutically acceptable salt" refers to any salt of a stabilizing agent that is useful for stabilizing the radiopharmaceutical compositions. As used herein, a "pharmaceutically acceptable salt" refers to any salt of a stabilizing agent that is useful for preventing or delaying the decomposition of the radiopharmaceutical within the compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral acid, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid, metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, the compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts, and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates.

In some embodiments, the compounds described herein exist as solvates. Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein. Accordingly, one aspect of the present disclosure pertains to hydrates and solvates of compounds of the present disclosure and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like.

Preparation of the Compositions

The disclosure provides methods of preparing and making the compositions described herein. In some embodiments, the method of making the radiopharmaceutical composition comprises combining a radionuclide (such as $^{225}$Ac) with a pre-labeled conjugate (e.g., DOTATATE or DOTATOC) in the presence of one or more stabilizer agents, wherein the pre-labeled conjugate comprises a targeting ligand and a metal chelator covalently attached to the targeting ligand, thereby producing a mixture comprising a labeled conjugate (e.g., $^{225}$Ac-DOTATATE or $^{225}$Ac-DOTATOC), and optionally combining one or more stabilizing agents to the mixture. In some embodiments, the method of making the radiopharmaceutical composition comprises combining a radionuclide with a pre-labeled conjugate, wherein the pre-labeled conjugate comprises a targeting ligand and a metal chelator covalently attached to the targeting ligand, thereby producing a labeled conjugate, and combining the one or more stabilizing agents with the labeled conjugate.

In some embodiments, the method of making the radiopharmaceutical composition comprises combining a radionuclide with a pre-labeled conjugate, which further comprises a targeting ligand and a metal chelator covalently attached to the targeting ligand, thereby producing a labeled conjugate, and adding the one or more stabilizing agents to the labeled conjugate. In some embodiments, the method of making the radiopharmaceutical composition comprises combining a radionuclide with a pre-labeled conjugate which further comprises a targeting ligand and a metal chelator covalently attached to the targeting ligand, in the presence of one or more stabilizer agents, thereby producing a labeled conjugate, and optionally adding one or more stabilizing agents to the labeled conjugate.

The method of making the compositions can comprise one or multiple steps. One or more such steps can comprise diluting a radionuclide-containing solution or mixture to a desired concentration (i.e., a dilution step). The radionuclide-containing solution or mixture can be diluted by 2 to 1000 fold, e.g., 10-50 fold, 2-40 fold, 25-75 fold, or 50-100 fold. One or more such steps can comprise adding one or more stabilizing agents during the process of dilution. One or more such steps can comprise optionally adding one or more stabilizing agents during the process of dilution. One or more such steps can comprise diluting a pre-labeled conjugate solution or mixture to a desired concentration. One or more such steps can comprise adding one or more stabilizing agents before the process of dilution. One or more such steps can comprise adding one or more stabilizing agents after the process of dilution. The pre-labeled conjugate can comprise a targeting ligand and a metal chelator. The targeting ligand and the metal chelator can be linked covalently. One or more such steps can comprise dilution using a liquid solution or mixture.

A method of making a radiopharmaceutical composition can comprise reacting or combining a radionuclide with a pre-labeled conjugate solution or mixture to obtain a labeled conjugate solution or mixture (i.e., a labeling process). In some embodiments, the method comprises maintaining a temperature during the labeling process. In some embodiments, the method comprises maintaining a temperature ranging from 0° C. to 100° C., from 10° C. to 100° C., from 20° C. to 100° C., from 30° C. to 100° C., from 40° C. to 100° C., from 50° C. to 100° C., from 60° C. to 100° C., from 70° C. to 100° C., or from 80° C. to 100° C. In some embodiments, the method comprises reacting the radionuclide with the pre-labeled conjugate for a period of time. In some embodiments, the period of time is from about 1 minute to about 3 hours, from about 2 minutes to about 2.5 hours, from about 3 minutes to about 2 hours, from about 5 minutes to about 1.5 hours, from about 8 minutes to about 1 hours, or from about 10 minutes to about 30 minutes. In some embodiments, the method comprises mixing the radionuclide with the pre-labeled conjugate during the labeling process. One or more such steps can comprise mixing using laboratory mixing equipment such as a mixer, a vortex mixer, a stirrer, a magnetic stirrer, a spinner, a shaker, a centrifuge, or a homogenizer. One or more such steps can comprise shaking the reaction solution or mixture. One or more such steps can comprise shaking the reaction solution or mixture at a speed ranging from about 10 rpm to about 5000 rpm, from about 100 rpm to about 2500 rpm, from about 200 rpm to about 1000 rpm, from about 300 rpm to about 800 rpm, or from about 400 rpm to about 600 rpm. One or more such steps can comprise further diluting the labeled conjugate solution or mixture. One or more such steps can comprise adding one or more stabilizing agents during the process of dilution. One or more such steps can comprise optionally adding one or more stabilizing agents after the process of dilution.

In some embodiments, a radiopharmaceutical composition comprising [$^{225}$Ac]Ac-DOTA-TATE (or $^{225}$Ac-DOTA-TATE) can be prepared by reacting DOTA-TATE with [$^{225}$Ac]AcCl$_3$ from HCl (e.g., 0.04M, aqueous) solution. Accordingly, provide herein are methods of making a radiopharmaceutical composition comprising $^{225}$Ac-DOTA-TATE. In some embodiments, the method comprises one or more of the following steps: diluting DOTA-TATE with sodium acetate/acetic acid buffer solution, adding [$^{225}$Ac] AcCl$_3$ HCl solution to the diluted DOTA-TATE, mixing the mixture, heating the mixture, and diluting into a formulation buffer with one or more stabilizing agents described herein. In some embodiments, the concentration of [$^{225}$Ac]AcCl$_3$ in the HCl solution is about 10 µCi/µl HCl. In some embodiments, the concentration of [$^{225}$Ac]AcCl$_3$ in the HCl solution is about 1 to 50 µCi/µl HCl.

In some embodiments, a method of making a radiopharmaceutical composition comprising [$^{225}$Ac]Ac-DOTA-TATE or [$^{225}$Ac]Ac-DOTA-TOC comprises one or more of the following steps: providing [$^{225}$Ac]AcCl$_3$ solution in a first vial, transferring such solution into a reactor, providing a reaction buffer solution into the first vial containing [$^{225}$Ac]AcCl$_3$ solution, transferring the reaction buffer solution and residual [$^{225}$Ac]AcCl$_3$ solution from the first vial to the rector, transferring a DOTA-TATE or a DOTA-TOC solution into the reactor, reacting the DOTA-TATE or DOTA-TOC solution with [$^{225}$Ac]AcCl$_3$ solution in the reactor to obtain [$^{225}$Ac]Ac-DOTA-TATE or [$^{225}$Ac]Ac-DOTA-TOC, and diluting the [$^{225}$Ac]Ac-DOTA-TATE or [$^{225}$Ac]Ac-DOTA-TOC in a formulation buffer comprising one or more stabilizing agents described herein to form the radiopharmaceutical composition. In some embodiments, the molar ratio of $^{225}$Ac to DOTA-TATE or DOTA-TOC is from 1:1 to 1:10, from 1:1 to 1:8, from 1:1 to 1:5, from 1:1 to 1:3.5, from 1:1 to 1:2, or from 1:1 to 1.25. In some embodiments, the molar ratio of $^{225}$Ac to DOTA-TATE or DOTA-TOC is about 1:1, 1:2, 1:25, 1:3, 1:3.5 or 1:4.

The compounds used in the reactions and compositions described herein are made according to organic synthesis techniques known to those skilled in this art, starting from commercially available chemicals and/or from compounds described in the chemical literature. "Commercially available chemicals" are obtained from standard commercial sources including ABX advanced biochemical compounds GmbH (Radeberg, Germany), Acros Organics (Pittsburgh, PA), Aldrich Chemical (Milwaukee, WI, including Sigma Chemical and Fluka), Apin Chemicals Ltd. (Milton Park, UK), Avidity Science (U.S.A.), Avocado Research (Lancashire, U.K.), BDH, Inc. (Toronto, Canada), Bionet (Cornwall, U.K.), Chem Service Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), ITM (Munich, Germany), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Sigma-Aldrich (U.S.A.), Spectrum Quality Product, Inc. (New Brunswick, NJ), TCI America (Portland, OR), Trans World Chemicals, Inc. (Rockville, MD), VWR (Radnor, PA, USA), Wako Chemicals USA, Inc. (Richmond, VA), and Wuxi-Apptech Inc. (Shanghai, China).

Method of Treatment

In one aspect, the disclosure provides methods of treating a disease or condition in a subject in need thereof. The methods can comprise administering a radiopharmaceutical composition to the subject in need thereof. The methods can provide a therapeutic and/or prophylactic benefit to a subject in need thereof comprising administering a radiopharmaceutical composition described herein.

The methods can comprise administering to a subject a radiopharmaceutical composition that comprise a therapeutically effective amount of a conjugate or a pharmaceutically acceptable salt or solvate thereof. In some embodiments, the subject has cancer. The cancer can be a solid tumor and/or an SSR-associated cancer.

In some embodiments, provided herein are methods for killing a cell comprising contacting the cell with a conjugate or a pharmaceutically acceptable salt or solvate thereof. In some embodiments, the cell expresses a receptor described herein. In some embodiments, the conjugate or pharmaceutically acceptable salt or solvate thereof binds to a structure on the cell. In some embodiments, the conjugate or pharmaceutically acceptable salt or solvate thereof releases a number of alpha particles by natural radioactive decay. In some embodiments, the conjugate or pharmaceutically acceptable salt or solvate thereof releases a number of beta particles, gamma rays, and/or Auger electrons by natural radioactive decay. The conjugate described herein can kill a cell by radiation. In some embodiments, the conjugate kills the cell directly by radiation. In some embodiments, the radiation creates, in the cell, oxidized bases, abasic sites, single-stranded breaks, double-stranded breaks, DNA crosslink, chromosomal rearrangement, or a combination thereof. The conjugate can kill the cell by inducing double-stranded DNA breaks. The released alpha particles can be sufficient to kill the cell. The released alpha particles can be sufficient to stop cell growth. The conjugate can also kill the cell indirectly via the production of reactive oxygen species (ROS) such as free hydroxyl radicals. In some embodiments, the conjugate kills the cell indirectly by releasing tumor antigens from one or more different cells, which can have vaccine effect. The conjugate can kill the cell by abscopal effect. The cell can be a cancer cell. In some embodiments, the method comprises killing a cell with an alpha-particle emitting radionuclide.

After contacting a cell, the described conjugate can be internalized by the cell. The internalization can be mediated by cell receptors, cell membrane endocytosis, etc. In some embodiments, rapid internalization rate into cancer cells accompanied by a slow externalization rate can offer therapeutic benefit.

In one aspect, the disclosed conjugate or a pharmaceutically acceptable salt or solvate thereof is configured to treat cancer by ablating tumor cells. The conjugate or a pharmaceutically acceptable salt or solvate thereof may not modulate the biology of the tumor cell and/or the surrounding stroma. The conjugate or a pharmaceutically acceptable salt or solvate thereof may not modulate immune cells. The ablating of tumor cells can lead to a downstream immunological cascade.

Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, a subject or population of subjects to be treated with a radiopharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a subject or population of subjects to be treated with a radiopharmaceutical composition of the present disclosure have a hematological cancer. In some embodiments, the subject has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a subject or population of subjects to be treated having the cancer selected from the group consisting of ovarian cancer, lung cancer and melanoma. The cancer can be an SSTR1-associated cancer. The cancer can be an SSTR2-associated cancer. The cancer can be an SSTR3-associated cancer. The cancer can be an SSTR4-associated cancer. The cancer can be an SSTR5-associated cancer. The cancer can be a neuroendocrine cancer, a lymphatic cancer, a pancreatic cancer, a pituitary cancer, a breast cancer, a stomach cancer, medulloblastoma, or neuroblastoma. The cancer can be a neuroendocrine cancer. The neuroendocrine cancer can be recurrent. The neuroendocrine cancer can be refractory to a radiotherapy that comprises beta-particle emitting radionuclide. The neuroendocrine cancer can be a neuroendocrine lung cancer or a neuroendocrine pancreatic cancer. The neuroendocrine cancer can be a Carcinoid tumor in the lungs, gastrointestinal tract or thymus, Pancreatic neuroendocrine tumor (e.g., Gastrinoma, Insulinoma, Glucagonoma, VIPoma) Medullary thyroid carcinoma, Merkel cell carcinoma, Pheochromocytoma of the adrenal gland, Adrenal cancer, Small cell carcinoma (such as in the lungs), or Large cell carcinoid tumor (such as in the lungs). In some embodiments, the neuroendocrine cancer can be a pancreatic neuroendocrine tumor (e.g. gastroenteropancreatic neuroendocrine tumor (GEP-NET)). In some embodiments, the neuroendocrine cancer can be a gastrointestinal neuroendocrine tumor (GI-NET). In some embodiments, the neuroendocrine cancer can be gastroesophageal pancreatic neuroendocrine tumor.

Gastroenteropancreatic neuroendocrine tumors, or GEP-NETs, are rare tumors with an incidence in the U.S. of 5.45 cases per 100,000. Despite this low incidence, many GEP-NETs follow a more indolent disease course than other epithelial malignancies and thus the prevalence of GEP-NETs in the U.S. is approximately 100,000. GEP-NET tumors can be aggressive and resistant to therapy and based on the Surveillance, Epidemiology, and End Results database, metastatic disease is present at diagnosis in 40-76% of cases. Depending on their morphology and proliferative activity, GEP-NETs can be classified as well-differentiated tumors or poorly differentiated carcinomas. Well-differentiated GEP-NETs can include low-grade (Grade 1, defined as tumors with a mitotic rate of 0-1 per 10 high power field, or HPF, or a Ki67 index from 0-2%) and intermediate-grade tumors (Grade 2, defined as tumors with a mitotic rate from 2-20 per 10 HPF or a Ki67 index from 3-20%), whereas poorly differentiated GEP-NETs can be high-grade (Grade 3, with a mitotic rate greater than 20 per 10 HPF or a Ki67 index greater than 20%).

In some embodiments, the site of primary NETs in the digestive tract is the rectum, small intestine, pancreas, stomach, colon, and/or appendix. In some embodiments, the GEP-NET is categorized as hormonally functional (associated with signs and symptoms consistent with excess hormone secretion). In some embodiments, the GEP-NET is categorized as non-functional tumors, with clinical features and aggressiveness depending on the primary tumor site. In some embodiments, the cancer is pancreatic neuroendocrine tumors (pNETs).

In some cases, a subject having GEP-NET has been treated with surgery. In some cases, a subject having GEP-NET is not suitable for surgery treatment. In some cases, a subject having GEP-NET has developed metastatic disease. In some embodiments, the GEP-NET overexpresses somatostatin receptor 2, or SSTR2 on the cell surface. In some embodiments, the subject has been previously treated with Somatostatin analogs, or SSAs. In some embodiments, SSA is administered in combination with a conjugate described herein. In some embodiments, the subject has been previously treated with chemotherapy and molecularly targeted therapies such as everolimus or sunitinib. In some embodiments, chemotherapy and molecularly targeted therapies such as everolimus or sunitinib is administered in combination with a conjugate described herein.

In some embodiments, provided herein are methods and compositions for treating a disease or condition. Exemplary disease or condition includes refractory or recurrent malignancies whose growth may be inhibited using the methods of treatment of the present disclosure. In some embodiments, the disease or condition is a cancer. In some embodiments, the cancer is breast cancer, head and neck squamous cell carcinoma, non-small cell lung cancer, hepatocellular cancer, colorectal cancer, gastric adenocarcinoma, pancreatic neuroendocrine tumor (e.g. gastroenteropancreatic neuroendocrine tumor), melanoma, or advanced cancer. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, pancreatic neuroendocrine tumors, gastroenteropancreatic neuroendocrine tumors, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, the cancer is GEP-NET. In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is pancreatic cancer. In some embodiments, a cancer to be treated by the methods of treatment of the present disclosure is a pancreatic neuroendocrine tumor. In some embodiments, a cancer to be treated by the methods of treatment of the present disclosure is a gastroenteropancreatic neuroendocrine tumor. In some embodiments, a cancer to be treated by the methods of treatment of the present disclosure is GEP-NET. In some embodiments, a cancer to be treated by the methods of treatment of the present disclosure is gastroesophageal pancreatic neuroendocrine tumor.

In addition to the methods of treatment described above, the radiopharmaceutical compositions described herein can be used to image, and/or as part of a treatment for diseases. Conjugates for imaging applications, e.g., single-photon emission computed tomography (SPECT) and positron emission tomography (PET), can comprise a radionuclide suitable for use as imaging isotopes such as the isotopes in Table 5B. Accordingly, the conjugate can be administered as a companion diagnostic.

In one aspect, provided herein are methods for diagnosing a patient harboring an SSR expressing cancer or tumor comprising administering to the patient a radiopharmaceutical described herein, or a pharmaceutically acceptable salt or solvate thereof, or a pharmaceutical composition comprising the same. In one aspect, provided herein are methods for imaging an SSR expressing cancer or tumor comprising administering to the patient a radiopharmaceutical described herein, or a pharmaceutically acceptable salt or solvate thereof, or a pharmaceutical composition comprising the same. In some embodiments, the method further comprises selecting or confirming that a tumor in the patient expresses SSR. In some embodiments, the SSR expressing cancer is an SSTR2 expressing cancer. In some embodiments, the method further comprises measuring the concentration of the radiopharmaceutical accumulated in the patient. In some embodiments, the method further comprises measuring the amount of radiation emitted from the radionuclide. In some embodiments, the method further comprises analyzing the elimination or clearance profile of the radiopharmaceutical in the patient. In some embodiments, the method further comprises measuring an elimination half-life of the radiopharmaceutical in the patient. In some embodiments, the method further comprises analyzing the clearance profile of the radiopharmaceutical in the patient. In some embodiments, the method of imaging or diagnosing cancer comprises administering a radiopharmaceutical that comprises a radionuclide of Table 5B, such as 68Ga. For example, radiopharmaceuticals of the present disclosure can be administered for patient selection purposes, such as to confirm the tumor has the appropriate expression of the SSR target (e.g., SSTR2). As another example, radiopharmaceuticals of the present disclosure can be administered to a patient so that the patient's care team can make sure the radiopharmaceutical is cleared from the body in a suitable timeframe so that undesired irradiation of other tissues is minimized.

In some embodiments, a method described herein comprises administering to a patient two radiopharmaceuticals of the present disclosure. In some embodiments, the two radiopharmaceuticals can have the same targeting ligand. In some embodiments, a method described herein comprises administering (i) a radiopharmaceutical of the present disclosure that comprises a radionuclide of Table 5B, and followed by (i) a radiopharmaceutical of the present disclosure that comprises a radionuclide of Table 5A. In some embodiments, the method comprises administering $^{68}$Ga-DOTA-TATE and followed by the administering of $^{225}$Ac-DOTA-TATE.

The subject can be 4 to 120 years old. The subject can be 5 to 10, 5 to 15, 5 to 18, 5 to 25, 5 to 35, 5 to 45, 5 to 55, 5 to 65, 5 to 75, 10 to 15, 10 to 18, 10 to 25, 10 to 35, 10 to 45, 10 to 55, 10 to 65, 10 to 75, 15 to 18, 15 to 25, 15 to 35, 15 to 45, 15 to 55, 15 to 65, 15 to 75, 18 to 25, 18 to 35, 18 to 45, 18 to 55, 18 to 65, 18 to 75, 25 to 35, 25 to 45, 25 to 55, 25 to 65, 25 to 75, 35 to 45, 35 to 55, 35 to 65, 35 to 75, 45 to 55, 45 to 65, 45 to 75, 55 to 65, 55 to 75, or 65 to 75 years old. The subject can be at least 5, 10, 15, 18, 25, 35, 45, 55, or 65 years old. The subject can be at most 10, 15, 18, 25, 35, 45, 55, 65, or 75 years old. In some embodiments, the subject has not received a radiotherapy that comprises beta-particle emitting radionuclide prior to the administering of the radiopharmaceutical composition. In some embodiments, the subject has not received a radiotherapy that comprises alpha-particle emitting radionuclide prior to the administering of the radiopharmaceutical composition. In some embodiments, the subject has received a radiotherapy that comprises alpha-particle emitting radionuclide prior to the administering of the radiopharmaceutical composition. In some embodiments, the subject has received a radiotherapy that comprises beta-particle emitting radionuclide prior to the administering of the radiopharmaceutical composition. In some embodiments, the subject has progressive disease following a radiotherapy treatment that comprises beta-particle emitting radionuclide (e.g., a $^{177}$Lu labeled somatostatin analog) prior to the administering of the radiopharmaceutical composition. In some embodiments, the subject has previously received $^{177}$Lu-DOTA-TATE treatment. In some embodiments, the subject has previously received $^{177}$Lu-DOTA-TOC treatment. In some embodiments, the subject has not received a therapy comprising a platinum based therapeutic prior to the administering of the radiopharmaceutical composition. In some embodiments, the subject has not received a therapy comprising an immune checkpoint inhibitor prior to the administering of the radiopharmaceutical composition.

Combination Therapy

In some embodiments, the radiopharmaceutical composition described herein can be administered alone or in combination with one or more additional therapeutic agents. For example, the combination therapy can include a composition comprising a radiopharmaceutical composition described herein co-formulated with, and/or co-administered with, one or more additional therapeutic agents, e.g., one or more anti-cancer agents, e.g., cytotoxic or cytostatic agents, immune checkpoint inhibitors, hormone treatment, vaccines, and/or immunotherapies. In some embodiments, the radiopharmaceutical composition is administered in combination with other therapeutic treatment modalities, including surgery, cryosurgery, and/or chemotherapy. Such combination therapies may advantageously utilize lower dosages of the administered therapeutic agents, thus avoiding possible toxicities or complications associated with the various monotherapies.

When administered in combination, two (or more) different treatments can be delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In some embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the herein-described conjugate is used in combination with a chemotherapeutic agent, e.g., a DNA damaging chemotherapeutic agent. Non-limiting examples of DNA damaging chemotherapeutic agents include topoisomerase I inhibitors, topoisomerase II inhibitors; alkylating agents; DNA intercalators; DNA intercalators and free radical generators such as bleomycin; and nucleoside mimetics. In some embodiments, the herein-described conjugate is used in combination with a radiation sensitizer, which makes tumor cells more sensitive to radiation therapy. In some embodiments, the herein-described conjugate is used in combination with a DNA damage repair inhibitor (or DNA damage response (DDR) inhibitor).

In some embodiments, a herein-described conjugate is used in combination with one or more of a chemotherapeutic agents (e.g., Everolimus, Sunitinib). In some embodiments, a herein-described conjugate (such as $^{225}$Ac-DOTA-TATE) is used in combination with Everolimus. In some embodiments, a herein-described conjugate (such as $^{225}$Ac-DOTA-TATE) is used in combination with Sunitinib.

In some embodiments, a herein-described conjugate is used in combination with a Somatostatin analog, such as octreotide and lanreotide Co-administration of amino acids with a radiopharmaceutical described herein may reduce kidney update of the radiopharmaceutical. In some embodiments, a radiopharmaceutical composition described herein is concurrently administered with an intravenous infusion of one or more amino acids. In some embodiments, a radiopharmaceutical composition described herein is administered after an intravenous infusion of one or more amino acids. In some embodiments, the infusion of the one or more amino acids is administered at least 30 minutes prior to administering a radiopharmaceutical composition described herein. In some embodiments, the infusion of the one or more amino acids is administered at least 6 hours, 3 hours, 1 hour, 30 minutes, 20 minutes, 10 minutes, or 5 minutes prior to administering a radiopharmaceutical composition described herein. In some embodiments, the infusion of the one or more amino acids is administered 10 to 60 minutes prior to administering a radiopharmaceutical composition described herein. In some embodiments, the concentration of the one or more amino acids is about 0.5% to about 10% w/v. In some embodiments, the concentration of the one or more amino acids is about 0.1% to about 25% w/v. In some embodiments, the concentration of the one or more amino acids is about 1% to about 5% w/v. In some embodiments, the concentration of the one or more amino acids is about 1% to about 3% w/v. In some embodiments, a radiopharmaceutical described herein is concurrently administered with an infusion of arginine and lysine. In some embodiments, a radiopharmaceutical described herein is concurrently administered with an intravenous infusion of arginine hydrochloride and lysine hydrochloride, where the concentration of arginine hydrochloride and lysine hydrochloride is about 2% w/v to about 5% w/v. In some embodiments, a radiopharmaceutical described herein is concurrently administered with an intravenous infusion of arginine hydrochloride and lysine hydrochloride, where the concentration of arginine hydrochloride and lysine hydrochloride is about 2.5% w/v. In some embodiments, the intravenous infusion of arginine and lysine is administered before administering a radiopharmaceutical described herein. In some embodiments, the intravenous infusion is administered at least 30 minutes prior to administering a radiopharmaceutical described herein. In some embodiments, the intravenous infusion is administered at least 30 minutes prior to administering a radiopharmaceutical described herein and is continually administered for up to 4 hours total.

Administration

The radiopharmaceutical compositions of the current disclosure can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. The term parenteral as used herein includes e.g., subcutaneous, intravenous, intramuscular, intrasternal, intraperitoneal, and infusion techniques. The term parenteral also includes injections, into the eye or ocular, intravitreal, intrabuccal, transdermal, intranasal, into the brain, including intracranial and intradural, into the joints, including ankles, knees, hips, shoulders, elbows, wrists, and the like, and in suppository form. The radiopharmaceutical compositions can be administered orally. The radiopharmaceutical compositions can be administered by systemic administration. The radiopharmaceutical compositions can be administered parenterally. The radiopharmaceutical compositions can be administered locally at a targeted site.

The radiopharmaceutical compositions described herein can be administered via parenteral injection as liquid solution, which can include other chemical components, such as carriers, stabilizers, diluents, dispersing agents, suspending agents, thickening agents, preservatives, or excipients. Parenteral injections can be formulated for bolus injection or continuous infusion. The radiopharmaceutical compositions can be formulated in a form suitable for parenteral injection as a sterile suspension, solution or emulsion in oily or aqueous vehicles, and can contain formulatory agents such as suspending, stabilizing or dispersing agents. The radiopharmaceutical formulations for parenteral administration can comprise aqueous solutions of the active compounds in water soluble form. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid, gentisic acid, or sodium bisulfate; chelating agents such as ethylenediaminetetraacetic acid; buffers such as acetates, citrates or phosphates; surfactants such as polysorbate 80; and agents for the adjustment of tonicity such as sodium chloride or dextrose. pH can be adjusted with acids or bases, such as hydrochloric acid or sodium hydroxide. In some embodiments, the radiopharmaceutical composition comprises a reductant. The presence of a reductant can help minimize potential radiolysis. In some embodiments, the reductant is ascorbic acid, gentisic acid, sodium thiosulfate, citric acid, tartaric acid, or a combination thereof.

The radiopharmaceutical compositions can be administered in a manner appropriate to the disease to be treated. An appropriate dose and a suitable duration and frequency of administration can be determined by such factors as the condition of the subject, the type and severity of the subject's disease, the particular form of the active ingredient, and the method of administration. In some embodiments, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the subject. In some embodiments, the radiopharmaceutical compositions can be administered as part of a first-line therapy. In some embodiments, the radiopharmaceutical compositions can be administered as part of a first-line therapy with existing standard of care, for example, immune checkpoint blockers and DNA damaging agents.

The radiopharmaceutical compositions administered can comprise amounts of conjugates or pharmaceutically acceptable salts or solvates thereof sufficient to deliver a therapeutically effective dose of the particular subject. In some embodiments, the dosage of the conjugate is between about 0.1 µg and about 50 mg per kilogram of body weight, between about 1 µg and about 50 mg per kilogram of body weight, or between about 0.1 and about 10 mg per kilogram of body weight. Therapeutically effective dosages can also be determined at the discretion of a physician. By way of example only, the radiopharmaceutical compositions administered can comprise dose of the conjugate or a pharmaceutically acceptable salt or solvate thereof for methods of treating a disease as described herein is about 0.001 mg/kg to about 1 mg/kg body weight of the subject per dose. In some embodiments, the dose of conjugate or a pharmaceutically acceptable salt or solvate thereof for the described methods is about 0.001 mg to about 1000 mg per dose for the subject being treated. In some embodiments, a conjugate or a pharmaceutically acceptable salt or solvate thereof described herein is administered to a subject at a dosage of from about 0.01 mg to about 500 mg, from about 0.01 mg to about 100 mg, or from about 0.01 mg to about 50 mg. In some embodiments, a conjugate or a pharmaceutically acceptable salt or solvate thereof described herein is administered to a subject at a dosage of about 0.01 picomole to about 1 mole, about 0.1 picomole to about 0.1 mole, about 1 nanomole to about 0.1 mole, or about 0.01 micromole to about 0.1 millimole. In some embodiments, a conjugate or a pharmaceutically acceptable salt or solvate thereof described herein is administered to a subject at a dosage of about 0.0001 Gbq to about 1000 Gbq, 0.01 Gbq to about 1000 Gbq, about 0.5 Gbq to about 100 Gbq, or about 1 Gbq to about 50 Gbq. In some embodiments, the radiopharmaceutical composition (or a conjugate or a pharmaceutically acceptable salt or solvate thereof) is administered to a subject in an amount equivalent to about 1 kBq/kg to about 100,000 kBq/kg, about 5 kBq/kg to about 50,000 kBq/kg, about 20 k Bq/kg to about 5,000 kBq/kg, about 50 k Bq/kg to about 500 kBq/kg, about 50 k Bq/kg to about 200 kBq/kg, or about 70 kBq/kg to about 150 kBq/kg body weight per dose. In some embodiments, the radiopharmaceutical composition (or a conjugate or a pharmaceutically acceptable salt or solvate thereof) is administered in an amount equivalent to about 1 kBq/kg to about 100,000 kBq/kg body weight per dose. The radiopharmaceutical compositions administered to a subject can comprise a conjugate or a pharmaceutically acceptable salt or solvate thereof in an amount equivalent to about 5 kBq/kg to about 50,000 kBq/kg body weight per dose. The radiopharmaceutical compositions administered to a subject can comprise a conjugate or a pharmaceutically acceptable salt or solvate thereof in an amount equivalent to about 20 kBq/kg to about 5,000 kBq/kg body weight per dose. The radiopharmaceutical compositions administered to a subject can comprise a conjugate or a pharmaceutically acceptable salt or solvate thereof in an amount equivalent to about 50 k Bq/kg to about 500 kBq/kg body weight per dose. The radiopharmaceutical compositions administered to a subject can comprise a conjugate or a pharmaceutically acceptable salt or solvate thereof in an amount equivalent to about 70 kBq/kg to about 150 kBq/kg body weight per dose. In some embodiments, the radiopharmaceutical compositions administered to a subject can comprise a conjugate or a pharmaceutically acceptable salt or solvate thereof in an amount equivalent to about 30 kBq/kg to about 150 kBq/kg body weight per dose. In some embodiments, the radiopharmaceutical compositions administered to a subject can comprise a conjugate or a pharmaceutically acceptable salt or solvate thereof in an amount equivalent to about 90 kBq/kg to about 180 kBq/kg body weight per dose. In some embodiments, the radiopharmaceutical compositions administered to a subject can comprise a conjugate or a pharmaceutically acceptable salt or solvate thereof in an amount equivalent to about 30 kBq/kg to about 240 kBq/kg body weight per dose. In some embodiments, the radiopharmaceutical compositions administered to a subject can comprise a conjugate or a pharmaceutically acceptable salt or solvate thereof in an amount equivalent to about 60 kBq/kg to about 120 kBq/kg body weight per dose. In some embodiments, the radiopharmaceutical composition (or a conjugate or a pharmaceutically acceptable salt or solvate thereof) is administered to a subject in an amount equivalent to about 120 kBq/kg body weight per dose. In some embodiments, the radiopharmaceutical composition (or a conjugate or a pharmaceutically acceptable salt or solvate thereof) is administered to a subject in an amount equivalent to about 90 kBq/kg body weight per dose. In some embodiments, the radiopharmaceutical composition (or a conjugate or a pharmaceutically acceptable salt or solvate thereof) is administered to a subject in an amount equivalent to about 60 kBq/kg body weight per dose. The radiopharmaceutical composition can be administered to the subject to achieve a cumulative dose of conjugate or pharmaceutically acceptable salt of solvate thereof in an equivalent of about 1,000 kBq to about 5,000,000 kBq. The radiopharmaceutical composition can be administered to the subject to achieve a cumulative dose of conjugate or pharmaceutically acceptable salt of solvate thereof in an equivalent of about 5,000 kBq to about 1,000,000 kBq. The radiopharmaceutical composition can be administered to the subject to achieve a cumulative dose of conjugate or pharmaceutically acceptable salt of solvate thereof in an equivalent of about 8,000 kBq to about 5,000,000 kBq. The radiopharmaceutical composition can be administered to the subject to achieve a cumulative dose of conjugate or pharmaceutically acceptable salt of solvate thereof in an equivalent of about 10,000 kBq to about 100,000 kBq. The radiopharmaceutical composition can be administered to the subject to achieve a cumulative dose of conjugate or pharmaceutically acceptable salt of solvate thereof in an equivalent of about 20,000 kBq to about 90,000 kBq. The radiopharmaceutical composition can be administered to the subject to achieve a cumulative dose of conjugate or pharmaceutically acceptable salt of solvate thereof in an equivalent of about 40,000 kBq to about 70,000 kBq. In some embodiments, the radiopharmaceutical composition can be administered to the subject to achieve a cumulative dose of conjugate or pharmaceutically acceptable salt or solvate thereof in an equivalent of about 400 kBq to about 4,000,000 kBq. In some embodiments, the radiopharmaceutical composition can be administered to the subject to achieve a cumulative dose of conjugate or pharmaceutically acceptable salt or solvate thereof in an equivalent of about 20,000 kBq to about 40,000 kBq. In some embodiments, the radiopharmaceutical composition can be administered to the subject to achieve a cumulative dose of conjugate or pharmaceutically acceptable salt or solvate thereof in an equivalent of about 20,000 kBq to about 30,000 kBq. In some embodiments, the radiopharmaceutical composition can be administered to the subject to achieve a cumulative dose of conjugate or pharmaceutically acceptable salt or solvate thereof in an equivalent of about 30,000 kBq to about 40,000 kBq. In some embodiments, the radiopharmaceutical composition can be administered to the subject to achieve a cumulative dose of conjugate or pharmaceutically acceptable salt or solvate thereof in an equivalent of about 40,000 kBq to about 50,000 kBq. In some embodiments, the radiopharmaceutical composition can be administered to the subject to achieve a cumulative dose of conjugate or pharmaceutically acceptable salt or solvate thereof in an equivalent of about 40,000 kBq to about 100,000 kBq. In some embodiments, the radiopharmaceutical composition can be administered to the subject to achieve a maximum cumulative dose of conjugate or pharmaceutically acceptable salt or solvate thereof in an equivalent of about 60,000 kBq. In some embodiments, the radiopharmaceutical composition can be administered to the subject to achieve a maximum cumulative dose of conjugate or pharmaceutically acceptable salt or solvate thereof in an equivalent of about 40,800 kBq. In some embodiments, the dose is administered once a day, 1 to 3 times a week, 1 to 4 times a month, or 1 to 12 times a year. The radiopharmaceutical compositions can be administered at a 2-week interval. The radiopharmaceutical compositions can be administered at a 4-week interval. The radiopharmaceutical compositions can be administered at a 6-week interval. The radiopharmaceutical compositions can be administered at an 8-week interval. The radiopharmaceutical compositions can be administered at a 10-week interval. The radiopharmaceutical compositions can be administered at a 12-week interval. The radiopharmaceutical compositions can be administered at a 15-week interval. The radiopharmaceutical composition can be administered at a 20-week interval. The radiopharmaceutical composition can be administered in cycles. For example, the radiopharmaceutical composition can be administered in 1-20 cycles. In some embodiments, the radiopharmaceutical composition is administered for 1-10 cycles. In some embodiments, the radiopharmaceutical composition is administered for 1-5 cycles. In some embodiments, the radiopharmaceutical composition is administered for 3-9 cycles. In some embodiments, the radiopharmaceutical composition is administered for 1 cycle. In some embodiments, the radiopharmaceutical composition is administered for 2 cycles. In some embodiments, the radiopharmaceutical composition is administered for 3 cycles. In some embodiments, the radiopharmaceutical composition is administered for 4 cycles. In some embodiments, the radiopharmaceutical composition is administered for 5 cycles. In some embodiments, the radiopharmaceutical composition is administered for 6 cycles. In some embodiments, the radiopharmaceutical composition is administered for 7 cycles. In some embodiments, the radiopharmaceutical composition is administered for 8 cycles. In some embodiments, the radiopharmaceutical composition is administered for 9 cycles. In some embodiments, the radiopharmaceutical composition is administered for 10 cycles. In some embodiments, the radiopharmaceutical composition is administered for 11 cycles. In some embodiments, the radiopharmaceutical composition is administered for 12 cycles. In some embodiments, each cycle includes one administration every 8 weeks. In some embodiments, each cycle includes one administration every 4 weeks. In some embodiments, each cycle includes one administration every 6 weeks. In some embodiments, each cycle includes one administration every 12 weeks. In some embodiments, the radiopharmaceutical composition comprises $^{225}$Ac-DOTA-TATE.

The pharmaceutical compositions can be packaged in unit dosage form for ease of administration and uniformity of dosage. A unit dosage form can refer to physically discrete units suited as unitary dosages for the subject to be treated; each unit containing a predetermined quantity of active compound calculated to produce the desired therapeutic effect in association with the pharmaceutical carrier or excipient. In some embodiments, the unit dosage has a volume of 5 to 25 mL. In some embodiments, the unit dosage has a volume of 1 to 10 mL. In some embodiments, the unit dosage has a volume of 8 to 15 mL. In some embodiments, the unit dosage has a volume of 10 to 15 mL. In some embodiments, the unit dosage has a volume of 8 mL. In some embodiments, the unit dosage has a volume of 9 mL. In some embodiments, the unit dosage has a volume of 10 mL. In some embodiments, the unit dosage has a volume of 11 mL. In some embodiments, the unit dosage has a volume of 12 mL. In some embodiments, the unit dosage has a volume of 13 mL. In some embodiments, the unit dosage has a volume of 14 mL. In some embodiments, the unit dosage has a volume of 15 mL. In some embodiments, the unit dosage has a volume of 16 mL. In some embodiments, the unit dosage has a volume of 17 mL. In some embodiments, the unit dosage has a volume of 18 mL. In some embodiments, the unit dosage has a volume of 19 mL. In some embodiments, the unit dosage has a volume of 20 mL. In some embodiments, the unit dosage comprises $^{225}$Ac-DOTA-TATE in an amount equivalent to 146-275 µCi. In some embodiments, the unit dosage comprises $^{225}$Ac-DOTA-TATE in an amount equivalent to 100-300 µCi.

In some embodiments, the unit dosage comprises $^{225}$Ac-DOTA-TATE in an amount equivalent to 10-500 µCi. In some embodiments, the unit dosage comprises $^{225}$Ac-DOTA-TATE in an amount equivalent to more than 500 µCi. In some embodiments, the unit dosage comprises $^{225}$Ac-DOTA-TATE in an amount equivalent to 10-100 µCi. In some embodiments, the unit dosage comprises $^{225}$Ac-DOTA-TATE in an amount equivalent to 10-50 µCi. In some embodiments, the unit dosage comprises $^{225}$Ac-DOTA-TATE in an amount equivalent to 100-200 µCi. In some embodiments, the unit dosage comprises $^{225}$Ac-DOTA-TATE in an amount equivalent to 120-300 µCi. In some embodiments, the unit dosage comprises $^{225}$Ac-DOTA-TATE in an amount equivalent to 200-400 µCi. In some embodiments, the unit dosage comprises $^{225}$Ac-DOTA-TATE in an amount equivalent to 200-500 µCi. In some embodiments, the unit dosage comprises $^{225}$Ac-DOTA-TATE in an amount equivalent to 146-275 µCi. In some embodiments, the unit dosage comprises $^{225}$Ac-DOTA-TATE in an amount equivalent to 146-275 µCi in a 12 mL solution.

In some embodiments, the unit dosage comprises $^{225}$Ac-DOTA-TATE in an amount equivalent to 45-114 µg of DOTATATE. In some embodiments, the unit dosage comprises $^{225}$Ac-DOTA-TATE in an amount equivalent to 5 to 1000 µg of DOTATATE. In some embodiments, the unit dosage comprises $^{225}$Ac-DOTA-TATE in an amount equivalent to 0.5 to 10,000 µg of DOTATATE. In some embodiments, the unit dosage comprises $^{225}$Ac-DOTA-TATE in an amount equivalent to 20 to 200 µg of DOTATATE. In some embodiments, the unit dosage comprises $^{225}$Ac-DOTA-TATE in an amount equivalent to 10 to 50 µg of DOTATATE. In some embodiments, the unit dosage comprises $^{225}$Ac-DOTA-TATE in an amount equivalent to 50 to 150 µg of DOTATATE. In some embodiments, the unit dosage comprises $^{225}$Ac-DOTA-TATE in an amount equivalent to 1 to 100 µg of DOTATATE. In some embodiments, the unit dosage comprises $^{225}$Ac-DOTA-TATE in an amount equivalent to 1 to 200 µg of DOTATATE. In some embodiments, the unit dosage comprises $^{225}$Ac-DOTA-TATE in an amount equivalent to 100 to 500 µg of DOTATATE. In some embodiments, the unit dosage comprises $^{225}$Ac-DOTA-TATE in an amount equivalent to 25 to 150 µg of DOTATATE. In some embodiments, the unit dosage comprises $^{225}$Ac-DOTA-TATE in an amount equivalent to about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, or 160 µg of DOTATATE.

In some embodiments, radiopharmaceutical compositions described herein are formulated in a unit dosage form stored in a glass vial.

In some embodiments, the radiopharmaceutical compositions described herein can comprise compounds exist as solvates. This disclosure provides for methods of treating diseases by administering such solvates. This disclosure further provides for methods of treating diseases by administering such solvates as radiopharmaceutical compositions.

Although the present disclosure and its advantages have been described in detail, it should be understood that various changes, substitutions and alterations can be made herein without departing from the spirit and scope of the disclosure as defined in the appended claims.

The present disclosure is further illustrated in the following Examples which are given for illustration purposes only and are not intended to limit the disclosure in any way.

EXAMPLES

Example 1. Conjugate Synthesis

A typical procedure to synthesize of [$^{225}$Ac]Ac-DOTA-TATE was achieved by reacting DOTA-TATE acetate (28 µg, 28 µL) from 1.0 mg/mL water solution) with [$^{225}$Ac]AcCl$_3$ (6.8 MBq or 0.2 mCi, 22 µl) from 10 µCi/µl HCl (0.04M, aqueous) solution. The DOTA-TATE acetate was diluted to 150 µL with sodium acetate/acetic acid buffer solution (0.4 M, pH=6.50). [$^{225}$Ac]AcCl$_3$ HCl solution was added. The reaction mixture of total volume of 200 µl was mixed with vortex mixture, then heated at 90° C. for 15 min at a shaking speed of 500 rpm. Upon completion, the mixture was directly diluted into the desired formulation described below.

Radio-TLC was performed at time 0 hour to determine radiochemical yield of the labeling reaction with the following protocol: 1 µL of the reaction mixture was spotted onto a TLC plate (Agilent A120B12, plate size 11.4×2.0 cm) at 1.5 cm from the bottom edge. The TLC was developed with 10 mM DTPA water solution (pH=7.0, adjusted by 1.0 M NaOH) until the eluent reaches 1.5 cm from the top edge (or in 15 mins). After drying in an incubator at a temperature of 38° C., the radio-TLC conversion was analyzed at different time points with a radio-TLC reader (Eckert & Ziegler AR-2000) set at High Voltage=1000 (to ensure alpha detection) until the ratio between labeled product and the free Ac225 ion no longer change (typically after 6-8 hours of TLC separation to ensure equilibrium between Ac225 and daughter nuclides). The typical radiochemical yield of [$^{225}$Ac]Ac-DOTA-TATE syntheses were found >99.0 (±0.5) %, Molar activity is 10 mCi/µmol.

Example 2. Broad Scope Screening of Excipients

Upon completion of the radiolabeling, the reaction mixture described in example 1 was immediately diluted in the stabilizing formulation in 30× fold (v/v), or to 0.03 mCi/ml. The formulations were buffered with sodium acetate-acetic acid 0.4 M solution to pH 5.80 (±0.10). A signal component excipient as stabilizing agent at 1 mg/ml in the buffer, except EtOH where 10% (v/v) was presented. Sodium L-Ascorbate/L-Ascorbic acid buffer was adjusted to pH 5.80 (±0.10). Water for Injection (WFI) with the same dilution without any excipient is used as the control formulation. The mixture was kept at room temperature (25° C.). Purity of [$^{225}$Ac]Ac-DOTA-TATE was checked at different time points by radio-TLC as described in the table below. Purity is described as the $^{225}$Ac present in [$^{225}$Ac]Ac-DOTA-TATE divided by total $^{225}$Ac content at that time point.

| Excipients | Percentage of $^{225}$Ac present in [$^{225}$Ac]Ac-DOTA-TATE | | |
|---|---|---|---|
| | 0 hour after mixing | 24 hours after mixing | 48 hours after mixing |
| Water for injection (WFI) | 99.42 | 92.43 | 88.85 |
| Sodium Ascorbate, pH 5.8 | 99.42 | 95.42 | 92.21 |
| Dextran (60-90), Clinical grade | 99.42 | 94.91 | 86.80 |
| DTPA | 99.42 | 95.77 | 91.38 |
| L-Methionine | 99.42 | 93.39 | 89.58 |
| Thiourea | 99.42 | 94.87 | 89.97 |
| L-Lysine | 99.42 | 95.45 | 89.52 |
| Catechin hydrate | 99.42 | 95.41 | 95.64 |
| N-Acetyl-L-Cysteine | 99.42 | 91.19 | 87.41 |
| L-Glutathione | 99.42 | 91.18 | 85.56 |
| 10% EtOH | 99.42 | 96.35 | 92.16 |
| Citric Acid | 99.42 | 90.20 | 82.18 |
| Salicylic Acid | 99.42 | 93.08 | 87.65 |
| Sodium Bisulfite | 98.61 | 0 | N/A |
| Lipoic Acid | 98.61 | 92.97 | 87.93 |
| D-Cysteine | 98.61 | 93.45 | 87.66 |
| Phenol | 98.61 | 94.44 | 87.88 |
| Albumin | 98.61 | 94.44 | 89.39 |

The degradation of Ac-225-DOTATATE in pure WFI was found significant even at the most diluted concentration for bolus injection.

Example 3. Control Formulation without Excipient

The reaction mixture described in example 1 was immediately diluted to 50× fold of volume with water for injection (WFI) or to 0.02 mCi/ml. pH was tested to be 6.13. The mixture was kept at room temperature (25° C.). At different time points, purity of [$^{225}$Ac]Ac-DOTA-TATE in the formulated dose were measured by radio-TLC as described in the table below:

| Time after formulation (hours) | Percentage of $^{225}$Ac present in [$^{225}$Ac]Ac-DOTA-TATE | Notes |
|---|---|---|
| 0 hour | 99.5% | 0.5% free Actinium |
| 24 hours | 94.8% | 2.0% free Actinium, 3.2% fragments |
| 48 hours | 91.8% | 3.5% free Actinium, 4.8% fragments |
| 72 hours | 83.5% | 8.8% free Actinium, 7.7% fragments |
| 96 hours | 79.1% | 9.2% free Actinium, 11.8% fragments |

Example 4. Radioactivity Concentration Optimization

The reaction mixture described in example 1 was immediately diluted into Sodium Ascorbate (100 mM or 19.8 mg/ml aqueous solution, pH adjusted to 5.80) aqueous solution at different concentrations; DTPA was added into the formulation accordingly to reach the final concentration at 0.05 mg/ml. The mixture was kept at room temperature (25° C.) and protected from light to prevent photodegradation. At different time points, purity of [$^{225}$Ac]Ac-DOTA-TATE in the formulated dose were measured by radio-TLC as described in the table below:

| Radioactivity concentration | Percentage of $^{225}$Ac present in [$^{225}$Ac]Ac-DOTA-TATE | | | | | |
|---|---|---|---|---|---|---|
| | 0 hour | 24 hours | 48 hours | 72 hours | 96 hours | 120 hours |
| 15 μCi/ml | 99.37 | 96.92 | 96.08 | 98.74 | 94.83 | 93.49 |
| 32 μCi/ml | 99.39 | 97.92 | 97.13 | 95.31 | 92.52 | 85.90 |
| 68 μCi/ml | 99.06 | 98.22 | 95.93 | 95.36 | 86.92 | n/a |
| 126 μCi/ml | 99.11 | 95.77 | 84.99 | n/a | n/a | n/a |
| 301 μCi/ml | 99.09 | 97.53 | 88.78 | n/a | n/a | n/a |
| 550 μCi/ml | 98.87 | 97.04 | 85.63 | n/a | n/a | n/a |

Example 5. DTPA Concentration Optimization

The reaction mixture described in example 1 was immediately diluted to 50× fold of volume (or to 20 μCi/ml) with Sodium Ascorbate (100 mM or 19.8 mg/ml aqueous solution, pH adjusted to 5.80) aqueous solution. Different concentrations of DTPA were added. The mixture was kept at room temperature (25° C.). At different time points, radioactive components of the formulated dose were measured by radio-TLC as described in the table below:

| DTPA concentration | Percentage of $^{225}$Ac present in [$^{225}$Ac]Ac-DOTA-TATE | | | |
|---|---|---|---|---|
| | 0 hour | 24 hours | 48 hours | 72 hours |
| 0.05 mg/ml | 98.74 | 97.67 | 95.34 | 94.62 |
| 0.1 mg/ml | 97.52 | 98.30 | 96.74 | 94.36 |
| 0.3 mg/ml | 98.06 | 97.19 | 96.11 | 93.60 |
| 0.5 mg/ml | 98.40 | 97.28 | 95.07 | 92.73 |
| 0.8 mg/ml | 98.02 | 97.60 | 96.57 | 93.11 |
| 1.0 mg/ml | 98.25 | 97.37 | 96.14 | 94.14 |

Example 6. Sodium Ascorbate Concentration Optimization

The reaction mixture described in example 1 was immediately diluted to 50× fold of volume (or to 0.02 mCi/ml) with sodium ascorbate (100 mM, pH adjusted, with 0.05 mg/ml DTPA). pH was tested to be 5.83. The mixture was kept at room temperature (25° C.). At different time points, radioactive components of the formulated dose were measured by radio-TLC as described in the table below:

| Sodium ascorbate concentration | Percentage of $^{225}$Ac present in [$^{225}$Ac]Ac-DOTA-TATE | | | | | | |
|---|---|---|---|---|---|---|---|
| | 0 hour | 24 hours | 48 hours | 72 hours | 96 hours | 120 hours | 144 hours |
| 200 mM | 99.22 | 98.16 | 97.12 | 95.63 | 95.51 | 94.38 | 91.27 |
| 100 mM | 99.15 | 98.76 | 96.94 | 96.16 | 95.84 | 95.44 | 95.34 |
| 10 mM* | 99.78 | 92.21 | 86.11 | n/a | n/a | n/a | n/a |
| 1 mM* | 99.76 | 91.11 | 52.06 | n/a | n/a | n/a | n/a |

*Radioactivity concentration at 1 mCi/ml

Example 7. Dextran Ratio Optimization

The reaction mixture described in example 1 was immediately diluted to 40× fold of volume (or to 25 μCi/ml) with sodium ascorbate (100 mM, pH adjusted, with 0.05 mg/ml DTPA) in pre-mixed dextran saline solution. pH was tested to be 5.80. The mixture was kept at room temperature (25° C.). At different time points, radioactive components of the formulated dose were measured by radio-TLC as described in the table below:

| Dextran percentage | Percentage of $^{225}$Ac present in [$^{225}$Ac]Ac-DOTA-TATE | | | | | | |
|---|---|---|---|---|---|---|---|
| | 0 hour | 24 hours | 48 hours | 72 hours | 96 hours | 120 hours | 144 hours |
| 10% w/w | 99.67 | 99.02 | 98.75 | 97.83 | 96.42 | 96.58 | 95.37 |
| 6% w/w | 100 | 99.08 | 98.83 | 98.29 | 96.99 | 97.00 | 96.41 |
| 3% w/w | 99.86 | 98.62 | 98.48 | 97.91 | 96.48 | 96.67 | 95.77 |
| 0% w/w | 99.90 | 99.42 | 98.73 | 97.77 | 97.13 | 98.09* | 94.64 |
| 10% w/w, no L-ascorbate | 100 | 95.38 | 93.36 | 89.11 | 87.20 | n/a | n/a |

*non-homogeneous sampling

Example 8. EGCg Concentration

The reaction mixture described in example 1 was immediately diluted to 40× fold of volume (or to 25 µCi/ml) with sodium ascorbate (100 mM, pH adjusted 5.80, with 0.05 mg/ml DTPA) in saline solution with different concentration of EGCg. The mixture was kept at room temperature (25° C.). At different time points, radioactive components of the formulated dose were measured by radio-TLC as described in the table below:

| | Percentage of $^{225}$Ac present in [$^{225}$Ac]Ac-DOTA-TATE | | | | | | |
|---|---|---|---|---|---|---|---|
| EGCg concentration | 0 hour | 24 hours | 48 hours | 72 hours | 96 hours | 120 hours | 144 hours |
| 3 mg/ml | 99.81 | 98.57 | 98.00 | 96.55 | 96.42 | 96.05 | 90.71 |
| 1 mg/ml | 99.76 | 99.14 | 98.83 | 98.04 | 97.15 | 94.82 | 95.65 |
| 0.5 mg/ml | 99.61 | 98.92 | 98.48 | 97.97 | 96.44 | 95.65 | 93.04 |
| 0 mg/ml | 99.90 | 99.42 | 98.73 | 97.77 | 97.13 | 98.09* | 94.64 |

*non-homogeneous sampling

Example 9. A Preparation of [$^{225}$Ac]Ac-DOTA-TATE at a Single Patient Dose Scale, its Formulation and Stability Study For a 300 µCi (11.1 MBq) batch size, a [$^{225}$Ac]Ac(NO$_3$)$_3$ solution (40 µl, 11.4 MBq, assayed) was diluted with sodium acetate buffer solution (250 µl, 0.4 M, pH=5.50). The DOTA-TATE acetate solution (200 µl, 1.0 mg/ml water solution, 200 µg) was added. The mixture was mixed with vortex mixture, then heated at 90° C. for 15 min at shaking speed of 500 round per minute on a thermal mixer. After completion, the reaction was removed from the mixture and allowed to cool to room temperature in 3 minutes. The reaction solution was diluted with pre-mixed intravenous formulation (9.5 ml). The Actinium-225 radioactive contains concentration was 30 mCi/L (total volume 10.0 ml). The calculated 5-day dose activity was 211 µCi (7.8 MBq, or 7.4MBq±10%). The starting molar activity of the dose was 2.2 mCi/µmol. The formulated product was dispensed into a 30-ml sterile vial and sealed with Wheaton's septa and crimp seal. The vial was wrapped with aluminum foil and stored away from light at room temperature (about 20° C. to about 25° C.) for stability sampling every 24 hours. Intravenous formulation is either Formulation A or Formulation B as described below.

Formulation A:

To prepare a 100 grams of 100 mM sodium L-ascorbate, 5% w/w Dextran 40, 0.9% w/w sodium chloride saline solution, pH 5.80, 5.000 g of DEXTRAN 40, 1.980 g of Sodium L-ascorbate and 5.0 mg of DTPA were dissolved in 93 ml of 0.9% w/w saline. The solution container was placed on a vortex shaker and mixed for 15 minutes to completely dissolve the solid. 24 µl of HCl (conc. 12 M) was added. Final pH was measured to between 5.75-5.85. The formulation solution was stored at 2-8° C. and protected from exposure of light up to 12 hours before consumption.

Formulation B:

To prepare 250 ml of a 100 mM sodium L-ascorbate, 0.9% w/w sodium chloride saline solution, pH 5.80, 4.950 g of Sodium L-ascorbate and 12.5 mg of DTPA were dissolved in 250 ml of 0.9% w/w saline. The solution container was placed on a vortex shaker and mixed for 15 minutes to completely dissolve the solid. 60 µl of HCl (conc. 12 M) was added. Final pH was measured to between 5.75-5.85. The formulation solution was stored at 2-8° C. and protected from exposure of light up to 12 hours before consumption.

At different time points, percentage purity of [$^{225}$Ac]Ac-DOTA-TATE in the formulated dose were measured by radio-TLC as described in the table below. Purity is described as the $^{225}$Ac present in [$^{225}$Ac]Ac-DOTA-TATE divided by total $^{225}$Ac content at that time point.

| | Percentage of $^{225}$Ac present in [$^{225}$Ac]Ac-DOTA-TATE | | | | | | | | |
|---|---|---|---|---|---|---|---|---|---|
| Formulation | 0 hour | 24 hours | 48 hours | 72 hours | 96 hours | 120 hours | 144 hours | 168 hours | 192 hours |
| A | 98.75 | 98.86 | 98.40 | 98.29 | 96.88 | 96.14 | 95.92 | 94.77 | 94.67 |
| B | 98.41 | 98.67 | 98.34 | 97.67 | 96.22 | 96.22 | 95.24 | 94.35 | 93.52 |

As illustrated in the table above, both Formulations A and B retain at least 95% of the $^{225}$Ac content as $^{225}$Ac-DOTA-TATE after 120 hours and at least 93% of the $^{225}$Ac content as $^{225}$Ac-DOTA-TATE after 192 hours.

Example 10. Preparation of [$^{225}$Ac]Ac-DOTA-TATE for In Vivo Administration

[$^{225}$Ac]Ac(NO$_3$)$_3$ was dissolved in 0.001M HCl to achieve a concentration of 1mCi in 100 µL. A 1.0-1.1 mCi aliquot of 10 µCi/µL $^{225}$Ac-chloride solution was combined with 285 µg of 1 µg/4 DOTA-TATE solution in 0.4M sodium acetate buffer. The combined solution was brought to 2.0 mL with 0.4M sodium acetate buffer and a final pH range of 6.0 to 6.5. The radioactive concentration of the combined solution was between 0.5mCi/mL and 0.55mCi/mL. The solution was heated and mixed with a thermal mixer at 90±3° C. for 15±2 minutes. To a separate, sterile, intermediary vial was added 28 mL of formulation buffer (100 mM sodium ascorbate, 0.05 mg/mL DTPA, 0.9% normal saline). The total contents of the combined [$^{225}$Ac]Ac-DOTA-TATE solution was transferred into the intermediary vial with the formulation buffer, further reducing the total radioactive concentration to 0.033-0.0367 mCi/mL in the formulation vial.

The required volume to fill to the requested patient activity dose is calculated with appropriate decay factor to time of calibration and dose range between 146-275 µCi. If necessary, after activity has been aliquoted to the patient vial, the vial is brought to a total volume of 12 mL with formulation buffer (100 mM sodium ascorbate, 0.05 mg/mL DTPA, 0.9% normal saline) for injection. Final excipient description [$^{225}$Ac]Ac-DOTA-TATE for in vivo administration was formulated in a sodium ascorbate concentration of 18.5±4.63 mg/mL, total DOTA-TATE peptide concentration of ≤11.5 µg/mL, 0.05 mg/mL DTPA, 0.9% normal saline, pH=5.5-7.0, with a dose range of 146-275 µCi at time of calibration in 12 mL total volume, and dose concentration at time of calibration between 0.012-0.023 µCi/µL. Stability up to 120 hours was initially verified with the bulk formulated vial and subsequently with the dose range between 146-275 µCi.

Example 11. Preparation of $^{225}$Ac-DOTA-TATE Formulation in Unit Dosage Form The unit dosage form formulation was manufactured in a continuous process from radiolabeling of $^{225}$Ac into the DOTA moiety of DOTATATE, to the final formulation with excipients. The unlabeled precursor DOTATATE was a lyophilized powder that was reconstituted in sodium acetate buffer prior to labeling with $^{225}$Ac. DOTATATE acetate was labeled with 229Th (thorium-229)-generator-derived $^{225}$Ac under a specified temperature and reaction time to produce $^{225}$Ac-DOTATATE. After radiolabeling was completed, the reaction mixture was further formulated in a buffer with selected excipients deemed necessary to mitigate radiolysis and breakdown of the drug product:

- 18.5 mg/mL L-sodium ascorbate (e.g., to mitigate radiolysis of the radiopharmaceutical preparation and extend stability)
- 0.05 mg/mL diethylenetriamine pentaacetate (e.g., to scavenge free unbound $^{225}$Ac)
- 0.9% normal saline (to further dilute to a total infusion volume of 12 mL)
- Other suitable excipients may also be used.

Example 12. Clinical Trial Design and Dosing Schedule

The clinical trial design is a Phase 1b/Phase 3 global, multicenter, randomized, controlled, open-label trial comparing treatment with [$^{225}$Ac]Ac-DOTA-TATE to standard of care therapy in subjects with inoperable, advanced, Grade 1-2, well-differentiated, somatostatin receptor positive (SSTR+) GEP-NETs that have progressed according to RECIST v.1.1 following prior treatment with $^{177}$Lu-DOTA-TATE or $^{177}$Lu-DOTA-TOC.

Part 1 of the study is to determine the recommended Phase 3 dose (RP3D), with dose de-escalation/re-escalation rules based on the Bayesian optimal interval (BOIN) design (Liu and Yuan 2015; Yuan 2016). Six subjects are planned to be enrolled in 3 dose cohorts for a total of 18 subjects if all 3 dose levels are initiated. A cohort may be expanded e.g., to a maximum of 10 subjects. The starting dose of [$^{225}$Ac]Ac-DOTA-TATE will be 120 kBq/kg (3.2 µCi/kg). Subjects will receive up to 4 cycles of [$^{225}$Ac]Ac-DOTA-TATE every 8 weeks. Dose de-escalation (between cohorts) and potential re-escalation will be decided by the DRC based on the dose limiting toxicity rate observed during the first 56 days following the first administration of [$^{225}$Ac]Ac-DOTA-TATE. Concomitant IV amino acids (solution containing L-arginine and L-lysine) will be given with each [$^{225}$Ac]Ac-DOTA-TATE administration for renal protection, starting 30 minutes before the [$^{225}$Ac]Ac-DOTA-TATE infusion and continuing for a total of 4 hours.

Figure 19:
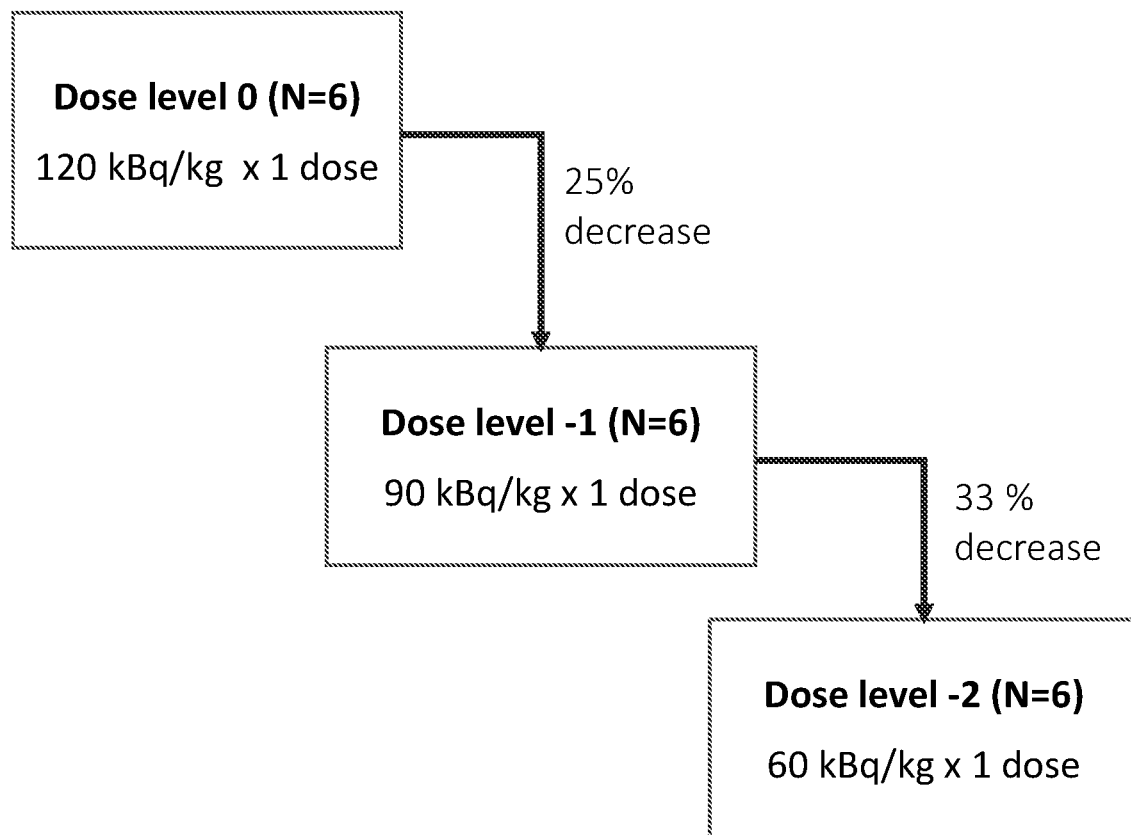
FIG. 19 depicts a clinical treatment dosing schedule using $^{225}$Ac-DOTA-TATE. Patients receive a de-escalating dose scheme and will receive up to 4 cycles of $^{225}$Ac-DOTA-TATE every 8 weeks.

A representative dosing scheme for Part I is illustrated in FIG. 19.

The Eligibility Criteria of the Part I study can include one or more of the following:
- Age≥18
- Histologically proven, G1-3 well-differentiated GEP-NETs
- Ki-67≤55%
- Progressive GEP-NET based on RECIST v.1.1 (centrally confirmed) following 177Lu-DOTATATE or 177Lu-DOTATOC
- RECIST v1.1 measurable SSTR+disease within 4 weeks prior to dose (centrally confirmed; no SSTR-neg metastatic disease)
- CrCl≥50 mL/min
- Subjects with p-NET have also received an additional non-SSA antineoplastic agent in addition to prior PRRT The end point of the Part I study can include one or more of the following:
Primary: Dose Limiting Toxicities (DLTs)
Secondary/exploratory:
- Recommended Phase 2 dose (RP2D)
- Safety
- objective response rate (ORR)
- PK Part 2 (randomized, controlled Phase 3) is to determine if treatment with [$^{225}$Ac]Ac-DOTA-TATE prolongs progression free survival as assessed by blinded independent central review (BICR) (primary objective) and OS (key secondary objective) compared with standard of care therapy. A total of 210 subjects are planned for randomization at a 1:1 ratio to receive [$^{225}$Ac]Ac-DOTA-TATE administered at the RP3D every 8 weeks for up to 4 cycles or standard of care therapy selected by the Investigator prior to randomization and given according to local labeling (standard of care options may include oral everolimus, oral sunitinib, high dose octreotide long-acting release (LAR), and high dose lanreotide). Following radiographic progressive disease confirmed by BICR, subjects randomized to the standard of care therapy group may be eligible to cross over and receive [$^{225}$Ac]Ac-DOTA-TATE. Pharmacokinetic evaluations of [$^{225}$Ac]Ac-DOTA-TATE in blood and urine will be completed in Part 1 of the study (all subjects) and in a subset of subjects randomized to [$^{225}$Ac]Ac-DOTA-TATE in Part 2 of the study. In addition, a PK/ECG substudy will be conducted in a subset of subjects randomized to [$^{225}$Ac]Ac-DOTA-TATE during Part 2.

The Eligibility Criteria of the Part 2 study can include one or more of the following:
- Age≥18
- Histologically proven, well-differentiated, G1-2 GEP-NETs
- Ki-67≤20%
- Progressive GEP-NET based on RECIST v.1.1 (centrally confirmed) following 177Lu-DOTATATE or 177Lu-DOTATOC
- RECIST v1.1 measurable SSTR+disease within 4 weeks prior to dose (centrally confirmed; no RECIST measurable SSTR-neg metastatic disease)
- ECOG≤2
- CrCl≥50 mL/min The end point of the Part 2 study can include one or more of the following: Primary: blinded independent central review (BICR) progression-free survival (PFS) Secondary/exploratory:
- overall survival (OS)
- objective response rate (ORR)
- duration of Response
- Disease Control Rate
- Safety
- PK
- Biomarkers
- QOL

Example 13: Preparation of [$^{225}$Ac]Ac-DOTA-TATE at a 1 mCi Batch Size, its Formulation and Stability Study For a 1 mCi (37 MBq) batch size, a [$^{225}$Ac]Ac(NO$_3$)$_3$ solution (93 µL, 995 µCi assayed) was diluted with sodium acetate buffer solution (1401 µL, 0.4M, pH=5.53). The DOTA-TATE acetate solution (285 µg, 0.964 µg/µL sodium acetate buffer, 296 µL) was added for a molar activity of 5.009 Ci/mmol. The target reaction radioactive concentration was 0.556 µCi/µL with a total reaction volume of 1,789 µL. The mixture was mixed with a vortexer, then heated at 90° C. for 15 minutes at shaking speed of 500 rounds per minute on a thermal mixer. After completion, the reaction vial was removed from the thermal mixer and cooled to room temperature (about 20° C. to about 25° C.) in 3 minutes. The entire reaction mixture was then added to 28.2 mL of a pre-mixed formulation buffer (Formulation B) consisting of 100 mM sodium L-ascorbate, 0.05 mg/mL DTPA in 0.9% saline (pH=5.79). The final assay of the bulk vial solution was 984 µCi in a total volume of 30,000 µL, for a final product radioactive concentration of 0.033 µCi/µL and final pH of 5.67. A total of 3 aliquots from the bulk vial was distributed to 3 separate vials, simulating patient dose activity levels of 307.5 µCi in 9 mL, 309.5 µCi in 9 mL, and 310 µCi in 9 mL. Each of the simulated patient vial was protected from light and stored in room temperature (20-25° C.). Stability sampling was taken every 24 hours from the 309.5 µCi vial, with an end specification of ≥95% by t=120 hours from end of synthesis.

At different time points, percentage purity of [$^{225}$Ac]Ac-DOTA-TATE in the formulated dose were measured by radio-TLC as described in the table below. Purity is described as the $^{225}$Ac present in [$^{225}$Ac]Ac-DOTA-TATE divided by total $^{225}$Ac content at that time point.

| | Percentage of $^{225}$Ac present in [$^{225}$Ac]Ac-DOTA-TATE | | | | | |
|---|---|---|---|---|---|---|
| | 0 hour | 24 hours | 48 hours | 72 hours | 96 hours | 120 hours | 144 hours |
| 1 mCi Formulation | 99.21% | 98.87% | 97.21% | 96.54% | Not measured | 95.52% | 94.81% |

As illustrated in the table above, the formulation of Example 13 retains at least 95% of the $^{225}$Ac content as $^{225}$Ac-DOTA-TATE after 120 hours.

Example 14: [225Ac]Ac-DOTA-TATE Dosing Calculation Based on Patient Weight

An 85 kg patient is treated with a dose of 3.24 µCi/kg (120 kBq/kg) [$^{225}$Ac]Ac-DOTA-TATE representing a total radiation dose of 275 µCi (10,200 kBq) at time of injection. The final product after synthesis and formulation has a radioactive concentration of 0.033 µCi/µL. Given the half-life of $^{225}$Ac, the dose is formulated to contain a certain amount of radioactivity dependent upon when the dose will be administered according to the following table:

| | Days before administration | | | | |
|---|---|---|---|---|---|
| | 1 | 2 | 3 | 4 | 5 |
| µCi in radiopharmaceutical | 295 | 317 | 340 | 364 | 391 |
| Volume of radiopharmaceutical (mL) | 8.9 | 9.6 | 10.3 | 11.0 | 11.8 |

The dose is then brought up to 12 mL total volume with formulation buffer for administration. Patients less than 85 kg receive the same 3.24 µCi/kg (120 kBq/kg) dose of [$^{225}$Ac]Ac-DOTA-TATE brought up to 12 mL total volume with formulation buffer for administration.

Further, the table below summaries the dose calculation for patients having different weights at a dose of 120 kBq/kg:

| Patent weight (kg) | 40 | 45 | 50 | 55 | 60 | 65 | 70 | 75 | 80 | 85 |
|---|---|---|---|---|---|---|---|---|---|---|
| Dose at time of injection (in µCi) | 130 | 146 | 162 | 178 | 194 | 211 | 227 | 243 | 259 | 275 |
| Dose at time of injection (in kBq) | 4800 | 5400 | 6000 | 6600 | 7200 | 7800 | 8400 | 9000 | 9600 | 10200 |

| Days before administration | Activity needed (in µCi) at day of manufacture if injected x days later | | | | | | | | | |
|---|---|---|---|---|---|---|---|---|---|---|
| 1 | 139 | 156 | 174 | 191 | 208 | 226 | 243 | 261 | 278 | 295 |
| 2 | 149 | 168 | 186 | 205 | 224 | 242 | 261 | 279 | 298 | 317 |
| 3 | 160 | 180 | 200 | 220 | 240 | 260 | 280 | 300 | 320 | 340 |
| 4 | 171 | 193 | 214 | 236 | 257 | 278 | 300 | 321 | 343 | 364 |
| 5 | 184 | 207 | 230 | 253 | 276 | 299 | 322 | 345 | 368 | 391 |

| Days before administration | Volume needed (in mL) if bulk drug product concentration = 0.033 µCi/uL | | | | | | | | | |
|---|---|---|---|---|---|---|---|---|---|---|
| 1 | 4.2 | 4.7 | 5.3 | 5.8 | 6.3 | 6.8 | 7.4 | 7.9 | 8.4 | 8.9 |
| 2 | 4.5 | 5.1 | 5.6 | 6.2 | 6.8 | 7.3 | 7.9 | 8.5 | 9.0 | 9.6 |
| 3 | 4.8 | 5.4 | 6.1 | 6.7 | 7.3 | 7.9 | 8.5 | 9.1 | 9.7 | 10.3 |
| 4 | 5.2 | 5.8 | 6.5 | 7.1 | 7.8 | 8.4 | 9.1 | 9.7 | 10.4 | 11.0 |
| 5 | 5.6 | 6.3 | 7.0 | 7.7 | 8.4 | 9.0 | 9.7 | 10.4 | 11.1 | 11.8 |

Disclosure of the present application is further illustrated in the following list of embodiments, which are given for illustration purposes only and are not intended to limit the disclosure in any way:

Embodiment 1: A liquid radiopharmaceutical composition comprising:
  a. a conjugate, wherein the conjugate is $^{225}$Ac-DOTA-TATE;
  b. one or more stabilizing agents; and
  c. an aqueous vehicle.

Embodiment 2: A liquid radiopharmaceutical composition comprising:
  d. a conjugate, wherein the conjugate is $^{225}$Ac-DOTA-TOC;
  e. one or more stabilizing agents; and
  f. an aqueous vehicle.

Embodiment 3: A liquid radiopharmaceutical composition comprising:
  a) a conjugate that comprises
    i. a targeting ligand,
    ii. a metal chelator covalently attached to the targeting ligand, and
    iii. a radionuclide, wherein the radionuclide is bound to the metal chelator;
  b) one or more stabilizing agents; and
  c) an aqueous vehicle.

Embodiment 4: The radiopharmaceutical composition of Embodiment 3, wherein the targeting ligand binds to a somatostatin receptor (SSR).

Embodiment 5: The radiopharmaceutical composition of Embodiment 4, wherein the targeting ligand binds to a somatostatin receptor type 1 (SSTR1), somatostatin receptor type 2 (SSTR2), somatostatin receptor type 3 (SSTR3), somatostatin receptor type 4 (SSTR4), and/or somatostatin receptor type 5 (SSTR5).

Embodiment 6: The radiopharmaceutical composition of Embodiment 4, wherein the targeting ligand binds to a somatostatin receptor type 2 (SSTR2).

Embodiment 7: The radiopharmaceutical composition of Embodiments 3 to 6, wherein the targeting ligand is a binding peptide.

Embodiment 8: The radiopharmaceutical composition of Embodiment 7, wherein the binding peptide comprises 6 to 14 amino acid residues.

Embodiment 9: The radiopharmaceutical composition of Embodiment 7 or 8, wherein the binding peptide comprises an amino acid sequence with at least 90% identity to a sequence selected from SEQ IDs 1 to 96.

Embodiment 10: The radiopharmaceutical composition of Embodiment 7 or 8, wherein the binding peptide comprises an amino acid sequence selected from SEQ IDs 1 to 96.

Embodiment 11: The radiopharmaceutical composition of Embodiment 3 to 6, wherein the targeting ligand is octreotate, octreotide, D-Phe$^1$-cyclo(Cys$^2$-Tyra-D-Trp$^4$-Lys$^5$-Thr$^6$-Cys$^7$)Thr$^8$ (SEQ ID NO: 97) (tyr3-octreotate or TATE), D-Phe$^1$-cyclo(Cys$^2$-Tyra-D-Trp$^4$-Lys$^5$-Thr$^6$-Cys$^7$)Thr(ol)$^8$ (SEQ ID NO: 98) (Phe$^1$-Tyr$^3$octreotide, edotreotide, or TOC), D-Phe$^1$-cyclo(Cys$^2$-Phe$^3$-D-Trp$^4$-Lys$^5$-Thr$^6$-Cys$^7$)Thr(ol)$^8$ (SEQ ID NO: 99) (OC), D-Phe$^1$-cyclo(Cys$^2$-1-Nal-D-Trp$^4$-Lys$^5$-Thr$^6$-Cys$^7$)Thr(ol)$^8$ (SEQ ID NO: 100) (NOC), p-Cl-Phe-cyclo(D-Cys-Aph(Hor)-D-Aph(Cbm)-Lys-Thr-Cys)D-Tyr-NH$_2$) (SEQ ID NO: 101) (JR11), or p-Cl-Phe-cyclo(D-Cys-Tyr-D-Aph(Cbm)-Lys-Thr-Cys)-D-Tyr-NH$_2$ (SEQ ID NO: 102) (LM3).

Embodiment 12: The radiopharmaceutical composition of Embodiment 3 to 6, wherein the targeting ligand is tyr3-octreotate, edotreotide, octreotate, or octreotide.

Embodiment 13: The radiopharmaceutical composition of Embodiment 3 to 6, wherein the targeting ligand is tyr3-octreotate.

Embodiment 14: The radiopharmaceutical composition of Embodiments 4 to 13, wherein targeting ligand is an agonist of the SSR.

Embodiment 15: The radiopharmaceutical composition of Embodiments 4 to 13, wherein targeting ligand is an antagonist of the SSR.

Embodiment 16: The radiopharmaceutical composition of Embodiments 3 to 6, wherein the targeting ligand is a small molecule compound.

Embodiment 17: The radiopharmaceutical composition of Embodiment 16, wherein the small molecule compound is L-797,591, L-779,976, L-796,778, L-803,087, or L-817,818.

Embodiment 18: The radiopharmaceutical composition of Embodiments 4 to 17, wherein a binding affinity of the targeting ligand to a human SSR is not more than 250 nM, as determined by half maximal inhibitory concentration (IC$_{50}$).

Embodiment 19: The radiopharmaceutical composition of Embodiments 4 to 18, wherein the binding affinity of the targeting ligand to a human SSR is not more than 100 nM, as determined by half maximal inhibitory concentration (IC$_{50}$).

Embodiment 20: The radiopharmaceutical composition of Embodiments 4 to 19, wherein the binding affinity of the targeting ligand to a human SSR is not more than 50 nM, as determined by half maximal inhibitory concentration (IC$_{50}$).

Embodiment 21: The radiopharmaceutical composition of Embodiments 4 to 20, wherein the binding affinity of the targeting ligand to a human SSR is not more than 5 nM, as determined by half maximal inhibitory concentration (IC$_{50}$).

Embodiment 22: The radiopharmaceutical composition of Embodiments 4 to 21, wherein the binding affinity of the targeting ligand to a human SSR is not more than 2 nM, as determined by half maximal inhibitory concentration (IC$_{50}$).

Embodiment 23: The radiopharmaceutical composition of Embodiments 18 to 22, wherein the human SSR is SSTR2.

Embodiment 24: The radiopharmaceutical composition of Embodiments 3 to 23, wherein the targeting ligand is covalently linked to the metal chelator through a linker.

Embodiment 25: The radiopharmaceutical composition of Embodiments 3 to 24, wherein the metal chelator is selected from AAZTA, BAT, BAT-TM, Crown, Cyclen, DO2A, CB-DO2A, DO3A, H3HP-DO3A, Oxo-DO3A, p-NH$_2$-Bn-Oxo-DO3A, DOTA, DOTA-3py, DOTA-PA, DOTA-GA, DOTA-4AMP, DOTA-2py, DOTA-1py, p-SCN-Bn-DOTA, CHX-A"-EDTA, MeO-DOTA-NCS EDTA, DOTAMAP, DOTAGA, DOTAGA-anhydride, DOTMA, DOTASA, DOTAM, DOTP, CB-Cyclam, TE2A, CB-TE2A, CB-TE2P, DM-TE2A, MM-TE2A, NOTA, NOTP, HEHA, HEHA-NCS, p-SCN-Bn-HEHA, DTPA, CHX-A"-DTPA, p-NH$_2$-Bn-CHX-A"-DTPA, p-SCN-DTPA, p-SCN-Bz-Mx-DTPA, 1B4M-DTPA-DTPA, p-SCN-Bn1B-DTPA, p-SCN-Bn-1B4M-DTPA, p-SCN-Bn-CHX-A"-DTPA, PEPA, p-SCN-Bn-PEPA, TETPA, DOTPA, DOTMP, DOTPM, t-Bu-calix[4]arene-tetracarboxylic acid, macropa, macropa-NCS, macropid, $H_3L^1$, $H_3L^4$, H2azapa, H5decapa, bispa2, H4pypa, H4octapa, H4CHXoctapa, p-SCN-Bn-H4octapa, p-SCN-Bn-H4octapa, TTHA, p-NO$_2$-Bn-neunpa, H4octox, H2macropa, H2bispa2, H4phospa, H6phospa, p-SCN-Bn-H6phospa, TETA, p-NO$_2$-Bn-TETA, TRAP, TRAP-Pr, TPA, HBED, SHBED, HBED-CC, (HBED-CC)TFP, DMSA, DMPS, DHLA, lipoic acid, TGA, BAL, Bis-thioseminarabazones, p-SCN-NOTA, nNOTA, NODAGA, CB-TE1A1P, 3P-C-NETA-NCS, 3p-C-DEPA, 3P-C-DEPA-NCS, TCMC, PCTA, NODIA-Me, TACN, pycuplAiB, pycup2A, THP, DEDPA, H2DEDPA, p-SCN-Bn-H2DEDPA, p-SCN-Bn-TCMC, motexafin, NTA, NOC, 3p-C-NETA, p-NH$_2$-Bn-TE3A, SarAr, DiAmSar, SarAr-NCS, AmBaSar, BaBaSar, TACN-TM, CP256, C-NE3TA, C-NE3TA-NCS, NODASA, NETA-monoamide, C-NETA, TACN-HSB, NOPO, BPCA, p-SCN-Bn-DRO, DRO-ChX-Mal, DFO, DFO-IAC, DFO-BAC, DiP-LICAM, EC, SBAD, BAPEN, TACHPYR, NEC-SP, $L^{py}$, L1, L2, L3, and EuK-106.

Embodiment 26: The radiopharmaceutical composition of Embodiments 3 to 24, wherein the metal chelator is a metal chelator in FIG. 3 to FIG. 17.

Embodiment 27: The radiopharmaceutical composition of Embodiments 3 to 26, wherein the metal chelator is DOTA, HEHA, or macropa.

Embodiment 28: The radiopharmaceutical composition of Embodiments 3 to 27, wherein the metal chelator is DOTA.

Embodiment 29: The radiopharmaceutical composition of Embodiments 1 to 28, wherein the one or more stabilizing agents comprise a radiolysis stabilizer.

Embodiment 30: The radiopharmaceutical composition of Embodiment 29, wherein the radiolysis stabilizer is
a) an amino acid or a peptide or a derivative thereof,
b) a vitamin or a derivative thereof,
c) a lipid or a derivative thereof,
d) a carbohydrate or a derivative thereof,
e) a volume expander or
f) an antioxidant.

Embodiment 31: The radiopharmaceutical composition of Embodiment 30, wherein the amino acid or peptide is selected from N-Acetyl-L-cysteine, Glutathione, L-Lysine, Selenol-L-methionine, Glutathione, Albumin, Melatonin, Taurine, Alanine, Arginine, Asparagine, Aspartic acid, Cysteine, Glutamine, Glutamic acid, Glycine, Histidine, Isoleucine, Lysine, Methionine, Phenylalanine, Proline, Serine, Threonine, Tryptophan, Tyrosine, Valine, and derivatives thereof.

Embodiment 32: The radiopharmaceutical composition of Embodiment 31, wherein the amino acid is Methionine.

Embodiment 33: The radiopharmaceutical composition of Embodiment 30, wherein the radiolysis stabilizer is an antioxidant.

Embodiment 34: The radiopharmaceutical composition of Embodiment 33, wherein the antioxidant is a flavonoid or a derivative thereof.

Embodiment 35: The radiopharmaceutical composition of Embodiment 34, wherein the flavonoid is (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), 3,3',4',5,5',7-Hexahydroxyflavylium chloride, (−)-cis-3,3',4',5,7-Pentahydroxyflavane (Epi-Catechin or EC), 7-Hydroxy-3-(4'-methoxyphenyl)-4H-benzopyran-4-one, 3,4,5-Trihydroxybenzoic acid (Gallic acid), 3,4',5,7-Tetrahydroxyflavone (Kaempferol), Luteolin, 2-(3,4-dihydroxyphenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl] oxymethyl]oxan-2-yl] oxychromen-4-one (Rutin hydrate), Quercetin, (2R, 3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), or (2R,3S)-2-(3,4,5-trihydroxyphenyl)-3,4-dihydro-2H-chromene-3,5,7-triol (Gallo-Catechin or GC).

Embodiment 36: The radiopharmaceutical composition of Embodiment 34, wherein the flavonoid is a catechin or a derivative thereof.

Embodiment 37: The radiopharmaceutical composition of Embodiment 36, wherein the catechin or catechin derivative is (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), (−)-cis-3,3',4',5,7-Pentahydroxyflavane (Epi-Catechin or EC), 3,4,5-Trihydroxybenzoic acid (Gallic acid), (2R,3R)-5,7-Dihydroxy-2-(3,4,5-trihydroxyphenyl)-3,4-dihydro-2H-1-benzopyran-3-yl 3,4,5-trihydroxybenzoate (Epi-Gallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), or (2R,3S)-2-(3,4,5-trihydroxyphenyl)-3,4-dihydro-2H-chromene-3,5,7-triol (Gallo-Catechin or GC).

Embodiment 38: The radiopharmaceutical composition of Embodiment 33, wherein the antioxidant is a carotenoid or a derivative thereof.

Embodiment 39: The radiopharmaceutical composition of Embodiment 38, wherein the carotenoid is all-trans-Fucoxanthin, Lycopene, Xanthophyll, Beta carotene, Lycopene, or Lutein.

Embodiment 40: The radiopharmaceutical composition of Embodiment 33, wherein the antioxidant is N-acetyl cysteine, L-Ascorbic acid, N-tert-Butyl-α-phenylnitrone, 3-(3,4-Dihydroxyphenyl)-2-propenoic acid (Caffeic Acid), β-Carotene, Provitamin A, (2S,3R)-2-(3,4-Dihydroxyphenyl)-3,4-dihydro-1(2H)-benzopyran-3,5,7-triol 3-(3,4,5-trihydroxybenzoate ((−) Catechin gallate or CG), 1,4,5-Trihydroxycyclohexanecarboxylic acid, trans-4-Hydroxycinnamic acid (p-Coumaric acid), 3,3',4',5,5',7-Hexahydroxyflavylium chloride, Thiocytic Acid (Dihydrolipoic Acid, DHLA), 4,4',5,5',6,6'-Hexahydroxydiphenic acid 2,6,2',6'-dilactone (Ellagic acid), (−)-cis-3,3',4',5,7-Pentahydroxyflavane (Epi-Catechin or EC), 2-Methoxy-4-(2-propenyl) phenol, trans-4-Hydroxy-3-methoxycinnamic acid (Ferulic acid), 7-Hydroxy-3-(4'-methoxyphenyl)-4H-benzopyran-4-one, all-trans-Fucoxanthin, 3,4,5-Trihydroxybenzoic acid (Gallic acid), (2S,3R)-2-(3,4,5-Trihydroxyphenyl)-3,4-dihydro-1 (2H)-benzopyran-3,5,7-triol ((−)-Gallocatechin), Glutathione, 2-(3,4-Dihydroxyphenyl)ethanol, 3,4',5,7-Tetrahydroxyflavone (Kaempferol), (±)-1,2-Dithiolane-3-pentanoic acid, Luteolin, Lycopene, L-Lysine, Neochlorogenic acid, Oleic acid, trans-3,5,4'-Trihydroxystilbene (Resveratrol), 2-(3,4-dihydroxyphenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl] oxy methyl] oxan-2-yl]oxychromen-4-one, Rutin hydrate, Selenol-L-methionine, Thiourea, (+)-α-Tocopherol, Xanthophyll, Citric acid (CA), Gentisic acid (GA), Salicylic acid (SA), Erythorbic acid (EA), Phenol, Sodium bisulfite, Butylated hydroxy anisole, Butylated hydroxy toluene, Metabisulfite, Benzyl alcohol, Thymol, Lipoic acid (LA), Thioglycolic acid (TGA), 2,3 Dimercaptopropan-1-ol (BAL), Zinc, Selenium, Albumin, Ethanol, Mannitol, Sucrose, Melatonin, Ebselen, Pyruvic acid, Carboxy-PTIO, Trolox, Uric acid, Edaravone, Beta carotene, NADPH, Lycopene, Lutein, Catalase, Estrogen, Estradiol, Estriol, Ubiquinol, Copper, Quercetin, Cortisone, Taurine, (2R, 3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), (2R,3S)-2-(3,4,5-trihydroxyphenyl)-3,4-dihydro-2H-chromene-3,5,7-triol (Gallo-Catechin or GC), (—)-cis-2-(3,4,5-Trihydroxyphenyl)-3,4-dihydro-1(2H)-benzopyran-3,5,7-triol 3-gallate ((−)-Epigalocatechin-3-O-Gallate), 5-Aminolevulibic Acid hydrate, Ploysorbate 80, Garlic Acid, Sodium L-Ascorbate, Hyaluronic Acid, Dextran 60-90, Selenol, and LysaKare.

Embodiment 41: The radiopharmaceutical composition of Embodiment 30, wherein the radiolysis stabilizer is a vitamin or a derivative thereof.

Embodiment 42: The radiopharmaceutical composition of Embodiment 41, wherein the vitamin or a derivative thereof is selected from L-Ascorbic acid, β-Carotene, Provitamin A, (+)-α-Tocopherol, Erythorbic acid (EA), Trolox, and Lutein.

Embodiment 43: The radiopharmaceutical composition of Embodiment 30, wherein the radiolysis stabilizer is a lipid.

Embodiment 44: The radiopharmaceutical composition of Embodiment 43, wherein the lipid is a fatty acid.

Embodiment 45: The radiopharmaceutical composition of Embodiment 44, wherein the fatty acid is a saturated or unsaturated $C_6$ to $C_{30}$ fatty acid.

Embodiment 46: The radiopharmaceutical composition of Embodiment 45, wherein the fatty acid is oleic acid, Myristoleic acid, Palmitoleic acid, Sapienic acid, Elaidic acid, Vaccenic acid, or Linoleic acid, α-Linolenic acid.

Embodiment 47: The radiopharmaceutical composition of Embodiment 43, wherein the lipid is a steroid or derivatives thereof.

Embodiment 48: The radiopharmaceutical composition of Embodiment 47, wherein the steroid is Estrogen, Estradiol, Estriol, or Cortisone.

Embodiment 49: The radiopharmaceutical composition of Embodiment 30, wherein the radiolysis stabilizer is a carbohydrate or a derivative thereof.

Embodiment 50: The radiopharmaceutical composition of Embodiment 49, wherein the carbohydrate is Mannitol, Sucrose, Dextran (e.g., Dextran 40, Dextran 70), or Cyclodextrin (e.g., α-cyclodextrin, β-cyclodextrin, and γ-cyclodextrin).

Embodiment 51: The radiopharmaceutical composition of Embodiment 30, wherein the radiolysis stabilizer is a volume expander.

Embodiment 52: The radiopharmaceutical composition of Embodiment 51, wherein the volume expander is a polymer or a polymer mixture.

Embodiment 53: The radiopharmaceutical composition of Embodiment 52, wherein the polymer or the polymer mixture comprises PEG (e.g., Mn 2000 to 5000), Polygeline, Haemaccel, Gelofusine, PLENVU (polyethylene glycol 3350, sodium sulfate, ascorbic acid, sodium chloride and potassium chloride US FDA 2018 Label), or a combination thereof.

Embodiment 54: The radiopharmaceutical composition of Embodiment 51, wherein the volume expander is selected from Dextran (e.g., Dextran 40, Dextran 70), Cyclodextrins (e.g., α-cyclodextrin, β-cyclodextrin, and γ-cyclodextrin), PEG, Polygeline, Gelofusine, and PLENVU.

Embodiment 55: The radiopharmaceutical composition of Embodiment 29, wherein the radiolysis stabilizer is selected from N-Acetyl-L-cysteine, L-Ascorbic acid, N-tert-Butyl-α-phenylnitrone, 3-(3,4-Dihydroxyphenyl)-2-propenoic acid (Caffeic Acid), β-Carotene, Provitamin A, (2S,3R)-2-(3,4-Dihydroxyphenyl)-3,4-dihydro-1(2H)-benzopyran-3,5,7-triol 3-(3,4,5-trihydroxybenzoate ((−) Catechin gallate, or CG), 1,4,5-Trihydroxycyclohexanecarboxylic acid, trans-4-Hydroxycinnamic acid (p-Coumaric acid), 3,3',4',5,5',7-Hexahydroxyflavylium chloride, Thiocytic Acid (Dihydrolipoic Acid, DHLA), 4,4',5,5',6,6'-Hexahydroxydiphenic acid 2,6,2',6'-dilactone (Ellagic acid), (−)-cis-3,3',4',5,7-Pentahydroxyflavane (Epi-Catechin or EC), 2-Methoxy-4-(2-propenyl) phenol, trans-4-Hydroxy-3-methoxy cinnamic acid (Ferulic acid), 7-Hydroxy-3-(4'-methoxyphenyl)-4H-benzopyran-4-one, all-trans-Fucoxanthin, 3,4,5-Trihydroxybenzoic acid (Gallic acid), (2S,3R)-2-(3,4,5-Trihydroxyphenyl)-3,4-dihydro-1(2H)-benzopyran-3,5,7-triol ((−)-Gallocatechin), Glutathione, 2-(3,4-Dihydroxyphenyl)ethanol, 3,4',5,7-Tetrahydroxyflavone (Kaempferol), (±)-1,2-Dithiolane-3-pentanoic acid, Luteolin, Lycopene, L-Lysine, Neochlorogenic acid, Oleic acid, trans-3,5,4'-Trihydroxystilbene (Resveratrol), 2-(3,4-dihydroxyphenyl)-5,7-dihydroxy-3-[(2S,3R,4S,5S,6R)-3,4,5-trihydroxy-6-[[(2R,3R,4R,5R,6S)-3,4,5-trihydroxy-6-methyloxan-2-yl] oxy methyl] oxan-2-yl]oxychromen-4-one, Rutin hydrate, Selenol-L-methionine, Thiourea, (+)-α-Tocopherol, Xanthophyll, Alanine and its derivatives, Arginine and its derivatives, Asparagine and its derivatives, Aspartic acid and its derivatives, Cysteine and its derivatives, Glutamine and its derivatives, Glutamic acid and its derivatives, Glycine and its derivatives, Histidine and its derivatives, Isoleucine and its derivatives, Lysine and its derivatives, Methionine and its derivatives, Phenylalanine and its derivatives, Proline and its derivatives, Serine and its derivatives, Threonine and its derivatives, Tryptophan and its derivatives, Tyrosine and its derivatives, Valine and its derivatives, Citric acid (CA), Gentisic acid (GA), Salicylic acid (SA), Erythorbic acid (EA), Phenol, Sodium bisulfite, Butylated hydroxy anisole, Butylated hydroxy toluene, Glutathione, Metabisulfite, Benzyl alcohol, Thymol, Lipoic acid (LA), Thioglycolic acid (TGA), 2,3 Dimercaptopropan-1-ol (BAL), Zinc, Selenium, Albumin, Ethanol, Mannitol, Sucrose, Melatonin, Ebselen, Pyruvic acid, Carboxy-PTIO, Trolox, Uric acid, Edaravone, Beta carotene, NADPH, Lycopene, Lutein, Catalase, Estrogen, Estradiol, Estriol, Ubiquinol, Copper, Quercetin, Cortisone, 2,3-dimercaptosuccinic acid (DMSA), monisoamyl derivative (Mi-ADMSA), Taurine, Dextran (e.g., Dextran 40, Dextran 70), PEG (e.g., PEG 3350 and PEG 4000), Polygeline, Gelofusine, PLENVU (polyethylene glycol 3350, sodium sulfate, ascorbic acid, sodium chloride and potassium chloride US FDA 2018 Label), Cyclodextrins (e.g., α-cyclodextrin, β-cyclodextrin, and γ-cyclodextrin), (2R,3R)-5,7-Dihydroxy-2-(3,4,5-trihydroxyphenyl)-3,4-dihydro-2H-1-benzopyran-3-yl 3,4,5-trihydroxybenzoate (EpiGallo-Catechin gallate or EGCg), (2R,3R)-2-(3,4-dihydroxyphenyl)-5,7-dihydroxy-3,4-dihydro-2H-chromen-3-yl]3,4,5-trihydroxybenzoate or Epi-Catechin Gallate (ECG), (2R,3R)-2-(3,4,5-trihydroxyphenyl)-3,4-dihydro-2H-chromene-3,5,7-triol (Epigallo-Catechin or EGC), (2R,3S)-2-(3,4,5-trihydroxyphenyl)-3,4-dihydro-2H-chromene-3,5,7-triol (Gallo-Catechin or GC).

Embodiment 56: The radiopharmaceutical composition of Embodiments 29 to 55, wherein the one or more stabilizing agents comprise a first and a second radiolysis stabilizer.

Embodiment 57: The radiopharmaceutical composition of Embodiment 56, wherein a molar ratio of the first and the second radiolysis stabilizer is from 1:1000 to 1:1000, 1:100 to 1:100 or 1:20 to 20:1.

Embodiment 58: The radiopharmaceutical composition of Embodiment 56, wherein a molar ratio of the first and the second radiolysis stabilizer is from 1:5 to 5:1.

Embodiment 59: The radiopharmaceutical composition of Embodiments 29 to 58, wherein the radiolysis stabilizer is present in the radiopharmaceutical composition at about 0.01 mM to about 5 M.

Embodiment 60: The radiopharmaceutical composition of Embodiment 59, wherein the stabilizing agent is present in the radiopharmaceutical composition from about 5 mM, 10 mM, 25 mM, 50 mM, or 75 mM to about 80 mM, 100 mM, 125 mM, 150 mM, 175 mM, 200 mM, 250 mM, or 500 mM.

Embodiment 61: The radiopharmaceutical composition of Embodiment 59, wherein the stabilizing agent is present in the radiopharmaceutical composition at about 0.1 mM to about 500 mM.

Embodiment 62: The radiopharmaceutical composition of Embodiment 59, wherein the stabilizing agent is present in the radiopharmaceutical composition at about 10 mM to about 500 mM.

Embodiment 63: The radiopharmaceutical composition of Embodiment 59, wherein the stabilizing agent is present in the radiopharmaceutical composition at about 20 mM to about 100 mM.

Embodiment 64: The radiopharmaceutical composition of Embodiments 29 to 58, wherein the radiolysis stabilizer is present in the radiopharmaceutical composition at about 0.0001 wt % to about 10 wt %.

Embodiment 65: The radiopharmaceutical composition of Embodiment 64, wherein the radiolysis stabilizer is present in the radiopharmaceutical composition at about 0.01 wt % to about 5 wt %, about 0.05 wt % to about 2 wt %, or about 0.1 wt % to about 1 wt %.

Embodiment 66: The radiopharmaceutical composition of Embodiments 29 to 58, wherein the radiolysis stabilizer is present in the radiopharmaceutical composition at a concentration of from about 0.1 to 50 mg/mL.

Embodiment 67: The radiopharmaceutical composition of Embodiments 30 to 58, wherein the volume expander is present in the radiopharmaceutical composition at a concentration of from about 0.001 wt % to 80% wt %.

Embodiment 68: The radiopharmaceutical composition of Embodiments 1 to 66, wherein the one or more stabilizing agents comprise a free metal chelator, wherein the free metal chelator is not attached to the targeting ligand.

Embodiment 69: The radiopharmaceutical composition of Embodiment 67, wherein the free metal chelator is selected from Ethylenediaminetetraacetic acid (EDTA), Diethylenetriaminepentaacetic acid (DTPA), 2-S-(4-Isothiocyanatobenzyl)-1,4,7-triazacyclononane-1,4,7-tri acetic acid (NOTA), Triethylenetetramine (TETA), 1, 4, 7, 10, 13-pentaazacyclopentadecane-N, N', N'', N''', N''''-pentaacetic acid (PEPA), TETPA, 2,2',2''-(10-(2,6-dioxotetrahydro-2H-pyran-3-yl)-1,4,7,10-tetraazacyclododecane-1,4,7-triyl)triacetic acid (DOTA-GA), 1,4,7,10-Tetraazacyclododecane-1,4,7,10-tetra(methylene phosphonic acid (DOTP), Deferoxamine (DFO), N, N-bis(2-hydroxybenzyl)ethylenediamine-N,N-diacetic acid (HBED), 1,4,7,10-Tetraazacyclododecane-1,4,7,10-tetra(methylene phosphonic acid) (DOTP), 6,6'-((1,4,10,13-tetraoxa-7,16-diazacyclooctadecane-7,16-diyl)bis(methylene))dipicolinic acid (Macropa), Meso-2,3-dimercaptosuccinic acid (DMSA), Dimercaptopropane sulfonate (DMPS), Dihydrolipoic acid (DHLA), Lipoic acid (LA), Thioglycolic acid (TGA), 2,3 Dimercaptopropan-1-ol (BAL).

Embodiment 70: The radiopharmaceutical composition of Embodiment 69, wherein the free metal chelator is EDTA, DTPA, or Macropa.

Embodiment 71: The radiopharmaceutical composition of Embodiments 67 to 70, wherein the free metal chelator is present in the radiopharmaceutical composition at about 0.001 wt % to about 10 wt %.

Embodiment 72: The radiopharmaceutical composition of Embodiment 71, wherein the free metal chelator is present in the radiopharmaceutical composition at about 0.01 wt % to about 5 wt %, about 0.05 wt % to about 2 wt %, or about 0.1 wt % to about 1 wt %.

Embodiment 73: The radiopharmaceutical composition of Embodiments 67 to 70, wherein the free metal chelator is present in the radiopharmaceutical composition at a concentration of from 0.01 to 50 mg/mL.

Embodiment 74: The radiopharmaceutical composition of Embodiments 67 to 70, wherein the free metal chelator is present in the radiopharmaceutical composition at about 10 mM to about 500 mM.

Embodiment 75: The radiopharmaceutical composition of Embodiments 67 to 70, wherein the free metal chelator is present in the radiopharmaceutical composition at about 5 mM to 10 mM, 10 mM to 25 mM, 25 mM to 50 mM, 50 mM to 75 mM, 75 mM to 100 mM, or 100 mM to 200 mM.

Embodiment 76: The radiopharmaceutical composition of Embodiments 1 to 75, wherein the one or more stabilizing agents comprise one or more pH stabilizers.

Embodiment 77: The radiopharmaceutical composition of Embodiment 76, wherein the one or more pH stabilizers function as a pH buffer.

Embodiment 78: The radiopharmaceutical composition of Embodiments 76 or 77, wherein the one or more pH stabilizers comprise an organic acid.

Embodiment 79: The radiopharmaceutical composition of Embodiment 78, wherein the organic acid is an acetic acid, fumaric acid, ascorbic acid, propionic acid, benzene sulfonic acid, carbonic acid, citrate acid, aspartic acid, maleic acid, methane sulfonic acid, or tartaric acid.

Embodiment 80: The radiopharmaceutical composition of Embodiments 76 to 79, wherein the one or more pH stabilizers comprise an inorganic acid.

Embodiment 81: The radiopharmaceutical composition of Embodiment 80, wherein the inorganic acid is hydrobromic acid, hydrochloric acid, phosphoric acid, boric acid, or sulfuric acid.

Embodiment 82: The radiopharmaceutical composition of Embodiments 76 to 81, wherein the one or more pH stabilizers comprise a base.

Embodiment 83: The radiopharmaceutical composition of Embodiment 82, wherein the base is tromethamine (Tris), ammonium hydroxide, diethanolamine, or sodium hydroxide.

Embodiment 84: The radiopharmaceutical composition of Embodiments 76 to 83, wherein the one or more pH stabilizers comprise an amino acid or a salt thereof Embodiment 85: The radiopharmaceutical composition of Embodiment 84, wherein the amino acid is glycine, lysine, arginine, histidine, or a salt thereof.

Embodiment 86: The radiopharmaceutical composition of Embodiments 76 to 85, wherein the one or more pH stabilizers comprise an alkaline salt.

Embodiment 87: The radiopharmaceutical composition of Embodiment 86, wherein the alkaline salt is sodium acetate, sodium ascorbate, sodium benzoate, sodium bicarbonate, sodium carbonate, tribasic sodium phosphate acid, dibasic sodium phosphate acid, monobasic sodium phosphate acid, sodium tartrate, sodium lactate, sodium succinate, or disodium succinate.

Embodiment 88: The radiopharmaceutical composition of Embodiments 76 to 85, wherein the one or more pH stabilizers comprise an acid salt.

Embodiment 89: The radiopharmaceutical composition of Embodiment 88, wherein the acid salt is ammonium sulfate.

Embodiment 90: The radiopharmaceutical composition of Embodiments 76, wherein the one or more pH stabilizers comprise Sodium acetate, Sodium ascorbate, Ascorbic acid, Acetic acid, Fumaric acid propionic acid, ascorbic acid, ammonium sulfate, ammonium hydroxide, arginine, aspartic acid, benzene sulfonic acid, sodium benzoate, sodium bicarbonate, boric acid, sodium carbonate, carbonic acid, diethanolamine, citrate acid, hydrobromic acid, glycine, histidine, sodium lactate, (1)-lysine, maleic acid, methane sulfonic acid, phosphate acid, monobasic sodium phosphate acid, tribasic sodium phosphate acid, dibasic sodium phosphate acid, sodium hydroxide, sodium/disodium succinate, sulfuric acid, sodium tartrate, tartaric acid, tromethamine (tris), or a combination thereof.

Embodiment 91: The radiopharmaceutical composition of Embodiments 76 to 90, wherein the one or more pH stabilizers are present in the radiopharmaceutical composition at about 0.001 wt % to about 10 wt %.

Embodiment 92: The radiopharmaceutical composition of Embodiment 91, wherein the one or more pH stabilizers are present in the radiopharmaceutical composition at about 0.01 wt % to about 5 wt %, about 0.05 wt % to about 2 wt %, or about 0.1 wt % to about 1 wt %.

Embodiment 93: The radiopharmaceutical composition of Embodiments 76 to 90, wherein the one or more pH stabilizers are present in the radiopharmaceutical composition at a concentration of from 0.1 to 5 mg/mL.

Embodiment 94: The radiopharmaceutical composition of Embodiments 76 to 90, wherein the one or more pH stabilizers are present in the radiopharmaceutical composition at about 10 mM to about 500 mM.

Embodiment 95: The radiopharmaceutical composition of Embodiments 76 to 90, wherein the one or more pH stabilizers are present in the radiopharmaceutical composition at about 0.1 mM to 2 mM, 1 mM to 2 mM, 1 mM to 10 mM, 5 mM to 10 mM, 5 mM to 15 mM, 1 mM to 15 mM or 1 mM to 25 mM.

Embodiment 96: The radiopharmaceutical composition of Embodiments 76 to 95, wherein the one or more pH stabilizers are configured to maintain a pH of the radiopharmaceutical composition at about 4 to about 8.

Embodiment 97: The radiopharmaceutical composition of Embodiments 76 to 95, wherein the one or more pH stabilizers are configured to maintain a pH of the radiopharmaceutical composition at about 5 to about 7.

Embodiment 98: The radiopharmaceutical composition of Embodiments 1 to 95, wherein the pH of the radiopharmaceutical composition is within a range of about 4 to about 8.

Embodiment 99: The radiopharmaceutical composition of Embodiments 1 to 95, wherein the pH of the radiopharmaceutical composition is about 5.5 to about 6.0.

Embodiment 100: The radiopharmaceutical composition of Embodiments 1 to 99, wherein the composition comprises one or more stabilizing agents selected from Table 2, Table 3, and Table 4.

Embodiment 101: The radiopharmaceutical composition of Embodiments 1 to 100, wherein the aqueous vehicle comprises water, saline solution, dextrose in water, dextrose in saline solution, Ringer's solution, or lactated Ringer's solution.

Embodiment 102: The radiopharmaceutical composition of Embodiments 1 to 100, wherein the radiopharmaceutical composition is isotonic.

Embodiment 103: The radiopharmaceutical composition of Embodiments 1 to 102, wherein the radiopharmaceutical composition is a solution or suspension.

Embodiment 104: The radiopharmaceutical composition of Embodiments 1 to 103, wherein the radiopharmaceutical composition is formulated for IV infusion or bolus injection.

Embodiment 105: The radiopharmaceutical composition of Embodiments 1 to 104, wherein the radiopharmaceutical composition further comprises one or more excipients selected from: a tonicity adjusting agent, a preservative, an antimicrobial agent, a solubilizing agent, a suspending agent, and a surfactant.

Embodiment 106: The radiopharmaceutical composition of Embodiments 24 to 105, wherein the linker comprises one or more groups selected from: substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Embodiment 107: The radiopharmaceutical composition of Embodiment 106, wherein the targeting ligand is a binding peptide, and the linker is attached to the binding peptide via the N terminus of the peptide.

Embodiment 108: The radiopharmaceutical composition of Embodiment 106, wherein the targeting ligand is a binding peptide, and the linker is attached to the binding peptide via the C terminus of the peptide.

Embodiment 109: The radiopharmaceutical composition of Embodiment 106, wherein the targeting ligand is a binding peptide, and the linker is attached to the binding peptide via a non-terminal amino acid of the peptide.

Embodiment 110: The radiopharmaceutical composition of Embodiments 1 to 109, wherein the radionuclide is an alpha particle-emitting radionuclide.

Embodiment 111: The radiopharmaceutical composition of Embodiment 110, wherein the alpha particle-emitting radionuclide is actinium-225, astatine-211, thorium-227, or radium-223.

Embodiment 112: The radiopharmaceutical composition of Embodiment 110, wherein the alpha particle-emitting radionuclide is actinium-225.

Embodiment 113: The radiopharmaceutical composition of Embodiment 112, wherein the actinium-225 is present in the radiopharmaceutical composition that it provides a volumetric radioactivity of about 5 to 20 MBq/mL.

Embodiment 114: The radiopharmaceutical composition of Embodiments 1 to 113, wherein the composition retains at least 90 mol % of the initial conjugate after 168 hours at room temperature (25° C.).

Embodiment 115: The radiopharmaceutical composition of Embodiments 1 to 113, wherein the composition retains at least 95 mol % of the initial conjugate after 168 hours at room temperature (25° C.).

Embodiment 116: The radiopharmaceutical composition of Embodiments 1 to 113, wherein the composition retains at least 98 mol % of the initial conjugate after 168 hours at room temperature (25° C.).

Embodiment 117: The radiopharmaceutical composition of Embodiments 1 to 116, wherein the composition retains at least 85 mol %, at least 90 mol %, at least 92 mol %, at least 95 mol %, at least 98 mol % or at least 99 mol % of the initial conjugate after 120 hours at room temperature (25° C.).

Embodiment 118: The radiopharmaceutical composition of Embodiments 1 to 114, wherein the composition retains 95 mol % or more of the initial conjugate after 48 hours, 72 hours, 96 hours, 120 hours, 148 hours, 168 hours, 192 hours, or 216 hours at room temperature (25° C.).

Embodiment 119: The radiopharmaceutical composition of Embodiments 1 to 118, wherein the radionuclide is actinium-225, and wherein the composition contains no more than about 5% free actinium after 168 hours at room temperature (25° C.), compared to the total amount of the initial chelated actinium content in the composition.

Embodiment 120: The radiopharmaceutical composition of Embodiments 1 to 118, wherein the radionuclide is actinium-225, and wherein the composition contains no more than about 2% or about 1% free actinium after 168 hours at room temperature (25° C.), compared to the total amount of the initial chelated actinium content in the composition.

Embodiment 121: The radiopharmaceutical composition of Embodiments 1 to 120, wherein the radionuclide is actinium-225, and wherein the composition contains no more than a total of 5 mol % of daughter isotopes of actinium-225 after 168 hours at room temperature (25° C.), compared to the total amount of the initial chelated actinium content in the composition.

Embodiment 122: The radiopharmaceutical composition of Embodiments 1 to 120, wherein the radionuclide is actinium-225, and wherein the composition contains no more than a total of 1 mol % of un-chelated daughter isotopes of actinium-225 after 168 hours at room temperature (25° C.), compared to the total amount of the initial chelated actinium content in the composition.

Embodiment 123: The radiopharmaceutical composition of Embodiments 1 to 28, comprising: (a) the conjugate, wherein the conjugate is present in the radiopharmaceutical composition at a concentration equivalent to about 10 to 45 mCi/L; (b) a pH stabilizer, wherein the pH stabilizer is present in the radiopharmaceutical composition at a concentration of about 80 to about 120 mM; (c) optionally a radiolysis stabilizer, wherein the radiolysis stabilizer is present in the radiopharmaceutical composition at concentration of about 1 wt % to about 10 wt %; (d) a free metal chelator, therein the free metal chelator is present in the radiopharmaceutical composition at concentration of about 0.01 mg/mL to about 1 mg/mL; and (e) an aqueous vehicle.

Embodiment 124: The radiopharmaceutical composition of Embodiment 123, comprising: (a) the conjugate, wherein the conjugate is present in the radiopharmaceutical composition at a concentration equivalent to about 10 to 45 mCi/L; (b) a pH stabilizer, wherein the pH stabilizer is sodium L-ascorbate and is present in the radiopharmaceutical composition at a concentration of about 80 to about 120 mM; (c) optionally a radiolysis stabilizer, wherein the radiolysis stabilizer is Dextran 40 and is present in the radiopharmaceutical composition at a concentration of about 1 wt % to about 10 wt %; (d) a free metal chelator, wherein the free metal chelator is DTPA and is present in the radiopharmaceutical composition at a concentration of about 0.01 mg/mL to about 1 mg/mL; and (e) an aqueous vehicle, wherein the aqueous vehicle is saline solution.

Embodiment 125: The radiopharmaceutical composition of Embodiment 123 or 124, comprising: (a) the conjugate, wherein the conjugate is present in the radiopharmaceutical composition at a concentration equivalent to about 10 to 25 mCi/L; (b) a pH stabilizer, wherein the pH stabilizer is sodium L-ascorbate and is present in the radiopharmaceutical composition at a concentration of about 90-110 mM; (c) a radiolysis stabilizer, wherein the radiolysis stabilizer is Dextran 40 and is present in the radiopharmaceutical composition at a concentration of about 4-6 wt %; (d) a free metal chelator, wherein the free metal chelator is DTPA and is present in the radiopharmaceutical composition at a concentration of about 0.01-0.03 mg/mL; and (e) an aqueous vehicle, wherein the aqueous vehicle is sodium chloride saline solution at a concentration of about 0.9% w/w.

Embodiment 126: The radiopharmaceutical composition of Embodiment 123 or 124, comprising: (a) the conjugate, wherein the conjugate is present in the radiopharmaceutical composition at a concentration equivalent to about 10 to 25 mCi/L; (b) a pH stabilizer, wherein the pH stabilizer is sodium L-ascorbate and is present in the radiopharmaceutical composition at a concentration of about 90-110 mM; (c) a free metal chelator, wherein the free metal chelator is DTPA and is present in the radiopharmaceutical composition at a concentration of about 0.04-0.06 mg/mL; and (d) an aqueous vehicle, wherein the aqueous vehicle is sodium chloride saline solution at a concentration of about 0.9% w/w.

Embodiment 127: The radiopharmaceutical composition of Embodiment 123 or 124, comprising: (a) the conjugate, wherein the conjugate is present in the radiopharmaceutical composition at a concentration equivalent to about 25 to 35 mCi/L; (b) a pH stabilizer, wherein the pH stabilizer is sodium L-ascorbate and is present in the radiopharmaceutical composition at a concentration of about 90-110 mM; (c) a free metal chelator, wherein the free metal chelator is DTPA and is present in the radiopharmaceutical composition at a concentration of about 0.04-0.06 mg/mL; and (d) an aqueous vehicle, wherein the aqueous vehicle is sodium chloride saline solution at a concentration of about 0.9% w/w.

Embodiment 128: The liquid radiopharmaceutical composition of Embodiment 1, comprising or consisting essentially of: (a) the $^{225}$Ac-DOTA-TATE, wherein the $^{225}$Ac-DOTA-TATE is present in the radiopharmaceutical composition at a concentration equivalent to about 10 mCi/L to about 25 mCi/L; (b) the sodium ascorbate, wherein the sodium ascorbate is sodium L-ascorbate and is present in the radiopharmaceutical composition at a concentration of about 100 mM; (c) the DTPA, wherein the DTPA is present in the radiopharmaceutical composition at a concentration of about 0.05 mg/mL; and (d) the aqueous vehicle, wherein the aqueous vehicle is sodium chloride saline solution at a concentration of about 0.9% w/w; wherein the radiopharmaceutical composition retains at least 90 mol % of the initial $^{225}$Ac-DOTA-TATE after stored for 120 hours at 25° C.

Embodiment 129: The liquid radiopharmaceutical composition of Embodiment 1, comprising or consisting essentially of: (a) the $^{225}$Ac-DOTA-TATE, wherein the $^{225}$Ac-DOTA-TATE is present in the radiopharmaceutical composition in an amount of 146-275 µCi in a 12 mL solution; (b) the sodium ascorbate, wherein the sodium ascorbate is sodium L-ascorbate and is present in the radiopharmaceutical composition at a concentration of about 18.5 mg/mL; (c) the DTPA, wherein the DTPA is present in the radiopharmaceutical composition at a concentration of about 0.05 mg/mL; and (d) the aqueous vehicle, wherein the aqueous vehicle is sodium chloride saline solution at a concentration of about 0.9% w/w; wherein the radiopharmaceutical composition retains at least 90 mol % of the initial $^{225}$Ac-DOTA-TATE after stored for 120 hours at 25° C.

Embodiment 130: The liquid radiopharmaceutical composition of Embodiment 1, comprising or consisting essentially of: (a) the $^{225}$Ac-DOTA-TATE, wherein the $^{225}$Ac-DOTA-TATE is present in the radiopharmaceutical composition in an amount of 146-275 µCi in a 12 mL solution; (b) the sodium ascorbate, wherein the sodium ascorbate is sodium L-ascorbate and is present in the radiopharmaceutical composition at a concentration of about 18.5±4.63 mg/mL; (c) the DTPA, wherein the DTPA is present in the radiopharmaceutical composition at a concentration of about 0.05 mg/mL; and (d) the aqueous vehicle, wherein the aqueous vehicle is sodium chloride saline solution at a concentration of about 0.9% w/w; wherein the radiopharmaceutical composition retains at least 90 mol % of the initial $^{225}$Ac-DOTA-TATE after stored for 120 hours at 25° C.

Embodiment 128: A method of making a radiopharmaceutical composition of Embodiments 1 to 127, comprising: (a) combining a radionuclide with a pre-labeled conjugate, wherein the pre-labeled conjugate comprises a targeting ligand and a metal chelator covalently attached to the targeting ligand, thereby producing a labeled conjugate, and (b) combining the one or more stabilizing agents with the labeled conjugate.

Embodiment 129: A method of making a radiopharmaceutical composition of Embodiments 1 to 127, comprising: (a) combining a radionuclide with a pre-labeled conjugate in the presence of one or more stabilizer agents, wherein the pre-labeled conjugate comprises a targeting ligand and a metal chelator covalently attached to the targeting ligand, thereby producing a mixture comprising a labeled conjugate, and (b) optionally combining one or more stabilizing agents to the mixture.

Embodiment 130: A method of treating a disease in a subject in need thereof, comprising administering to the subject the radiopharmaceutical composition of Embodiments 1 to 127.

Embodiment 131: The method of Embodiment 130, wherein the disease is a cancer.

Embodiment 132: The method of Embodiment 131, wherein the cancer is an SSR-associated cancer.

Embodiment 133: The method of Embodiments 130 to 132, wherein the cancer is an SSTR2-associated cancer.

Embodiment 134: The method of Embodiments 130 to 133, wherein the cancer is a neuroendocrine cancer, a lymphatic cancer, a pancreatic cancer, a pituitary cancer, a breast cancer, a stomach cancer, medulloblastoma, or neuroblastoma.

Embodiment 135: The method of Embodiments 130 to 134, wherein the cancer is a neuroendocrine cancer.

Embodiment 136: The method of Embodiment 135, comprising administering to the subject the radiopharmaceutical composition, wherein the neuroendocrine cancer is recurrent.

Embodiment 137: The method of Embodiment 134 or 135, wherein the neuroendocrine cancer is refractory to a radiotherapy that comprises beta-particle emitting radionuclide.

Embodiment 138: The method of Embodiment 137, wherein the subject has received a radiotherapy that comprises beta-particle emitting radionuclide (e.g., $^{177}$Lu-DOTA-TATE or $^{177}$Lu-DOTA-TOC) prior to the administering of the radiopharmaceutical composition.

Embodiment 139: The method of Embodiment 134 to 138, wherein the neuroendocrine cancer is a neuroendocrine lung cancer or a neuroendocrine pancreatic cancer.

Embodiment 140: The method of Embodiment 134 to 138, wherein the neuroendocrine cancer is a Carcinoid tumor in the lungs, gastrointestinal tract or thymus, Pancreatic neuroendocrine tumor (e.g., Gastrinoma, Insulinoma, Glucagonoma, VIPoma) Medullary thyroid carcinoma, Merkel cell carcinoma, Pheochromocytoma of the adrenal gland, Adrenal cancer, Small cell carcinoma (such as in the lungs), or Large cell carcinoid tumor (such as in the lungs).

Embodiment 141: The method of Embodiments 130 to 140, wherein the radiopharmaceutical composition is administered to the subject in an amount equivalent to about 1 kBq/kg to about 0.2GBq/kg body weight per dose.

Embodiment 142: The method of Embodiments 130 to 140, wherein the radiopharmaceutical composition is administered to the subject in an amount equivalent to about 5 kBq/kg to about 50,000 kBq/kg body weight per dose.

Embodiment 143: The method of Embodiments 130 to 140, wherein the radiopharmaceutical composition is administered to the subject in an amount equivalent to about 20 k Bq/kg to about 5,000 kBq/kg body weight per dose.

Embodiment 144: The method of Embodiments 130 to 140, wherein the radiopharmaceutical composition is administered to the subject in an amount equivalent to about 50 k Bq/kg to about 500 kBq/kg body weight per dose.

Embodiment 145: The method of Embodiments 130 to 140, wherein the radiopharmaceutical composition is administered to the subject in an amount equivalent to about 50 k Bq/kg to about 200 kBq/kg body weight per dose.

Embodiment 146: The method of Embodiments 130 to 140, comprising administering to the subject the radiopharmaceutical composition wherein the radiopharmaceutical composition is administered to the subject in an amount equivalent to about 70 kBq/kg to about 150 kBq/kg body weight per dose.

Embodiment 147: The method of Embodiments 130 to 146, comprising administering to the subject the radiopharmaceutical composition, wherein the radiopharmaceutical composition is administered at an 8-week interval.

Embodiment 148: The method of Embodiments 130 to 147, comprising administering to the subject the radiopharmaceutical composition, wherein the radiopharmaceutical composition is administered to achieve a cumulative dose in the subject of about 10,000 kBq to about 100,000 kBq.

Embodiment 149: The method of Embodiments 130 to 147, comprising administering to the subject the radiopharmaceutical composition, wherein the radiopharmaceutical composition is administered to achieve a cumulative dose in the subject of about 40,000 kBq to about 70,000 kBq.

SEQUENCE LISTING

```
Sequence total quantity: 104
SEQ ID NO: 1            moltype = AA  length = 8
FEATURE                 Location/Qualifiers
source                  1..8
                        mol_type = protein
                        organism = synthetic construct
SITE                    1
                        note = D-Phenylalanine
SITE                    4
                        note = D-Tryptophan
SEQUENCE: 1
FCYWKVCW                                                                   8

SEQ ID NO: 2            moltype = AA  length = 8
FEATURE                 Location/Qualifiers
source                  1..8
                        mol_type = protein
                        organism = synthetic construct
SITE                    1
                        note = D-Pyridyl-L-alanine
SITE                    4
                        note = D-Tryptophan
SEQUENCE: 2
ACYWKVCT                                                                   8

SEQ ID NO: 3            moltype = AA  length = 8
FEATURE                 Location/Qualifiers
source                  1..8
                        mol_type = protein
                        organism = synthetic construct
SITE                    1
                        note = D-Phenylalanine
SITE                    4
                        note = D-Tryptophan
SITE                    8
                        note = (2R,3R)-2-aminobutane-1,3-diol
SEQUENCE: 3
FCFWKTCX                                                                   8

SEQ ID NO: 4            moltype = AA  length = 8
FEATURE                 Location/Qualifiers
source                  1..8
                        mol_type = protein
                        organism = synthetic construct
SITE                    1
                        note = L-3-(1-Naphthyl)alanine
SITE                    2
                        note = D-Cysteine
SITE                    3
                        note = Pyridyl-L-alanine
```

-continued

```
SITE            4
                note = D-Tryptophan
SITE            8
                note = L-3-(1-Naphthyl)alanine
SEQUENCE: 4
XCAWKACX                                                                           8

SEQ ID NO: 5    moltype = AA  length = 8
FEATURE         Location/Qualifiers
source          1..8
                mol_type = protein
                organism = synthetic construct
SITE            1
                note = L-3-(1-Naphthyl)alanine
SITE            2
                note = D-Cysteine
SITE            3
                note = Pyridyl-L-alanine
SITE            4
                note = D-Tryptophan
SITE            8
                note = L-3-(1-Naphthyl)alanine
SEQUENCE: 5
XCAWKGCX                                                                           8

SEQ ID NO: 6    moltype = AA  length = 8
FEATURE         Location/Qualifiers
source          1..8
                mol_type = protein
                organism = synthetic construct
SITE            1
                note = L-3-(1-Naphthyl)alanine
SITE            2
                note = D-Cysteine
SITE            3
                note = Pyridyl-L-alanine
SITE            4
                note = D-Tryptophan
SITE            8
                note = L-3-(1-Naphthyl)alanine
SEQUENCE: 6
XCAWKICX                                                                           8

SEQ ID NO: 7    moltype = AA  length = 8
FEATURE         Location/Qualifiers
source          1..8
                mol_type = protein
                organism = synthetic construct
SITE            1
                note = L-3-(1-Naphthyl)alanine
SITE            2
                note = D-Cysteine
SITE            3
                note = Pyridyl-L-alanine
SITE            4
                note = D-Tryptophan
SITE            8
                note = L-3-(1-Naphthyl)alanine
SEQUENCE: 7
XCAWKLCX                                                                           8

SEQ ID NO: 8    moltype = AA  length = 8
FEATURE         Location/Qualifiers
source          1..8
                mol_type = protein
                organism = synthetic construct
SITE            1
                note = L-3-(1-Naphthyl)alanine
SITE            2
                note = D-Cysteine
SITE            3
                note = Pyridyl-L-alanine
SITE            4
                note = D-Tryptophan
SITE            8
                note = L-3-(1-Naphthyl)alanine
SEQUENCE: 8
XCAWKVCX                                                                           8
```

-continued

```
SEQ ID NO: 9              moltype = AA   length = 11
FEATURE                   Location/Qualifiers
source                    1..11
                          mol_type = protein
                          organism = synthetic construct
SITE                      5
                          note = D-Tryptophan
SITE                      6
                          note = 4-aminomethylphenylalanine
SEQUENCE: 9
CKFFWFTFTS C                                                                   11

SEQ ID NO: 10             moltype = AA   length = 28
FEATURE                   Location/Qualifiers
source                    1..28
                          mol_type = protein
                          organism = synthetic construct
SEQUENCE: 10
SANSNPAMAP RERKAGCKNF FWKTFTSC                                                 28

SEQ ID NO: 11             moltype = AA   length = 8
FEATURE                   Location/Qualifiers
source                    1..8
                          mol_type = protein
                          organism = synthetic construct
SEQUENCE: 11
CFFWKTFC                                                                        8

SEQ ID NO: 12             moltype = AA   length = 8
FEATURE                   Location/Qualifiers
source                    1..8
                          mol_type = protein
                          organism = synthetic construct
SITE                      4
                          note = D-Tryptophan
SEQUENCE: 12
CFFWKTFC                                                                        8

SEQ ID NO: 13             moltype = AA   length = 8
FEATURE                   Location/Qualifiers
source                    1..8
                          mol_type = protein
                          organism = synthetic construct
SITE                      2
                          note = (S)-2-amino-2-(N-methylbenzamido)acetic acid
SITE                      4
                          note = D-Tryptophan
SEQUENCE: 13
CXFWKTFC                                                                        8

SEQ ID NO: 14             moltype = AA   length = 8
FEATURE                   Location/Qualifiers
source                    1..8
                          mol_type = protein
                          organism = synthetic construct
SITE                      2
                          note = (R)-2-amino-2-(N-methylbenzamido)acetic acid
SITE                      4
                          note = D-Tryptophan
SEQUENCE: 14
CXFWKTFC                                                                        8

SEQ ID NO: 15             moltype = AA   length = 8
FEATURE                   Location/Qualifiers
source                    1..8
                          mol_type = protein
                          organism = synthetic construct
SITE                      3
                          note = (S)-2-amino-2-(N-methylbenzamido)acetic acid
SEQUENCE: 15
CFXWKTFC                                                                        8
```

```
SEQ ID NO: 16            moltype = AA  length = 8
FEATURE                  Location/Qualifiers
source                   1..8
                         mol_type = protein
                         organism = synthetic construct
SITE                     3
                         note = (R)-2-amino-2-(N-methylbenzamido)acetic acid
SEQUENCE: 16
CFXWKTFC                                                                    8

SEQ ID NO: 17            moltype = AA  length = 8
FEATURE                  Location/Qualifiers
source                   1..8
                         mol_type = protein
                         organism = synthetic construct
SITE                     3
                         note = (S)-2-amino-2-(N-methylbenzamido)acetic acid
SITE                     4
                         note = D-Tryptophan
SEQUENCE: 17
CFXWKTFC                                                                    8

SEQ ID NO: 18            moltype = AA  length = 8
FEATURE                  Location/Qualifiers
source                   1..8
                         mol_type = protein
                         organism = synthetic construct
SITE                     3
                         note = (R)-2-amino-2-(N-methylbenzamido)acetic acid
SITE                     4
                         note = D-Tryptophan
SEQUENCE: 18
CFXWKTFC                                                                    8

SEQ ID NO: 19            moltype = AA  length = 8
FEATURE                  Location/Qualifiers
source                   1..8
                         mol_type = protein
                         organism = synthetic construct
SITE                     1
                         note = D-Cysteine
SITE                     3
                         note = (S)-2-amino-2-(N-methylbenzamido)acetic acid
SITE                     4
                         note = D-Tryptophan
SEQUENCE: 19
CFXWKTFC                                                                    8

SEQ ID NO: 20            moltype = AA  length = 8
FEATURE                  Location/Qualifiers
source                   1..8
                         mol_type = protein
                         organism = synthetic construct
SITE                     1
                         note = D-Cysteine
SITE                     3
                         note = (R)-2-amino-2-(N-methylbenzamido)acetic acid
SITE                     4
                         note = D-Tryptophan
SEQUENCE: 20
CFXWKTFC                                                                    8

SEQ ID NO: 21            moltype = AA  length = 9
FEATURE                  Location/Qualifiers
source                   1..9
                         mol_type = protein
                         organism = synthetic construct
SITE                     4
                         note = (S)-2-amino-2-(N-methylbenzamido)acetic acid
SEQUENCE: 21
YCFXWKTFC                                                                   9
```

```
SEQ ID NO: 22           moltype = AA  length = 9
FEATURE                 Location/Qualifiers
source                  1..9
                        mol_type = protein
                        organism = synthetic construct
SITE                    4
                        note = (R)-2-amino-2-(N-methylbenzamido)acetic acid
SEQUENCE: 22
YCFXWKTFC                                                                  9

SEQ ID NO: 23           moltype = AA  length = 9
FEATURE                 Location/Qualifiers
source                  1..9
                        mol_type = protein
                        organism = synthetic construct
SITE                    4
                        note = (S)-2-amino-2-(N-methylbenzamido)acetic acid
SITE                    5
                        note = D-Tryptophan
SEQUENCE: 23
YCFXWKTFC                                                                  9

SEQ ID NO: 24           moltype = AA  length = 9
FEATURE                 Location/Qualifiers
source                  1..9
                        mol_type = protein
                        organism = synthetic construct
SITE                    4
                        note = (R)-2-amino-2-(N-methylbenzamido)acetic acid
SITE                    5
                        note = D-Tryptophan
SEQUENCE: 24
YCFXWKTFC                                                                  9

SEQ ID NO: 25           moltype = AA  length = 8
FEATURE                 Location/Qualifiers
source                  1..8
                        mol_type = protein
                        organism = synthetic construct
SITE                    4
                        note = D-Tryptophan
SITE                    5
                        note = (S)-2-amino-2-((S)-2-aminopropanamido)acetic acid
SEQUENCE: 25
CFFWXTFC                                                                   8

SEQ ID NO: 26           moltype = AA  length = 8
FEATURE                 Location/Qualifiers
source                  1..8
                        mol_type = protein
                        organism = synthetic construct
SITE                    4
                        note = D-Tryptophan
SITE                    5
                        note = (R)-2-amino-2-((S)-2-aminopropanamido)acetic acid
SEQUENCE: 26
CFFWXTFC                                                                   8

SEQ ID NO: 27           moltype = AA  length = 8
FEATURE                 Location/Qualifiers
source                  1..8
                        mol_type = protein
                        organism = synthetic construct
SITE                    4
                        note = D-Tryptophan
SITE                    5
                        note =
                        (S)-2-amino-2-((S)-2-amino-N-methylpropanamido)acetic acid
SEQUENCE: 27
CFFWXTFC                                                                   8
```

```
SEQ ID NO: 28          moltype = AA   length = 8
FEATURE                Location/Qualifiers
source                 1..8
                       mol_type = protein
                       organism = synthetic construct
SITE                   4
                       note = D-Tryptophan
SITE                   5
                       note =
                       (R)-2-amino-2-((S)-2-amino-N-methylpropanamido)acetic acid
SEQUENCE: 28
CFFWXTFC                                                                        8

SEQ ID NO: 29          moltype = AA   length = 8
FEATURE                Location/Qualifiers
source                 1..8
                       mol_type = protein
                       organism = synthetic construct
SITE                   4
                       note = D-Tryptophan
SITE                   6
                       note = (S)-2-amino-2-(2-hydroxy-N-methylacetamido)acetic
                       acid
SEQUENCE: 29
CFFWKXFC                                                                        8

SEQ ID NO: 30          moltype = AA   length = 8
FEATURE                Location/Qualifiers
source                 1..8
                       mol_type = protein
                       organism = synthetic construct
SITE                   4
                       note = D-Tryptophan
SITE                   6
                       note = (R)-2-amino-2-(2-hydroxy-N-methylacetamido)acetic
                       acid
SEQUENCE: 30
CFFWKXFC                                                                        8

SEQ ID NO: 31          moltype = AA   length = 8
FEATURE                Location/Qualifiers
source                 1..8
                       mol_type = protein
                       organism = synthetic construct
SITE                   4
                       note = D-Tryptophan
SITE                   7
                       note = (S)-2-amino-2-(N-methylbenzamido)acetic acid
SEQUENCE: 31
CFFWKTXC                                                                        8

SEQ ID NO: 32          moltype = AA   length = 8
FEATURE                Location/Qualifiers
source                 1..8
                       mol_type = protein
                       organism = synthetic construct
SITE                   4
                       note = D-Tryptophan
SITE                   7
                       note = (S)-2-amino-2-(N-methylbenzamido)acetic acid
SEQUENCE: 32
CFFWKTXC                                                                        8

SEQ ID NO: 33          moltype = AA   length = 8
FEATURE                Location/Qualifiers
source                 1..8
                       mol_type = protein
                       organism = synthetic construct
SITE                   4
                       note = D-Tryptophan
SEQUENCE: 33
CFFWKTYC                                                                        8
```

```
SEQ ID NO: 34           moltype = AA   length = 8
FEATURE                 Location/Qualifiers
source                  1..8
                        mol_type = protein
                        organism = synthetic construct
SEQUENCE: 34
CFFWKTYC                                                                    8

SEQ ID NO: 35           moltype = AA   length = 8
FEATURE                 Location/Qualifiers
source                  1..8
                        mol_type = protein
                        organism = synthetic construct
VARIANT                 3
                        note = Isoleucine or Leucine
SEQUENCE: 35
CFXWKTFC                                                                    8

SEQ ID NO: 36           moltype = AA   length = 8
FEATURE                 Location/Qualifiers
source                  1..8
                        mol_type = protein
                        organism = synthetic construct
SITE                    4
                        note = D-Tryptophan
SEQUENCE: 36
CFYWKTFC                                                                    8

SEQ ID NO: 37           moltype = AA   length = 8
FEATURE                 Location/Qualifiers
source                  1..8
                        mol_type = protein
                        organism = synthetic construct
SEQUENCE: 37
CFYWKTFC                                                                    8

SEQ ID NO: 38           moltype = AA   length = 9
FEATURE                 Location/Qualifiers
source                  1..9
                        mol_type = protein
                        organism = synthetic construct
SITE                    5
                        note = D-Tryptophan
SEQUENCE: 38
YCFAWKTFC                                                                   9

SEQ ID NO: 39           moltype = AA   length = 9
FEATURE                 Location/Qualifiers
source                  1..9
                        mol_type = protein
                        organism = synthetic construct
SEQUENCE: 39
YCFAWKTFC                                                                   9

SEQ ID NO: 40           moltype = AA   length = 9
FEATURE                 Location/Qualifiers
source                  1..9
                        mol_type = protein
                        organism = synthetic construct
SEQUENCE: 40
YCFFWKTFC                                                                   9

SEQ ID NO: 41           moltype = AA   length = 9
FEATURE                 Location/Qualifiers
source                  1..9
                        mol_type = protein
                        organism = synthetic construct
VARIANT                 4
                        note = Isoleucine or Leucine
SEQUENCE: 41
YCFXWKTFC                                                                   9
```

```
SEQ ID NO: 42           moltype = AA   length = 14
FEATURE                 Location/Qualifiers
source                  1..14
                        mol_type = protein
                        organism = synthetic construct
SEQUENCE: 42
AGCKNFFWKT FTSC                                                          14

SEQ ID NO: 43           moltype = AA   length = 8
FEATURE                 Location/Qualifiers
source                  1..8
                        mol_type = protein
                        organism = synthetic construct
SITE                    4
                        note = D-Tryptophan
SEQUENCE: 43
CFAWKTAC                                                                  8

SEQ ID NO: 44           moltype = AA   length = 8
FEATURE                 Location/Qualifiers
source                  1..8
                        mol_type = protein
                        organism = synthetic construct
SITE                    4
                        note = D-Tryptophan
SEQUENCE: 44
CFAWKTFC                                                                  8

SEQ ID NO: 45           moltype = AA   length = 8
FEATURE                 Location/Qualifiers
source                  1..8
                        mol_type = protein
                        organism = synthetic construct
SITE                    4
                        note = D-Tryptophan
SEQUENCE: 45
CFFWKTFC                                                                  8

SEQ ID NO: 46           moltype = AA   length = 8
FEATURE                 Location/Qualifiers
source                  1..8
                        mol_type = protein
                        organism = synthetic construct
SEQUENCE: 46
CFFWKTFC                                                                  8

SEQ ID NO: 47           moltype = AA   length = 11
FEATURE                 Location/Qualifiers
source                  1..11
                        mol_type = protein
                        organism = synthetic construct
SITE                    1
                        note = N-methylcysteine
SITE                    5
                        note = D-3-(1-Naphthyl)alanine
SITE                    6
                        note = 4-aminomethylphenylalanine
SEQUENCE: 47
CKFFXFTFTS C                                                             11

SEQ ID NO: 48           moltype = AA   length = 11
FEATURE                 Location/Qualifiers
source                  1..11
                        mol_type = protein
                        organism = synthetic construct
SITE                    1
                        note = N-methylcysteine
SITE                    5
                        note = D-Tryptophan
SITE                    6
                        note = 4-aminomethylphenylalanine
SEQUENCE: 48
CKFFWFTFTS C                                                             11
```

```
SEQ ID NO: 49            moltype = AA   length = 11
FEATURE                  Location/Qualifiers
source                   1..11
                         mol_type = protein
                         organism = synthetic construct
SITE                     1
                         note = N-methylcysteine
SITE                     5
                         note = D-Tryptophan
SITE                     6
                         note = 4-methylaminomethyl-L-phenylalanine
SEQUENCE: 49
CKFFWFTFTS C                                                                   11

SEQ ID NO: 50            moltype = AA   length = 11
FEATURE                  Location/Qualifiers
source                   1..11
                         mol_type = protein
                         organism = synthetic construct
SITE                     5
                         note = D-3-(1-Naphthyl)alanine
SITE                     6
                         note = 4-aminomethylphenylalanine
SEQUENCE: 50
CKFFXFTFTS C                                                                   11

SEQ ID NO: 51            moltype = AA   length = 11
FEATURE                  Location/Qualifiers
source                   1..11
                         mol_type = protein
                         organism = synthetic construct
SITE                     5
                         note = D-Tryptophan
SEQUENCE: 51
CKFFWKTYTS C                                                                   11

SEQ ID NO: 52            moltype = AA   length = 11
FEATURE                  Location/Qualifiers
source                   1..11
                         mol_type = protein
                         organism = synthetic construct
SITE                     6
                         note = Pyridyl-L-alanine
SEQUENCE: 52
CKFFWATYTS C                                                                   11

SEQ ID NO: 53            moltype = AA   length = 7
FEATURE                  Location/Qualifiers
source                   1..7
                         mol_type = protein
                         organism = synthetic construct
SITE                     3
                         note = D-Tryptophan
SEQUENCE: 53
CFWKTFC                                                                         7

SEQ ID NO: 54            moltype = AA   length = 7
FEATURE                  Location/Qualifiers
source                   1..7
                         mol_type = protein
                         organism = synthetic construct
SITE                     4
                         note = D-Tryptophan
SEQUENCE: 54
CFFWKFC                                                                         7

SEQ ID NO: 55            moltype = AA   length = 7
FEATURE                  Location/Qualifiers
source                   1..7
                         mol_type = protein
                         organism = synthetic construct
SITE                     4
                         note = D-Tryptophan
SEQUENCE: 55
CFFWKTC                                                                         7
```

```
SEQ ID NO: 56            moltype = AA  length = 9
FEATURE                  Location/Qualifiers
source                   1..9
                         mol_type = protein
                         organism = synthetic construct
SITE                     4
                         note = D-Tryptophan
SEQUENCE: 56
CFFWKTFTC                                                                  9

SEQ ID NO: 57            moltype = AA  length = 9
FEATURE                  Location/Qualifiers
source                   1..9
                         mol_type = protein
                         organism = synthetic construct
SITE                     4
                         note = D-Tryptophan
SEQUENCE: 57
CFFWKTFTC                                                                  9

SEQ ID NO: 58            moltype = AA  length = 9
FEATURE                  Location/Qualifiers
source                   1..9
                         mol_type = protein
                         organism = synthetic construct
SITE                     5
                         note = D-Tryptophan
SITE                     6
                         note = Pyridyl-L-alanine
SEQUENCE: 58
CKFFWATFC                                                                  9

SEQ ID NO: 59            moltype = AA  length = 9
FEATURE                  Location/Qualifiers
source                   1..9
                         mol_type = protein
                         organism = synthetic construct
SITE                     5
                         note = D-Tryptophan
SEQUENCE: 59
CKFFWKTFC                                                                  9

SEQ ID NO: 60            moltype = AA  length = 9
FEATURE                  Location/Qualifiers
source                   1..9
                         mol_type = protein
                         organism = synthetic construct
SITE                     5
                         note = D-Tryptophan
SEQUENCE: 60
CNFFWKTFC                                                                  9

SEQ ID NO: 61            moltype = AA  length = 10
FEATURE                  Location/Qualifiers
source                   1..10
                         mol_type = protein
                         organism = synthetic construct
SITE                     5
                         note = D-Tryptophan
SEQUENCE: 61
CNFFWKTFTC                                                                10

SEQ ID NO: 62            moltype = AA  length = 8
FEATURE                  Location/Qualifiers
source                   1..8
                         mol_type = protein
                         organism = synthetic construct
SITE                     4
                         note = D-Tryptophan
SEQUENCE: 62
YCFWKTFC                                                                   8
```

```
SEQ ID NO: 63            moltype = AA  length = 10
FEATURE                  Location/Qualifiers
source                   1..10
                         mol_type = protein
                         organism = synthetic construct
SITE                     5
                         note = D-Tryptophan
SITE                     6
                         note = Pyridyl-L-alanine
SEQUENCE: 63
YCKFWATFTC                                                                 10

SEQ ID NO: 64            moltype = AA  length = 12
FEATURE                  Location/Qualifiers
source                   1..12
                         mol_type = protein
                         organism = synthetic construct
SITE                     6
                         note = D-Tryptophan
SITE                     7
                         note = Pyridyl-L-alanine
SEQUENCE: 64
YCKEFWATFK SC                                                              12

SEQ ID NO: 65            moltype = AA  length = 13
FEATURE                  Location/Qualifiers
source                   1..13
                         mol_type = protein
                         organism = synthetic construct
SITE                     7
                         note = D-Tryptophan
SITE                     8
                         note = Pyridyl-L-alanine
SEQUENCE: 65
YCKFEFWATF KSC                                                             13

SEQ ID NO: 66            moltype = AA  length = 8
FEATURE                  Location/Qualifiers
source                   1..8
                         mol_type = protein
                         organism = synthetic construct
SITE                     3
                         note = 4-aminophenyl propanoic acid
SEQUENCE: 66
CFXWKTFC                                                                   8

SEQ ID NO: 67            moltype = AA  length = 8
FEATURE                  Location/Qualifiers
source                   1..8
                         mol_type = protein
                         organism = synthetic construct
SITE                     3
                         note = 4-aminophenyl propanoic acid
SITE                     4
                         note = D-Tryptophan
SEQUENCE: 67
CFXWKTFC                                                                   8

SEQ ID NO: 68            moltype = AA  length = 8
FEATURE                  Location/Qualifiers
source                   1..8
                         mol_type = protein
                         organism = synthetic construct
SITE                     1
                         note = Cysteine with an N-term carbamoyl moiety
SITE                     3
                         note = 4-aminophenyl propanoic acid
SEQUENCE: 68
CFXWKTFC                                                                   8
```

```
SEQ ID NO: 69            moltype = AA  length = 8
FEATURE                  Location/Qualifiers
source                   1..8
                         mol_type = protein
                         organism = synthetic construct
SITE                     1
                         note = Cysteine with an N-term carbamoyl moiety
SITE                     3
                         note = 4-aminophenyl propanoic acid
SITE                     4
                         note = D-Tryptophan
SEQUENCE: 69
CFXWKTFC                                                                    8

SEQ ID NO: 70            moltype = AA  length = 8
FEATURE                  Location/Qualifiers
source                   1..8
                         mol_type = protein
                         organism = synthetic construct
SITE                     3
                         note = 4-aminophenyl propanoic acid
SITE                     4
                         note = L-3-(2-Naphthyl)alanine
SEQUENCE: 70
CFXXKTFC                                                                    8

SEQ ID NO: 71            moltype = AA  length = 9
FEATURE                  Location/Qualifiers
source                   1..9
                         mol_type = protein
                         organism = synthetic construct
SITE                     4
                         note = 4-aminophenyl propanoic acid
SEQUENCE: 71
YCFXWKTFC                                                                   9

SEQ ID NO: 72            moltype = AA  length = 9
FEATURE                  Location/Qualifiers
source                   1..9
                         mol_type = protein
                         organism = synthetic construct
SITE                     4
                         note = 4-aminophenyl propanoic acid
SITE                     5
                         note = D-Tryptophan
SEQUENCE: 72
YCFXWKTFC                                                                   9

SEQ ID NO: 73            moltype = AA  length = 9
FEATURE                  Location/Qualifiers
source                   1..9
                         mol_type = protein
                         organism = synthetic construct
SITE                     1
                         note = Tyrosine with an N-term carbamoyl moiety
SITE                     4
                         note = 4-aminophenyl propanoic acid
SEQUENCE: 73
YCFXWKTFC                                                                   9

SEQ ID NO: 74            moltype = AA  length = 8
FEATURE                  Location/Qualifiers
source                   1..8
                         mol_type = protein
                         organism = synthetic construct
SITE                     3
                         note = 4-aminophenyl propanoic acid
SEQUENCE: 74
CFXWKTYC                                                                    8
```

```
SEQ ID NO: 75           moltype = AA   length = 8
FEATURE                 Location/Qualifiers
source                  1..8
                        mol_type = protein
                        organism = synthetic construct
SITE                    1
                        note = Cysteine with an N-term carbamoyl moiety
SITE                    3
                        note = 4-aminophenyl propanoic acid
SEQUENCE: 75
CFXWKTYC                                                                  8

SEQ ID NO: 76           moltype = AA   length = 8
FEATURE                 Location/Qualifiers
source                  1..8
                        mol_type = protein
                        organism = synthetic construct
SEQUENCE: 76
CFAWKTFC                                                                  8

SEQ ID NO: 77           moltype = AA   length = 9
FEATURE                 Location/Qualifiers
source                  1..9
                        mol_type = protein
                        organism = synthetic construct
SEQUENCE: 77
YCFAWKTFC                                                                 9

SEQ ID NO: 78           moltype = AA   length = 9
FEATURE                 Location/Qualifiers
source                  1..9
                        mol_type = protein
                        organism = synthetic construct
SITE                    5
                        note = D-Tryptophan
SEQUENCE: 78
YCFAWKTFC                                                                 9

SEQ ID NO: 79           moltype = AA   length = 9
FEATURE                 Location/Qualifiers
source                  1..9
                        mol_type = protein
                        organism = synthetic construct
SITE                    4
                        note = 4-aminomethylphenylalanine
SEQUENCE: 79
YCFFWKTFC                                                                 9

SEQ ID NO: 80           moltype = AA   length = 9
FEATURE                 Location/Qualifiers
source                  1..9
                        mol_type = protein
                        organism = synthetic construct
SITE                    1
                        note = D-Cysteine
SITE                    4
                        note = O-methyl-D-threonine
SITE                    5
                        note = L-3-(2-Naphthyl)alanine
SEQUENCE: 80
CFYTXKTFC                                                                 9

SEQ ID NO: 81           moltype = AA   length = 9
FEATURE                 Location/Qualifiers
source                  1..9
                        mol_type = protein
                        organism = synthetic construct
SITE                    4
                        note = O-methyl-D-threonine
SITE                    5
                        note = L-3-(2-Naphthyl)alanine
SEQUENCE: 81
CFYTXKTFC                                                                 9
```

```
SEQ ID NO: 82           moltype = AA  length = 8
FEATURE                 Location/Qualifiers
source                  1..8
                        mol_type = protein
                        organism = synthetic construct
SITE                    1
                        note = Cysteine with an N-term carbamoyl moiety
SITE                    3
                        note = 4-aminophenyl propanoic acid
SITE                    4
                        note = D-Tryptophan
SEQUENCE: 82
CFXWKTYC                                                                8

SEQ ID NO: 83           moltype = AA  length = 8
FEATURE                 Location/Qualifiers
source                  1..8
                        mol_type = protein
                        organism = synthetic construct
SITE                    4
                        note = D-Tryptophan
SEQUENCE: 83
CFVWKTFC                                                                8

SEQ ID NO: 84           moltype = AA  length = 8
FEATURE                 Location/Qualifiers
source                  1..8
                        mol_type = protein
                        organism = synthetic construct
SEQUENCE: 84
CFAWKTAC                                                                8

SEQ ID NO: 85           moltype = AA  length = 8
FEATURE                 Location/Qualifiers
source                  1..8
                        mol_type = protein
                        organism = synthetic construct
SITE                    4
                        note = D-Tryptophan
SEQUENCE: 85
CFAWKTAC                                                                8

SEQ ID NO: 86           moltype = AA  length = 8
FEATURE                 Location/Qualifiers
source                  1..8
                        mol_type = protein
                        organism = synthetic construct
SEQUENCE: 86
CFAWKTFC                                                                8

SEQ ID NO: 87           moltype = AA  length = 9
FEATURE                 Location/Qualifiers
source                  1..9
                        mol_type = protein
                        organism = synthetic construct
SITE                    1
                        note = Gamma-Aminobutyric acid
SEQUENCE: 87
XCFAWKTFC                                                               9

SEQ ID NO: 88           moltype = AA  length = 8
FEATURE                 Location/Qualifiers
source                  1..8
                        mol_type = protein
                        organism = synthetic construct
SEQUENCE: 88
CFAWKTVC                                                                8

SEQ ID NO: 89           moltype = AA  length = 8
FEATURE                 Location/Qualifiers
source                  1..8
                        mol_type = protein
                        organism = synthetic construct
SEQUENCE: 89
CFVWKTVC                                                                8
```

```
SEQ ID NO: 90              moltype = AA   length = 8
FEATURE                    Location/Qualifiers
source                     1..8
                           mol_type = protein
                           organism = synthetic construct
SEQUENCE: 90
CFAWKTGC                                                                    8

SEQ ID NO: 91              moltype = AA   length = 9
FEATURE                    Location/Qualifiers
source                     1..9
                           mol_type = protein
                           organism = synthetic construct
SEQUENCE: 91
FCFAWKTFC                                                                   9

SEQ ID NO: 92              moltype = AA   length = 9
FEATURE                    Location/Qualifiers
source                     1..9
                           mol_type = protein
                           organism = synthetic construct
SITE                       1
                           note = Tyrosine with an N-term carbamoyl moiety
SEQUENCE: 92
YCFAWKTFC                                                                   9

SEQ ID NO: 93              moltype = AA   length = 9
FEATURE                    Location/Qualifiers
source                     1..9
                           mol_type = protein
                           organism = synthetic construct
SITE                       1
                           note = Tyrosine with an N-term carbamoyl moiety
SITE                       4
                           note = 4-aminomethylphenylalanine
SEQUENCE: 93
YCFFWKTFC                                                                   9

SEQ ID NO: 94              moltype = AA   length = 9
FEATURE                    Location/Qualifiers
source                     1..9
                           mol_type = protein
                           organism = synthetic construct
SITE                       4
                           note = 4-(N-isopropyl)-aminomethylphenylalanine
SEQUENCE: 94
YCFFWKTFC                                                                   9

SEQ ID NO: 95              moltype = AA   length = 9
FEATURE                    Location/Qualifiers
source                     1..9
                           mol_type = protein
                           organism = synthetic construct
SITE                       1
                           note = D-Cysteine
SITE                       4
                           note = O-methyl-L-threonine
SITE                       5
                           note = L-3-(2-Naphthyl)alanine
SEQUENCE: 95
CFYTXKTFC                                                                   9

SEQ ID NO: 96              moltype = AA   length = 9
FEATURE                    Location/Qualifiers
source                     1..9
                           mol_type = protein
                           organism = synthetic construct
SITE                       4
                           note = O-methyl-L-threonine
SITE                       5
                           note = L-3-(2-Naphthyl)alanine
SEQUENCE: 96
CFYTXKTFC                                                                   9
```

```
SEQ ID NO: 97          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-Tryptophan
SEQUENCE: 97
FCYWKTCT                                                                  8

SEQ ID NO: 98          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-Tryptophan
SITE                   8
                       note = (2R,3R)-2-aminobutane-1,3-diol
SEQUENCE: 98
FCYWKTCX                                                                  8

SEQ ID NO: 99          moltype = AA  length = 8
FEATURE                Location/Qualifiers
source                 1..8
                       mol_type = protein
                       organism = synthetic construct
SITE                   1
                       note = D-Phenylalanine
SITE                   4
                       note = D-Tryptophan
SITE                   8
                       note = (2R,3R)-2-aminobutane-1,3-diol
SEQUENCE: 99
FCFWKTCX                                                                  8

SEQ ID NO: 100         moltype = AA  length = 8
FEATURE                Location/Qualifiers
source                 1..8
                       mol_type = protein
                       organism = synthetic construct
SITE                   1
                       note = D-Phenylalanine
SITE                   3
                       note = L-3-(1-Naphthyl)alanine
SITE                   4
                       note = D-Tryptophan
SITE                   8
                       note = (2R,3R)-2-aminobutane-1,3-diol
SEQUENCE: 100
FCXWKTCX                                                                  8

SEQ ID NO: 101         moltype = AA  length = 8
FEATURE                Location/Qualifiers
source                 1..8
                       mol_type = protein
                       organism = synthetic construct
SITE                   1
                       note = (S)-2-amino-3-(4-chlorophenyl)propanoic acid
SITE                   2
                       note = D-Cysteine
SITE                   3
                       note =
                       (2S)-2-amino-3-(4-(2,6-dioxohexahydropyrimidine-4-carboxami
                       do)phenyl)propanoic acid
SITE                   4
                       note = (R)-2-amino-3-(4-ureidophenyl)propanoic acid
SITE                   8
                       note = D-Tyrosine
SEQUENCE: 101
XCXXKTCY                                                                  8
```

```
SEQ ID NO: 102          moltype = AA  length = 8
FEATURE                 Location/Qualifiers
source                  1..8
                        mol_type = protein
                        organism = synthetic construct
SITE                    1
                        note = (S)-2-amino-3-(4-chlorophenyl)propanoic acid
SITE                    2
                        note = D-Cysteine
SITE                    4
                        note = (R)-2-amino-3-(4-ureidophenyl)propanoic acid
SITE                    8
                        note = D-Tyrosine
SEQUENCE: 102
XCYXKTCY                                                                     8

SEQ ID NO: 103          moltype = AA  length = 13
FEATURE                 Location/Qualifiers
source                  1..13
                        mol_type = protein
                        organism = synthetic construct
SITE                    1
                        note = 18F-Lysine
SEQUENCE: 103
KYNDRLPLYI SNP                                                              13

SEQ ID NO: 104          moltype = AA  length = 5
FEATURE                 Location/Qualifiers
source                  1..5
                        mol_type = protein
                        organism = synthetic construct
SEQUENCE: 104
EAAAK                                                                        5
```

We claim:

1. A liquid radiopharmaceutical composition comprising:
   (a) $^{225}$Ac-DOTA-TATE or a pharmaceutically acceptable salt thereof, wherein the $^{225}$Ac-DOTA-TATE or the pharmaceutically acceptable salt thereof is present in the radiopharmaceutical composition at a concentration equivalent to 10 mCi/L to 50 mCi/L;
   (b) a pH stabilizer, wherein the pH stabilizer is present in the radiopharmaceutical composition at a concentration of 10 mM to 500 mM;
   (c) a free metal chelator, wherein the free metal chelator is present in the radiopharmaceutical composition at a concentration of 0.01 mg/mL to 5 mg/mL; and
   (d) water;
   wherein the radiopharmaceutical composition is a solution, and
   wherein the radiopharmaceutical composition retains at least 85% of the $^{225}$Ac content as $^{225}$Ac-DOTA-TATE or the pharmaceutically acceptable salt thereof after 48 hours.

2. The liquid radiopharmaceutical composition of claim 1, wherein a pH of the liquid radiopharmaceutical composition is about 4.0 to about 8.0.

3. The liquid radiopharmaceutical composition of claim 1, wherein the $^{225}$Ac-DOTA-TATE or the pharmaceutically acceptable salt thereof is present in the radiopharmaceutical composition at a concentration equivalent to 10 mCi/L to 25 mCi/L.

4. The liquid radiopharmaceutical composition of claim 1, wherein the $^{225}$Ac-DOTA-TATE or the pharmaceutically acceptable salt thereof is present in the radiopharmaceutical composition at a concentration equivalent to about 12 mCi/L to about 23 mCi/L.

5. The liquid radiopharmaceutical composition of claim 1, wherein the $^{225}$Ac-DOTA-TATE or the pharmaceutically acceptable salt thereof is present in the radiopharmaceutical composition at a concentration equivalent to about 25 µg to about 150 µg of the DOTA-TATE.

6. The liquid radiopharmaceutical composition of claim 1, wherein the pH stabilizer is sodium acetate, sodium ascorbate, ascorbic acid, acetic acid, fumaric acid, propionic acid, ascorbic acid, ammonium sulfate, ammonium hydroxide, arginine, aspartic acid, benzene sulfonic acid, sodium benzoate, sodium bicarbonate, boric acid, sodium carbonate, carbonic acid, diethanolamine, citrate acid, hydrobromic acid, glycine, histidine, sodium lactate, lysine, maleic acid, methane sulfonic acid, phosphate acid, monobasic sodium phosphate acid, tribasic sodium phosphate acid, dibasic sodium phosphate acid, sodium hydroxide, sodium/disodium succinate, sulfuric acid, sodium tartrate, tartaric acid, tromethamine (tris), or a combination thereof.

7. The liquid radiopharmaceutical composition of claim 1, wherein the pH stabilizer is sodium acetate, acetic acid, sodium ascorbate, ascorbic acid, or a combination thereof.

8. The liquid radiopharmaceutical composition of claim 1, wherein the pH stabilizer is present in the radiopharmaceutical composition at a concentration of 80 mM to 125 mM.

9. The liquid radiopharmaceutical composition of claim 1, wherein the free metal chelator is selected from Ethylenediaminetetraacetic acid (EDTA), Diethylenetriaminepentaacetic acid (DTPA), 2-S-(4-Isothiocyanatobenzyl)-1,4,7-triazacyclononane-1,4,7-triacetic acid (NOTA), Triethylenetetramine (TETA), 1, 4, 7, 10, 13-pentaazacyclopentadecane-N, N', N", N''', N''''-pentaacetic acid (PEPA), 1,4,8,11-tetraazacyclo tetradecane-1,4,8,11-tetrapropionic acid (TETPA1 2,2',2''-(10-(2,6-dioxotetrahydro-2H-pyran-3-yl)-1,4,7,10-tetraazacyclododecane-1,4,7-triyl)triacetic acid (DOTA-GA), Deferoxamine (DFO), N, N-bis(2-hydroxybenzyl)ethylenediamine-N,N-diacetic acid (HBED), 1,4,7,10-Tetraazacyclododecane-1,4,7,10-tetra(methylene phosphonic acid) (DOTP), 6,6'-((1,4,10,13-tetraoxa-7,16-diazacyclooctadecane-7,16-diyl)bis(methylene))dipicolinic acid (Macropa), Meso-2,3-dimercaptosuccinic acid (DMSA), Dimercaptopropane sulfonate (DMPS), Dihydrolipoic acid (DHLA), Lipoic acid (LA), Thioglycolic acid (TGA), and 2,3 Dimercaptopropan-1-ol (BAL).

10. The liquid radiopharmaceutical composition of claim 1, wherein the free metal chelator is EDTA, DTPA, or Macropa.

11. The liquid radiopharmaceutical composition of claim 1, wherein the free metal chelator is present in the radiopharmaceutical composition at a concentration of 0.02 mg/mL to 2.5 mg/mL.

12. The liquid radiopharmaceutical composition of claim 1, wherein the radiopharmaceutical composition retains at least 85% of the $^{225}$Ac content as $^{225}$Ac-DOTA-TATE or the pharmaceutically acceptable salt thereof after 48 hours at about 4° C.

13. The liquid radiopharmaceutical composition of claim 1, wherein the radiopharmaceutical composition retains at least 85% of the $^{225}$Ac content as $^{225}$Ac-DOTA-TATE or the pharmaceutically acceptable salt thereof after 48 hours at about 20° C. to about 25° C.

14. The liquid radiopharmaceutical composition of claim 1, wherein the composition retains at least 90% of the $^{225}$Ac content as $^{225}$Ac-DOTA-TATE or the pharmaceutically acceptable salt thereof after 120 hours at about 20° C. to about 25° C.

15. The liquid radiopharmaceutical composition of claim 1, wherein the radiopharmaceutical composition is formulated as a unit dose form that contains about 5-25 mL of the solution.

16. The liquid radiopharmaceutical composition of claim 1, wherein the radiopharmaceutical composition is formulated for IV infusion.

17. The liquid radiopharmaceutical composition of claim 1, wherein the $^{225}$Ac-DOTA-TATE or the pharmaceutically acceptable salt thereof has a structure illustrated as

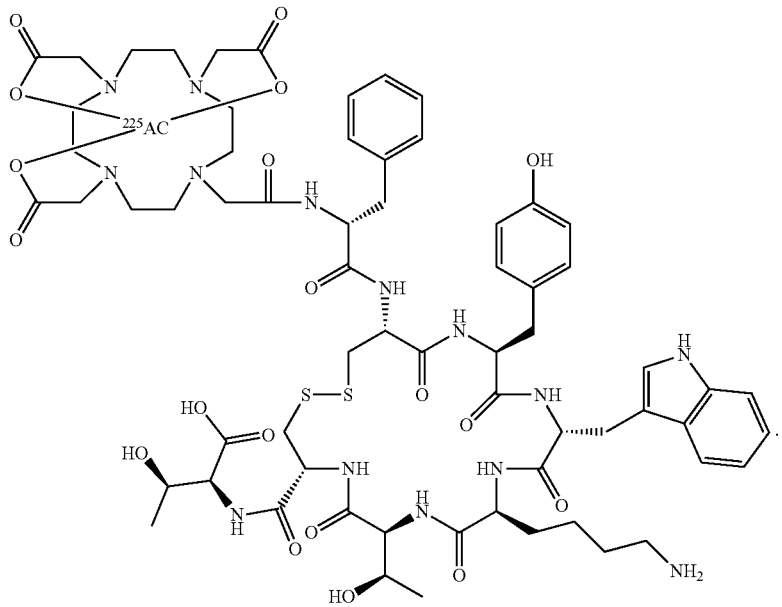

18. A method of treating a somatostatin receptor-positive (SSTR+) tumor in a subject in need thereof, comprising administering to the subject an effective amount of a liquid radiopharmaceutical composition of claim 1.

19. The method of claim 18, wherein the SSTR+tumor is gastroenteropancreatic neuroendocrine tumor (GEP-NET).

20. The method of claim 18, wherein, prior to the administrating of the liquid radiopharmaceutical composition, the subject received $^{177}$Lu based radiotherapy.

21. The method of claim 18, wherein, prior to the administrating of the liquid radiopharmaceutical composition, the subject received $^{177}$Lu-DOTA-TATE or $^{177}$Lu-DOTA-TOC treatment.

22. The method of claim 18, wherein the radiopharmaceutical composition is administered to the subject in an amount equivalent to about 60 kBq/kg body weight to about 120 kBq/kg body weight per dose.

* * * * *

UNITED STATES PATENT AND TRADEMARK OFFICE
CERTIFICATE OF CORRECTION

PATENT NO. : 11,819,556 B2
APPLICATION NO. : 18/324420
DATED : November 21, 2023
INVENTOR(S) : Daniel Kim et al.

It is certified that error appears in the above-identified patent and that said Letters Patent is hereby corrected as shown below:

In the Specification

Column 1; Lines 6-15, should read:
--This application is a continuation of U.S. Application No. 17/976,664, filed on October 28, 2022, which is a continuation of U.S. Application No. 17/858,859, filed July 6, 2022, now issued as U.S. Patent No. 11,497,822 on November 15, 2022, which is a divisional of U.S. Application No. 17/665,202, filed on February 4, 2022, now issued as U.S. Patent No. 11,541,134 on January 3, 2023, which claims the benefit of U.S. Provisional Application No. 63/228,535, filed on August 2, 2021, each of which is incorporated herein by reference in their entirety.--

In the Claims

Column 146; Line 53, "SSTR+tumor" should read --SSTR+ tumor--

Signed and Sealed this
Twenty-third Day of January, 2024

Katherine Kelly Vidal
*Director of the United States Patent and Trademark Office*